US011413340B2

(12) United States Patent
Brogdon et al.

(10) Patent No.: US 11,413,340 B2
(45) Date of Patent: Aug. 16, 2022

(54) MESOTHELIN CHIMERIC ANTIGEN RECEPTOR (CAR) AND ANTIBODY AGAINST PD-L1 INHIBITOR FOR COMBINED USE IN ANTICANCER THERAPY

(71) Applicants: Novartis AG, Basel (CH); The Trustees of the University of Pennsylvania, Philadelphia, PA (US); DANA-FARBER CANCER INSTITUTE, INC., Boston, MA (US); PRESIDENT AND FELLOWS OF HARVARD COLLEGE, Cambridge, MA (US)

(72) Inventors: Jennifer Brogdon, Sudbury, MA (US); Hwai Wen Chang, San Marcos, CA (US); Boris Engels, Arlington, MA (US); Gordon James Freeman, Brookline, MA (US); Gerhard Johann Frey, San Diego, CA (US); Jennifer Marie Mataraza, Cambridge, MA (US); Reshma Singh, Cambridge, MA (US); Arlene Helen Sharpe, Brookline, MA (US)

(73) Assignees: Novartis AG, Basel (CH); The Trustees of the University of Pennsylvania, Philadelphia, PA (US); Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 1070 days.

(21) Appl. No.: 16/065,387

(22) PCT Filed: Dec. 21, 2016

(86) PCT No.: PCT/US2016/067957

§ 371 (c)(1),
(2) Date: Jun. 22, 2018

(87) PCT Pub. No.: WO2017/112741

PCT Pub. Date: Jun. 29, 2017

(65) Prior Publication Data

US 2019/0000944 A1 Jan. 3, 2019

Related U.S. Application Data

(60) Provisional application No. 62/270,780, filed on Dec. 22, 2015.

(51) Int. Cl.

| | |
|---|---|
| ***A61K 39/395*** | (2006.01) |
| ***A61K 39/00*** | (2006.01) |
| ***A61P 35/00*** | (2006.01) |
| ***A61K 45/06*** | (2006.01) |

(52) U.S. Cl.

CPC .. *A61K 39/001168* (2018.08); *A61K 39/3955* (2013.01); *A61K 45/06* (2013.01); *A61P 35/00* (2018.01); *A61K 2039/505* (2013.01); *A61K 2039/5158* (2013.01); *A61K 2039/545* (2013.01)

(58) Field of Classification Search

None

See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |
| 5,712,149 | A | 1/1998 | Roberts |
| 5,874,240 | A | 2/1999 | Ni et al. |
| 5,906,936 | A | 5/1999 | Eshhar et al. |
| 6,103,521 | A | 8/2000 | Capon et al. |
| 6,319,494 | B1 | 11/2001 | Capon et al. |
| 6,355,779 | B1 | 3/2002 | Goodwin et al. |
| 6,410,319 | B1 | 6/2002 | Raubitschek et al. |
| 6,569,997 | B1 | 5/2003 | Kwon |
| 7,049,136 | B2 | 5/2006 | Seed et al. |
| 7,052,906 | B1 | 5/2006 | Lawson et al. |
| 7,070,995 | B2 | 7/2006 | Jensen |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |
| 7,514,537 | B2 | 4/2009 | Jensen |

(Continued)

FOREIGN PATENT DOCUMENTS

| | | | |
|---|---|---|---|
| CN | 103347897 | A | 10/2013 |
| EP | 0574512 | A1 | 12/1993 |

(Continued)

OTHER PUBLICATIONS

Morello et al. (Cancer Discovery 2015, pp OF1-OF15; DOI: 10, 1158/2159-8290. CD-15-0583) (cited on IDS filed Jan. 25, 2019) (Year: 2015).*

(Continued)

*Primary Examiner* — Meera Natarajan

(74) *Attorney, Agent, or Firm* — Saul Ewing Arnstein & Lehr LLP; Kathryn Doyle

(57) ABSTRACT

Provided are compositions for use in methods for treating diseases associated with expression of mesothelin comprising administering a cell that expresses a chimeric antigen receptor (CAR) specific to mesothelin in combination with a PD-L1 inhibitor.

32 Claims, 10 Drawing Sheets

Specification includes a Sequence Listing.

(56) References Cited

U.S. PATENT DOCUMENTS

| | | | |
|---|---|---|---|
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |
| 7,994,298 | B2 | 8/2011 | Zhang et al. |
| 8,211,422 | B2 | 7/2012 | Eshhar et al. |
| 8,252,914 | B2 | 8/2012 | Zhang et al. |
| 8,268,970 | B2 | 9/2012 | Terrett et al. |
| 8,389,282 | B2 | 3/2013 | Sadelain et al. |
| 8,399,645 | B2 | 3/2013 | Campana et al. |
| 8,465,743 | B2 | 6/2013 | Rosenberg et al. |
| 8,637,307 | B2 | 1/2014 | June et al. |
| 8,722,400 | B2 | 5/2014 | Riley et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,394,368 | B2 | 7/2016 | Brogdon et al. |
| 9,573,988 | B2 | 2/2017 | Brogdon et al. |
| 9,745,368 | B2 | 8/2017 | Milone et al. |
| 9,777,061 | B2 | 10/2017 | Ebersbach et al. |
| 9,815,901 | B2 | 11/2017 | Brogdon et al. |
| 2003/0060444 | A1 | 3/2003 | Finney et al. |
| 2003/0077249 | A1 | 4/2003 | Bebbington et al. |
| 2003/0148982 | A1 | 8/2003 | Brenner et al. |
| 2003/0224520 | A1 | 12/2003 | June et al. |
| 2004/0038886 | A1 | 2/2004 | Finney et al. |
| 2004/0043401 | A1 | 3/2004 | Sadelain et al. |
| 2005/0113564 | A1 | 5/2005 | Campana et al. |
| 2005/0129671 | A1 | 6/2005 | Cooper et al. |
| 2007/0036773 | A1 | 2/2007 | Cooper et al. |
| 2008/0131415 | A1 | 6/2008 | Riddell et al. |
| 2009/0257994 | A1 | 10/2009 | Jensen |
| 2011/0052554 | A1 | 3/2011 | Zakrzewski et al. |
| 2012/0107933 | A1 | 5/2012 | Ho et al. |
| 2012/0148552 | A1 | 6/2012 | Jensen |
| 2012/0321667 | A1 | 12/2012 | Sentman |
| 2013/0071409 | A1 | 3/2013 | Riley et al. |
| 2013/0071414 | A1 | 3/2013 | Dotti et al. |
| 2013/0149337 | A1 | 6/2013 | Cooper et al. |
| 2013/0155909 | A1 | 6/2013 | Jackson et al. |
| 2013/0287748 | A1 | 10/2013 | June et al. |
| 2014/0050708 | A1 | 2/2014 | Powell et al. |
| 2014/0099309 | A1 | 4/2014 | Powell, Jr. et al. |
| 2014/0099340 | A1 | 4/2014 | June et al. |
| 2014/0106449 | A1 | 4/2014 | June et al. |
| 2014/0186947 | A1 | 7/2014 | June et al. |
| 2014/0212446 | A1 | 7/2014 | Riley et al. |
| 2014/0219975 | A1 | 8/2014 | June et al. |
| 2014/0227237 | A1 | 8/2014 | June et al. |
| 2014/0271635 | A1 | 9/2014 | Brogdon et al. |
| 2014/0322169 | A1 | 10/2014 | Harper et al. |
| 2014/0322183 | A1 | 10/2014 | Milone et al. |
| 2014/0322212 | A1 | 10/2014 | Brogdon et al. |
| 2014/0322275 | A1 | 10/2014 | Brogdon et al. |
| 2014/0370045 | A1 | 12/2014 | June et al. |
| 2015/0017141 | A1 | 1/2015 | June et al. |
| 2015/0140019 | A1 | 5/2015 | June et al. |
| 2015/0190428 | A1 | 7/2015 | June et al. |
| 2015/0202286 | A1 | 7/2015 | June et al. |
| 2015/0283178 | A1 | 10/2015 | June et al. |
| 2015/0290244 | A1 | 10/2015 | June et al. |
| 2015/0342994 | A1 | 12/2015 | Riley et al. |
| 2016/0046724 | A1 | 2/2016 | Brogdon et al. |
| 2016/0051651 | A1 | 2/2016 | Brogdon et al. |
| 2016/0068601 | A1 | 3/2016 | Brogdon et al. |
| 2016/0096892 | A1 | 4/2016 | Brogdon et al. |
| 2016/0185861 | A1 | 6/2016 | Bedoya et al. |
| 2016/0311907 | A1 | 10/2016 | Brogdon et al. |
| 2016/0311917 | A1 | 10/2016 | Beatty et al. |
| 2016/0340406 | A1 | 11/2016 | Zhao et al. |
| 2016/0362472 | A1 | 12/2016 | Bitter et al. |
| 2017/0008963 | A1 | 1/2017 | Brogdon et al. |
| 2017/0081411 | A1 | 3/2017 | Engels et al. |
| 2017/0137783 | A1 | 5/2017 | Bedoya et al. |
| 2017/0183415 | A1 | 6/2017 | Brogdon et al. |
| 2017/0209492 | A1 | 7/2017 | June et al. |
| 2017/0211055 | A1 | 7/2017 | Brogdon et al. |
| 2017/0226495 | A1 | 8/2017 | Guimaraes |
| 2017/0239294 | A1 | 8/2017 | Thomas-Tikhonenko et al. |
| 2017/0260268 | A1 | 9/2017 | Beatty et al. |
| 2017/0274014 | A1 | 9/2017 | Brogdon et al. |
| 2017/0306416 | A1 | 10/2017 | Bedoya et al. |
| 2017/0335281 | A1 | 11/2017 | Loew et al. |
| 2018/0022795 | A1 | 1/2018 | Milone et al. |
| 2018/0044423 | A1 | 2/2018 | Ebersbach et al. |
| 2018/0044424 | A1 | 2/2018 | June et al. |
| 2018/0118834 | A1 | 5/2018 | Brogdon et al. |
| 2018/0125892 | A1 | 5/2018 | Brannetti et al. |
| 2018/0133296 | A1 | 5/2018 | Barrett |
| 2018/0140602 | A1 | 5/2018 | Angst et al. |
| 2018/0230193 | A1 | 8/2018 | Loew et al. |
| 2018/0252727 | A1 | 9/2018 | Garfall et al. |
| 2018/0258149 | A1 | 9/2018 | Motz et al. |
| 2018/0298068 | A1 | 10/2018 | Albelda |
| 2018/0312595 | A1 | 11/2018 | Brogdon et al. |

FOREIGN PATENT DOCUMENTS

| | | | |
|---|---|---|---|
| EP | 0871495 | A1 | 10/1998 |
| EP | 1226244 | A2 | 7/2002 |
| WO | 1992015322 | A1 | 9/1992 |
| WO | 199530014 | A1 | 11/1995 |
| WO | 9623814 | A1 | 8/1996 |
| WO | 9624671 | A1 | 8/1996 |
| WO | 1997015669 | A1 | 5/1997 |
| WO | 9723613 | A2 | 7/1997 |
| WO | 9818809 | A1 | 5/1998 |
| WO | 9900494 | A2 | 1/1999 |
| WO | 9957268 | A1 | 11/1999 |
| WO | 0014257 | A1 | 3/2000 |
| WO | 2002033101 | A1 | 4/2002 |
| WO | 02077029 | A2 | 10/2002 |
| WO | 02088334 | A1 | 11/2002 |
| WO | 2003057171 | A2 | 7/2003 |
| WO | 2005019429 | A2 | 3/2005 |
| WO | 2005044996 | A2 | 5/2005 |
| WO | 2005/118788 | A2 | 12/2005 |
| WO | 2006060878 | A1 | 6/2006 |
| WO | 2008045437 | A2 | 4/2008 |
| WO | 2009045957 | A1 | 4/2009 |
| WO | 2010085660 | A2 | 7/2010 |
| WO | 2010111282 | A1 | 9/2010 |
| WO | 2011059836 | A2 | 5/2011 |
| WO | 2011097477 | A1 | 8/2011 |
| WO | 2012058460 | A2 | 5/2012 |
| WO | 2012079000 | A1 | 6/2012 |
| WO | 2012082841 | A2 | 6/2012 |
| WO | 2012/099973 | A2 | 7/2012 |
| WO | 2012127464 | A2 | 9/2012 |
| WO | 2012129514 | A1 | 9/2012 |
| WO | 2012135854 | A2 | 10/2012 |
| WO | 2012138858 | A1 | 10/2012 |
| WO | 2013019615 | A2 | 2/2013 |
| WO | 2013033626 | A2 | 3/2013 |
| WO | 2013040371 | A2 | 3/2013 |
| WO | 2013040557 | A2 | 3/2013 |
| WO | 2013059593 | A1 | 4/2013 |
| WO | 2013063419 | A2 | 5/2013 |
| WO | 2013074916 | A1 | 5/2013 |
| WO | 2013/126712 | A1 | 8/2013 |
| WO | 2013126729 | A1 | 8/2013 |
| WO | 2013126733 | A1 | 8/2013 |
| WO | 2013142034 | A1 | 9/2013 |
| WO | 2014/011984 | A1 | 1/2014 |
| WO | 2014/011987 | A1 | 1/2014 |
| WO | 2014/011993 | A2 | 1/2014 |
| WO | 2014/012001 | A2 | 1/2014 |
| WO | 2014011988 | A2 | 1/2014 |
| WO | 2014011996 | A1 | 1/2014 |
| WO | 2014031687 | A1 | 2/2014 |

(56) References Cited

FOREIGN PATENT DOCUMENTS

| | | | |
|---|---|---|---|
| WO | 2014039513 | A2 | 3/2014 |
| WO | 2014/055442 | A2 | 4/2014 |
| WO | 2014052064 | A1 | 4/2014 |
| WO | 2014055657 | A1 | 4/2014 |
| WO | 2014130635 | A1 | 8/2014 |
| WO | 2014/145252 | A2 | 9/2014 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | 2015157252 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |
| WO | 2017/112741 | A1 | 6/2017 |

OTHER PUBLICATIONS

Almagro & Fransson, Frontiers in Bioscience 2008; 13:1619-33 (Year: 2008).*

Padlan (Advances in Protein Chemistry, 1996, 49:57-133) (Year: 1996).*

Berglund et al, Protein Science, 2008, 17:606-613 (Year: 2008).*

Corada (Blood, 2001; 97:1679-84) (Year: 2001).*

Kulkarni-Kale et al. Nucleic Acid Research, 2005, 33:W168-W171 (Year: 2005).*

Kim et al., "Human 4-1BB regulates CD28 co-stimulation to promote Th1 cell responses" Eur. J. Immunol. (1998) vol. 28 pp. 881-890.

Kochenderfer et al, "A Phase I Clinical Trial of Treatment of B-Cell Malignancies with Autologous Anti-Cd19-CAR-Transduced T Cells" Blood (2010) vol. 116 No 21 pp. 1179-1180 & 52nd Annual Meeting of the American-Society-of-Hematology (ASH); Orlando, FL, USA; Dec. 4-7, 2010 abstract.

Kochenderfer et al. "Construction and Pre-clinical Evaluation of an Anti-CD19 Chimeric Antigen Receptor", J Immunother (2009) vol. 32, No. 7, pp. 689-702.

Kochenderfer et al., "Eradication of B-lineage cells and regression of lymphoma in a patient treated with autologous T cells genetically-engineered to recognize CD19," Blood 116:4099-4102 (2010).

Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.

Kwon et al., "cDNA sequences of two inducible T-cell genes". Proc. Natl. Acad. Sci. U.S.A. 86(6): 1963-1967 (1989).

Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.

Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).

Lanitis et al., "Redirected Antitumor Activity of Primary Human Lymphocytes Transduced With a Fully Human Anti-mesothelin Chimeric Receptor" Molecular Therapy, 20(3):633-643 (2012).

Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.

Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.

Lee et al., "The Future is Now: Chimeric Antigen Receptors as New Targeted Therapies for Childhood Cancer," Clin. Dancer Res. 18:2780-2790 (2012).

Letourneur et al., "T-cell and basophil activation through the cytoplasmic tail of T-cell-receptor zeta family proteins," Proc. Natl. Acad. Sci. U.S.A 88: 8905-8909 (1991).

Levine et al., "Gene transfer in humans using a conditionally replicating lentiviral vector" PNAS (2006) vol. 103 No. 46 pp. 17372-17377.

Macallan et al., "Measurement and modeling of human T cell kinetics" European Journal of Immunology (2003) vol. 33 pp. 2316-2326.

Maher et al., "Human T lymphocyte cytotoxicity and proliferation directed by a single chimeric TCRzeta/CD28 receptor," Nat. Biotechnol. 20: 70-75 (2002).

Maus et al., "T cells expressing chimeric antigen receptors can cause anaphylaxis in humans" Cancel Immunol Res, 1:26-31 (2013).

McGuinness et al., "Anti-tumor activity of human T cells expressing the CC49-zeta chimeric immune receptor," Hum. Gene Ther. 10: 165-173 (1999).

Milone et al., "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.

Molina, "A Decade of Rituximab: Improving Survival Outcomes in Non-Hodgkin's Lymphoma" Annu. Rev. Med. (2008) vol. 59 pp. 237-250.

Morello et al. "Mesothelin-Targeted CARs: Driving T Cells to Solid Tumors" Cancer Discovery (2015) pp. OF1-OF15; DOI: 10.1158/2159-8290.CD-15-0583.

Morgan et al., "Case Report of a Serious Adverse Event Following the Administration of T Cells Transduced With a Chimeric Anitgen Receptor Recognizing ErbB2," Mol. Ther. 18(4): 843-851 (2010).

Moritz and Groner, "A spacer region between the single chain antibody- and the CD3 zeta-chain domain of chimeric T cell receptor components is required for efficient ligand binding and signaling activity," Gene Therapy 2(8): 539-546 (1995).

Moritz et al., "Cytotoxic T lymphocytes with a grafted recognition specificity for ERBB2-expressing tumor cells" Proc. Natl. Acad. Sci (1994) vol. 91 pp. 4318-4322.

Naldini et al., "In Vivo Gene Delivery and Stable Transduction of Nondividing Cells by a Lentiviral Vector" Science (1996) vol. 272 pp. 263-267.

NCBI accession HM_852952 accessed Sep. 29, 2015 from http://www.ncbi.nlm.nih.gov/nuccore/hm852952.

Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).

Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.

Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.

Patel et al., "Impact of chimeric immune receptor extracellular protein domains on T cell function" Gene Therapy (1999) vol. 6 pp. 412-419.

Porter et al. "Chimeric Antigen Receptor-Modified T Cells in Chronic Lymphoid Leukemia", The New England Journal of Medicine (2011) vol. 365 No. 8 pp. 725-733.

Porter et al., "A phase 1 trial of donor lumphocyte infusions expanded and activated ex vivo via CD3/CD28 costimulation" Blood (2006) vol. 107 No. 4 pp. 1325-1331.

Porter et al., "Chimeric Antigen Receptor Therapy for B-cell Malignancies" Journal of Cancer (2011) vol. 2 pp. 331-332.

(56) References Cited

OTHER PUBLICATIONS

Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer Architecture and Outcomes," AntiCancer Res. 32: 2377-2384 (2012).
Singapore Search Report and Written Opinion for Singapore Application No. 11201604815R dated Jul. 26, 2018.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Supplementary European Search Report for European Application No. EP14871351.4 dated May 23, 2017.
Tanyi et al. "Abstract CT105: Safety and feasibility of chimeric antigen receptor modified T cells directed against mesothelin (CART-meso) in patients with mesothelin expressing cancers" Cancer Research; Proceedings: AACR 106th Annual Meeting 2015; Apr. 18-22, 2015; Philadelphia, PA (2015) vol. 75, No. 15.
Tchou et al "Mesothelin, a novel immunotherapy target for triple negative breast cancer" Breast Cancer Research and Treatment (2012) vol. 133, Iss 2, pp. 799-804.
Till et al., "Adoptive immunotherapy for indolent non-Hodgkin lymphoma and mantle cell lymphoma using genetically modified autologous CD20-specificT cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Baeksgaard & Sorensen, "Acute tumor lysis syndrome in solid tumors—a case report and review of the iterature" Cancer Chemotherapy Pharmacology (2003) vol. 51 pp. 187-192.
Bondanza et al. "Suicide gene therapy of graft-versus-host disease induced by central memory human T ymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interieukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Dall & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Acad Sci USA (2009) vol. 106 pp. 3360-3365.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al., "A Third-Generation Lentivirus Vector with a Conditional Packaging System" Journal of Virology (1998) vol. 72 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093(2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.

(56) References Cited

OTHER PUBLICATIONS

GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Hornback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International application No. PCT/CN2014/094393, dated Mar. 30, 2015.
International Search Report and Written Opinion for International Application No. PCT/US2016/067957 dated Apr. 7, 2017.
International Search Report for International Application No. PCT/CN2013/089979 dated Sep. 26, 2014.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
John et al. "Blockade of PD-1 immunosuppression boosts CAR T-cell therapy" OncoImmunology (2013) vol. 2, No. 10, e26286, pp. 1-3.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kaneko et al. "A Binding Domain on Mesothelin for CA125/MUC16" The Journal of Biological Chemistry (2009) vol. 284, No. 6, pp. 3739-3749.
Kershaw et al., "A Phase I Study on Adoptive Immunotherapy Using Gene-Modified T Cells for Ovarian Cancer," Clin. Cancer Res. 12(20 Pt 1): 6106-6115 (2006).

* cited by examiner

\# First antibody dose (q5d)
* CAR dose (two doses total)
☆ Tissue harvest n=8 after PD takedowns

* indicates day of CAR dose
# indicates day of first antibody dose

Oral administration of RAD001: Day 0 PK in NSG mouse

Oral administration of RAD001: Day 14 PK in NSG mouse

```
                         SEQUENCE LISTING


<160> NUMBER OF SEQ ID NOS: 613

<210> SEQ ID NO 1
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Met Ala Leu Pro Val Thr Ala Leu Leu Leu Pro Leu Ala Leu Leu Leu
1               5                   10                  15

His Ala Ala Arg Pro
            20


<210> SEQ ID NO 2
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 3
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110
```

```
Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230


<210> SEQ ID NO 4
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
```

```
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Gly Gly Ser Gly Gly Gly Gly Ser
1               5                   10


<210> SEQ ID NO 6
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 7
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 8
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Arg Arg Lys Tyr Arg Ser Asn Lys Gly Glu Ser Pro Val Glu Pro
1               5                   10                  15
```

Ala Glu Pro Cys Arg Tyr Ser Cys Pro Arg Glu Glu Glu Gly Ser Thr
20 25 30

Ile Pro Ile Gln Glu Asp Tyr Arg Lys Pro Glu Pro Ala Cys Ser Pro
35 40 45

<210> SEQ ID NO 9
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 11
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
cgtgaggctc cggtgcccgt cagtgggcag agcgcacatc gcccacagtc cccgagaagt 60
tggggggagg ggtcggcaat tgaaccggtg cctagagaag gtggcgcggg gtaaactggg 120
aaagtgatgt cgtgtactgg ctccgccttt ttcccgaggg tgggggagaa ccgtatataa 180
gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300
gaattacttc cacctggctg cagtacgtga ttcttgatcc cgagcttcgg gttggaagtg 360
ggtgggagag ttcgaggcct tgcgcttaag gagccccttc gcctcgtgct tgagttgagg 420
cctggcctgg gcgctggggc cgccgcgtgc gaatctggtg gcaccttcgc gcctgtctcg 480
ctgctttcga taagtctcta gccatttaaa atttttgatg acctgctgcg acgctttttt 540
tctggcaaga tagtcttgta aatgcgggcc aagatctgca cactggtatt tcggtttttg 600
gggccgcggg cggcgacggg gcccgtgcgt cccagcgcac atgttcggcg aggcggggcc 660
tgcgagcgcg gccaccgaga atcggacggg ggtagtctca agctggccgg cctgctctgg 720
tgcctggcct cgcgccgccg tgtatcgccc cgccctgggc ggcaaggctg gcccggtcgg 780
caccagttgc gtgagcggaa agatggccgc ttcccggccc tgctgcaggg agctcaaaat 840
ggaggacgcg gcgctcggga gagcgggcgg gtgagtcacc cacacaaagg aaaagggcct 900
ttccgtcctc agccgtcgct tcatgtgact ccacggagta ccgggcgccg tccaggcacc 960
tcgattagtt ctcgagcttt tggagtacgt cgtctttagg ttggggggag gggttttatg 1020
cgatggagtt tccccacact gagtgggtgg agactgaagt taggccagct tggcacttga 1080
tgtaattctc cttggaattt gccctttttg agtttggatc ttggttcatt ctcaagcctc 1140
agacagtggt tcaaagtttt tttcttccat ttcaggtgtc gtga 1184

<210> SEQ ID NO 12
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12
atggccctgc ctgtgacagc cctgctgctg cctctggctc tgctgctgca tgccgctaga 60
ccc 63

<210> SEQ ID NO 13
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 14
<211> LENGTH: 690

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
gagagcaagt acggccctcc ctgccccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 15
<211> LENGTH: 847
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
aggtggcccg aaagtcccaa ggcccaggca tctagtgttc ctactgcaca gccccaggca 60
gaaggcagcc tagccaaagc tactactgca cctgccacta cgcgcaatac tggccgtggc 120
ggggaggaga agaaaaagga gaaagagaaa gaagaacagg aagagaggga gaccaagacc 180
cctgaatgtc catcccatac ccagccgctg ggcgtctatc tcttgactcc cgcagtacag 240
gacttgtggc ttagagataa ggccaccttt acatgtttcg tcgtgggctc tgacctgaag 300
gatgcccatt tgacttggga ggttgccgga aaggtaccca caggggggggt tgaggaaggg 360 ttgctggagc gccattccaa tggctctcag agccagcact caagactcac ccttccgaga 420
tccctgtgga acgccgggac ctctgtcaca tgtactctaa atcatcctag cctgcccccca 480 cagcgtctga tggcccttag agagccagcc gcccaggcac cagttaagct tagcctgaat 540
ctgctcgcca gtagtgatcc cccagaggcc gccagctggc tcttatgcga agtgtccggc 600
tttagcccgc ccaacatctt gctcatgtgg ctggaggacc agcgagaagt gaacaccagc 660
ggcttcgctc cagcccggcc cccaccccag ccgggttcta ccacattctg ggcctggagt 720
gtcttaaggg tcccagcacc acctagcccc cagccagcca catacacctg tgttgtgtcc 780
catgaagata gcaggaccct gctaaatgct tctaggagtc tggaggtttc ctacgtgact 840
gaccatt 847

<210> SEQ ID NO 16
<211> LENGTH: 30
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ggtggcggag gttctggagg tggaggttcc 30

<210> SEQ ID NO 17
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
atctacatct gggcgccctt ggccgggact tgtggggtcc ttctcctgtc actggttatc 60
accctttact gc 72

<210> SEQ ID NO 18
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 19
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 20
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180

```
gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 21
<211> LENGTH: 336
<212> TYPE: DNA
<213> ORGANISM: Homo  sapiens

<400> SEQUENCE: 21

agagtgaagt tcagcaggag cgcagacgcc cccgcgtacc agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 22
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
```

```
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370
```

<210> SEQ ID NO 23
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
atggccctcc ctgtcactgc cctgcttctc cccctcgcac tcctgctcca cgccgctaga     60

ccacccggat ggtttctgga ctctccggat cgcccgtgga atcccccaac cttctcaccg    120

gcactcttgg ttgtgactga gggcgataat gcgaccttca cgtgctcgtt ctccaacacc    180

tccgaatcat tcgtgctgaa ctggtaccgc atgagcccgt caaaccagac cgacaagctc    240

gccgcgtttc cggaagatcg gtcgcaaccg ggacaggatt gtcggttccg cgtgactcaa    300

ctgccgaatg gcagagactt ccacatgagc gtggtccgcg ctaggcgaaa cgactccggg    360

acctacctgt gcggagccat ctcgctggcg cctaaggccc aaatcaaaga gagcttgagg    420

gccgaactga gagtgaccga gcgcagagct gaggtgccaa ctgcacatcc atccccatcg    480

cctcggcctg cggggcagtt tcagaccctg gtcacgacca ctccggcgcc gcgcccaccg    540

actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720

aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960

cgcggccggg accccgaaat gggcgggaag cctagaagaa agaaccctca ggaaggcctg   1020

tataacgagc tgcagaagga caagatggcc gaggcctact ccgaaattgg gatgaaggga   1080
```

gagcggcgga ggggaaaggg gcacgacggc ctgtaccaag gactgtccac cgccaccaag 1140
gacacatacg atgccctgca catgcaggcc cttccccctc gc 1182

<210> SEQ ID NO 24
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Met Ala Leu Pro Val Thr Ala Leu Leu Leu Pro Leu Ala Leu Leu Leu
1 5 10 15

His Ala Ala Arg Pro Pro Gly Trp Phe Leu Asp Ser Pro Asp Arg Pro
20 25 30

Trp Asn Pro Pro Thr Phe Ser Pro Ala Leu Leu Val Val Thr Glu Gly
35 40 45

Asp Asn Ala Thr Phe Thr Cys Ser Phe Ser Asn Thr Ser Glu Ser Phe
50 55 60

Val Leu Asn Trp Tyr Arg Met Ser Pro Ser Asn Gln Thr Asp Lys Leu
65 70 75 80

Ala Ala Phe Pro Glu Asp Arg Ser Gln Pro Gly Gln Asp Cys Arg Phe
85 90 95

Arg Val Thr Gln Leu Pro Asn Gly Arg Asp Phe His Met Ser Val Val
100 105 110

Arg Ala Arg Arg Asn Asp Ser Gly Thr Tyr Leu Cys Gly Ala Ile Ser
115 120 125

Leu Ala Pro Lys Ala Gln Ile Lys Glu Ser Leu Arg Ala Glu Leu Arg
130 135 140

Val Thr Glu Arg Arg Ala Glu Val Pro Thr Ala His Pro Ser Pro Ser
145 150 155 160

Pro Arg Pro Ala Gly Gln Phe Gln Thr Leu Val Thr Thr Thr Pro Ala
165 170 175

Pro Arg Pro Pro Thr Pro Ala Pro Thr Ile Ala Ser Gln Pro Leu Ser
180 185 190

Leu Arg Pro Glu Ala Cys Arg Pro Ala Ala Gly Gly Ala Val His Thr
195 200 205

Arg Gly Leu Asp Phe Ala Cys Asp Ile Tyr Ile Trp Ala Pro Leu Ala
210 215 220

Gly Thr Cys Gly Val Leu Leu Leu Ser Leu Val Ile Thr Leu Tyr Cys
225 230 235 240

Lys Arg Gly Arg Lys Lys Leu Leu Tyr Ile Phe Lys Gln Pro Phe Met
245 250 255

Arg Pro Val Gln Thr Thr Gln Glu Glu Asp Gly Cys Ser Cys Arg Phe
260 265 270

Pro Glu Glu Glu Glu Gly Gly Cys Glu Leu Arg Val Lys Phe Ser Arg
275 280 285

Ser Ala Asp Ala Pro Ala Tyr Lys Gln Gly Gln Asn Gln Leu Tyr Asn
290 295 300

Glu Leu Asn Leu Gly Arg Arg Glu Glu Tyr Asp Val Leu Asp Lys Arg
305 310 315 320

Arg Gly Arg Asp Pro Glu Met Gly Gly Lys Pro Arg Arg Lys Asn Pro
325 330 335

```
Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390


<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Gly Gly Gly Ser
1               5


<210> SEQ ID NO 26
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 1-6
      "Gly Gly Gly Gly Ser" repeating units"

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 27
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Gly Gly Gly Ser Gly Gly Gly Gly Ser Gly Gly Gly Gly Ser Gly
1               5                   10                  15

Gly Gly Gly Ser
            20


<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 28

Gly Gly Gly Gly Ser Gly Gly Gly Gly Ser Gly Gly Gly Gly Ser
1 5 10 15

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

Gly Gly Gly Ser
1

<210> SEQ ID NO 30
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"
<220> FEATURE:
<221> NAME/KEY: source
<223> OTHER INFORMATION: /note="See specification as filed for detailed description of substitutions and preferred embodiments"

<400> SEQUENCE: 30
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140

-continued aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 31
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31
tttttttttt tttttttttt tttttttttt tttttttttt tttttttttt tttttttttt 60
tttttttttt tttttttttt tttttttttt tttttttttt 100

<210> SEQ ID NO 32
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)

<223> OTHER INFORMATION: /note="This sequence may encompass 50-5000 nucleotides"
<220> FEATURE:
<221> NAME/KEY: source
<223> OTHER INFORMATION: /note="See specification as filed for detailed description of substitutions and preferred embodiments"

<400> SEQUENCE: 32
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300
tttttttttt tttttttttt tttttttttt tttttttttt tttttttttt tttttttttt 360
tttttttttt tttttttttt tttttttttt tttttttttt tttttttttt tttttttttt 420
tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660
tttttttttt tttttttttt tttttttttt tttttttttt tttttttttt tttttttttt 720
tttttttttt tttttttttt tttttttttt tttttttttt tttttttttt tttttttttt 780
tttttttttt tttttttttt tttttttttt tttttttttt tttttttttt tttttttttt 840
tttttttttt tttttttttt tttttttttt tttttttttt tttttttttt tttttttttt 900
tttttttttt tttttttttt tttttttttt tttttttttt tttttttttt tttttttttt 960
tttttttttt tttttttttt tttttttttt tttttttttt tttttttttt tttttttttt 1020
tttttttttt tttttttttt tttttttttt tttttttttt tttttttttt tttttttttt 1080
tttttttttt tttttttttt tttttttttt tttttttttt tttttttttt tttttttttt 1140
tttttttttt tttttttttt tttttttttt tttttttttt tttttttttt tttttttttt 1200
tttttttttt tttttttttt tttttttttt tttttttttt tttttttttt tttttttttt 1260
tttttttttt tttttttttt tttttttttt tttttttttt tttttttttt tttttttttt 1320
tttttttttt tttttttttt tttttttttt tttttttttt tttttttttt tttttttttt 1380
tttttttttt tttttttttt tttttttttt tttttttttt tttttttttt tttttttttt 1440
tttttttttt tttttttttt tttttttttt tttttttttt tttttttttt tttttttttt 1500
tttttttttt tttttttttt tttttttttt tttttttttt tttttttttt tttttttttt 1560
tttttttttt tttttttttt tttttttttt tttttttttt tttttttttt tttttttttt 1620
tttttttttt tttttttttt tttttttttt tttttttttt tttttttttt tttttttttt 1680
tttttttttt tttttttttt tttttttttt tttttttttt tttttttttt tttttttttt 1740
tttttttttt tttttttttt tttttttttt tttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttttt tttttttttt tttttttttt tttttttttt tttttttttt 2040
tttttttttt tttttttttt tttttttttt tttttttttt tttttttttt tttttttttt 2100

-continued tttttttttt tttttttttt tttttttttt tttttttttt tttttttttt tttttttttt 2160
tttttttttt tttttttttt tttttttttt tttttttttt tttttttttt tttttttttt 2220
tttttttttt tttttttttt tttttttttt tttttttttt tttttttttt tttttttttt 2280
tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640
tttttttttt tttttttttt tttttttttt tttttttttt tttttttttt tttttttttt 2700
tttttttttt tttttttttt tttttttttt tttttttttt tttttttttt tttttttttt 2760
tttttttttt tttttttttt tttttttttt tttttttttt tttttttttt tttttttttt 2820
tttttttttt tttttttttt tttttttttt tttttttttt tttttttttt tttttttttt 2880
tttttttttt tttttttttt tttttttttt tttttttttt tttttttttt tttttttttt 2940
tttttttttt tttttttttt tttttttttt tttttttttt tttttttttt tttttttttt 3000
tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720
tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500

```
tttttttttt tttttttttt tttttttttt tttttttttt tttttttttt tttttttttt   4560

tttttttttt tttttttttt tttttttttt tttttttttt tttttttttt tttttttttt   4620

tttttttttt tttttttttt tttttttttt tttttttttt tttttttttt tttttttttt   4680

tttttttttt tttttttttt tttttttttt tttttttttt tttttttttt tttttttttt   4740

tttttttttt tttttttttt tttttttttt tttttttttt tttttttttt tttttttttt   4800

tttttttttt tttttttttt tttttttttt tttttttttt tttttttttt tttttttttt   4860

tttttttttt tttttttttt tttttttttt tttttttttt tttttttttt tttttttttt   4920

tttttttttt tttttttttt tttttttttt tttttttttt tttttttttt tttttttttt   4980

tttttttttt tttttttttt                                               5000


<210> SEQ ID NO 33
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 100-5000
      nucleotides"
<220> FEATURE:
<221> NAME/KEY: source
<223> OTHER INFORMATION: /note="See specification as filed for detailed
      description of substitutions and preferred embodiments"

<400> SEQUENCE: 33

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200
```

-continued aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 34
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(400)
<223> OTHER INFORMATION: /note="This sequence may encompass 100-400 nucleotides"
<220> FEATURE:
<221> NAME/KEY: source
<223> OTHER INFORMATION: /note="See specification as filed for detailed description of substitutions and preferred embodiments"

<400> SEQUENCE: 34
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa 400

<210> SEQ ID NO 35
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(2000)
<223> OTHER INFORMATION: /note="This sequence may encompass 50-2000 nucleotides"
<220> FEATURE:
<221> NAME/KEY: source
<223> OTHER INFORMATION: /note="See specification as filed for detailed description of substitutions and preferred embodiments"

<400> SEQUENCE: 35
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560

```
aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000


<210> SEQ ID NO 36
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 37
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123


<210> SEQ ID NO 38
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35


<210> SEQ ID NO 39
<211> LENGTH: 244
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

Gln Val Gln Leu Gln Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Arg Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Glu Asp Thr Ala Val Tyr Tyr Cys
85 90 95

Ala Arg Gly Arg Tyr Tyr Gly Met Asp Val Trp Gly Gln Gly Thr Met
100 105 110

Val Thr Val Ser Ser Gly Gly Gly Gly Ser Gly Gly Gly Gly Ser Gly
115 120 125

Gly Gly Gly Ser Gly Gly Gly Gly Ser Glu Ile Val Leu Thr Gln Ser
130 135 140

Pro Ala Thr Leu Ser Leu Ser Pro Gly Glu Arg Ala Thr Ile Ser Cys
145 150 155 160

Arg Ala Ser Gln Ser Val Ser Ser Asn Phe Ala Trp Tyr Gln Gln Arg
165 170 175

Pro Gly Gln Ala Pro Arg Leu Leu Ile Tyr Asp Ala Ser Asn Arg Ala
180 185 190

Thr Gly Ile Pro Pro Arg Phe Ser Gly Ser Gly Ser Gly Thr Asp Phe
195 200 205

Thr Leu Thr Ile Ser Ser Leu Glu Pro Glu Asp Phe Ala Ala Tyr Tyr
210 215 220

Cys His Gln Arg Ser Asn Trp Leu Tyr Thr Phe Gly Gln Gly Thr Lys
225 230 235 240

Val Asp Ile Lys

<210> SEQ ID NO 40
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Arg Arg Thr Val Val Thr Pro Arg Ala Tyr Tyr Gly
            100                 105                 110

Met Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Leu Thr Gln Ser Pro Ser Thr Leu Ser Ala Ser
145                 150                 155                 160

Val Gly Asp Arg Val Thr Ile Thr Cys Gln Ala Ser Gln Asp Ile Ser
                165                 170                 175

Asn Ser Leu Asn Trp Tyr Gln Gln Lys Ala Gly Lys Ala Pro Lys Leu
            180                 185                 190

Leu Ile Tyr Asp Ala Ser Thr Leu Glu Thr Gly Val Pro Ser Arg Phe
        195                 200                 205

Ser Gly Ser Gly Ser Gly Thr Asp Phe Ser Phe Thr Ile Ser Ser Leu
    210                 215                 220

Gln Pro Glu Asp Ile Ala Thr Tyr Tyr Cys Gln Gln His Asp Asn Leu
225                 230                 235                 240

Pro Leu Thr Phe Gly Gln Gly Thr Lys Val Glu Ile Lys
                245                 250


<210> SEQ ID NO 41
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Trp Asp Gly Ser Tyr Tyr Tyr Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Val Leu
    130                 135                 140

Thr Gln Thr Pro Ser Ser Leu Ser Ala Ser Val Gly Asp Arg Val Thr
145                 150                 155                 160
```

-continued

```
Ile Thr Cys Arg Ala Ser Gln Ser Ile Asn Thr Tyr Leu Asn Trp Tyr
                165                 170                 175

Gln His Lys Pro Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Phe Ser Pro Leu Thr Phe Gly Gly Gly
225                 230                 235                 240

Thr Lys Leu Glu Ile Lys
                245


<210> SEQ ID NO 42
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Val Pro Gly Lys Gly Leu Val Trp Val
        35                  40                  45

Ser Arg Ile Asn Thr Asp Gly Ser Thr Thr Thr Tyr Ala Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Asp Asp Asp Thr Ala Val Tyr Tyr Cys
                85                  90                  95

Val Gly Gly His Trp Ala Val Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Val Gly Asp Arg Val Thr Ile Thr Cys Arg Ala Ser
145                 150                 155                 160

Gln Ser Ile Ser Asp Arg Leu Ala Trp Tyr Gln Gln Lys Pro Gly Lys
                165                 170                 175

Ala Pro Lys Leu Leu Ile Tyr Lys Ala Ser Ser Leu Glu Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Val Tyr Tyr Cys Gln Gln
    210                 215                 220

Tyr Gly His Leu Pro Met Tyr Thr Phe Gly Gln Gly Thr Lys Val Glu
225                 230                 235                 240

Ile Lys


<210> SEQ ID NO 43
```

```
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys


<210> SEQ ID NO 44
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
```

```
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Arg Leu Ile Ala Val Ala Gly Asp Tyr Tyr Tyr Tyr Gly
            100                 105                 110

Met Asp Val Trp Gly Gln Gly Thr Met Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Met Thr Gln Ser Pro Ser Ser Val Ser Ala Ser
145                 150                 155                 160

Val Gly Asp Arg Val Thr Ile Thr Cys Arg Ala Ser Gln Gly Val Gly
                165                 170                 175

Arg Trp Leu Ala Trp Tyr Gln Gln Lys Pro Gly Thr Ala Pro Lys Leu
            180                 185                 190

Leu Ile Tyr Ala Ala Ser Thr Leu Gln Ser Gly Val Pro Ser Arg Phe
        195                 200                 205

Ser Gly Ser Gly Ser Gly Thr Asp Phe Thr Leu Thr Ile Asn Asn Leu
    210                 215                 220

Gln Pro Glu Asp Phe Ala Thr Tyr Tyr Cys Gln Gln Ala Asn Ser Phe
225                 230                 235                 240

Pro Leu Thr Phe Gly Gly Gly Thr Arg Leu Glu Ile Lys
                245                 250


<210> SEQ ID NO 45
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Lys Val Ser Ser Ser Ser Pro Ala Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160
```

```
Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
    210                 215                 220

Phe Ala Val Tyr Tyr Cys Gln His Tyr Gly Gly Ser Pro Leu Ile Thr
225                 230                 235                 240

Phe Gly Gln Gly Thr Arg Leu Glu Ile Lys
                245                 250


<210> SEQ ID NO 46
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Pro Phe Thr Gly Tyr
            20                  25                  30

Ser Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Tyr Gly Gly Asn Ser Leu Phe Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ser Ser Ile Ser Ala Ser Val Gly Asp Thr Val Ser Ile
145                 150                 155                 160

Thr Cys Arg Ala Ser Gln Asp Ser Gly Thr Trp Leu Ala Trp Tyr Gln
                165                 170                 175

Gln Lys Pro Gly Lys Ala Pro Asn Leu Leu Met Tyr Asp Ala Ser Thr
            180                 185                 190

Leu Glu Asp Gly Val Pro Ser Arg Phe Ser Gly Ser Ala Ser Gly Thr
        195                 200                 205

Glu Phe Thr Leu Thr Val Asn Arg Leu Gln Pro Glu Asp Ser Ala Thr
    210                 215                 220

Tyr Tyr Cys Gln Gln Tyr Asn Ser Tyr Pro Leu Thr Phe Gly Gly Gly
225                 230                 235                 240

Thr Lys Val Asp Ile Lys
                245
```

<210> SEQ ID NO 47
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Gly Tyr Ala Gln Lys Phe
    50                  55                  60

Gln Gly Arg Val Thr Met Thr Arg Asp Thr Ser Thr Ser Thr Val His
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Ser Ser Asp Ala Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Pro Ser Leu Ser Ala Ser Val Gly Asp Arg Val
145                 150                 155                 160

Thr Ile Thr Cys Arg Ala Ser Gln Asp Ile Ser Ser Ala Leu Ala Trp
                165                 170                 175

Tyr Gln Gln Lys Pro Gly Thr Pro Pro Lys Leu Leu Ile Tyr Asp Ala
            180                 185                 190

Ser Ser Leu Glu Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Phe Ser Ser Tyr Pro Leu Thr Phe Gly
225                 230                 235                 240

Gly Gly Thr Arg Leu Glu Ile Lys
                245
```

<210> SEQ ID NO 48
<211> LENGTH: 255
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
```

```
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Gly Gly Ile Tyr Tyr Tyr Tyr Gly Met Asp Val Trp
            100                 105                 110

Gly Gln Gly Thr Thr Ile Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Val Met Thr Gln Thr Pro Asp Ser Leu Ala Val Ser Leu Gly Glu Arg
145                 150                 155                 160

Ala Thr Ile Ser Cys Lys Ser Ser His Ser Val Leu Tyr Asn Arg Asn
                165                 170                 175

Asn Lys Asn Tyr Leu Ala Trp Tyr Gln Gln Lys Pro Gly Gln Pro Pro
            180                 185                 190

Lys Leu Leu Phe Tyr Trp Ala Ser Thr Arg Lys Ser Gly Val Pro Asp
        195                 200                 205

Arg Phe Ser Gly Ser Gly Ser Gly Thr Asp Phe Thr Leu Thr Ile Ser
    210                 215                 220

Ser Leu Gln Pro Glu Asp Phe Ala Thr Tyr Phe Cys Gln Gln Thr Gln
225                 230                 235                 240

Thr Phe Pro Leu Thr Phe Gly Gln Gly Thr Arg Leu Glu Ile Asn
                245                 250                 255


<210> SEQ ID NO 49
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Arg Met Thr Gln Ser Pro Ser
    130                 135                 140
```

Ser Leu Ser Ala Ser Val Gly Asp Arg Val Thr Ile Thr Cys Arg Ala
145 150 155 160

Ser Gln Ser Ile Arg Tyr Tyr Leu Ser Trp Tyr Gln Gln Lys Pro Gly
165 170 175

Lys Ala Pro Lys Leu Leu Ile Tyr Thr Ala Ser Ile Leu Gln Asn Gly
180 185 190

Val Pro Ser Arg Phe Ser Gly Ser Gly Ser Gly Thr Asp Phe Thr Leu
195 200 205

Thr Ile Ser Ser Leu Gln Pro Glu Asp Phe Ala Thr Tyr Tyr Cys Leu
210 215 220

Gln Thr Tyr Thr Thr Pro Asp Phe Gly Pro Gly Thr Lys Val Glu Ile
225 230 235 240

Lys

<210> SEQ ID NO 50
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Arg Ile Asn Pro Asn Ser Gly Gly Thr Asn Tyr Ala Gln Lys Phe
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Thr Thr Thr Ser Tyr Ala Phe Asp Ile Trp Gly Gln Gly Thr
100 105 110

Met Val Thr Val Ser Ser Gly Gly Gly Gly Ser Gly Gly Gly Gly Ser
115 120 125

Gly Gly Gly Gly Ser Gly Gly Gly Gly Ser Asp Ile Gln Leu Thr Gln
130 135 140

Ser Pro Ser Thr Leu Ser Ala Ser Val Gly Asp Arg Val Thr Ile Thr
145 150 155 160

Cys Arg Ala Ser Gln Ser Ile Ser Thr Trp Leu Ala Trp Tyr Gln Gln
165 170 175

Lys Pro Gly Lys Ala Pro Asn Leu Leu Ile Tyr Lys Ala Ser Thr Leu
180 185 190

Glu Ser Gly Val Pro Ser Arg Phe Ser Gly Ser Gly Ser Gly Thr Glu
195 200 205

Phe Thr Leu Thr Ile Ser Ser Leu Gln Pro Asp Asp Phe Ala Thr Tyr
210 215 220

Tyr Cys Gln Gln Tyr Asn Thr Tyr Ser Pro Tyr Thr Phe Gly Gln Gly
225 230 235 240

Thr Lys Leu Glu Ile Lys

245

<210> SEQ ID NO 51
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

Gln Val Gln Leu Val Gln Ser Gly Gly Gly Leu Val Lys Pro Gly Gly
1 5 10 15

Ser Leu Arg Leu Ser Cys Glu Ala Ser Gly Phe Ile Phe Ser Asp Tyr
20 25 30

Tyr Met Gly Trp Ile Arg Gln Ala Pro Gly Lys Gly Leu Glu Trp Val
35 40 45

Ser Tyr Ile Gly Arg Ser Gly Ser Ser Met Tyr Tyr Ala Asp Ser Val
50 55 60

Lys Gly Arg Phe Thr Phe Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Ala Ser Pro Val Val Ala Ala Thr Glu Asp Phe Gln His Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Asp Ile Val
130 135 140

Met Thr Gln Thr Pro Ala Thr Leu Ser Leu Ser Pro Gly Glu Arg Ala
145 150 155 160

Thr Leu Ser Cys Arg Ala Ser Gln Ser Val Thr Ser Asn Tyr Leu Ala
165 170 175

Trp Tyr Gln Gln Lys Pro Gly Gln Ala Pro Arg Leu Leu Leu Phe Gly
180 185 190

Ala Ser Thr Arg Ala Thr Gly Ile Pro Asp Arg Phe Ser Gly Ser Gly
195 200 205

Ser Gly Thr Asp Phe Thr Leu Thr Ile Asn Arg Leu Glu Pro Glu Asp
210 215 220

Phe Ala Met Tyr Tyr Cys Gln Gln Tyr Gly Ser Ala Pro Val Thr Phe
225 230 235 240

Gly Gln Gly Thr Lys Leu Glu Ile Lys
245

<210> SEQ ID NO 52
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Gln Val Gln Leu Val Gln Ser Gly Ala Glu Val Arg Ala Pro Gly Ala
1 5 10 15

Ser Val Lys Ile Ser Cys Lys Ala Ser Gly Phe Thr Phe Arg Gly Tyr
20 25 30

```
Tyr Ile His Trp Val Arg Gln Ala Pro Gly Gln Gly Leu Glu Trp Met
        35                  40                  45

Gly Ile Ile Asn Pro Ser Gly Gly Ser Arg Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Met Tyr Tyr Cys
                85                  90                  95

Ala Arg Thr Ala Ser Cys Gly Gly Asp Cys Tyr Tyr Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Pro Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
        195                 200                 205

Ser Gly Ala Glu Phe Thr Leu Thr Ile Ser Ser Leu Gln Pro Asp Asp
    210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
                245


<210> SEQ ID NO 53
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Ser Trp Ser Trp Gly Tyr Phe Asp Tyr Trp
            100                 105                 110

Gly Gln Gly Thr Leu Val Thr Val Ser Ser Gly Gly Gly Gly Ser Gly
        115                 120                 125
```

Gly Gly Gly Ser Gly Gly Gly Gly Ser Ser Ser Glu Leu Thr Gln Asp
130 135 140

Pro Ala Val Ser Val Ala Leu Gly Gln Thr Val Arg Thr Thr Cys Gln
145 150 155 160

Gly Asp Ala Leu Arg Ser Tyr Tyr Ala Ser Trp Tyr Gln Gln Lys Pro
165 170 175

Gly Gln Ala Pro Met Leu Val Ile Tyr Gly Lys Asn Asn Arg Pro Ser
180 185 190

Gly Ile Pro Asp Arg Phe Ser Gly Ser Asp Ser Gly Asp Thr Ala Ser
195 200 205

Leu Thr Ile Thr Gly Ala Gln Ala Glu Asp Glu Ala Asp Tyr Tyr Cys
210 215 220

Asn Ser Arg Asp Ser Ser Gly Tyr Pro Val Phe Gly Thr Gly Thr Lys
225 230 235 240

Val Thr Val Leu

<210> SEQ ID NO 54
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Ser Ser Ser Trp Tyr Gly Gly Gly Ser Ala Phe Asp Ile
100 105 110

Trp Gly Gln Gly Thr Met Val Thr Val Ser Ser Gly Gly Gly Gly Ser
115 120 125

Gly Gly Gly Gly Ser Gly Gly Gly Gly Ser Ser Ser Glu Leu Thr Gln
130 135 140

Glu Pro Ala Val Ser Val Ala Leu Gly Gln Thr Val Arg Ile Thr Cys
145 150 155 160

Gln Gly Asp Ser Leu Arg Ser Tyr Tyr Ala Ser Trp Tyr Gln Gln Lys
165 170 175

Pro Gly Gln Ala Pro Val Leu Val Ile Phe Gly Arg Ser Arg Arg Pro
180 185 190

Ser Gly Ile Pro Asp Arg Phe Ser Gly Ser Ser Ser Gly Asn Thr Ala
195 200 205

Ser Leu Ile Ile Thr Gly Ala Gln Ala Glu Asp Glu Ala Asp Tyr Tyr
210 215 220

Cys Asn Ser Arg Asp Asn Thr Ala Asn His Tyr Val Phe Gly Thr Gly
225 230 235 240

Thr Lys Leu Thr Val Leu
245

<210> SEQ ID NO 55
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Ser Ser Ser Trp Tyr Gly Gly Gly Ser Ala Phe Asp Ile
100 105 110

Trp Gly Gln Gly Thr Met Val Thr Val Ser Ser Gly Gly Gly Gly Ser
115 120 125

Gly Gly Gly Gly Ser Gly Gly Gly Gly Ser Ser Ser Glu Leu Thr Gln
130 135 140

Asp Pro Ala Val Ser Val Ala Leu Gly Gln Thr Val Arg Ile Thr Cys
145 150 155 160

Gln Gly Asp Ser Leu Arg Ser Tyr Tyr Ala Ser Trp Tyr Gln Gln Lys
165 170 175

Pro Gly Gln Ala Pro Val Leu Val Ile Tyr Gly Lys Asn Asn Arg Pro
180 185 190

Ser Gly Ile Pro Asp Arg Phe Ser Gly Ser Ser Ser Gly Asn Thr Ala
195 200 205

Ser Leu Thr Ile Thr Gly Ala Gln Ala Glu Asp Glu Ala Asp Tyr Tyr
210 215 220

Cys Asn Ser Arg Gly Ser Ser Gly Asn His Tyr Val Phe Gly Thr Gly
225 230 235 240

Thr Lys Val Thr Val Leu
245

<210> SEQ ID NO 56
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

Gln Val Gln Leu Val Gln Ser Gly Gly Gly Leu Val Gln Pro Gly Gly
1 5 10 15

```
Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Thr Gly Trp Val Gly Ser Tyr Tyr Tyr Tyr Met Asp Val Trp
            100                 105                 110

Gly Lys Gly Thr Thr Val Thr Val Ser Ser Gly Gly Gly Gly Ser Gly
        115                 120                 125

Gly Gly Gly Ser Gly Gly Gly Gly Ser Gly Gly Gly Gly Ser Glu Ile
    130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Ser Val Ser Ser Asn Tyr Leu
                165                 170                 175

Ala Trp Tyr Gln Gln Lys Pro Gly Gln Pro Pro Arg Leu Leu Ile Tyr
            180                 185                 190

Asp Val Ser Thr Arg Ala Thr Gly Ile Pro Ala Arg Phe Ser Gly Gly
        195                 200                 205

Gly Ser Gly Thr Asp Phe Thr Leu Thr Ile Ser Ser Leu Glu Pro Glu
    210                 215                 220

Asp Phe Ala Val Tyr Tyr Cys Gln Gln Arg Ser Asn Trp Pro Pro Trp
225                 230                 235                 240

Thr Phe Gly Gln Gly Thr Lys Val Glu Ile Lys
                245                 250


<210> SEQ ID NO 57
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Ser Arg Tyr Tyr Tyr Tyr Gly Met Asp Val Trp Gly
            100                 105                 110

Gln Gly Thr Thr Val Thr Val Ser Ser Gly Gly Gly Gly Ser Gly Gly
```

```
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
    210                 215                 220

Phe Ala Val Tyr Tyr Cys Gln His Tyr Gly Gly Ser Pro Leu Ile Thr
225                 230                 235                 240

Phe Gly Gln Gly Thr Lys Val Asp Ile Lys
                245                 250


<210> SEQ ID NO 58
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Glu Ala Ala Ala Gly His Asp Trp Tyr Phe Asp Leu Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Arg Val Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220
```

```
Phe Ala Thr Tyr Tyr Cys Gln Gln Ser Tyr Ser Ile Pro Leu Thr Phe
225                 230                 235                 240

Gly Gln Gly Thr Lys Val Glu Ile Lys
                245


<210> SEQ ID NO 59
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Gln Val Gln Leu Val Gln Ser Trp Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Ser Pro Arg Val Thr Thr Gly Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Leu
    130                 135                 140

Thr Gln Ser Pro Ser Thr Leu Ser Ala Ser Val Gly Asp Arg Val Thr
145                 150                 155                 160

Ile Thr Cys Arg Ala Ser Gln Ser Ile Ser Ser Trp Leu Ala Trp Tyr
                165                 170                 175

Gln Gln Lys Pro Gly Lys Ala Pro Lys Leu Leu Ile Tyr Lys Ala Ser
            180                 185                 190

Ser Leu Glu Ser Gly Val Pro Ser Arg Phe Ser Gly Ser Gly Ser Gly
        195                 200                 205

Thr Glu Phe Thr Leu Thr Ile Ser Ser Leu Gln Pro Asp Asp Phe Ala
    210                 215                 220

Thr Tyr Tyr Cys Gln Gln Tyr Ser Ser Tyr Pro Leu Thr Phe Gly Gly
225                 230                 235                 240

Gly Thr Arg Leu Glu Ile Lys
                245


<210> SEQ ID NO 60
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60
```

```
Gln Val Gln Leu Val Gln Ser Gly Ala Glu Val Arg Arg Pro Gly Ala
1               5                   10                  15

Ser Val Lys Ile Ser Cys Arg Ala Ser Gly Asp Thr Ser Thr Arg His
            20                  25                  30

Tyr Ile His Trp Leu Arg Gln Ala Pro Gly Gln Gly Pro Glu Trp Met
        35                  40                  45

Gly Val Ile Asn Pro Thr Thr Gly Pro Ala Thr Gly Ser Pro Ala Tyr
    50                  55                  60

Ala Gln Met Leu Gln Gly Arg Val Thr Met Thr Arg Asp Thr Ser Thr
65                  70                  75                  80

Arg Thr Val Tyr Met Glu Leu Arg Ser Leu Arg Phe Glu Asp Thr Ala
                85                  90                  95

Val Tyr Tyr Cys Ala Arg Ser Val Val Gly Arg Ser Ala Pro Tyr Tyr
            100                 105                 110

Phe Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Gly Ile Ser
                165                 170                 175

Asp Tyr Ser Ala Trp Tyr Gln Gln Lys Pro Gly Lys Ala Pro Lys Leu
            180                 185                 190

Leu Ile Tyr Ala Ala Ser Thr Leu Gln Ser Gly Val Pro Ser Arg Phe
        195                 200                 205

Ser Gly Ser Gly Ser Gly Thr Asp Phe Thr Leu Thr Ile Ser Tyr Leu
    210                 215                 220

Gln Ser Glu Asp Phe Ala Thr Tyr Tyr Cys Gln Gln Tyr Tyr Ser Tyr
225                 230                 235                 240

Pro Leu Thr Phe Gly Gly Gly Thr Lys Val Asp Ile Lys
                245                 250


<210> SEQ ID NO 61
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Tyr Thr Thr Tyr Ala Gln Lys Phe
    50                  55                  60

Gln Gly Arg Leu Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Arg Ser Cys Gly Gly Asp Cys Tyr Tyr Phe Asp Asn Trp
```

```
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Leu Thr Gln Ser Pro Ser Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
        195                 200                 205

Ser Gly Ala Glu Phe Thr Leu Thr Ile Ser Ser Leu Gln Pro Asp Asp
    210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
                245


<210> SEQ ID NO 62
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Ile Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Val His Val Gly Trp Ile Arg Gln Pro Pro Gly Lys Ala Leu Glu
        35                  40                  45

Trp Leu Ala Leu Ile Ser Trp Ala Asp Asp Lys Arg Tyr Arg Pro Ser
    50                  55                  60

Leu Arg Ser Arg Leu Asp Ile Thr Arg Val Thr Ser Lys Asp Gln Val
65                  70                  75                  80

Val Leu Ser Met Thr Asn Met Gln Pro Glu Asp Thr Ala Thr Tyr Tyr
                85                  90                  95

Cys Ala Leu Gln Gly Phe Asp Gly Tyr Glu Ala Asn Trp Gly Pro Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Ser Ser Leu Ser Ala Ser Ala Gly Asp Arg Val Thr Ile
145                 150                 155                 160

Thr Cys Arg Ala Ser Arg Gly Ile Ser Ser Ala Leu Ala Trp Tyr Gln
                165                 170                 175

Gln Lys Pro Gly Lys Pro Pro Lys Leu Leu Ile Tyr Asp Ala Ser Ser
            180                 185                 190

Leu Glu Ser Gly Val Pro Ser Arg Phe Ser Gly Ser Gly Ser Gly Thr
        195                 200                 205
```

```
Asp Phe Thr Leu Thr Ile Asp Ser Leu Glu Pro Glu Asp Phe Ala Thr
    210                 215                 220

Tyr Tyr Cys Gln Gln Ser Tyr Ser Thr Pro Trp Thr Phe Gly Gln Gly
225                 230                 235                 240

Thr Lys Val Asp Ile Lys
                245


<210> SEQ ID NO 63
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Arg Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Glu Asp Thr
            100                 105                 110

Ala Val Tyr Tyr Cys Ala Arg Gly Arg Tyr Tyr Gly Met Asp Val Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Ile Ser Cys Arg Ala Ser Gln Ser Val Ser Ser Asn Phe Ala
            180                 185                 190

Trp Tyr Gln Gln Arg Pro Gly Gln Ala Pro Arg Leu Leu Ile Tyr Asp
        195                 200                 205

Ala Ser Asn Arg Ala Thr Gly Ile Pro Pro Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Ala Tyr Tyr Cys His Gln Arg Ser Asn Trp Leu Tyr Thr Phe
                245                 250                 255

Gly Gln Gly Thr Lys Val Asp Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300
```

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Lys Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser
435 440 445

Glu Ile Gly Met Lys Gly Glu Arg Arg Arg Gly Lys Gly His Asp Gly
450 455 460

Leu Tyr Gln Gly Leu Ser Thr Ala Thr Lys Asp Thr Tyr Asp Ala Leu
465 470 475 480

His Met Gln Ala Leu Pro Pro Arg
485

<210> SEQ ID NO 64
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ala Ser Val Lys Val Ser Cys Lys Ala Ser Gly Tyr
35 40 45

Thr Phe Thr Gly Tyr Tyr Met His Trp Val Arg Gln Ala Pro Gly Gln
50 55 60

Gly Leu Glu Trp Met Gly Trp Ile Asn Pro Asn Ser Gly Gly Thr Asn
65 70 75 80

Tyr Ala Gln Lys Phe Gln Gly Arg Val Thr Met Thr Arg Asp Thr Ser
85 90 95

Ile Ser Thr Ala Tyr Met Glu Leu Ser Arg Leu Arg Ser Asp Asp Thr
100 105 110

Ala Val Tyr Tyr Cys Ala Arg Asp Leu Arg Arg Thr Val Val Thr Pro
115 120 125

Arg Ala Tyr Tyr Gly Met Asp Val Trp Gly Gln Gly Thr Thr Val Thr
130 135 140

Val Ser Ser Gly Gly Gly Gly Ser Gly Gly Gly Gly Ser Gly Gly Gly
145 150 155 160

Gly Ser Gly Gly Gly Gly Ser Asp Ile Gln Leu Thr Gln Ser Pro Ser

```
                165                 170                 175

Thr Leu Ser Ala Ser Val Gly Asp Arg Val Thr Ile Thr Cys Gln Ala
            180                 185                 190

Ser Gln Asp Ile Ser Asn Ser Leu Asn Trp Tyr Gln Gln Lys Ala Gly
        195                 200                 205

Lys Ala Pro Lys Leu Leu Ile Tyr Asp Ala Ser Thr Leu Glu Thr Gly
    210                 215                 220

Val Pro Ser Arg Phe Ser Gly Ser Gly Ser Gly Thr Asp Phe Ser Phe
225                 230                 235                 240

Thr Ile Ser Ser Leu Gln Pro Glu Asp Ile Ala Thr Tyr Tyr Cys Gln
                245                 250                 255

Gln His Asp Asn Leu Pro Leu Thr Phe Gly Gln Gly Thr Lys Val Glu
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 65
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Met Ala Leu Pro Val Thr Ala Leu Leu Leu Pro Leu Ala Leu Leu Leu
1               5                   10                  15
```

-continued

```
His Ala Ala Arg Pro Gln Val Gln Leu Val Gln Ser Gly Ala Glu Val
            20                  25                  30

Lys Lys Pro Gly Ala Pro Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Gly Glu Trp Asp Gly Ser Tyr Tyr Tyr
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Val Leu Thr Gln Thr Pro Ser Ser Leu Ser Ala Ser Val
                165                 170                 175

Gly Asp Arg Val Thr Ile Thr Cys Arg Ala Ser Gln Ser Ile Asn Thr
            180                 185                 190

Tyr Leu Asn Trp Tyr Gln His Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ser Phe Ser Pro Leu
                245                 250                 255

Thr Phe Gly Gly Gly Thr Lys Leu Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
```

```
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 66
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Trp Met His Trp Val Arg Gln Val Pro Gly Lys
    50                  55                  60

Gly Leu Val Trp Val Ser Arg Ile Asn Thr Asp Gly Ser Thr Thr Thr
65                  70                  75                  80

Tyr Ala Asp Ser Val Glu Gly Arg Phe Thr Ile Ser Arg Asp Asn Ala
                85                  90                  95

Lys Asn Thr Leu Tyr Leu Gln Met Asn Ser Leu Arg Asp Asp Asp Thr
            100                 105                 110

Ala Val Tyr Tyr Cys Val Gly Gly His Trp Ala Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Thr Leu Ser Ala Ser Val Gly Asp Arg Val Thr Ile
                165                 170                 175

Thr Cys Arg Ala Ser Gln Ser Ile Ser Asp Arg Leu Ala Trp Tyr Gln
            180                 185                 190

Gln Lys Pro Gly Lys Ala Pro Lys Leu Leu Ile Tyr Lys Ala Ser Ser
        195                 200                 205

Leu Glu Ser Gly Val Pro Ser Arg Phe Ser Gly Ser Gly Ser Gly Thr
    210                 215                 220

Glu Phe Thr Leu Thr Ile Ser Ser Leu Gln Pro Asp Asp Phe Ala Val
225                 230                 235                 240

Tyr Tyr Cys Gln Gln Tyr Gly His Leu Pro Met Tyr Thr Phe Gly Gln
                245                 250                 255

Gly Thr Lys Val Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300
```

```
Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 67
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Glu Lys Pro Gly Ala Ser Val Lys Val Ser Cys Lys Ala Ser Gly Tyr
        35                  40                  45

Thr Phe Thr Asp Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Ser Gly Trp Asp Phe Asp Tyr Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Gly Gly Gly Gly Ser Asp Ile Val Met
145                 150                 155                 160
```

```
Thr Gln Ser Pro Ser Ser Leu Ser Ala Ser Val Gly Asp Arg Val Thr
                165                 170                 175

Ile Thr Cys Arg Ala Ser Gln Ser Ile Arg Tyr Tyr Leu Ser Trp Tyr
            180                 185                 190

Gln Gln Lys Pro Gly Lys Ala Pro Lys Leu Leu Ile Tyr Thr Ala Ser
        195                 200                 205

Ile Leu Gln Asn Gly Val Pro Ser Arg Phe Ser Gly Ser Gly Ser Gly
    210                 215                 220

Thr Asp Phe Thr Leu Thr Ile Ser Ser Leu Gln Pro Glu Asp Phe Ala
225                 230                 235                 240

Thr Tyr Tyr Cys Leu Gln Thr Tyr Thr Thr Pro Asp Phe Gly Pro Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 68
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
```

```
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Tyr Arg Leu Ile Ala Val Ala Gly Asp
        115                 120                 125

Tyr Tyr Tyr Tyr Gly Met Asp Val Trp Gly Gln Gly Thr Met Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Gln Met Thr Gln Ser Pro Ser
                165                 170                 175

Ser Val Ser Ala Ser Val Gly Asp Arg Val Thr Ile Thr Cys Arg Ala
            180                 185                 190

Ser Gln Gly Val Gly Arg Trp Leu Ala Trp Tyr Gln Gln Lys Pro Gly
        195                 200                 205

Thr Ala Pro Lys Leu Leu Ile Tyr Ala Ala Ser Thr Leu Gln Ser Gly
    210                 215                 220

Val Pro Ser Arg Phe Ser Gly Ser Gly Ser Gly Thr Asp Phe Thr Leu
225                 230                 235                 240

Thr Ile Asn Asn Leu Gln Pro Glu Asp Phe Ala Thr Tyr Tyr Cys Gln
                245                 250                 255

Gln Ala Asn Ser Phe Pro Leu Thr Phe Gly Gly Gly Thr Arg Leu Glu
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445
```

```
Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg


<210> SEQ ID NO 69
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Trp Lys Val Ser Ser Ser Ser Pro Ala
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Ile Leu Ser Cys Arg Ala Ser Gln Ser Val Tyr
            180                 185                 190

Thr Lys Tyr Leu Gly Trp Tyr Gln Gln Lys Pro Gly Gln Ala Pro Arg
        195                 200                 205

Leu Leu Ile Tyr Asp Ala Ser Thr Arg Ala Thr Gly Ile Pro Asp Arg
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Val Tyr Tyr Cys Gln His Tyr Gly Gly
                245                 250                 255

Ser Pro Leu Ile Thr Phe Gly Gln Gly Thr Arg Leu Glu Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
```

```
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 70
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Thr Ser Gly Tyr
        35                  40                  45

Pro Phe Thr Gly Tyr Ser Leu His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp His Tyr Gly Gly Asn Ser Leu Phe
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160
```

```
Asp Ile Gln Leu Thr Gln Ser Pro Ser Ser Ile Ser Ala Ser Val Gly
                165                 170                 175

Asp Thr Val Ser Ile Thr Cys Arg Ala Ser Gln Asp Ser Gly Thr Trp
            180                 185                 190

Leu Ala Trp Tyr Gln Gln Lys Pro Gly Lys Ala Pro Asn Leu Leu Met
        195                 200                 205

Tyr Asp Ala Ser Thr Leu Glu Asp Gly Val Pro Ser Arg Phe Ser Gly
    210                 215                 220

Ser Ala Ser Gly Thr Glu Phe Thr Leu Thr Val Asn Arg Leu Gln Pro
225                 230                 235                 240

Glu Asp Ser Ala Thr Tyr Tyr Cys Gln Gln Tyr Asn Ser Tyr Pro Leu
                245                 250                 255

Thr Phe Gly Gly Gly Thr Lys Val Asp Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 71
<211> LENGTH: 492
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Met Ala Leu Pro Val Thr Ala Leu Leu Leu Pro Leu Ala Leu Leu Leu
1               5                   10                  15
```

```
His Ala Ala Arg Pro Gln Val Gln Leu Val Gln Ser Gly Ala Glu Val
            20                  25                  30

Lys Lys Pro Gly Ala Ser Val Glu Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Gly
65                  70                  75                  80

Tyr Ala Gln Lys Phe Gln Gly Arg Val Thr Met Thr Arg Asp Thr Ser
                85                  90                  95

Thr Ser Thr Val His Met Glu Leu Ser Ser Leu Arg Ser Glu Asp Thr
            100                 105                 110

Ala Val Tyr Tyr Cys Ala Arg Gly Gly Tyr Ser Ser Ser Ser Asp Ala
        115                 120                 125

Phe Asp Ile Trp Gly Gln Gly Thr Met Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Asp Ile Gln Met Thr Gln Ser Pro Pro Ser Leu Ser Ala Ser
                165                 170                 175

Val Gly Asp Arg Val Thr Ile Thr Cys Arg Ala Ser Gln Asp Ile Ser
            180                 185                 190

Ser Ala Leu Ala Trp Tyr Gln Gln Lys Pro Gly Thr Pro Pro Lys Leu
        195                 200                 205

Leu Ile Tyr Asp Ala Ser Ser Leu Glu Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Phe Ser Ser Tyr
                245                 250                 255

Pro Leu Thr Phe Gly Gly Gly Thr Arg Leu Glu Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
```

```
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 72
<211> LENGTH: 499
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Gly Ile Ser Trp Val Arg Gln Ala Pro Gly Gln
    50                  55                  60

Gly Leu Glu Trp Met Gly Trp Ile Ser Ala Tyr Asn Gly Asn Thr Asn
65                  70                  75                  80

Tyr Ala Gln Lys Leu Gln Gly Arg Val Thr Met Thr Thr Asp Thr Ser
                85                  90                  95

Thr Ser Thr Ala Tyr Met Glu Leu Arg Ser Leu Arg Ser Asp Asp Thr
            100                 105                 110

Ala Val Tyr Tyr Cys Ala Arg Val Ala Gly Gly Ile Tyr Tyr Tyr Tyr
        115                 120                 125

Gly Met Asp Val Trp Gly Gln Gly Thr Thr Ile Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Val Met Thr Gln Thr Pro Asp Ser Leu Ala Val
                165                 170                 175

Ser Leu Gly Glu Arg Ala Thr Ile Ser Cys Lys Ser Ser His Ser Val
            180                 185                 190

Leu Tyr Asn Arg Asn Asn Lys Asn Tyr Leu Ala Trp Tyr Gln Gln Lys
        195                 200                 205

Pro Gly Gln Pro Pro Lys Leu Leu Phe Tyr Trp Ala Ser Thr Arg Lys
    210                 215                 220

Ser Gly Val Pro Asp Arg Phe Ser Gly Ser Gly Ser Gly Thr Asp Phe
225                 230                 235                 240

Thr Leu Thr Ile Ser Ser Leu Gln Pro Glu Asp Phe Ala Thr Tyr Phe
                245                 250                 255

Cys Gln Gln Thr Gln Thr Phe Pro Leu Thr Phe Gly Gln Gly Thr Arg
            260                 265                 270

Leu Glu Ile Asn Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300
```

```
Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400

Lys Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg


<210> SEQ ID NO 73
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Asn Phe Gln Gly Arg Val Thr Met Thr Arg Asp Thr Ser
                85                  90                  95

Ile Ser Thr Ala Tyr Met Glu Leu Arg Arg Leu Arg Ser Asp Asp Thr
            100                 105                 110

Ala Val Tyr Tyr Cys Ala Ser Gly Trp Asp Phe Asp Tyr Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Gly Gly Gly Gly Ser Asp Ile Arg Met
```

```
145                 150                 155                 160

Thr Gln Ser Pro Ser Ser Leu Ser Ala Ser Val Gly Asp Arg Val Thr
                165                 170                 175

Ile Thr Cys Arg Ala Ser Gln Ser Ile Arg Tyr Tyr Leu Ser Trp Tyr
            180                 185                 190

Gln Gln Lys Pro Gly Lys Ala Pro Lys Leu Leu Ile Tyr Thr Ala Ser
        195                 200                 205

Ile Leu Gln Asn Gly Val Pro Ser Arg Phe Ser Gly Ser Gly Ser Gly
    210                 215                 220

Thr Asp Phe Thr Leu Thr Ile Ser Ser Leu Gln Pro Glu Asp Phe Ala
225                 230                 235                 240

Thr Tyr Tyr Cys Leu Gln Thr Tyr Thr Thr Pro Asp Phe Gly Pro Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 74
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

```
Met Ala Leu Pro Val Thr Ala Leu Leu Leu Pro Leu Ala Leu Leu Leu
1               5                   10                  15
```

```
His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Arg Ile Asn Pro Asn Ser Gly Gly Thr Asn
65                  70                  75                  80

Tyr Ala Gln Lys Phe Gln Gly Arg Val Thr Met Thr Thr Asp Thr Ser
                85                  90                  95

Thr Ser Thr Ala Tyr Met Glu Leu Arg Ser Leu Arg Ser Asp Asp Thr
            100                 105                 110

Ala Val Tyr Tyr Cys Ala Arg Thr Thr Thr Ser Tyr Ala Phe Asp Ile
        115                 120                 125

Trp Gly Gln Gly Thr Met Val Thr Val Ser Ser Gly Gly Gly Gly Ser
    130                 135                 140

Gly Gly Gly Gly Ser Gly Gly Gly Gly Ser Gly Gly Gly Gly Ser Asp
145                 150                 155                 160

Ile Gln Leu Thr Gln Ser Pro Ser Thr Leu Ser Ala Ser Val Gly Asp
                165                 170                 175

Arg Val Thr Ile Thr Cys Arg Ala Ser Gln Ser Ile Ser Thr Trp Leu
            180                 185                 190

Ala Trp Tyr Gln Gln Lys Pro Gly Lys Ala Pro Asn Leu Leu Ile Tyr
        195                 200                 205

Lys Ala Ser Thr Leu Glu Ser Gly Val Pro Ser Arg Phe Ser Gly Ser
    210                 215                 220

Gly Ser Gly Thr Glu Phe Thr Leu Thr Ile Ser Ser Leu Gln Pro Asp
225                 230                 235                 240

Asp Phe Ala Thr Tyr Tyr Cys Gln Gln Tyr Asn Thr Tyr Ser Pro Tyr
                245                 250                 255

Thr Phe Gly Gln Gly Thr Lys Leu Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430
```

```
Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 75
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Lys Pro Gly Gly Ser Leu Arg Leu Ser Cys Glu Ala Ser Gly Phe
        35                  40                  45

Ile Phe Ser Asp Tyr Tyr Met Gly Trp Ile Arg Gln Ala Pro Gly Lys
    50                  55                  60

Gly Leu Glu Trp Val Ser Tyr Ile Gly Arg Ser Gly Ser Ser Met Tyr
65                  70                  75                  80

Tyr Ala Asp Ser Val Lys Gly Arg Phe Thr Phe Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Ala Ser Pro Val Val Ala Ala Thr Glu Asp
        115                 120                 125

Phe Gln His Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Asp Ile Val Met Thr Gln Thr Pro Ala Thr Leu Ser Leu Ser
                165                 170                 175

Pro Gly Glu Arg Ala Thr Leu Ser Cys Arg Ala Ser Gln Ser Val Thr
            180                 185                 190

Ser Asn Tyr Leu Ala Trp Tyr Gln Gln Lys Pro Gly Gln Ala Pro Arg
        195                 200                 205

Leu Leu Leu Phe Gly Ala Ser Thr Arg Ala Thr Gly Ile Pro Asp Arg
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Met Tyr Tyr Cys Gln Gln Tyr Gly Ser
                245                 250                 255

Ala Pro Val Thr Phe Gly Gln Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
```

290 295 300

Val His Thr Arg Gly Leu Asp Phe Ala Cys Asp Ile Tyr Ile Trp Ala
305 310 315 320

Pro Leu Ala Gly Thr Cys Gly Val Leu Leu Leu Ser Leu Val Ile Thr
325 330 335

Leu Tyr Cys Lys Arg Gly Arg Lys Lys Leu Leu Tyr Ile Phe Lys Gln
340 345 350

Pro Phe Met Arg Pro Val Gln Thr Thr Gln Glu Glu Asp Gly Cys Ser
355 360 365

Cys Arg Phe Pro Glu Glu Glu Glu Gly Gly Cys Glu Leu Arg Val Lys
370 375 380

Phe Ser Arg Ser Ala Asp Ala Pro Ala Tyr Lys Gln Gly Gln Asn Gln
385 390 395 400

Leu Tyr Asn Glu Leu Asn Leu Gly Arg Arg Glu Glu Tyr Asp Val Leu
405 410 415

Asp Lys Arg Arg Gly Arg Asp Pro Glu Met Gly Gly Lys Pro Arg Arg
420 425 430

Lys Asn Pro Gln Glu Gly Leu Tyr Asn Glu Leu Gln Lys Asp Lys Met
435 440 445

Ala Glu Ala Tyr Ser Glu Ile Gly Met Lys Gly Glu Arg Arg Arg Gly
450 455 460

Lys Gly His Asp Gly Leu Tyr Gln Gly Leu Ser Thr Ala Thr Lys Asp
465 470 475 480

Thr Tyr Asp Ala Leu His Met Gln Ala Leu Pro Pro Arg
485 490

<210> SEQ ID NO 76
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Arg Ala Pro Gly Ala Ser Val Lys Ile Ser Cys Lys Ala Ser Gly Phe
35 40 45

Thr Phe Arg Gly Tyr Tyr Ile His Trp Val Arg Gln Ala Pro Gly Gln
50 55 60

Gly Leu Glu Trp Met Gly Ile Ile Asn Pro Ser Gly Gly Ser Arg Ala
65 70 75 80

Tyr Ala Gln Lys Phe Gln Gly Arg Val Thr Met Thr Arg Asp Thr Ser
85 90 95

Thr Ser Thr Val Tyr Met Glu Leu Ser Ser Leu Arg Ser Asp Asp Thr
100 105 110

Ala Met Tyr Tyr Cys Ala Arg Thr Ala Ser Cys Gly Gly Asp Cys Tyr
115 120 125

Tyr Leu Asp Tyr Trp Gly Gln Gly Thr Leu Val Thr Val Ser Ser Gly
130 135 140

Gly Gly Gly Ser Gly Gly Gly Gly Ser Gly Gly Gly Gly Ser Gly Gly
145 150 155 160

```
Gly Gly Ser Asp Ile Gln Met Thr Gln Ser Pro Pro Thr Leu Ser Ala
                165                 170                 175

Ser Val Gly Asp Arg Val Thr Ile Thr Cys Arg Ala Ser Glu Asn Val
            180                 185                 190

Asn Ile Trp Leu Ala Trp Tyr Gln Gln Lys Pro Gly Lys Ala Pro Lys
        195                 200                 205

Leu Leu Ile Tyr Lys Ser Ser Ser Leu Ala Ser Gly Val Pro Ser Arg
    210                 215                 220

Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
                245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 77
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

```
Met Ala Leu Pro Val Thr Ala Leu Leu Leu Pro Leu Ala Leu Leu Leu
1               5                   10                  15
```

His Ala Ala Arg Pro Gln Val Gln Leu Val Gln Ser Gly Gly Gly Leu
20 25 30

Val Gln Pro Gly Arg Ser Leu Arg Leu Ser Cys Ala Ala Ser Gly Phe
35 40 45

Thr Phe Asp Asp Tyr Ala Met His Trp Val Arg Gln Ala Pro Gly Lys
50 55 60

Gly Leu Glu Trp Val Ser Gly Ile Ser Trp Asn Ser Gly Ser Ile Gly
65 70 75 80

Tyr Ala Asp Ser Val Lys Gly Arg Phe Thr Ile Ser Arg Asp Asn Ala
85 90 95

Lys Asn Ser Leu Tyr Leu Gln Met Asn Ser Leu Arg Ala Glu Asp Thr
100 105 110

Ala Val Tyr Tyr Cys Ala Lys Asp Gly Ser Ser Ser Trp Ser Trp Gly
115 120 125

Tyr Phe Asp Tyr Trp Gly Gln Gly Thr Leu Val Thr Val Ser Ser Gly
130 135 140

Gly Gly Gly Ser Gly Gly Gly Gly Ser Gly Gly Gly Gly Ser Ser Ser
145 150 155 160

Glu Leu Thr Gln Asp Pro Ala Val Ser Val Ala Leu Gly Gln Thr Val
165 170 175

Arg Thr Thr Cys Gln Gly Asp Ala Leu Arg Ser Tyr Tyr Ala Ser Trp
180 185 190

Tyr Gln Gln Lys Pro Gly Gln Ala Pro Met Leu Val Ile Tyr Gly Lys
195 200 205

Asn Asn Arg Pro Ser Gly Ile Pro Asp Arg Phe Ser Gly Ser Asp Ser
210 215 220

Gly Asp Thr Ala Ser Leu Thr Ile Thr Gly Ala Gln Ala Glu Asp Glu
225 230 235 240

Ala Asp Tyr Tyr Cys Asn Ser Arg Asp Ser Ser Gly Tyr Pro Val Phe
245 250 255

Gly Thr Gly Thr Lys Val Thr Val Leu Thr Thr Thr Pro Ala Pro Arg
260 265 270

Pro Pro Thr Pro Ala Pro Thr Ile Ala Ser Gln Pro Leu Ser Leu Arg
275 280 285

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Lys Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser

```
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485


<210> SEQ ID NO 78
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Thr Gly
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Leu Tyr Tyr Cys Ala Lys Asp Ser Ser Ser Trp Tyr Gly Gly Gly
        115                 120                 125

Ser Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Ser
145                 150                 155                 160

Ser Glu Leu Thr Gln Glu Pro Ala Val Ser Val Ala Leu Gly Gln Thr
                165                 170                 175

Val Arg Ile Thr Cys Gln Gly Asp Ser Leu Arg Ser Tyr Tyr Ala Ser
            180                 185                 190

Trp Tyr Gln Gln Lys Pro Gly Gln Ala Pro Val Leu Val Ile Phe Gly
        195                 200                 205

Arg Ser Arg Arg Pro Ser Gly Ile Pro Asp Arg Phe Ser Gly Ser Ser
    210                 215                 220

Ser Gly Asn Thr Ala Ser Leu Ile Ile Thr Gly Ala Gln Ala Glu Asp
225                 230                 235                 240

Glu Ala Asp Tyr Tyr Cys Asn Ser Arg Asp Asn Thr Ala Asn His Tyr
                245                 250                 255

Val Phe Gly Thr Gly Thr Lys Leu Thr Val Leu Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300
```

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 79
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Arg Ser Leu Arg Leu Ser Cys Ala Ala Ser Gly Phe
35 40 45

Thr Phe Asp Asp Tyr Ala Met His Trp Val Arg Gln Ala Pro Gly Lys
50 55 60

Gly Leu Glu Trp Val Ser Gly Ile Ser Trp Asn Ser Gly Ser Thr Gly
65 70 75 80

Tyr Ala Asp Ser Val Lys Gly Arg Phe Thr Ile Ser Arg Asp Asn Ala
85 90 95

Lys Asn Ser Leu Tyr Leu Gln Met Asn Ser Leu Arg Ala Glu Asp Thr
100 105 110

Ala Leu Tyr Tyr Cys Ala Lys Asp Ser Ser Ser Trp Tyr Gly Gly Gly
115 120 125

Ser Ala Phe Asp Ile Trp Gly Gln Gly Thr Met Val Thr Val Ser Ser
130 135 140

Gly Gly Gly Gly Ser Gly Gly Gly Gly Ser Gly Gly Gly Gly Ser Ser
145 150 155 160

Ser Glu Leu Thr Gln Asp Pro Ala Val Ser Val Ala Leu Gly Gln Thr
165 170 175

Val Arg Ile Thr Cys Gln Gly Asp Ser Leu Arg Ser Tyr Tyr Ala Ser
180 185 190

Trp Tyr Gln Gln Lys Pro Gly Gln Ala Pro Val Leu Val Ile Tyr Gly
195 200 205

Lys Asn Asn Arg Pro Ser Gly Ile Pro Asp Arg Phe Ser Gly Ser Ser
210 215 220

Ser Gly Asn Thr Ala Ser Leu Thr Ile Thr Gly Ala Gln Ala Glu Asp
225 230 235 240

Glu Ala Asp Tyr Tyr Cys Asn Ser Arg Gly Ser Ser Gly Asn His Tyr
245 250 255

Val Phe Gly Thr Gly Thr Lys Val Thr Val Leu Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 80
<211> LENGTH: 495
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Gly Gly Leu

-continued

```
            20                  25                  30

Val Gln Pro Gly Gly Ser Leu Arg Leu Ser Cys Ala Ala Ser Gly Phe
        35                  40                  45

Thr Phe Ser Ser Tyr Trp Met His Trp Val Arg Gln Ala Pro Gly Lys
    50                  55                  60

Gly Leu Val Trp Val Ser Arg Ile Asn Ser Asp Gly Ser Ser Thr Ser
65                  70                  75                  80

Tyr Ala Asp Ser Val Lys Gly Arg Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Val Arg Thr Gly Trp Val Gly Ser Tyr Tyr Tyr
        115                 120                 125

Tyr Met Asp Val Trp Gly Lys Gly Thr Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Glu Ile Val Leu Thr Gln Ser Pro Gly Thr Leu Ser Leu
                165                 170                 175

Ser Pro Gly Glu Arg Ala Thr Leu Ser Cys Arg Ala Ser Gln Ser Val
            180                 185                 190

Ser Ser Asn Tyr Leu Ala Trp Tyr Gln Gln Lys Pro Gly Gln Pro Pro
        195                 200                 205

Arg Leu Leu Ile Tyr Asp Val Ser Thr Arg Ala Thr Gly Ile Pro Ala
    210                 215                 220

Arg Phe Ser Gly Gly Gly Ser Gly Thr Asp Phe Thr Leu Thr Ile Ser
225                 230                 235                 240

Ser Leu Glu Pro Glu Asp Phe Ala Val Tyr Tyr Cys Gln Gln Arg Ser
                245                 250                 255

Asn Trp Pro Pro Trp Thr Phe Gly Gln Gly Thr Lys Val Glu Ile Lys
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445
```

Lys Met Ala Glu Ala Tyr Ser Glu Ile Gly Met Lys Gly Glu Arg Arg
450 455 460

Arg Gly Lys Gly His Asp Gly Leu Tyr Gln Gly Leu Ser Thr Ala Thr
465 470 475 480

Lys Asp Thr Tyr Asp Ala Leu His Met Gln Ala Leu Pro Pro Arg
485 490 495

<210> SEQ ID NO 81
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Gly Gly Val
20 25 30

Val Gln Pro Gly Arg Ser Leu Arg Leu Ser Cys Ala Ala Ser Gly Phe
35 40 45

Thr Phe Ser Ser Tyr Gly Met His Trp Val Arg Gln Ala Pro Gly Lys
50 55 60

Gly Leu Glu Trp Val Ala Val Ile Ser Tyr Asp Gly Ser Asn Lys Tyr
65 70 75 80

Tyr Ala Asp Ser Val Lys Gly Arg Phe Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Ala Lys Gly Tyr Ser Arg Tyr Tyr Tyr Tyr Gly
115 120 125

Met Asp Val Trp Gly Gln Gly Thr Thr Val Thr Val Ser Ser Gly Gly
130 135 140

Gly Gly Ser Gly Gly Gly Gly Ser Gly Gly Gly Gly Ser Gly Gly Gly
145 150 155 160

Gly Ser Glu Ile Val Met Thr Gln Ser Pro Ala Thr Leu Ser Leu Ser
165 170 175

Pro Gly Glu Arg Ala Ile Leu Ser Cys Arg Ala Ser Gln Ser Val Tyr
180 185 190

Thr Lys Tyr Leu Gly Trp Tyr Gln Gln Lys Pro Gly Gln Ala Pro Arg
195 200 205

Leu Leu Ile Tyr Asp Ala Ser Thr Arg Ala Thr Gly Ile Pro Asp Arg
210 215 220

Phe Ser Gly Ser Gly Ser Gly Thr Asp Phe Thr Leu Thr Ile Asn Arg
225 230 235 240

Leu Glu Pro Glu Asp Phe Ala Val Tyr Tyr Cys Gln His Tyr Gly Gly
245 250 255

Ser Pro Leu Ile Thr Phe Gly Gln Gly Thr Lys Val Asp Ile Lys Thr
260 265 270

Thr Thr Pro Ala Pro Arg Pro Pro Thr Pro Ala Pro Thr Ile Ala Ser
275 280 285

Gln Pro Leu Ser Leu Arg Pro Glu Ala Cys Arg Pro Ala Ala Gly Gly
290 295 300

Ala Val His Thr Arg Gly Leu Asp Phe Ala Cys Asp Ile Tyr Ile Trp
305 310 315 320

Ala Pro Leu Ala Gly Thr Cys Gly Val Leu Leu Leu Ser Leu Val Ile
325 330 335

Thr Leu Tyr Cys Lys Arg Gly Arg Lys Lys Leu Leu Tyr Ile Phe Lys
340 345 350

Gln Pro Phe Met Arg Pro Val Gln Thr Thr Gln Glu Glu Asp Gly Cys
355 360 365

Ser Cys Arg Phe Pro Glu Glu Glu Glu Gly Gly Cys Glu Leu Arg Val
370 375 380

Lys Phe Ser Arg Ser Ala Asp Ala Pro Ala Tyr Lys Gln Gly Gln Asn
385 390 395 400

Gln Leu Tyr Asn Glu Leu Asn Leu Gly Arg Arg Glu Glu Tyr Asp Val
405 410 415

Leu Asp Lys Arg Arg Gly Arg Asp Pro Glu Met Gly Gly Lys Pro Arg
420 425 430

Arg Lys Asn Pro Gln Glu Gly Leu Tyr Asn Glu Leu Gln Lys Asp Lys
435 440 445

Met Ala Glu Ala Tyr Ser Glu Ile Gly Met Lys Gly Glu Arg Arg Arg
450 455 460

Gly Lys Gly His Asp Gly Leu Tyr Gln Gly Leu Ser Thr Ala Thr Lys
465 470 475 480

Asp Thr Tyr Asp Ala Leu His Met Gln Ala Leu Pro Pro Arg
485 490

<210> SEQ ID NO 82
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Gly Gly Leu
20 25 30

Val Gln Pro Gly Gly Ser Leu Arg Leu Ser Cys Ala Ala Ser Gly Phe
35 40 45

Thr Phe Ser Ser Tyr Ala Met Ser Trp Val Arg Gln Ala Pro Gly Lys
50 55 60

Gly Leu Glu Trp Val Ser Ala Ile Ser Gly Ser Gly Gly Ser Thr Tyr
65 70 75 80

Tyr Ala Asp Ser Val Lys Gly Arg Phe Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Ala Lys Arg Glu Ala Ala Ala Gly His Asp Trp
115 120 125

Tyr Phe Asp Leu Trp Gly Arg Gly Thr Leu Val Thr Val Ser Ser Gly
130 135 140

Gly Gly Gly Ser Gly Gly Gly Gly Ser Gly Gly Gly Gly Ser Gly Gly
145 150 155 160

Gly Gly Ser Asp Ile Arg Val Thr Gln Ser Pro Ser Ser Leu Ser Ala

```
                165                 170                 175

Ser Val Gly Asp Arg Val Thr Ile Thr Cys Arg Ala Ser Gln Ser Ile
            180                 185                 190

Ser Ser Tyr Leu Asn Trp Tyr Gln Gln Lys Pro Gly Lys Ala Pro Lys
        195                 200                 205

Leu Leu Ile Tyr Ala Ala Ser Ser Leu Gln Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Tyr Cys Gln Gln Ser Tyr Ser
                245                 250                 255

Ile Pro Leu Thr Phe Gly Gln Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 83
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Trp Ala Glu Val
            20                  25                  30
```

```
Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Asn Leu Arg Ser Glu Asp Thr
            100                 105                 110

Ala Val Tyr Tyr Cys Ala Arg Ser Pro Arg Val Thr Thr Gly Tyr Phe
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Gln Leu Thr Gln Ser Pro Ser Thr Leu Ser Ala Ser Val
                165                 170                 175

Gly Asp Arg Val Thr Ile Thr Cys Arg Ala Ser Gln Ser Ile Ser Ser
            180                 185                 190

Trp Leu Ala Trp Tyr Gln Gln Lys Pro Gly Lys Ala Pro Lys Leu Leu
        195                 200                 205

Ile Tyr Lys Ala Ser Ser Leu Glu Ser Gly Val Pro Ser Arg Phe Ser
    210                 215                 220

Gly Ser Gly Ser Gly Thr Glu Phe Thr Leu Thr Ile Ser Ser Leu Gln
225                 230                 235                 240

Pro Asp Asp Phe Ala Thr Tyr Tyr Cys Gln Gln Tyr Ser Ser Tyr Pro
                245                 250                 255

Leu Thr Phe Gly Gly Gly Thr Arg Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445
```

```
Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 84
<211> LENGTH: 497
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Arg Arg Pro Gly Ala Ser Val Lys Ile Ser Cys Arg Ala Ser Gly Asp
        35                  40                  45

Thr Ser Thr Arg His Tyr Ile His Trp Leu Arg Gln Ala Pro Gly Gln
    50                  55                  60

Gly Pro Glu Trp Met Gly Val Ile Asn Pro Thr Thr Gly Pro Ala Thr
65                  70                  75                  80

Gly Ser Pro Ala Tyr Ala Gln Met Leu Gln Gly Arg Val Thr Met Thr
                85                  90                  95

Arg Asp Thr Ser Thr Arg Thr Val Tyr Met Glu Leu Arg Ser Leu Arg
            100                 105                 110

Phe Glu Asp Thr Ala Val Tyr Tyr Cys Ala Arg Ser Val Val Gly Arg
        115                 120                 125

Ser Ala Pro Tyr Tyr Phe Asp Tyr Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Gln Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Gly Ile Ser Asp Tyr Ser Ala Trp Tyr Gln Gln Lys Pro Gly
        195                 200                 205

Lys Ala Pro Lys Leu Leu Ile Tyr Ala Ala Ser Thr Leu Gln Ser Gly
    210                 215                 220

Val Pro Ser Arg Phe Ser Gly Ser Gly Ser Gly Thr Asp Phe Thr Leu
225                 230                 235                 240

Thr Ile Ser Tyr Leu Gln Ser Glu Asp Phe Ala Thr Tyr Tyr Cys Gln
                245                 250                 255

Gln Tyr Tyr Ser Tyr Pro Leu Thr Phe Gly Gly Gly Thr Lys Val Asp
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
```

```
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg


<210> SEQ ID NO 85
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Asn Tyr Tyr Met His Trp Val Arg Gln Ala Pro Gly Gln
    50                  55                  60

Gly Leu Glu Trp Met Gly Ile Ile Asn Pro Ser Gly Gly Tyr Thr Thr
65                  70                  75                  80

Tyr Ala Gln Lys Phe Gln Gly Arg Leu Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Ile Arg Ser Cys Gly Gly Asp Cys Tyr
        115                 120                 125

Tyr Phe Asp Asn Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160
```

```
Gly Gly Ser Asp Ile Gln Leu Thr Gln Ser Pro Ser Thr Leu Ser Ala
                165                 170                 175

Ser Val Gly Asp Arg Val Thr Ile Thr Cys Arg Ala Ser Glu Asn Val
            180                 185                 190

Asn Ile Trp Leu Ala Trp Tyr Gln Gln Lys Pro Gly Lys Ala Pro Lys
        195                 200                 205

Leu Leu Ile Tyr Lys Ser Ser Ser Leu Ala Ser Gly Val Pro Ser Arg
    210                 215                 220

Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
                245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 86
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

```
Met Ala Leu Pro Val Thr Ala Leu Leu Leu Pro Leu Ala Leu Leu Leu
1               5                   10                  15

His Ala Ala Arg Pro Gln Ile Thr Leu Lys Glu Ser Gly Pro Ala Leu
```

-continued

```
            20                  25                  30

Val Lys Pro Thr Gln Thr Leu Thr Leu Thr Cys Thr Phe Ser Gly Phe
        35                  40                  45

Ser Leu Ser Thr Ala Gly Val His Val Gly Trp Ile Arg Gln Pro Pro
    50                  55                  60

Gly Lys Ala Leu Glu Trp Leu Ala Leu Ile Ser Trp Ala Asp Asp Lys
65                  70                  75                  80

Arg Tyr Arg Pro Ser Leu Arg Ser Arg Leu Asp Ile Thr Arg Val Thr
                85                  90                  95

Ser Lys Asp Gln Val Val Leu Ser Met Thr Asn Met Gln Pro Glu Asp
            100                 105                 110

Thr Ala Thr Tyr Tyr Cys Ala Leu Gln Gly Phe Asp Gly Tyr Glu Ala
        115                 120                 125

Asn Trp Gly Pro Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Asp Ile Val Met Thr Gln Ser Pro Ser Ser Leu Ser Ala Ser Ala Gly
                165                 170                 175

Asp Arg Val Thr Ile Thr Cys Arg Ala Ser Arg Gly Ile Ser Ser Ala
            180                 185                 190

Leu Ala Trp Tyr Gln Gln Lys Pro Gly Lys Pro Pro Lys Leu Leu Ile
        195                 200                 205

Tyr Asp Ala Ser Ser Leu Glu Ser Gly Val Pro Ser Arg Phe Ser Gly
    210                 215                 220

Ser Gly Ser Gly Thr Asp Phe Thr Leu Thr Ile Asp Ser Leu Glu Pro
225                 230                 235                 240

Glu Asp Phe Ala Thr Tyr Tyr Cys Gln Gln Ser Tyr Ser Thr Pro Trp
                245                 250                 255

Thr Phe Gly Gln Gly Thr Lys Val Asp Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445
```

```
Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 87
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87

caagtccaac tgcagcagtc aggagcggaa gtgaagaaac caggagcgtc agtcaaagtg      60

tcgtgcaagg ctagcggcta caccttcacc ggctactaca tgcactgggt tcgacaggct     120

ccagggcagg gtctggagtg gatgggccgc atcaacccga attccggtgg gactaactac     180

gcccagaagt tccagggaag agtgaccatg actagggaca cgtcgatcag cactgcgtac     240

atggaactga gccgcctgcg gtccgaggat actgccgtct actactgcgc acgcggaagg     300

tactatggaa tggacgtgtg gggccaaggg actatggtga ctgtgagctc gggagggga     360

ggctccggtg gcgggggatc aggaggagga ggatcagggg gaggaggttc cgaaattgtc     420

ctcacccaga gcccggcaac cctctcactt tccccgggag agcgcgcaac catctcttgc     480

cgggctagcc aatccgtgtc gtccaatttc gcctggtacc agcaacggcc gggacaagcc     540

cctagactcc tgatctacga cgccagcaac agagcgactg gaattcctcc acgcttttcg     600

ggatcaggct ccggtaccga cttcaccctg actatctcgt cgctcgaacc cgaggatttc     660

gccgcctact actgtcatca gcggtcgaac tggttgtata cgtttggcca gggcaccaag     720

gtggatatca ag                                                         732


<210> SEQ ID NO 88
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88

caagtccaac tcgtccagtc aggagcagaa gtcaagaaac caggtgctag cgtgaaagtg      60

tcgtgcaagg cgtcgggata cactttcacc ggatactaca tgcactgggt ccgccaggcc     120

cccggacaag gactggaatg gatgggctgg atcaacccga atagcggggg aactaattac     180

gcccagaagt ttcagggacg agtgaccatg acccgcgata cctctatctc gaccgcctac     240

atggagctct ccagactgcg ctccgacgat actgcagtgt actactgcgc ccgggacctg     300

aggcggactg tggttactcc tcgcgcctat tatggcatgg acgtgtgggg ccaaggaact     360

actgtgactg tgagctcggg aggcggtggg tcaggcggag gagggtcggg cggtggtggc     420

tcgggagggg gaggaagcga cattcaactt acgcagagcc cgtcaaccct gtcagcgtca     480

gtgggagatc gggtgaccat cacgtgtcag gccagccagg atatctccaa ctcgctcaac     540

tggtaccagc aaaaggcggg taaagctccg aagctgctga tctacgacgc ttccaccctc     600
```

gagactggag tcccatccag attttccggg tcaggaagcg gcaccgattt ctccttcacc 660
atttcgtcct tgcaaccgga ggacatcgca acctactact gccagcagca tgacaacttg 720
cctctgacgt tcgggcaggg caccaaggtg gaaatcaag 759

<210> SEQ ID NO 89
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89
caagtccaac tcgtccaatc aggagcggaa gtcaaaaagc ccggagctcc agtgaaagtg 60
tcatgcaagg cctccggcta caccttcacc ggttactata tgcactgggt gcggcaggcc 120
ccgggccagg ggttggaatg gatgggatgg atcaatccaa actcgggtgg gactaactac 180
gcccagaagt tccaaggacg ggtgaccatg actagggaca cctcgatctc caccgcatac 240
atggagctta gcagactccg ctccgacgat accgcagtct actattgcgc gcggggagag 300
tgggacggat cgtactacta cgattactgg ggccagggaa ctctggtgac tgtttcctcg 360
ggtggaggag gttcaggcgg aggcggctcg ggcgggggag gatctggagg aggagggtcc 420
gacattgtgc tgacccaaac tccttcgtcc ctgtcggcca gcgtgggcga ccgcgtgacg 480
attacgtgca gagctagcca atccatcaat acttacctca actggtacca gcataagccg 540
gggaaagcac caaagctgct gatctacgcc gcctcatcct tgcagagcgg tgtgccttca 600
cgctttagcg gatcgggatc gggaacggat ttcaccctga ctatcagctc cctccagccg 660
gaggattttg cgacctacta ctgtcagcag agcttctcac cgctgacttt cggcggcggg 720
accaagctgg aaatcaag 738

<210> SEQ ID NO 90
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 90
caagtgcaac tcgttgaatc aggtggaggt ttggtgcaac ccggaggatc tctcagactg 60
tcgtgtgcgg cgtccgggtt caccttttcg tcctactgga tgcactgggt gcgccaggtg 120
ccgggaaaag gactggtgtg ggtgtccaga atcaacaccg acgggtcaac gactacctac 180
gcagatagcg tggaaggtcg gttcaccatt tcgcgggaca acgctaaaaa cactctgtac 240
cttcagatga attcactgcg cgatgacgac accgcagtct actactgcgt cggtggacac 300
tgggcggtct ggggacaggg aactacggtg actgtgtcca gcggcggggg aggaagcggc 360
ggagggggga gcggaggcgg aggatcagga ggaggcggct ccgatatcca gatgacccag 420
tcgccatcga ccctctccgc tagcgtgggg gatagggtca ctatcacttg ccgagccagc 480
caatccatta gcgaccggct tgcctggtac caacagaaac ctggaaaggc cccgaagctg 540
ctcatctaca aggcctcgtc actggagtcg ggagtcccgt cccgcttttc cggctcgggc 600
tcaggcaccg agttcactct gaccatctcg agcctgcagc cggacgattt cgccgtgtat 660

```
tactgccagc aatacggaca tctcccaatg tacacgttcg gtcagggcac caaggtcgaa    720

atcaag                                                               726


<210> SEQ ID NO 91
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91

caagtccaac tcgttcaatc aggcgcagaa gtcgaaaagc ccggagcatc agtcaaagtc     60

tcttgcaagg cttccggcta caccttcacg gactactaca tgcactgggt gcgccaggct    120

ccaggccagg gactggagtg gatgggatgg atcaacccga attccggggg aactaactac    180

gcccagaagt ttcagggccg ggtgactatg actcgcgata cctcgatctc gactgcgtac    240

atggagctca gccgcctccg gtcggacgat accgccgtgt actattgtgc gtcgggatgg    300

gacttcgact actgggggca gggcactctg gtcactgtgt caagcggagg aggtggatca    360

ggtggaggtg gaagcggggg aggaggttcc ggcggcggag gatcagatat cgtgatgacg    420

caatcgcctt cctcgttgtc cgcatccgtg ggagacaggg tgaccattac ttgcagagcg    480

tcccagtcca ttcggtacta cctgtcgtgg taccagcaga agccggggaa agccccaaaa    540

ctgcttatct atactgcctc gatcctccaa aacggcgtgc catcaagatt cagcggttcg    600

ggcagcggga ccgactttac cctgactatc agcagcctgc agccggaaga tttcgccacg    660

tactactgcc tgcaaaccta caccaccccg gacttcggac ctggaaccaa ggtggagatc    720

aag                                                                  723


<210> SEQ ID NO 92
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92

caagtgcaac tcgtccagtc aggtgcagaa gtgaagaaac ccggagcgtc agtcaaagtg     60

tcatgcaagg cgtcaggcta caccttcacc agctactaca tgcactgggt gcggcaggcc    120

ccaggccaag gcttggagtg gatgggaatc attaacccgt caggaggctc cacctcctac    180

gcccagaagt ttcagggaag agtgacgatg actcgggata cgtcgacctc gaccgtgtac    240

atggaactga gctcgctgcg ctccgaggac actgctgtgt actactgcgc acggtacaga    300

ctcattgccg tggcaggaga ctactactac tatggcatgg acgtctgggg gcagggcact    360

atggtcactg tgtcgtccgg cggaggaggc tcgggtggag gaggtagcgg aggaggggga    420

agcggagggg ggggctccga tatccagatg actcagtcgc cttcctccgt gtcggcctcg    480

gttggagatc gcgtcaccat cacttgtcga gcttcccaag gagtcggtag gtggctggcg    540

tggtaccagc aaaagccggg aactgccccg aagctcctga tctacgcggc tagcaccctg    600

cagtcgggag tgccatcccg cttcagcgga tctgggtcag gtaccgactt cacccttacg    660

atcaacaatc tccagccgga ggactttgcc acctattact gccaacaggc caacagcttc    720

cctctgactt tcggaggggg cactcgcctg gaaatcaag                           759
```

<210> SEQ ID NO 93
<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93
caagtgcaat tggttcaatc aggaggagga gtggtgcaac ctggaagatc tctcagactg 60
tcgtgtgcgg catcgggatt cactttctca tcatacgcaa tgcactgggt ccgccaggcc 120
ccgggcaaag gcttggaatg ggtggcggtc atttcatacg acggctcgaa caagtactac 180
gctgacagcg tgaagggacg ctttactatt tcccgggaca attcgaagaa cactctgtac 240
ctccagatga actcccttag ggctgaggac accgccgtct actactgcgc acgctggaaa 300
gtgtcgtcca gctccccagc ttttgactac tggggacagg gaacccttgt gaccgtgtcg 360
tccggtggag gggaagcgg cggagggga tcaggtggcg gcggatcggg aggcggggga 420
tcagaaatcg tgctgactca gtccccggcc acgctgtctc tcagcccggg agagagagcg 480
atcctgtcct gccgcgcctc gcagagcgtg tacactaagt acctggggtg gtaccagcag 540
aaaccgggtc aagcgcctcg gctgctgatc tacgatgcct ccacccgggc caccggaatc 600
cccgatcggt tctccggcag cggctcggga actgatttca cgctgaccat caatcgcctg 660
gagccggaag atttcgccgt ctattactgc cagcattacg gcgggagccc actcatcacc 720
ttcggtcaag gaacccgact cgaaatcaag 750

<210> SEQ ID NO 94
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94
caagtccaac tccagcagtc aggtgcagaa gtcaaaaagc caggagcatc cgtgaaggtt 60
tcgtgcaaga cttccggcta cccttttacc gggtactccc tccattgggt gagacaagca 120
ccgggccagg gactggagtg gatgggatgg atcaacccaa attcgggcgg caccaactat 180
gcgcagaagt tccagggacg ggtgaccatg actcgcgaca cttcgatctc cactgcctac 240
atggagctgt cccgcttgag atctgacgac acggccgtct actactgcgc ccgggatcac 300
tacggaggta attcgctgtt ctactggggg cagggaaccc ttgtgactgt gtcctcgggt 360
ggtggagggt caggaggcgg aggctcaggg ggaggaggta gcggaggagg cggatcagac 420
atccaactga cccagtcacc atcctccatc tcggctagcg tcggagacac cgtgtcgatt 480
acttgtaggg cctcccaaga ctcagggacg tggctggcgt ggtatcagca aaaaccgggc 540
aaagctccga acctgttgat gtacgacgcc agcaccctcg aagatggagt gcctagccgc 600
ttcagcggaa gcgcctcggg cactgaattc acgctgactg tgaatcggct ccagccggag 660
gattcggcga cctactactg ccagcagtac aacagctacc ccctgacctt tggaggcggg 720
accaaggtgg atatcaag 738

<210> SEQ ID NO 95

<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 95
caagtgcaac tcgtccagtc aggtgcagaa gtgaagaaac caggagcgtc cgtcgaagtg 60
tcgtgtaagg cgtccggcta cactttcacc tcgtactaca tgcactgggt gcggcaggcc 120
ccgggacaag gcctcgaatg gatgggaatc atcaacccga gcggaggctc gactggttac 180
gcccagaagt tccagggaag ggtgacgatg acccgcgata cctcgacttc gaccgttcat 240
atggagctct cgtccctgcg gagcgaggac actgctgtct actattgcgc gcggggagga 300
tactctagct cctccgatgc atttgacatt tggggccagg gaactatggt gaccgtgtca 360
tcaggcggag gtggatcagg aggaggaggg tcgggagggg gaggcagcgg cgggggtggg 420
tcggacattc agatgacgca gtcccctcct agcctgagcg cctcggtggg tgacagagtg 480
accatcactt gcagagcctc gcaagacatc tcctccgcat tggcttggta ccagcaaaag 540
ccgggcactc cgccgaaact gctcatctac gatgcctcct cactggagtc aggagtccca 600
tctcgcttct cggggtcagg aagcggcacc gattttaccc ttaccatctc cagcctgcag 660
cccgaggact tcgccacgta ctactgccaa cagttcagct cctacccact gaccttcggg 720
ggcggaactc gcctggaaat caag 744

<210> SEQ ID NO 96
<211> LENGTH: 765
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96
caagtgcaac tcgtccagag cggagcagaa gtcaagaagc caggagcgtc agtgaaagtg 60
tcatgcaagg ccagcggcta tacctttact tcgtatggga tctcctgggt gcggcaggca 120
ccgggccaag gactggagtg gatgggatgg atctcagcct acaacggtaa caccaactac 180
gcccagaagc tgcaaggacg cgtgaccatg actactgata cgagcacctc cactgcctac 240
atggaattgc ggtcccttcg gtcggacgat actgctgtgt actactgcgc aagagtcgcc 300
ggagggatct actactacta cggcatggac gtctggggac agggaaccac cattacggtg 360
tcgagcggag ggggaggctc ggggggagga ggaagcggag gtggcggctc cgggggcggc 420
ggatcggaca ttgtgatgac ccagactcct gactccctgg ctgtttcgtt gggagagcgc 480
gcgactatct cgtgtaagtc cagccactca gtcctgtaca atcgcaataa caagaactac 540
ctcgcgtggt accagcaaaa accgggtcag ccgcctaaac tcctgttcta ctgggcctcc 600
accagaaaga gcggggtgcc agatcgattc tctggatcag gatcaggtac cgactttacg 660
ctgaccatct cgtccctgca gccggaggat ttcgcgactt acttctgcca gcagactcag 720
actttccccc tcaccttcgg tcaaggcacc aggctggaaa tcaat 765

<210> SEQ ID NO 97
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 97

```
caagtccaat tgcagcagag cggagcagaa gtgaagaagc caggagcgtc agtcaaagtg     60

tcgtgtaagg cgtcaggata caccttcacg ggatactaca tgcactgggt gcgccaggcc    120

ccgggccaag gactcgagtg gatgggctgg atcaacccta actctggagg caccaactac    180

gcccagaatt tccaaggcag agtgaccatg acccgggaca cctccatctc gactgcctat    240

atggaactgc ggcggctgcg ctcggacgat actgctgtgt attactgcgc cagcggctgg    300

gactttgact actggggaca gggtactctg gtgactgttt cctcgggagg aggcggatcg    360

ggtggaggag gtagcggggg agggggtcg ggaggcggag gcagcgatat tcgcatgact    420

caatcgccgt cctccctgag cgctagcgtg ggagatcgag tcaccatcac ttgcagagcg    480

tcacagtcga ttcgctacta cctgtcctgg taccagcaga aaccgggaaa ggcaccaaag    540

cttctgatct acacggcctc catcctgcaa aatggtgtcc catcaaggtt ctccgggtca    600

gggagcggca ctgacttcac tctcaccatc tcctcactcc agcccgagga ctttgcaacc    660

tactactgcc tccagacgta caccaccccg gatttcggtc ctggaaccaa ggtggaaatc    720

aaa                                                                  723
```

<210> SEQ ID NO 98
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 98

```
caagtccaac tcgtccaaag cggagcagaa gtcaaaaagc caggagcgtc ggtgaaagtg     60

tcttgcaaag ccagcggcta caccttcacg ggttactaca tgcactgggt gcgccaggcg    120

ccgggccagg ggctggagtg gatgggccgg attaacccta acagcggggg aactaattac    180

gctcagaagt tccagggtag agtcaccatg actacggaca cttccacttc caccgcctat    240

atggaactgc gctccctccg ctcagatgat actgccgtgt attactgcgc gcggactacc    300

acgtcatacg catttgacat ctggggccag ggaactatgg tgaccgtgag ctcgggcgga    360

ggcggttcag gggaggaggg aagcggagga ggaggatcgg gaggaggtgg ctccgatatc    420

cagctgactc agtccccgag caccctgtcg gcgtcggtgg gggacagggt taccatcacc    480

tgtagagctt cccaatccat ttcgacttgg ctggcctggt accagcaaaa gccgggaaag    540

gcccctaatt tgcttatcta caaggcatcg accctcgaaa gcggtgtgcc ctcccggttt    600

tcgggatcag gatcagggac cgagttcacc ctgaccatct catccctcca gccggacgac    660

ttcgccactt actactgcca gcagtacaac acctactcgc catacacttt cggccaaggc    720

accaagctgg agatcaag                                                  738
```

<210> SEQ ID NO 99
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 99
caagttcaac tcgtgcaatc aggtggagga ctcgtcaaac ccggaggatc attgagactg 60
tcatgcgaag cgagcggttt tatcttctcc gattactata tgggatggat tcggcaggcc 120
ccgggaaagg gactcgaatg ggtgtcatac atcggaaggt caggctcgtc catgtactac 180
gcagactcgg tgaaaggcag attcaccttt agccgggaca acgccaagaa ttccctctac 240
ttgcagatga acagcctgcg agccgaggat actgctgtct actactgtgc cgcgtcgccg 300
gtggtggcag ctactgaaga tttccagcac tggggacagg gaactctggt cacggtgtcg 360
agcggtgggg gcggaagcgg aggcggagga tcgggcggcg gaggttcggg ggggggaggg 420
tctgacatcg tgatgaccca aaccccagcc accctgagcc tctcccctgg agagcgcgcg 480
actctttcgt gccgcgcttc ccagtcagtg accagcaatt acttggcttg gtaccaacag 540
aagccgggac aggcgccacg gctgctgctt tttggtgcca gcactcgcgc caccggaatc 600
ccggatcgct tctcgggctc agggtccggg acggacttca ccctgactat caaccggctg 660
gaacctgagg acttcgcgat gtactactgc cagcagtacg gctccgcacc agtcactttc 720
ggacaaggca ccaagctgga gatcaag 747

<210> SEQ ID NO 100
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 100
caagtccaac tcgtccagtc gggagcagaa gttagagcac caggagcgtc agtgaaaatc 60
tcatgcaagg cctcgggctt cacgttccgc ggatactaca tccactgggt gcgccaagcc 120
ccgggtcagg gattggagtg gatgggaatc attaacccat caggagggag ccgggcttac 180
gcgcagaagt tccagggacg cgtcactatg acccgagata cttccacctc gactgtgtac 240
atggaactct cgtccctgag gtccgacgac actgcgatgt attactgtgc tcggactgcc 300
agctgcggtg gggactgtta ctacctcgat tactggggcc agggaactct ggtgaccgtg 360
tccagcggag gtggcgggtc agggggtggc ggaagcggag gcggcggttc aggcggagga 420
ggctcggaca tccaaatgac gcaatcgccg cctaccctga gcgcttccgt gggagatcgg 480
gtgaccatta cttgcagagc atccgagaac gtcaatatct ggctggcctg gtaccaacag 540
aagccgggga aggcccctaa actgctgatc tacaagtcga gcagccttgc ctctggagtg 600
ccctcccgct tctcgggctc gggatcagga gcggaattca ccctcaccat ctcctccctg 660
cagccagatg actttgccac ctactactgc cagcagtacc agagctatcc gttgaccttt 720
gggggaggca ctaaagtgga catcaag 747

<210> SEQ ID NO 101
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 101
caagttcaac tcgttcaatc aggtggagga ctcgtgcaac caggaagatc actcagactc 60
agctgcgccg cgtcgggatt cactttcgat gactacgcaa tgcactgggt gcggcaggcc 120
ccgggcaaag gactggaatg ggtgagcgga attagctgga actcggggtc catcgggtac 180
gccgactcgg tgaagggacg ctttacgatc tcccgggaca atgccaagaa ctccctgtat 240
ttgcagatga actccttgag ggctgaggac accgccgtgt actactgcgc taaagatgga 300
tcatcgtcct ggtcctgggg atacttcgat tactggggcc agggcactct ggtgaccgtg 360
tcgtcaggcg gtggagggtc gggcggagga ggtagcggag gcggagggag cagctctgaa 420
ctgacccaag acccggcggt gtcggtcgcc cttggtcaga ctgtgcggac tacctgtcag 480
ggggacgcgc tgcgctcgta ctacgcttca tggtaccagc agaagcccgg acaggcacct 540
atgctggtca tctacggaaa gaataaccgc ccatccggca tcccggatcg cttctcgggt 600
tcggacagcg gcgacaccgc atccctgacg atcactggag cgcaggccga ggatgaagcc 660
gactactact gcaattcccg agattcaagc ggctaccctg tgtttgggac cggaactaag 720
gtcaccgtcc tg 732

<210> SEQ ID NO 102
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102
gaagtgcaac tcgtggaatc tggtggagga cttgtgcaac ctggaagatc gttgagactc 60
tcatgtgctg cctccgggtt cacctttgac gactacgcca tgcactgggt gcgccaggca 120
ccaggaaagg gtctggagtg ggtttcgggt atctcgtgga actccgggag cactggctac 180
gctgattcgg tgaaaggccg gtttaccatc tcccgagaca atgcgaagaa ttccctctat 240
ctgcagatga acagcctccg ggccgaggat actgccctgt actactgcgc caaggatagc 300
tcatcatggt acggaggtgg atcggctttc gatatctggg gccagggcac gatggtcacc 360
gtgtcctcgg ggggcggagg ctccggggga ggaggtagcg gaggaggagg atcgagctca 420
gagttgactc aagaacccgc agtgtccgtg gcactgggcc aaaccgtcag gatcacttgc 480
cagggagaca gcctgaggtc gtactacgcg tcctggtacc agcagaagcc gggacaggcc 540
ccggtcctgg tcattttcgg acgctcaaga cgcccatcgg gcatcccgga ccggttcagc 600
ggaagctcct cgggaaacac cgcgtcactt atcattaccg gcgcacaggc tgaggacgaa 660
gcggattact actgcaactc ccgcgacaat actgccaacc attacgtgtt cgggaccgga 720
acgaaactga ctgtcctg 738

<210> SEQ ID NO 103
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 103
gaagttcaat tggtggaatc tggaggagga cttgtgcaac ccggtagatc tctgagactg 60

```
tcctgtgcgg catcgggatt caccttcgac gactacgcta tgcactgggt gagacaagcc    120

cctggaaaag gactggagtg ggtgtcaggc atctcctgga atagcgggtc cactggatac    180

gccgattcgg tcaagggtcg cttcaccatt tcccgggaca atgccaagaa ctccctgtac    240

cttcaaatga actccctccg ggccgaggat accgccctct actactgcgc caaagacagc    300

tcgtcatggt atggcggagg gtcggcattt gacatctggg gacagggaac tatggtgact    360

gtgtcatcag gaggcggcgg aagcggcggc ggcgggtccg gcggaggagg gtcgtccagc    420

gaactcaccc aagatccagc agtgagcgtc gcgctgggcc agaccgtcag gatcacgtgc    480

cagggagatt cactgcgctc atactacgcg tcctggtacc agcagaagcc ggggcaggcc    540

ccggtcctcg tgatctacgg aaagaacaac cgcccgtcgg gtatcccaga ccgcttttcg    600

ggtagctcca gcggaaatac ggctagcctg accatcactg gagcacaggc tgaggatgaa    660

gcggactact actgcaattc gcggggctca tcggggaacc attacgtgtt cggaactggt    720

accaaggtga ctgtcctg                                                  738
```

<210> SEQ ID NO 104
<211> LENGTH: 753
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104

```
caagtgcagc tcgttcaatc aggcggagga ctcgttcaac caggaggatc attgcgactc     60

tcatgtgcgg cctctggatt cacgtttagc tcatattgga tgcactgggt gcggcaggcg    120

ccggggaaag gtctggtgtg ggtcagccgc atcaactcag acggctcctc gacttcgtac    180

gccgactccg tgaagggacg ctttaccatt tcccgcgaca acgccaagaa taccctttac    240

cttcagatga actccctccg cgctgaggat accgccgtgt actactgcgt gaggactggc    300

tgggtcggca gctactacta ctacatggac gtgtggggca aggaactac tgtcaccgtg    360

tcaagcggcg gtggaggttc cggcggggga ggatcggggg ggggcggatc gggtggcgga    420

ggatcggaga tcgtgttgac ccagtcgccg ggaaccctgt cgctgtcgcc tggggagaga    480

gcaactctgt cctgccgggc ttcccagtcg gtgtcgagca attacctggc atggtaccaa    540

cagaagccgg gacagccgcc acgcctgctg atctatgacg tgtcaactcg ggcaactgga    600

atccctgcgc ggttcagcgg cggagggagc ggtaccgatt tcaccctgac tatttcctcc    660

ctcgaaccag aagatttcgc cgtctactac tgccagcaga gaagcaactg gccgccctgg    720

acgttcggac aaggaaccaa ggtcgaaatc aag                                 753
```

<210> SEQ ID NO 105
<211> LENGTH: 750
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105

```
caagtgcaat tggttcaatc aggaggagga gtcgtgcagc ccggaagatc gttgagactg     60

tcatgtgccg cgagcggctt tactttctca agctacggaa tgcattgggt gcgacaggct    120

ccgggaaaag gactggaatg ggtcgcagtg atctcatacg acggctcgaa caagtactac    180
```

gccgactccg tcaagggtcg gttcacgatt tcgcgcgata attccaagaa cactctgtac 240
ctccaaatga acagcctccg ggcagaggac accgccgtct actactgcgc taagggatac 300
tcgcgctact actactatgg aatggatgtg tggggccagg gaactaccgt gacggtgtcg 360
tccggcggcg gtgggtcggg cggaggcgga tcaggtggag gtggaagcgg aggaggaggg 420
agcgaaatcg tcatgactca gtcccctgct accctttctc tgtcgccggg agaaagagcc 480
atcctgagct gccgggcctc ccagagcgtg tacaccaaat acctgggatg gtaccagcag 540
aagccggggc aggcaccaag gctcctgatc tacgatgcgt ccacccgcgc gactggtatc 600
ccagaccgct ttccggctc ggggtcaggg actgacttca cccttactat caatcggctc 660
gagcctgagg atttcgccgt gtattactgc cagcactacg gagggtcccc gctgattacc 720
ttcggccaag gcaccaaagt ggacatcaag 750

<210> SEQ ID NO 106
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106
caagtgcaac ttgttcaatc aggaggagga ctcgttcaac ccggaggatc actgcgactc 60
tcatgtgcag cgtcggggtt caccttctcc agctacgcaa tgtcctgggt gcgccaagcc 120
cctggaaaag gcctggagtg ggtgtcggcc atctctggga gcgggggatc aacttactac 180
gctgactccg tcaagggccg ctttaccatc tcccgggaca acagcaagaa cactctctat 240
ctccagatga actcgctgag agccgaagat accgctgtct actactgcgc gaagagagaa 300
gctgccgcag ggcacgattg gtacttcgac ttgtggggca ggggcaccct tgtgaccgtg 360
tcctccggtg gaggcggatc aggaggtggg ggatcgggtg gaggaggaag cggaggcggc 420
ggttcggaca ttcgcgtcac ccagtcaccg agctccctca gcgcatcggt gggcgaccgg 480
gtcactatca cttgccgggc gtcccagtcg atctcatcgt atctgaattg gtaccagcag 540
aaaccgggaa aggcgccgaa gctgttgatc tacgctgcca gctccctgca gtcgggtgtg 600
ccatcacgct tttccggctc gggatcggga accgatttca ctctgacgat ctctagcctg 660
cagccagaag atttcgccac ttactactgc cagcagtcct acagcatccc tctgactttc 720
ggacaaggga cgaaagtgga gattaag 747

<210> SEQ ID NO 107
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 107
caagtccaac tcgttcagtc atgggcagaa gtcaagaaac ccggtgcaag cgtcaaagtg 60
tcgtgtaagg cctccggcta cactttcact tcctactaca tgcactgggt gcgccaagcc 120
ccgggacagg gccttgaatg gatgggcatc atcaacccat caggaggttc cacgagctac 180
gcgcagaagt tccaggggag agtgacgatg actagagata cctccacgag caccgtctac 240

```
atggagctgt cgaatctgcg gtcagaggac actgctgtgt attactgcgc gcgctccccg    300

cgggtgacca ctggctactt tgactactgg ggacaaggga ccctggtgac cgtcagctcg    360

ggaggcggag gatcgggagg tggagggtcc ggtggaggcg gctctggagg aggcgggtcg    420

gacattcaat tgacccagag cccatccacc ctctcagcct cggtggggga tagggtgact    480

atcacttgcc gggcctccca gtcaatttcc agctggctgg cttggtacca gcaaaagcct    540

ggaaaggcac cgaagctcct gatctacaag gcctcatctc tggaatcagg agtgccttcg    600

cgcttcagcg gaagcggctc gggaactgag tttaccctga ccatctcgag cctgcagcca    660

gatgacttcg cgacctatta ctgccagcag tactcgtcct acccgttgac tttcggagga    720

ggtacccgcc tcgaaatcaa a                                              741
```

```
<210> SEQ ID NO 108
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108

caagtccaac tcgtccagtc cggtgcagaa gtcagaaggc caggagcaag cgtgaagatc     60

tcgtgtagag cgtcaggaga caccagcact cgccattaca tccactggct gcgccaggct    120

ccgggccaag ggccggagtg gatgggtgtg atcaacccga ctacgggacc ggctaccgga    180

agccctgcgt acgcacagat gctgcaggga cgggtgacta tgacccgcga tactagcact    240

aggaccgtgt acatggaact ccgctcgttg cggttcgaag ataccgccgt ctactactgc    300

gcccggtccg tggtgggccg aagcgcccct tactacttcg attactgggg acagggcact    360

ctggtgaccg ttagctccgg tgggggaggc tcgggtggag gcggatcggg aggaggaggc    420

agcggtggag gggggatcgga cattcagatg acccagtcac cctcctccct ctcagcctcg    480

gtcggggacc gggtgaccat tacgtgcaga gcctcacaag ggatctcgga ctactccgcc    540

tggtaccagc agaaaccggg aaaagcgcca aagctcctga tctacgccgc gagcaccctg    600

caatcaggag tgccatcgcg cttttctgga tcgggctcag ggactgactt cacgctgact    660

atctcctacc ttcagtccga ggatttcgct acctactact gccaacagta ttactcctat    720

cccctgacct ttggcggagg cactaaggtg gacatcaag                           759
```

```
<210> SEQ ID NO 109
<211> LENGTH: 747
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109

caagtccaac tccagcaatc gggagcagaa gtcaagaaac caggcgcatc ggtgaaagtg     60

tcgtgtaagg cgtcagggta caccttcacc aactactata tgcactgggt gcgccaggct    120

ccaggccagg ggttggagtg gatggggatc atcaatccgt caggtggcta caccacttac    180

gctcagaagt tccagggacg cctcactatg actcgcgata ctagcacctc cacggtgtac    240

atggaactgt catcgctgag gtccgaagat accgccgtct actactgcgc acggatcaga    300

tcctgcggag gagattgtta ctactttgac aactggggac agggcaccct tgttactgtg    360
```

tcatcgggag gagggggaag cggaggaggt ggatcaggcg gcggtggcag cgggggcgga 420
ggatcggaca ttcagctgac tcagtccccc tccactttgt cggccagcgt gggagacaga 480
gtgaccatca cttgccgggc gtccgagaac gtcaatatct ggctggcctg gtaccagcaa 540
aagcctggaa aagccccgaa gctgctcatc tataagtcat ccagcctggc gtctggtgtg 600
ccgtcgcggt tctccggcag cgggagcgga gccgagttca ctctcaccat ttcgagcctt 660
caaccggacg atttcgccac ctactactgc cagcagtacc aatcctaccc tctgacgttt 720
ggaggtggaa ccaaggtgga catcaag 747

<210> SEQ ID NO 110
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110
caaatcactc tgaaagaatc tggaccggcc ctggttaagc cgactcaaac gctcaccctt 60
acttgcacct tcagcggatt ctcactcagc actgctggtg tgcacgtcgg atggattaga 120
cagccgcctg gaaaggccct ggaatggctc gccctcatct cctgggccga tgacaagaga 180
tacaggccct cgcttcgatc ccggttggac attacccggg tgacctcgaa agatcaggtg 240
gtgctctcaa tgaccaatat gcagccggag gacaccgcta cgtactactg cgcactgcaa 300
ggatttgacg gctacgaggc taactgggga ccaggtactc tggtcaccgt gagctccggc 360
gggggaggat caggcggggg ggggtcagga ggcggaggct ccggtggagg aggatcggat 420
atcgtcatga cccagtcccc aagctcgctg agcgcgtcag cgggcgaccg cgtgactatc 480
acttgccggg ccagccgcgg catctcctcc gcactggcgt ggtaccagca gaagcctgga 540
aaaccgccaa agctcctgat ctatgatgcc tccagcctgg agtcaggtgt ccccagccgc 600
ttctcgggtt cgggctcggg aaccgacttc actttgacca tcgactcgct ggaaccggaa 660
gatttcgcaa cctactactg tcagcagtcc tactcgaccc cttggacttt tggacaaggg 720
acgaaggtgg acatcaag 738

<210> SEQ ID NO 111
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111
atggccctcc ctgtcaccgc cctgctgctt ccgctggctc ttctgctcca cgccgctcgg 60
ccccaagtcc aactgcagca gtcaggagcg gaagtgaaga aaccaggagc gtcagtcaaa 120
gtgtcgtgca aggctagcgg ctacaccttc accggctact acatgcactg ggttcgacag 180
gctccagggc agggtctgga gtggatgggc cgcatcaacc cgaattccgg tgggactaac 240
tacgcccaga agttccaggg aagagtgacc atgactaggg acacgtcgat cagcactgcg 300
tacatggaac tgagccgcct gcggtccgag gatactgccg tctactactg cgcacgcgga 360
aggtactatg gaatggacgt gtggggccaa gggactatgg tgactgtgag ctcgggaggg 420

```
ggaggctccg gtggcggggg atcaggagga ggaggatcag ggggaggagg ttccgaaatt    480
gtcctcaccc agagcccggc aaccctctca ctttccccgg gagagcgcgc aaccatctct    540
tgccgggcta gccaatccgt gtcgtccaat ttcgcctggt accagcaacg gccgggacaa    600
gcccctagac tcctgatcta cgacgccagc aacagagcga ctggaattcc tccacgcttt    660
tcgggatcag gctccggtac cgacttcacc ctgactatct cgtcgctcga acccgaggat    720
ttcgccgcct actactgtca tcagcggtcg aactggttgt atacgtttgg ccagggcacc    780
aaggtggata tcaagaccac taccccagca ccgaggccac ccaccccggc tcctaccatc    840
gcctcccagc ctctgtccct gcgtccggag gcatgtagac ccgcagctgg tggggccgtg    900
catacccggg gtcttgactt cgcctgcgat atctacattt gggcccctct ggctggtact    960
tgcggggtcc tgctgctttc actcgtgatc actctttact gtaagcgcgg tcggaagaag   1020
ctgctgtaca tctttaagca acccttcatg aggcctgtgc agactactca agaggaggac   1080
ggctgttcat gccggttccc agaggaggag gaaggcggct gcgaactgcg cgtgaaattc   1140
agccgcagcg cagatgctcc agcctacaag caggggcaga accagctcta caacgaactc   1200
aatcttggtc ggagagagga gtacgacgtg ctggacaagc ggagaggacg ggacccagaa   1260
atgggcggga agccgcgcag aaagaatccc caagagggcc tgtacaacga gctccaaaag   1320
gataagatgg cagaagccta tagcgagatt ggtatgaaag gggaacgcag aagaggcaaa   1380
ggccacgacg gactgtacca gggactcagc accgccacca aggacaccta tgacgctctt   1440
cacatgcagg ccctgccgcc tcgg                                           1464
```

<210> SEQ ID NO 112
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 112

```
atggccctcc ctgtcaccgc cctgctgctt ccgctggctc ttctgctcca cgccgctcgg     60
ccccaagtcc aactcgtcca gtcaggagca gaagtcaaga aaccaggtgc tagcgtgaaa    120
gtgtcgtgca aggcgtcggg atacactttc accggatact acatgcactg ggtccgccag    180
gcccccggac aaggactgga atggatgggc tggatcaacc cgaatagcgg gggaactaat    240
tacgcccaga agtttcaggg acgagtgacc atgacccgcg atacctctat ctcgaccgcc    300
tacatggagc tctccagact gcgctccgac gatactgcag tgtactactg cgcccgggac    360
ctgaggcgga ctgtggttac tcctcgcgcc tattatggca tggacgtgtg ggccaagga     420
actactgtga ctgtgagctc gggaggcggt gggtcaggcg gaggagggtc gggcggtggt    480
ggctcgggag ggggaggaag cgacattcaa cttacgcaga gcccgtcaac cctgtcagcg    540
tcagtgggag atcgggtgac catcacgtgt caggccagcc aggatatctc caactcgctc    600
aactggtacc agcaaaaggc gggtaaagct ccgaagctgc tgatctacga cgcttccacc    660
ctcgagactg gagtcccatc cagattttcc gggtcaggaa gcggcaccga tttctccttc    720
accatttcgt ccttgcaacc ggaggacatc gcaacctact actgccagca gcatgacaac    780
ttgcctctga cgttcgggca gggcaccaag gtggaaatca agaccactac cccagcaccg    840
aggccaccca ccccggctcc taccatcgcc tcccagcctc tgtccctgcg tccggaggca    900
tgtagacccg cagctggtgg ggccgtgcat acccggggtc ttgacttcgc ctgcgatatc    960
```

```
tacatttggg cccctctggc tggtacttgc ggggtcctgc tgctttcact cgtgatcact   1020

ctttactgta agcgcggtcg gaagaagctg ctgtacatct ttaagcaacc cttcatgagg   1080

cctgtgcaga ctactcaaga ggaggacggc tgttcatgcc ggttcccaga ggaggaggaa   1140

ggcggctgcg aactgcgcgt gaaattcagc cgcagcgcag atgctccagc ctacaagcag   1200

gggcagaacc agctctacaa cgaactcaat cttggtcgga gagaggagta cgacgtgctg   1260

gacaagcgga gaggacggga cccagaaatg ggcgggaagc cgcgcagaaa gaatccccaa   1320

gagggcctgt acaacgagct ccaaaaggat aagatggcag aagcctatag cgagattggt   1380

atgaaagggg aacgcagaag aggcaaaggc cacgacggac tgtaccaggg actcagcacc   1440

gccaccaagg acacctatga cgctcttcac atgcaggccc tgccgcctcg g            1491
```

<210> SEQ ID NO 113
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 113

```
atggccctcc ctgtcaccgc cctgctgctt ccgctggctc ttctgctcca cgccgctcgg     60

ccccaagtcc aactcgtcca atcaggagcg gaagtcaaaa agcccggagc tccagtgaaa    120

gtgtcatgca aggcctccgg ctacaccttc accggttact atatgcactg ggtgcggcag    180

gccccgggcc aggggttgga atggatggga tggatcaatc caaactcggg tgggactaac    240

tacgcccaga agttccaagg acgggtgacc atgactaggg acacctcgat ctccaccgca    300

tacatggagc ttagcagact ccgctccgac gataccgcag tctactattg cgcgcgggga    360

gagtgggacg gatcgtacta ctacgattac tggggccagg gaactctggt gactgtttcc    420

tcgggtggag gaggttcagg cggaggcggc tcgggcgggg gaggatctgg aggaggaggg    480

tccgacattg tgctgaccca aactccttcg tccctgtcgg ccagcgtggg cgaccgcgtg    540

acgattacgt gcagagctag ccaatccatc aatacttacc tcaactggta ccagcataag    600

ccggggaaag caccaaagct gctgatctac gccgcctcat ccttgcagag cggtgtgcct    660

tcacgcttta gcggatcggg atcgggaacg gatttcaccc tgactatcag ctccctccag    720

ccggaggatt ttgcgaccta ctactgtcag cagagcttct caccgctgac tttcggcggc    780

gggaccaagc tggaaatcaa gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440
```

gctcttcaca tgcaggccct gccgcctcgg 1470

<210> SEQ ID NO 114
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114
atggccctcc ctgtcaccgc cctgctgctt ccgctggctc ttctgctcca cgccgctcgg 60
ccccaagtgc aactcgttga atcaggtgga ggtttggtgc aacccggagg atctctcaga 120
ctgtcgtgtg cggcgtccgg gttcaccttt tcgtcctact ggatgcactg ggtgcgccag 180
gtgccgggaa aaggactggt gtgggtgtcc agaatcaaca ccgacgggtc aacgactacc 240
tacgcagata gcgtggaagg tcggttcacc atttcgcggg acaacgctaa aaacactctg 300
taccttcaga tgaattcact gcgcgatgac gacaccgcag tctactactg cgtcggtgga 360
cactgggcgg tctggggaca gggaactacg gtgactgtgt ccagcggcgg gggaggaagc 420
ggcggagggg ggagcggagg cggaggatca ggaggaggcg gctccgatat ccagatgacc 480
cagtcgccat cgaccctctc cgctagcgtg ggggataggg tcactatcac ttgccgagcc 540
agccaatcca ttagcgaccg gcttgcctgg taccaacaga aacctggaaa ggccccgaag 600
ctgctcatct acaaggcctc gtcactggag tcgggagtcc cgtcccgctt ttccggctcg 660
ggctcaggca ccgagttcac tctgaccatc tcgagcctgc agccggacga tttcgccgtg 720
tattactgcc agcaatacgg acatctccca atgtacacgt tcggtcaggg caccaaggtc 780
gaaatcaaga ccactacccc agcaccgagg ccacccaccc cggctcctac catcgcctcc 840
cagcctctgt ccctgcgtcc ggaggcatgt agacccgcag ctggtggggc cgtgcatacc 900
cggggtcttg acttcgcctg cgatatctac atttgggccc ctctggctgg tacttgcggg 960
gtcctgctgc tttcactcgt gatcactctt tactgtaagc gcggtcggaa gaagctgctg 1020
tacatcttta agcaaccctt catgaggcct gtgcagacta ctcaagagga ggacggctgt 1080
tcatgccggt tcccagagga ggaggaaggc ggctgcgaac tgcgcgtgaa attcagccgc 1140
agcgcagatg ctccagccta caagcagggg cagaaccagc tctacaacga actcaatctt 1200
ggtcggagag aggagtacga cgtgctggac aagcggagag gacgggaccc agaaatgggc 1260
gggaagccgc gcagaaagaa tccccaagag ggcctgtaca acgagctcca aaaggataag 1320
atggcagaag cctatagcga gattggtatg aaaggggaac gcagaagagg caaaggccac 1380
gacggactgt accagggact cagcaccgcc accaaggaca cctatgacgc tcttcacatg 1440
caggccctgc cgcctcgg 1458

<210> SEQ ID NO 115
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115
atggccctcc ctgtcaccgc cctgctgctt ccgctggctc ttctgctcca cgccgctcgg 60
ccccaagtcc aactcgttca atcaggcgca gaagtcgaaa agcccggagc atcagtcaaa 120
gtctcttgca aggcttccgg ctacaccttc acggactact acatgcactg ggtgcgccag 180
gctccaggcc agggactgga gtggatggga tggatcaacc cgaattccgg gggaactaac 240
tacgcccaga agtttcaggg ccgggtgact atgactcgcg atacctcgat ctcgactgcg 300
tacatggagc tcagccgcct ccggtcggac gataccgccg tgtactattg tgcgtcggga 360
tgggacttcg actactgggg gcagggcact ctggtcactg tgtcaagcgg aggaggtgga 420
tcaggtggag gtggaagcgg gggaggaggt tccggcggcg gaggatcaga tatcgtgatg 480
acgcaatcgc cttcctcgtt gtccgcatcc gtgggagaca gggtgaccat tacttgcaga 540
gcgtcccagt ccattcggta ctacctgtcg tggtaccagc agaagccggg gaaagcccca 600
aaactgctta tctatactgc ctcgatcctc caaaacggcg tgccatcaag attcagcggt 660
tcgggcagcg ggaccgactt taccctgact atcagcagcc tgcagccgga agatttcgcc 720
acgtactact gcctgcaaac ctacaccacc ccggacttcg gacctggaac caaggtggag 780
atcaagacca ctaccccagc accgaggcca cccaccccgg ctcctaccat cgcctcccag 840
cctctgtccc tgcgtccgga ggcatgtaga cccgcagctg gtggggccgt gcatacccgg 900
ggtcttgact tcgcctgcga tatctacatt tgggcccctc tggctggtac ttgcggggtc 960
ctgctgcttt cactcgtgat cactctttac tgtaagcgcg gtcggaagaa gctgctgtac 1020
atctttaagc aacccttcat gaggcctgtg cagactactc aagaggagga cggctgttca 1080
tgccggttcc cagaggagga ggaaggcggc tgcgaactgc gcgtgaaatt cagccgcagc 1140
gcagatgctc cagcctacaa gcaggggcag aaccagctct acaacgaact caatcttggt 1200
cggagagagg agtacgacgt gctggacaag cggagaggac gggacccaga aatgggcggg 1260
aagccgcgca gaaagaatcc ccaagagggc ctgtacaacg agctccaaaa ggataagatg 1320
gcagaagcct atagcgagat tggtatgaaa ggggaacgca gaagaggcaa aggccacgac 1380
ggactgtacc agggactcag caccgccacc aaggacacct atgacgctct tcacatgcag 1440
gccctgccgc ctcgg 1455

<210> SEQ ID NO 116
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116
atggccctcc ctgtcaccgc cctgctgctt ccgctggctc ttctgctcca cgccgctcgg 60
ccccaagtgc aactcgtcca gtcaggtgca gaagtgaaga aacccggagc gtcagtcaaa 120
gtgtcatgca aggcgtcagg ctacaccttc accagctact acatgcactg ggtgcggcag 180
gccccaggcc aaggcttgga gtggatggga atcattaacc cgtcaggagg ctccacctcc 240
tacgcccaga agtttcaggg aagagtgacg atgactcggg atacgtcgac ctcgaccgtg 300
tacatggaac tgagctcgct gcgctccgag gacactgctg tgtactactg cgcacggtac 360
agactcattg ccgtggcagg agactactac tactatggca tggacgtctg gggcagggc 420 actatggtca ctgtgtcgtc cggcggagga ggctcgggtg gaggaggtag cggaggaggg 480
ggaagcggag gggggggctc cgatatccag atgactcagt cgccttcctc cgtgtcggcc 540
tcggttggag atcgcgtcac catcacttgt cgagcttccc aaggagtcgg taggtggctg 600

```
gcgtggtacc agcaaaagcc gggaactgcc ccgaagctcc tgatctacgc ggctagcacc    660

ctgcagtcgg gagtgccatc ccgcttcagc ggatctgggt caggtaccga cttcaccctt    720

acgatcaaca atctccagcc ggaggacttt gccacctatt actgccaaca ggccaacagc    780

ttccctctga ctttcggagg gggcactcgc ctggaaatca agaccactac cccagcaccg    840

aggccaccca ccccggctcc taccatcgcc tcccagcctc tgtccctgcg tccggaggca    900

tgtagacccg cagctggtgg ggccgtgcat acccggggtc ttgacttcgc ctgcgatatc    960

tacatttggg cccctctggc tggtacttgc ggggtcctgc tgctttcact cgtgatcact   1020

ctttactgta agcgcggtcg gaagaagctg ctgtacatct ttaagcaacc cttcatgagg   1080

cctgtgcaga ctactcaaga ggaggacggc tgttcatgcc ggttcccaga ggaggaggaa   1140

ggcggctgcg aactgcgcgt gaaattcagc cgcagcgcag atgctccagc ctacaagcag   1200

gggcagaacc agctctacaa cgaactcaat cttggtcgga gagaggagta cgacgtgctg   1260

gacaagcgga gaggacggga cccagaaatg ggcgggaagc cgcgcagaaa gaatccccaa   1320

gagggcctgt acaacgagct ccaaaaggat aagatggcag aagcctatag cgagattggt   1380

atgaaagggg aacgcagaag aggcaaaggc cacgacggac tgtaccaggg actcagcacc   1440

gccaccaagg acacctatga cgctcttcac atgcaggccc tgccgcctcg g            1491
```

<210> SEQ ID NO 117
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 117

```
atggccctcc ctgtcaccgc cctgctgctt ccgctggctc ttctgctcca cgccgctcgg     60

ccccaagtgc aattggttca atcaggagga ggagtggtgc aacctggaag atctctcaga    120

ctgtcgtgtg cggcatcggg attcactttc tcatcatacg caatgcactg ggtccgccag    180

gccccgggca aaggcttgga atgggtggcg gtcatttcat acgacggctc gaacaagtac    240

tacgctgaca gcgtgaaggg acgctttact atttcccggg acaattcgaa gaacactctg    300

tacctccaga tgaactccct tagggctgag gacaccgccg tctactactg cgcacgctgg    360

aaagtgtcgt ccagctcccc agcttttgac tactggggac agggaaccct tgtgaccgtg    420

tcgtccggtg gagggggaag cggcggaggg ggatcaggtg gcggcggatc gggaggcggg    480

ggatcagaaa tcgtgctgac tcagtccccg gccacgctgt ctctcagccc gggagagaga    540

gcgatcctgt cctgccgcgc ctcgcagagc gtgtacacta agtacctggg gtggtaccag    600

cagaaaccgg gtcaagcgcc tcggctgctg atctacgatg cctccacccg ggccaccgga    660

atccccgatc ggttctccgg cagcggctcg ggaactgatt tcacgctgac catcaatcgc    720

ctggagccgg aagatttcgc cgtctattac tgccagcatt acggcgggag cccactcatc    780

accttcggtc aaggaacccg actcgaaatc aagaccacta ccccagcacc gaggccaccc    840

accccggctc ctaccatcgc ctcccagcct ctgtccctgc gtccggaggc atgtagaccc    900

gcagctggtg gggccgtgca tacccggggt cttgacttcg cctgcgatat ctacatttgg    960

gcccctctgg ctggtacttg cggggtcctg ctgctttcac tcgtgatcac tctttactgt   1020

aagcgcggtc ggaagaagct gctgtacatc tttaagcaac ccttcatgag gcctgtgcag   1080

actactcaag aggaggacgg ctgttcatgc cggttcccag aggaggagga aggcggctgc   1140
```

gaactgcgcg tgaaattcag ccgcagcgca gatgctccag cctacaagca ggggcagaac 1200
cagctctaca acgaactcaa tcttggtcgg agagaggagt acgacgtgct ggacaagcgg 1260
agaggacggg acccagaaat gggcgggaag ccgcgcagaa agaatcccca agagggcctg 1320
tacaacgagc tccaaaagga taagatggca gaagcctata gcgagattgg tatgaaaggg 1380
gaacgcagaa gaggcaaagg ccacgacgga ctgtaccagg gactcagcac cgccaccaag 1440
gacacctatg acgctcttca catgcaggcc ctgccgcctc gg 1482

<210> SEQ ID NO 118
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 118
atggccctcc ctgtcaccgc cctgctgctt ccgctggctc ttctgctcca cgccgctcgg 60
ccccaagtcc aactccagca gtcaggtgca gaagtcaaaa agccaggagc atccgtgaag 120
gtttcgtgca agacttccgg ctacccttt accgggtact ccctccattg ggtgagacaa 180
gcaccgggcc agggactgga gtggatggga tggatcaacc caaattcggg cggcaccaac 240
tatgcgcaga agttccaggg acgggtgacc atgactcgcg acacttcgat ctccactgcc 300
tacatggagc tgtcccgctt gagatctgac gacacggccg tctactactg cgcccgggat 360
cactacggag gtaattcgct gttctactgg gggcagggaa cccttgtgac tgtgtcctcg 420
ggtggtggag ggtcaggagg cggaggctca gggggaggag gtagcggagg aggcggatca 480
gacatccaac tgacccagtc accatcctcc atctcggcta gcgtcggaga caccgtgtcg 540
attacttgta gggcctccca agactcaggg acgtggctgg cgtggtatca gcaaaaaccg 600
ggcaaagctc cgaacctgtt gatgtacgac gccagcaccc tcgaagatgg agtgcctagc 660
cgcttcagcg gaagcgcctc gggcactgaa ttcacgctga ctgtgaatcg gctccagccg 720
gaggattcgg cgacctacta ctgccagcag tacaacagct accccctgac ctttggaggc 780
gggaccaagg tggatatcaa gaccactacc ccagcaccga ggccacccac cccggctcct 840
accatcgcct cccagcctct gtccctgcgt ccggaggcat gtagacccgc agctggtggg 900
gccgtgcata cccggggtct tgacttcgcc tgcgatatct acatttgggc ccctctggct 960
ggtacttgcg gggtcctgct gctttcactc gtgatcactc tttactgtaa gcgcggtcgg 1020
aagaagctgc tgtacatctt taagcaaccc ttcatgaggc ctgtgcagac tactcaagag 1080
gaggacggct gttcatgccg gttcccagag gaggaggaag gcggctgcga actgcgcgtg 1140
aaattcagcc gcagcgcaga tgctccagcc tacaagcagg ggcagaacca gctctacaac 1200
gaactcaatc ttggtcggag agaggagtac gacgtgctgg acaagcggag aggacgggac 1260
ccagaaatgg gcgggaagcc gcgcagaaag aatccccaag agggcctgta caacgagctc 1320
caaaaggata agatggcaga agcctatagc gagattggta tgaaagggga acgcagaaga 1380
ggcaaaggcc acgacggact gtaccaggga ctcagcaccg ccaccaagga cacctatgac 1440
gctcttcaca tgcaggccct gccgcctcgg 1470

<210> SEQ ID NO 119
<211> LENGTH: 1476
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 119
atggccctcc ctgtcaccgc cctgctgctt ccgctggctc ttctgctcca cgccgctcgg 60
ccccaagtgc aactcgtcca gtcaggtgca gaagtgaaga aaccaggagc gtccgtcgaa 120
gtgtcgtgta aggcgtccgg ctacactttc acctcgtact acatgcactg ggtgcggcag 180
gccccgggac aaggcctcga atggatggga atcatcaacc cgagcggagg ctcgactggt 240
tacgcccaga agttccaggg aagggtgacg atgacccgcg atacctcgac ttcgaccgtt 300
catatggagc tctcgtccct gcggagcgag gacactgctg tctactattg cgcgcgggga 360
ggatactcta gctcctccga tgcatttgac atttggggcc agggaactat ggtgaccgtg 420
tcatcaggcg gaggtggatc aggaggagga gggtcgggag ggggaggcag cggcgggggt 480
gggtcggaca ttcagatgac gcagtcccct cctagcctga gcgcctcggt gggtgacaga 540
gtgaccatca cttgcagagc ctcgcaagac atctcctccg cattggcttg gtaccagcaa 600
aagccgggca ctccgccgaa actgctcatc tacgatgcct cctcactgga gtcaggagtc 660
ccatctcgct tctcggggtc aggaagcggc accgatttta cccttaccat ctccagcctg 720
cagcccgagg acttcgccac gtactactgc caacagttca gctcctaccc actgaccttc 780
gggggcggaa ctcgcctgga aatcaagacc actaccccag caccgaggcc acccaccccg 840
gctcctacca tcgcctccca gcctctgtcc ctgcgtccgg aggcatgtag acccgcagct 900
ggtggggccg tgcatacccg gggtcttgac ttcgcctgcg atatctacat ttgggcccct 960
ctggctggta cttgcggggt cctgctgctt tcactcgtga tcactcttta ctgtaagcgc 1020
ggtcggaaga agctgctgta catctttaag caacccttca tgaggcctgt gcagactact 1080
caagaggagg acggctgttc atgccggttc ccagaggagg aggaaggcgg ctgcgaactg 1140
cgcgtgaaat tcagccgcag cgcagatgct ccagcctaca agcaggggca gaaccagctc 1200
tacaacgaac tcaatcttgg tcggagagag gagtacgacg tgctggacaa gcggagagga 1260
cgggacccag aaatgggcgg gaagccgcgc agaaagaatc cccaagaggg cctgtacaac 1320
gagctccaaa aggataagat ggcagaagcc tatagcgaga ttggtatgaa aggggaacgc 1380
agaagaggca aaggccacga cggactgtac cagggactca gcaccgccac caaggacacc 1440
tatgacgctc ttcacatgca ggccctgccg cctcgg 1476

<210> SEQ ID NO 120
<211> LENGTH: 1497
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 120
atggccctcc ctgtcaccgc cctgctgctt ccgctggctc ttctgctcca cgccgctcgg 60
ccccaagtgc aactcgtcca gagcggagca gaagtcaaga agccaggagc gtcagtgaaa 120
gtgtcatgca aggccagcgg ctataccttt acttcgtatg ggatctcctg ggtgcggcag 180
gcaccgggcc aaggactgga gtggatggga tggatctcag cctacaacgg taacaccaac 240
tacgcccaga agctgcaagg acgcgtgacc atgactactg atacgagcac ctccactgcc 300
tacatggaat tgcggtccct tcggtcggac gatactgctg tgtactactg cgcaagagtc 360
gccggaggga tctactacta ctacggcatg gacgtctggg gacagggaac caccattacg 420
gtgtcgagcg gagggggagg ctcgggggga ggaggaagcg gaggtggcgg ctccgggggc 480
ggcggatcgg acattgtgat gacccagact cctgactccc tggctgtttc gttgggagag 540
cgcgcgacta tctcgtgtaa gtccagccac tcagtcctgt acaatcgcaa taacaagaac 600
tacctcgcgt ggtaccagca aaaaccgggt cagccgccta aactcctgtt ctactgggcc 660
tccaccagaa agagcggggt gccagatcga ttctctggat caggatcagg taccgacttt 720
acgctgacca tctcgtccct gcagccggag gatttcgcga cttacttctg ccagcagact 780
cagactttcc ccctcacctt cggtcaaggc accaggctgg aaatcaatac cactacccca 840
gcaccgaggc cacccacccc ggctcctacc atcgcctccc agcctctgtc cctgcgtccg 900
gaggcatgta gacccgcagc tggtggggcc gtgcataccc ggggtcttga cttcgcctgc 960
gatatctaca tttgggcccc tctggctggt acttgcgggg tcctgctgct ttcactcgtg 1020
atcactcttt actgtaagcg cggtcggaag aagctgctgt acatctttaa gcaacccttc 1080
atgaggcctg tgcagactac tcaagaggag gacggctgtt catgccggtt cccagaggag 1140
gaggaaggcg gctgcgaact gcgcgtgaaa ttcagccgca gcgcagatgc tccagcctac 1200
aagcaggggc agaaccagct ctacaacgaa ctcaatcttg gtcggagaga ggagtacgac 1260
gtgctggaca agcggagagg acgggaccca gaaatgggcg ggaagccgcg cagaaagaat 1320
ccccaagagg gcctgtacaa cgagctccaa aaggataaga tggcagaagc ctatagcgag 1380
attggtatga aaggggaacg cagaagaggc aaaggccacg acggactgta ccagggactc 1440
agcaccgcca ccaaggacac ctatgacgct cttcacatgc aggccctgcc gcctcgg 1497

<210> SEQ ID NO 121
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 121
atggccctcc ctgtcaccgc cctgctgctt ccgctggctc ttctgctcca cgccgctcgg 60
ccccaagtcc aattgcagca gagcggagca gaagtgaaga agccaggagc gtcagtcaaa 120
gtgtcgtgta aggcgtcagg atacaccttc acgggatact acatgcactg ggtgcgccag 180
gccccgggcc aaggactcga gtggatgggc tggatcaacc ctaactctgg aggcaccaac 240
tacgcccaga atttccaagg cagagtgacc atgacccggg acacctccat ctcgactgcc 300
tatatggaac tgcggcggct gcgctcggac gatactgctg tgtattactg cgccagcggc 360
tgggactttg actactgggg acagggtact ctggtgactg tttcctcggg aggaggcgga 420
tcgggtggag gaggtagcgg gggagggggg tcgggaggcg gaggcagcga tattcgcatg 480
actcaatcgc cgtcctccct gagcgctagc gtgggagatc gagtcaccat cacttgcaga 540
gcgtcacagt cgattcgcta ctacctgtcc tggtaccagc agaaaccggg aaaggcacca 600
aagcttctga tctacacggc ctccatcctg caaaatggtg tcccatcaag gttctccggg 660
tcagggagcg gcactgactt cactctcacc atctcctcac tccagcccga ggactttgca 720
acctactact gcctccagac gtacaccacc ccggatttcg gtcctggaac caaggtggaa 780
atcaaaacca ctaccccagc accgaggcca cccaccccgg ctcctaccat cgcctcccag 840
cctctgtccc tgcgtccgga ggcatgtaga cccgcagctg gtggggccgt gcatacccgg 900
ggtcttgact tcgcctgcga tatctacatt tgggcccctc tggctggtac ttgcggggtc 960
ctgctgcttt cactcgtgat cactctttac tgtaagcgcg gtcggaagaa gctgctgtac 1020
atctttaagc aacccttcat gaggcctgtg cagactactc aagaggagga cggctgttca 1080
tgccggttcc cagaggagga ggaaggcggc tgcgaactgc gcgtgaaatt cagccgcagc 1140
gcagatgctc cagcctacaa gcaggggcag aaccagctct acaacgaact caatcttggt 1200
cggagagagg agtacgacgt gctggacaag cggagaggac gggacccaga aatgggcggg 1260
aagccgcgca gaaagaatcc ccaagagggc ctgtacaacg agctccaaaa ggataagatg 1320
gcagaagcct atagcgagat tggtatgaaa ggggaacgca gaagaggcaa aggccacgac 1380
ggactgtacc agggactcag caccgccacc aaggacacct atgacgctct tcacatgcag 1440
gccctgccgc ctcgg 1455

<210> SEQ ID NO 122
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122
atggccctcc ctgtcaccgc cctgctgctt ccgctggctc ttctgctcca cgccgctcgg 60
ccccaagtcc aactcgtcca aagcggagca gaagtcaaaa agccaggagc gtcggtgaaa 120
gtgtcttgca aagccagcgg ctacaccttc acgggttact acatgcactg ggtgcgccag 180
gcgccgggcc aggggctgga gtggatgggc cggattaacc ctaacagcgg gggaactaat 240
tacgctcaga agttccaggg tagagtcacc atgactacgg acacttccac ttccaccgcc 300
tatatggaac tgcgctccct ccgctcagat gatactgccg tgtattactg cgcgcggact 360
accacgtcat acgcatttga catctggggc cagggaacta tggtgaccgt gagctcgggc 420
ggaggcggtt cagggggagg aggaagcgga ggaggaggat cgggaggagg tggctccgat 480
atccagctga ctcagtcccc gagcaccctg tcggcgtcgg tgggggacag ggttaccatc 540
acctgtagag cttcccaatc catttcgact tggctggcct ggtaccagca aaagccggga 600
aaggccccta atttgcttat ctacaaggca tcgaccctcg aaagcggtgt gccctcccgg 660
ttttcgggat caggatcagg gaccgagttc accctgacca tctcatccct ccagccggac 720
gacttcgcca cttactactg ccagcagtac aacacctact cgccatacac tttcggccaa 780
ggcaccaagc tggagatcaa gaccactacc ccagcaccga ggccacccac cccggctcct 840
accatcgcct cccagcctct gtccctgcgt ccggaggcat gtagacccgc agctggtggg 900
gccgtgcata cccggggtct tgacttcgcc tgcgatatct acatttgggc ccctctggct 960
ggtacttgcg gggtcctgct gctttcactc gtgatcactc tttactgtaa gcgcggtcgg 1020
aagaagctgc tgtacatctt taagcaaccc ttcatgaggc ctgtgcagac tactcaagag 1080
gaggacggct gttcatgccg gttcccagag gaggaggaag gcggctgcga actgcgcgtg 1140
aaattcagcc gcagcgcaga tgctccagcc tacaagcagg ggcagaacca gctctacaac 1200
gaactcaatc ttggtcggag agaggagtac gacgtgctgg acaagcggag aggacgggac 1260
ccagaaatgg gcgggaagcc gcgcagaaag aatccccaag agggcctgta caacgagctc 1320

```
caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

```
<210> SEQ ID NO 123
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123

atggccctcc ctgtcaccgc cctgctgctt ccgctggctc ttctgctcca cgccgctcgg     60

ccccaagttc aactcgtgca atcaggtgga ggactcgtca aacccggagg atcattgaga    120

ctgtcatgcg aagcgagcgg ttttatcttc tccgattact atatgggatg gattcggcag    180

gccccgggaa agggactcga atgggtgtca tacatcggaa ggtcaggctc gtccatgtac    240

tacgcagact cggtgaaagg cagattcacc tttagccggg acaacgccaa gaattccctc    300

tacttgcaga tgaacagcct gcgagccgag gatactgctg tctactactg tgccgcgtcg    360

ccggtggtgg cagctactga agatttccag cactggggac agggaactct ggtcacggtg    420

tcgagcggtg gggcggaag cggaggcgga ggatcgggcg gcggaggttc gggggggga    480

gggtctgaca tcgtgatgac ccaaacccca gccaccctga gcctctcccc tggagagcgc    540

gcgactcttt cgtgccgcgc ttcccagtca gtgaccagca attacttggc ttggtaccaa    600

cagaagccgg gacaggcgcc acggctgctg ctttttggtg ccagcactcg cgccaccgga    660

atcccggatc gcttctcggg ctcagggtcc gggacggact tcaccctgac tatcaaccgg    720

ctggaacctg aggacttcgc gatgtactac tgccagcagt acggctccgc accagtcact    780

ttcggacaag gcaccaagct ggagatcaag accactaccc cagcaccgag gccacccacc    840

ccggctccta ccatcgcctc ccagcctctg tccctgcgtc cggaggcatg tagacccgca    900

gctggtgggg ccgtgcatac ccggggtctt gacttcgcct gcgatatcta catttgggcc    960

cctctggctg gtacttgcgg ggtcctgctg ctttcactcg tgatcactct ttactgtaag   1020

cgcggtcgga agaagctgct gtacatcttt aagcaaccct tcatgaggcc tgtgcagact   1080

actcaagagg aggacggctg ttcatgccgg ttcccagagg aggaggaagg cggctgcgaa   1140

ctgcgcgtga aattcagccg cagcgcagat gctccagcct acaagcaggg gcagaaccag   1200

ctctacaacg aactcaatct tggtcggaga gaggagtacg acgtgctgga caagcggaga   1260

ggacgggacc cagaaatggg cgggaagccg cgcagaaaga atccccaaga gggcctgtac   1320

aacgagctcc aaaaggataa gatggcagaa gcctatagcg agattggtat gaaaggggaa   1380

cgcagaagag gcaaaggcca cgacggactg taccagggac tcagcaccgc caccaaggac   1440

acctatgacg ctcttcacat gcaggccctg ccgcctcgg                          1479
```

```
<210> SEQ ID NO 124
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 124
atggccctcc ctgtcaccgc cctgctgctt ccgctggctc ttctgctcca cgccgctcgg 60
ccccaagtcc aactcgtcca gtcgggagca gaagttagag caccaggagc gtcagtgaaa 120
atctcatgca aggcctcggg cttcacgttc cgcggatact acatccactg ggtgcgccaa 180
gccccgggtc agggattgga gtggatggga atcattaacc catcaggagg gagccgggct 240
tacgcgcaga agttccaggg acgcgtcact atgacccgag atacttccac ctcgactgtg 300
tacatggaac tctcgtccct gaggtccgac gacactgcga tgtattactg tgctcggact 360
gccagctgcg gtggggactg ttactacctc gattactggg gccagggaac tctggtgacc 420
gtgtccagcg gaggtggcgg gtcagggggt ggcggaagcg gaggcggcgg ttcaggcgga 480
ggaggctcgg acatccaaat gacgcaatcg ccgcctaccc tgagcgcttc cgtgggagat 540
cgggtgacca ttacttgcag agcatccgag aacgtcaata tctggctggc ctggtaccaa 600
cagaagccgg ggaaggcccc taaactgctg atctacaagt cgagcagcct tgcctctgga 660
gtgccctccc gcttctcggg ctcgggatca ggagcggaat tcaccctcac catctcctcc 720
ctgcagccag atgactttgc cacctactac tgccagcagt accagagcta tccgttgacc 780
tttgggggag gcactaaagt ggacatcaag accactaccc cagcaccgag gccacccacc 840
ccggctccta ccatcgcctc ccagcctctg tccctgcgtc cggaggcatg tagacccgca 900
gctggtgggg ccgtgcatac ccggggtctt gacttcgcct gcgatatcta catttgggcc 960
cctctggctg gtacttgcgg ggtcctgctg ctttcactcg tgatcactct ttactgtaag 1020
cgcggtcgga agaagctgct gtacatcttt aagcaaccct tcatgaggcc tgtgcagact 1080
actcaagagg aggacggctg ttcatgccgg ttcccagagg aggaggaagg cggctgcgaa 1140
ctgcgcgtga aattcagccg cagcgcagat gctccagcct acaagcaggg gcagaaccag 1200
ctctacaacg aactcaatct tggtcggaga gaggagtacg acgtgctgga caagcggaga 1260
ggacgggacc cagaaatggg cgggaagccg cgcagaaaga atccccaaga gggcctgtac 1320
aacgagctcc aaaaggataa gatggcagaa gcctatagcg agattggtat gaaaggggaa 1380
cgcagaagag gcaaaggcca cgacggactg taccagggac tcagcaccgc caccaaggac 1440
acctatgacg ctcttcacat gcaggccctg ccgcctcgg 1479

<210> SEQ ID NO 125
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125
atggccctcc ctgtcaccgc cctgctgctt ccgctggctc ttctgctcca cgccgctcgg 60
ccccaagttc aactcgttca atcaggtgga ggactcgtgc aaccaggaag atcactcaga 120
ctcagctgcg ccgcgtcggg attcactttc gatgactacg caatgcactg ggtgcggcag 180
gccccgggca aaggactgga atgggtgagc ggaattagct ggaactcggg gtccatcggg 240
tacgccgact cggtgaaggg acgctttacg atctcccggg acaatgccaa gaactccctg 300
tatttgcaga tgaactcctt gagggctgag gacaccgccg tgtactactg cgctaaagat 360
ggatcatcgt cctggtcctg gggatacttc gattactggg gccagggcac tctggtgacc 420
gtgtcgtcag gcggtggagg gtcgggcgga ggaggtagcg gaggcggagg gagcagctct 480

```
gaactgaccc aagacccggc ggtgtcggtc gcccttggtc agactgtgcg gactacctgt    540

caggggggacg cgctgcgctc gtactacgct tcatggtacc agcagaagcc cggacaggca   600

cctatgctgg tcatctacgg aaagaataac cgcccatccg gcatcccgga tcgcttctcg    660

ggttcggaca gcggcgacac cgcatccctg acgatcactg gagcgcaggc cgaggatgaa    720

gccgactact actgcaattc ccgagattca agcggctacc ctgtgtttgg gaccggaact    780

aaggtcaccg tcctgaccac taccccagca ccgaggccac ccaccccggc tcctaccatc    840

gcctcccagc ctctgtccct gcgtccggag gcatgtagac ccgcagctgg tggggccgtg    900

catacccggg gtcttgactt cgcctgcgat atctacattt gggcccctct ggctggtact    960

tgcggggtcc tgctgctttc actcgtgatc actctttact gtaagcgcgg tcggaagaag   1020

ctgctgtaca tctttaagca acccttcatg aggcctgtgc agactactca agaggaggac   1080

ggctgttcat gccggttccc agaggaggag gaaggcggct gcgaactgcg cgtgaaattc   1140

agccgcagcg cagatgctcc agcctacaag caggggcaga accagctcta caacgaactc   1200

aatcttggtc ggagagagga gtacgacgtg ctggacaagc ggagaggacg ggacccagaa   1260

atgggcggga agccgcgcag aaagaatccc caagagggcc tgtacaacga gctccaaaag   1320

gataagatgg cagaagccta tagcgagatt ggtatgaaag gggaacgcag aagaggcaaa   1380

ggccacgacg gactgtacca gggactcagc accgccacca aggacaccta tgacgctctt   1440

cacatgcagg ccctgccgcc tcgg                                          1464
```

<210> SEQ ID NO 126
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 126

```
atggccctcc ctgtcaccgc cctgctgctt ccgctggctc ttctgctcca cgccgctcgg     60

cccgaagtgc aactcgtgga atctggtgga ggacttgtgc aacctggaag atcgttgaga    120

ctctcatgtg ctgcctccgg gttcaccttt gacgactacg ccatgcactg ggtgcgccag    180

gcaccaggaa agggtctgga gtgggtttcg ggtatctcgt ggaactccgg gagcactggc    240

tacgctgatt cggtgaaagg ccggtttacc atctcccgag acaatgcgaa gaattccctc    300

tatctgcaga tgaacagcct ccgggccgag gatactgccc tgtactactg cgccaaggat    360

agctcatcat ggtacggagg tggatcggct ttcgatatct ggggccaggg cacgatggtc    420

accgtgtcct cgggggggcgg aggctccggg ggaggaggta gcggaggagg aggatcgagc    480

tcagagttga ctcaagaacc cgcagtgtcc gtggcactgg gccaaaccgt caggatcact    540

tgccagggag acagcctgag gtcgtactac gcgtcctggt accagcagaa gccgggacag    600

gcccccggtcc tggtcatttt cggacgctca agacgcccat cgggcatccc ggaccggttc    660

agcggaagct cctcgggaaa caccgcgtca cttatcatta ccggcgcaca ggctgaggac    720

gaagcggatt actactgcaa ctcccgcgac aatactgcca accattacgt gttcgggacc    780

ggaacgaaac tgactgtcct gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960
```

-continued

```
ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

<210> SEQ ID NO 127
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127

```
atggccctcc ctgtcaccgc cctgctgctt ccgctggctc ttctgctcca cgccgctcgg     60

cccgaagttc aattggtgga atctggagga ggacttgtgc aacccggtag atctctgaga    120

ctgtcctgtg cggcatcggg attcaccttc gacgactacg ctatgcactg ggtgagacaa    180

gcccctggaa aaggactgga gtgggtgtca ggcatctcct ggaatagcgg gtccactgga    240

tacgccgatt cggtcaaggg tcgcttcacc atttcccggg acaatgccaa gaactccctg    300

taccttcaaa tgaactccct ccgggccgag gataccgccc tctactactg cgccaaagac    360

agctcgtcat ggtatggcgg agggtcggca tttgacatct ggggacaggg aactatggtg    420

actgtgtcat caggaggcgg cggaagcggc ggcggcgggt ccggcggagg agggtcgtcc    480

agcgaactca cccaagatcc agcagtgagc gtcgcgctgg gccagaccgt caggatcacg    540

tgccagggag attcactgcg ctcatactac gcgtcctggt accagcagaa gccggggcag    600

gccccggtcc tcgtgatcta cggaaagaac aaccgcccgt cgggtatccc agaccgcttt    660

tcgggtagct ccagcggaaa tacggctagc ctgaccatca ctggagcaca ggctgaggat    720

gaagcggact actactgcaa ttcgcggggc tcatcgggga accattacgt gttcggaact    780

ggtaccaagg tgactgtcct gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

<210> SEQ ID NO 128
<211> LENGTH: 1485
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 128
atggccctcc ctgtcaccgc cctgctgctt ccgctggctc ttctgctcca cgccgctcgg 60
ccccaagtgc agctcgttca atcaggcgga ggactcgttc aaccaggagg atcattgcga 120
ctctcatgtg cggcctctgg attcacgttt agctcatatt ggatgcactg ggtgcggcag 180
gcgccgggga aaggtctggt gtgggtcagc cgcatcaact cagacggctc ctcgacttcg 240
tacgccgact ccgtgaaggg acgctttacc atttcccgcg acaacgccaa gaataccctt 300
taccttcaga tgaactccct ccgcgctgag gataccgccg tgtactactg cgtgaggact 360
ggctgggtcg gcagctacta ctactacatg gacgtgtggg gcaaaggaac tactgtcacc 420
gtgtcaagcg gcggtggagg ttccggcggg ggaggatcgg ggggggcgg atcgggtggc 480
ggaggatcgg agatcgtgtt gacccagtcg ccgggaaccc tgtcgctgtc gcctggggag 540
agagcaactc tgtcctgccg ggcttcccag tcggtgtcga gcaattacct ggcatggtac 600
caacagaagc cgggacagcc gccacgcctg ctgatctatg acgtgtcaac tcgggcaact 660
ggaatccctg cgcggttcag cggcggaggg agcggtaccg atttcaccct gactatttcc 720
tccctcgaac cagaagattt cgccgtctac tactgccagc agagaagcaa ctggccgccc 780
tggacgttcg gacaaggaac caaggtcgaa atcaagacca ctaccccagc accgaggcca 840
cccaccccgg ctcctaccat cgcctcccag cctctgtccc tgcgtccgga ggcatgtaga 900
cccgcagctg gtggggccgt gcatacccgg ggtcttgact tcgcctgcga tatctacatt 960
tgggcccctc tggctggtac ttgcggggtc ctgctgcttt cactcgtgat cactctttac 1020
tgtaagcgcg gtcggaagaa gctgctgtac atctttaagc aacccttcat gaggcctgtg 1080
cagactactc aagaggagga cggctgttca tgccggttcc cagaggagga ggaaggcggc 1140
tgcgaactgc gcgtgaaatt cagccgcagc gcagatgctc cagcctacaa gcaggggcag 1200
aaccagctct acaacgaact caatcttggt cggagagagg agtacgacgt gctggacaag 1260
cggagaggac gggacccaga aatgggcggg aagccgcgca gaaagaatcc ccaagagggc 1320
ctgtacaacg agctccaaaa ggataagatg gcagaagcct atagcgagat tggtatgaaa 1380
ggggaacgca gaagaggcaa aggccacgac ggactgtacc agggactcag caccgccacc 1440
aaggacacct atgacgctct tcacatgcag gccctgccgc ctcgg 1485

<210> SEQ ID NO 129
<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 129
atggccctcc ctgtcaccgc cctgctgctt ccgctggctc ttctgctcca cgccgctcgg 60
ccccaagtgc aattggttca atcaggagga ggagtcgtgc agcccggaag atcgttgaga 120

```
ctgtcatgtg ccgcgagcgg ctttactttc tcaagctacg gaatgcattg ggtgcgacag    180
gctccgggaa aaggactgga atgggtcgca gtgatctcat acgacggctc gaacaagtac    240
tacgccgact ccgtcaaggg tcggttcacg atttcgcgcg ataattccaa gaacactctg    300
tacctccaaa tgaacagcct ccgggcagag gacaccgccg tctactactg cgctaaggga    360
tactcgcgct actactacta tggaatggat gtgtggggcc agggaactac cgtgacggtg    420
tcgtccggcg gcggtgggtc gggcggaggc ggatcaggtg gaggtggaag cggaggagga    480
gggagcgaaa tcgtcatgac tcagtcccct gctacccttt ctctgtcgcc gggagaaaga    540
gccatcctga gctgccgggc ctcccagagc gtgtacacca aatacctggg atggtaccag    600
cagaagccgg ggcaggcacc aaggctcctg atctacgatg cgtccacccg cgcgactggt    660
atcccagacc gcttttccgg ctcggggtca gggactgact tcacccttac tatcaatcgg    720
ctcgagcctg aggatttcgc cgtgtattac tgccagcact acggagggtc cccgctgatt    780
accttcggcc aaggcaccaa agtggacatc aagaccacta ccccagcacc gaggccaccc    840
accccggctc ctaccatcgc ctcccagcct ctgtccctgc gtccggaggc atgtagaccc    900
gcagctggtg gggccgtgca tacccggggt cttgacttcg cctgcgatat ctacatttgg    960
gcccctctgg ctggtacttg cggggtcctg ctgctttcac tcgtgatcac tctttactgt   1020
aagcgcggtc ggaagaagct gctgtacatc tttaagcaac ccttcatgag gcctgtgcag   1080
actactcaag aggaggacgg ctgttcatgc cggttcccag aggaggagga aggcggctgc   1140
gaactgcgcg tgaaattcag ccgcagcgca gatgctccag cctacaagca ggggcagaac   1200
cagctctaca acgaactcaa tcttggtcgg agagaggagt acgacgtgct ggacaagcgg   1260
agaggacggg acccagaaat gggcgggaag ccgcgcagaa agaatcccca agagggcctg   1320
tacaacgagc tccaaaagga taagatggca gaagcctata gcgagattgg tatgaaaggg   1380
gaacgcagaa gaggcaaagg ccacgacgga ctgtaccagg gactcagcac cgccaccaag   1440
gacacctatg acgctcttca catgcaggcc ctgccgcctc gg                       1482
```

<210> SEQ ID NO 130
<211> LENGTH: 1479
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130

```
atggccctcc ctgtcaccgc cctgctgctt ccgctggctc ttctgctcca cgccgctcgg     60
ccccaagtgc aacttgttca atcaggagga ggactcgttc aacccggagg atcactgcga    120
ctctcatgtg cagcgtcggg gttcaccttc tccagctacg caatgtcctg ggtgcgccaa    180
gcccctggaa aaggcctgga gtgggtgtcg gccatctctg ggagcggggg atcaacttac    240
tacgctgact ccgtcaaggg ccgctttacc atctcccggg acaacagcaa gaacactctc    300
tatctccaga tgaactcgct gagagccgaa gataccgctg tctactactg cgcgaagaga    360
gaagctgccg cagggcacga ttggtacttc gacttgtggg gcaggggcac ccttgtgacc    420
gtgtcctccg gtggaggcgg atcaggaggt gggggatcgg gtggaggagg aagcggaggc    480
ggcggttcgg acattcgcgt cacccagtca ccgagctccc tcagcgcatc ggtgggcgac    540
cgggtcacta tcacttgccg ggcgtcccag tcgatctcat cgtatctgaa ttggtaccag    600
cagaaaccgg gaaaggcgcc gaagctgttg atctacgctg ccagctccct gcagtcgggt    660
```

-continued

```
gtgccatcac gcttttccgg ctcgggatcg ggaaccgatt tcactctgac gatctctagc    720

ctgcagccag aagatttcgc cacttactac tgccagcagt cctacagcat ccctctgact    780

ttcggacaag ggacgaaagt ggagattaag accactaccc cagcaccgag gccacccacc    840

ccggctccta ccatcgcctc ccagcctctg tccctgcgtc cggaggcatg tagacccgca    900

gctggtgggg ccgtgcatac ccggggtctt gacttcgcct gcgatatcta catttgggcc    960

cctctggctg gtacttgcgg ggtcctgctg ctttcactcg tgatcactct ttactgtaag   1020

cgcggtcgga agaagctgct gtacatcttt aagcaaccct tcatgaggcc tgtgcagact   1080

actcaagagg aggacggctg ttcatgccgg ttcccagagg aggaggaagg cggctgcgaa   1140

ctgcgcgtga aattcagccg cagcgcagat gctccagcct acaagcaggg gcagaaccag   1200

ctctacaacg aactcaatct tggtcggaga gaggagtacg acgtgctgga caagcggaga   1260

ggacgggacc cagaaatggg cgggaagccg cgcagaaaga atccccaaga gggcctgtac   1320

aacgagctcc aaaaggataa gatggcagaa gcctatagcg agattggtat gaaaggggaa   1380

cgcagaagag gcaaaggcca cgacggactg taccagggac tcagcaccgc caccaaggac   1440

acctatgacg ctcttcacat gcaggccctg ccgcctcgg                          1479
```

<210> SEQ ID NO 131
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 131

```
atggccctcc ctgtcaccgc cctgctgctt ccgctggctc ttctgctcca cgccgctcgg     60

ccccaagtcc aactcgttca gtcatgggca gaagtcaaga aacccggtgc aagcgtcaaa    120

gtgtcgtgta aggcctccgg ctacactttc acttcctact acatgcactg ggtgcgccaa    180

gccccgggac agggccttga atggatgggc atcatcaacc catcaggagg ttccacgagc    240

tacgcgcaga agttccaggg gagagtgacg atgactagag atacctccac gagcaccgtc    300

tacatggagc tgtcgaatct gcggtcagag gacactgctg tgtattactg cgcgcgctcc    360

ccgcgggtga ccactggcta ctttgactac tggggacaag ggaccctggt gaccgtcagc    420

tcgggaggcg gaggatcggg aggtggaggg tccggtggag gcggctctgg aggaggcggg    480

tcggacattc aattgaccca gagcccatcc accctctcag cctcggtggg ggatagggtg    540

actatcactt gccgggcctc ccagtcaatt tccagctggc tggcttggta ccagcaaaag    600

cctggaaagg caccgaagct cctgatctac aaggcctcat ctctggaatc aggagtgcct    660

tcgcgcttca gcggaagcgg ctcgggaact gagtttaccc tgaccatctc gagcctgcag    720

ccagatgact tcgcgaccta ttactgccag cagtactcgt cctacccgtt gactttcgga    780

ggaggtaccc gcctcgaaat caaaaccact accccagcac cgaggccacc caccccggct    840

cctaccatcg cctcccagcc tctgtccctg cgtccggagg catgtagacc cgcagctggt    900

ggggccgtgc atacccgggg tcttgacttc gcctgcgata tctacatttg ggcccctctg    960

gctggtactt gcggggtcct gctgctttca ctcgtgatca ctctttactg taagcgcggt   1020

cggaagaagc tgctgtacat ctttaagcaa cccttcatga ggcctgtgca gactactcaa   1080

gaggaggacg gctgttcatg ccggttccca gaggaggagg aaggcggctg cgaactgcgc   1140
```

```
gtgaaattca gccgcagcgc agatgctcca gcctacaagc aggggcagaa ccagctctac   1200

aacgaactca atcttggtcg gagagaggag tacgacgtgc tggacaagcg gagaggacgg   1260

gacccagaaa tgggcgggaa gccgcgcaga aagaatcccc aagagggcct gtacaacgag   1320

ctccaaaagg ataagatggc agaagcctat agcgagattg gtatgaaagg ggaacgcaga   1380

agaggcaaag gccacgacgg actgtaccag ggactcagca ccgccaccaa ggacacctat   1440

gacgctcttc acatgcaggc cctgccgcct cgg                                1473


<210> SEQ ID NO 132
<211> LENGTH: 1491
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132

atggccctcc ctgtcaccgc cctgctgctt ccgctggctc ttctgctcca cgccgctcgg     60

ccccaagtcc aactcgtcca gtccggtgca gaagtcagaa ggccaggagc aagcgtgaag    120

atctcgtgta gagcgtcagg agacaccagc actcgccatt acatccactg gctgcgccag    180

gctccgggcc aagggccgga gtggatgggt gtgatcaacc cgactacggg accggctacc    240

ggaagccctg cgtacgcaca gatgctgcag ggacgggtga ctatgacccg cgatactagc    300

actaggaccg tgtacatgga actccgctcg ttgcggttcg aagataccgc cgtctactac    360

tgcgcccggt ccgtggtggg ccgaagcgcc ccttactact tcgattactg gggacagggc    420

actctggtga ccgttagctc cggtggggga ggctcgggtg gaggcggatc gggaggagga    480

ggcagcggtg gaggggggatc ggacattcag atgacccagt caccctcctc cctctcagcc    540

tcggtcgggg accgggtgac cattacgtgc agagcctcac aagggatctc ggactactcc    600

gcctggtacc agcagaaacc gggaaaagcg ccaaagctcc tgatctacgc cgcgagcacc    660

ctgcaatcag gagtgccatc gcgcttttct ggatcgggct cagggactga cttcacgctg    720

actatctcct accttcagtc cgaggatttc gctacctact actgccaaca gtattactcc    780

tatcccctga cctttggcgg aggcactaag gtggacatca agaccactac cccagcaccg    840

aggccaccca ccccggctcc taccatcgcc tcccagcctc tgtccctgcg tccggaggca    900

tgtagacccg cagctggtgg ggccgtgcat acccggggtc ttgacttcgc ctgcgatatc    960

tacatttggg cccctctggc tggtacttgc ggggtcctgc tgctttcact cgtgatcact   1020

ctttactgta agcgcggtcg gaagaagctg ctgtacatct ttaagcaacc cttcatgagg   1080

cctgtgcaga ctactcaaga ggaggacggc tgttcatgcc ggttcccaga ggaggaggaa   1140

ggcggctgcg aactgcgcgt gaaattcagc cgcagcgcag atgctccagc ctacaagcag   1200

gggcagaacc agctctacaa cgaactcaat cttggtcgga gagaggagta cgacgtgctg   1260

gacaagcgga gaggacggga cccagaaatg ggcgggaagc cgcgcagaaa gaatccccaa   1320

gagggcctgt acaacgagct ccaaaaggat aagatggcag aagcctatag cgagattggt   1380

atgaaagggg aacgcagaag aggcaaaggc cacgacggac tgtaccaggg actcagcacc   1440

gccaccaagg acacctatga cgctcttcac atgcaggccc tgccgcctcg g            1491


<210> SEQ ID NO 133
<211> LENGTH: 1479
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic polynucleotide"

<400> SEQUENCE: 133

```
atggccctcc ctgtcaccgc cctgctgctt ccgctggctc ttctgctcca cgccgctcgg     60

ccccaagtcc aactccagca atcgggagca gaagtcaaga aaccaggcgc atcggtgaaa    120

gtgtcgtgta aggcgtcagg gtacaccttc accaactact atatgcactg ggtgcgccag    180

gctccaggcc aggggttgga gtggatgggg atcatcaatc cgtcaggtgg ctacaccact    240

tacgctcaga agttccaggg acgcctcact atgactcgcg atactagcac ctccacggtg    300

tacatggaac tgtcatcgct gaggtccgaa gataccgccg tctactactg cgcacggatc    360

agatcctgcg gaggagattg ttactacttt gacaactggg gacagggcac ccttgttact    420

gtgtcatcgg gaggaggggg aagcggagga ggtggatcag gcggcggtgg cagcgggggc    480

ggaggatcgg acattcagct gactcagtcc ccctccactt tgtcggccag cgtgggagac    540

agagtgacca tcacttgccg ggcgtccgag aacgtcaata tctggctggc ctggtaccag    600

caaaagcctg gaaaagcccc gaagctgctc atctataagt catccagcct ggcgtctggt    660

gtgccgtcgc ggttctccgg cagcgggagc ggagccgagt tcactctcac catttcgagc    720

cttcaaccgg acgatttcgc cacctactac tgccagcagt accaatccta ccctctgacg    780

tttggaggtg gaaccaaggt ggacatcaag accactaccc cagcaccgag gccacccacc    840

ccggctccta ccatcgcctc ccagcctctg tccctgcgtc cggaggcatg tagacccgca    900

gctggtgggg ccgtgcatac ccggggtctt gacttcgcct gcgatatcta catttgggcc    960

cctctggctg gtacttgcgg ggtcctgctg ctttcactcg tgatcactct ttactgtaag   1020

cgcggtcgga agaagctgct gtacatcttt aagcaaccct tcatgaggcc tgtgcagact   1080

actcaagagg aggacggctg ttcatgccgg ttcccagagg aggaggaagg cggctgcgaa   1140

ctgcgcgtga aattcagccg cagcgcagat gctccagcct acaagcaggg gcagaaccag   1200

ctctacaacg aactcaatct tggtcggaga gaggagtacg acgtgctgga caagcggaga   1260

ggacgggacc cagaaatggg cgggaagccg cgcagaaaga atccccaaga gggcctgtac   1320

aacgagctcc aaaaggataa gatggcagaa gcctatagcg agattggtat gaaaggggaa   1380

cgcagaagag gcaaaggcca cgacggactg taccagggac tcagcaccgc caccaaggac   1440

acctatgacg ctcttcacat gcaggccctg ccgcctcgg                           1479
```

<210> SEQ ID NO 134
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 134

```
atggccctcc ctgtcaccgc cctgctgctt ccgctggctc ttctgctcca cgccgctcgg     60

ccccaaatca ctctgaaaga atctggaccg gccctggtta agccgactca aacgctcacc    120

cttacttgca ccttcagcgg attctcactc agcactgctg gtgtgcacgt cggatggatt    180

agacagccgc ctggaaaggc cctggaatgg ctcgccctca tctcctgggc cgatgacaag    240

agatacaggc cctcgcttcg atcccggttg gacattaccc gggtgacctc gaaagatcag    300
```

-continued

```
gtggtgctct caatgaccaa tatgcagccg gaggacaccg ctacgtacta ctgcgcactg    360

caaggatttg acggctacga ggctaactgg ggaccaggta ctctggtcac cgtgagctcc    420

ggcgggggag gatcaggcgg ggggggtca ggaggcggag gctccggtgg aggaggatcg    480

gatatcgtca tgacccagtc cccaagctcg ctgagcgcgt cagcgggcga ccgcgtgact    540

atcacttgcc gggccagccg cggcatctcc tccgcactgg cgtggtacca gcagaagcct    600

ggaaaaccgc caaagctcct gatctatgat gcctccagcc tggagtcagg tgtccccagc    660

cgcttctcgg gttcgggctc gggaaccgac ttcactttga ccatcgactc gctggaaccg    720

gaagatttcg caacctacta ctgtcagcag tcctactcga ccccttggac ttttggacaa    780

gggacgaagg tggacatcaa gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

<210> SEQ ID NO 135
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

```
Gly Gly Gly Gly Ser
1               5
```

<210> SEQ ID NO 136
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

```
Gly Tyr Thr Phe Thr Gly Tyr Tyr Met His
1               5                   10
```

<210> SEQ ID NO 137
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Gly Phe Thr Phe Ser Ser Tyr Trp Met His
1 5 10

<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 138

Gly Tyr Thr Phe Thr Asp Tyr Tyr Met His
1 5 10

<210> SEQ ID NO 139
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

Gly Tyr Thr Phe Thr Ser Tyr Tyr Met His
1 5 10

<210> SEQ ID NO 140
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 140

Gly Phe Thr Phe Ser Ser Tyr Ala Met His
1 5 10

<210> SEQ ID NO 141
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 141

Gly Tyr Pro Phe Thr Gly Tyr Ser Leu His
1 5 10

<210> SEQ ID NO 142
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 142

Gly Tyr Thr Phe Thr Ser Tyr Tyr Met His 1 5 10

<210> SEQ ID NO 143
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 143

Gly Tyr Thr Phe Thr Ser Tyr Gly Ile Ser
1 5 10

<210> SEQ ID NO 144
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 144

Gly Tyr Thr Phe Thr Gly Tyr Tyr Met His
1 5 10

<210> SEQ ID NO 145
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 145

Gly Phe Ile Phe Ser Asp Tyr Tyr Met Gly
1 5 10

<210> SEQ ID NO 146
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 146

Gly Phe Thr Phe Arg Gly Tyr Tyr Ile His
1 5 10

<210> SEQ ID NO 147
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 147

Gly Phe Thr Phe Asp Asp Tyr Ala Met His
1 5 10

<210> SEQ ID NO 148

<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Gly Phe Thr Phe Ser Ser Tyr Trp Met His
1 5 10

<210> SEQ ID NO 149
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Gly Phe Thr Phe Ser Ser Tyr Gly Met His
1 5 10

<210> SEQ ID NO 150
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 150

Gly Phe Thr Phe Ser Ser Tyr Ala Met Ser
1 5 10

<210> SEQ ID NO 151
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 151

Gly Tyr Thr Phe Thr Ser Tyr Tyr Met His
1 5 10

<210> SEQ ID NO 152
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 152

Gly Asp Thr Ser Thr Arg His Tyr Ile His
1 5 10

<210> SEQ ID NO 153
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 153

Gly Tyr Thr Phe Thr Asn Tyr Tyr Met His
1 5 10

<210> SEQ ID NO 154
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 154

Gly Phe Ser Leu Ser Thr Ala Gly Val His Val Gly
1 5 10

<210> SEQ ID NO 155
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 155

Arg Ile Asn Pro Asn Ser Gly Gly Thr Asn Tyr Ala Gln Lys Phe Gln
1 5 10 15

Gly

<210> SEQ ID NO 156
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 156

Trp Ile Asn Pro Asn Ser Gly Gly Thr Asn Tyr Ala Gln Lys Phe Gln
1 5 10 15

Gly

<210> SEQ ID NO 157
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 157

Arg Ile Asn Thr Asp Gly Ser Thr Thr Thr Tyr Ala Asp Ser Val Glu
1 5 10 15

Gly

<210> SEQ ID NO 158
<211> LENGTH: 16
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 158

Ile Ile Asn Pro Ser Gly Gly Ser Thr Ser Tyr Ala Gln Lys Phe Gln
1 5 10 15

<210> SEQ ID NO 159
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 159

Trp Ile Asn Pro Asn Ser Gly Gly Thr Asn Tyr Ala Gln Lys Phe Gln
1 5 10 15

Gly

<210> SEQ ID NO 160
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 160

Ile Ile Asn Pro Ser Gly Gly Ser Thr Gly Tyr Ala Gln Lys Phe Gln
1 5 10 15

Gly

<210> SEQ ID NO 161
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 161

Trp Ile Ser Ala Tyr Asn Gly Asn Thr Asn Tyr Ala Gln Lys Leu Gln
1 5 10 15

<210> SEQ ID NO 162
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 162

Trp Ile Asn Pro Asn Ser Gly Gly Thr Asn Tyr Ala Gln Asn Phe Gln
1 5 10 15

Gly

<210> SEQ ID NO 163

<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 163

Arg Ile Asn Pro Asn Ser Gly Gly Thr Asn Tyr Ala Gln Lys Phe Gln
1 5 10 15

Gly

<210> SEQ ID NO 164
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 164

Tyr Ile Gly Arg Ser Gly Ser Ser Met Tyr Tyr Ala Asp Ser Val Lys
1 5 10 15

Gly

<210> SEQ ID NO 165
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 165

Ile Ile Asn Pro Ser Gly Gly Ser Arg Ala Tyr Ala Gln Lys Phe Gln
1 5 10 15

Gly

<210> SEQ ID NO 166
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 166

Gly Ile Ser Trp Asn Ser Gly Ser Ile Gly Tyr Ala Asp Ser Val Lys
1 5 10 15

<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 167

Gly Ile Ser Trp Asn Ser Gly Ser Thr Gly Tyr Ala Asp Ser Val Lys
1 5 10 15

Gly

<210> SEQ ID NO 168
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 168

Arg Ile Asn Ser Asp Gly Ser Ser Thr Ser Tyr Ala Asp Ser Val Lys
1 5 10 15

Gly

<210> SEQ ID NO 169
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 169

Val Ile Ser Tyr Asp Gly Ser Asn Lys Tyr Tyr Ala Asp Ser Val Lys
1 5 10 15

Gly

<210> SEQ ID NO 170
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 170

Ala Ile Ser Gly Ser Gly Gly Ser Thr Tyr Tyr Ala Asp Ser Val Lys
1 5 10 15

Gly

<210> SEQ ID NO 171
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 171

Ile Ile Asn Pro Ser Gly Gly Ser Thr Ser Tyr Ala Gln Lys Phe Gln
1 5 10 15

Gly

<210> SEQ ID NO 172
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 172

Val Ile Asn Pro Thr Thr Gly Pro Ala Thr Gly Ser Pro Ala Tyr Ala
1               5                   10                  15

Gln Met Leu Gln Gly
            20

<210> SEQ ID NO 173
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Ile Ile Asn Pro Ser Gly Gly Tyr Thr Thr Tyr Ala Gln Lys Phe Gln
1               5                   10                  15

Gly

<210> SEQ ID NO 174
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Leu Ile Ser Trp Ala Asp Asp Lys Arg Tyr Arg Pro Ser Leu Arg Ser
1               5                   10                  15

<210> SEQ ID NO 175
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gly Arg Tyr Tyr Gly Met Asp Val
1               5

<210> SEQ ID NO 176
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Asp Leu Arg Arg Thr Val Val Thr Pro Arg Ala Tyr Tyr Gly Met Asp
1               5                   10                  15

Val

<210> SEQ ID NO 177
<211> LENGTH: 11
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 177

Gly Glu Trp Asp Gly Ser Tyr Tyr Tyr Asp Tyr
1               5                   10

<210> SEQ ID NO 178
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Gly His Trp Ala Val
1               5

<210> SEQ ID NO 179
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Gly Trp Asp Phe Asp Tyr
1               5

<210> SEQ ID NO 180
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Tyr Arg Leu Ile Ala Val Ala Gly Asp Tyr Tyr Tyr Tyr Gly Met Asp
1               5                   10                  15

Val

<210> SEQ ID NO 181
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Trp Lys Val Ser Ser Ser Ser Pro Ala Phe Asp Tyr
1               5                   10

<210> SEQ ID NO 182
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 182

Asp His Tyr Gly Gly Asn Ser Leu Phe Tyr
1 5 10

<210> SEQ ID NO 183
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 183

Gly Gly Tyr Ser Ser Ser Ser Asp Ala Phe Asp Ile
1 5 10

<210> SEQ ID NO 184
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 184

Val Ala Gly Gly Ile Tyr Tyr Tyr Tyr Gly Met Asp Val
1 5 10

<210> SEQ ID NO 185
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 185

Gly Trp Asp Phe Asp Tyr
1 5

<210> SEQ ID NO 186
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 186

Thr Thr Thr Ser Tyr Ala Phe Asp Ile
1 5

<210> SEQ ID NO 187
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 187

Ser Pro Val Val Ala Ala Thr Glu Asp Phe Gln His
1 5 10

<210> SEQ ID NO 188
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 188

Thr Ala Ser Cys Gly Gly Asp Cys Tyr Tyr Leu Asp Tyr
1 5 10

<210> SEQ ID NO 189
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 189

Asp Gly Ser Ser Ser Trp Ser Trp Gly Tyr Phe Asp Tyr
1 5 10

<210> SEQ ID NO 190
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Asp Ser Ser Ser Trp Tyr Gly Gly Gly Ser Ala Phe Asp Ile
1 5 10

<210> SEQ ID NO 191
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Asp Ser Ser Ser Trp Tyr Gly Gly Gly Ser Ala Phe Asp Ile
1 5 10

<210> SEQ ID NO 192
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 192

Thr Gly Trp Val Gly Ser Tyr Tyr Tyr Tyr Met Asp Val
1 5 10

-continued

<210> SEQ ID NO 193
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 193

Gly Tyr Ser Arg Tyr Tyr Tyr Tyr Gly Met Asp Val
1 5 10

<210> SEQ ID NO 194
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 194

Arg Glu Ala Ala Ala Gly His Asp Trp Tyr Phe Asp Leu
1 5 10

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 195

Ser Pro Arg Val Thr Thr Gly Tyr Phe Asp Tyr
1 5 10

<210> SEQ ID NO 196
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 196

Ser Val Val Gly Arg Ser Ala Pro Tyr Tyr Phe Asp Tyr
1 5 10

<210> SEQ ID NO 197
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 197

Ile Arg Ser Cys Gly Gly Asp Cys Tyr Tyr Phe Asp Asn
1 5 10

<210> SEQ ID NO 198
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Gln Gly Phe Asp Gly Tyr Glu Ala Asn
1               5

<210> SEQ ID NO 199
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Arg Ala Ser Gln Ser Val Ser Ser Asn Phe Ala
1               5                   10

<210> SEQ ID NO 200
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Gln Ala Ser Gln Asp Ile Ser Asn Ser Leu Asn
1               5                   10

<210> SEQ ID NO 201
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Arg Ala Ser Gln Ser Ile Asn Thr Tyr Leu Asn
1               5                   10

<210> SEQ ID NO 202
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Arg Ala Ser Gln Ser Ile Ser Asp Arg Leu Ala
1               5                   10

<210> SEQ ID NO 203
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Arg Ala Ser Gln Ser Ile Arg Tyr Tyr Leu Ser
1 5 10

<210> SEQ ID NO 204
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 204

Arg Ala Ser Gln Gly Val Gly Arg Trp Leu Ala
1 5 10

<210> SEQ ID NO 205
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 205

Arg Ala Ser Gln Ser Val Tyr Thr Lys Tyr Leu Gly
1 5 10

<210> SEQ ID NO 206
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 206

Arg Ala Ser Gln Asp Ser Gly Thr Trp Leu Ala
1 5 10

<210> SEQ ID NO 207
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 207

Arg Ala Ser Gln Asp Ile Ser Ser Ala Leu Ala
1 5 10

<210> SEQ ID NO 208
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 208

Lys Ser Ser His Ser Val Leu Tyr Asn Arg Asn Asn Lys Asn Tyr Leu 1 5 10 15

Ala

<210> SEQ ID NO 209
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 209

Arg Ala Ser Gln Ser Ile Arg Tyr Tyr Leu Ser
1 5 10

<210> SEQ ID NO 210
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 210

Arg Ala Ser Gln Ser Ile Ser Thr Trp Leu Ala
1 5 10

<210> SEQ ID NO 211
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 211

Arg Ala Ser Gln Ser Val Thr Ser Asn Tyr Leu Ala
1 5 10

<210> SEQ ID NO 212
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 212

Arg Ala Ser Glu Asn Val Asn Ile Trp Leu Ala
1 5 10

<210> SEQ ID NO 213
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 213

Gln Gly Asp Ala Leu Arg Ser Tyr Tyr Ala Ser
1 5 10

```
<210> SEQ ID NO 214
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Gln Gly Asp Ser Leu Arg Ser Tyr Tyr Ala Ser
1               5                   10


<210> SEQ ID NO 215
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Gln Gly Asp Ser Leu Arg Ser Tyr Tyr Ala Ser
1               5                   10


<210> SEQ ID NO 216
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Arg Ala Ser Gln Ser Val Ser Ser Asn Tyr Leu Ala
1               5                   10


<210> SEQ ID NO 217
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Arg Ala Ser Gln Ser Val Tyr Thr Lys Tyr Leu Gly
1               5                   10


<210> SEQ ID NO 218
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Arg Ala Ser Gln Ser Ile Ser Ser Tyr Leu Asn
1               5                   10


<210> SEQ ID NO 219
<211> LENGTH: 11
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Arg Ala Ser Gln Ser Ile Ser Ser Trp Leu Ala
1               5                   10

<210> SEQ ID NO 220
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Arg Ala Ser Gln Gly Ile Ser Asp Tyr Ser
1               5                   10

<210> SEQ ID NO 221
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Arg Ala Ser Glu Asn Val Asn Ile Trp Leu Ala
1               5                   10

<210> SEQ ID NO 222
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Arg Ala Ser Arg Gly Ile Ser Ser Ala Leu Ala
1               5                   10

<210> SEQ ID NO 223
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Asp Ala Ser Asn Arg Ala Thr
1               5

<210> SEQ ID NO 224
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 224

Asp Ala Ser Thr Leu Glu Thr
1 5

<210> SEQ ID NO 225
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 225

Ala Ala Ser Ser Leu Gln Ser
1 5

<210> SEQ ID NO 226
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 226

Lys Ala Ser Ser Leu Glu Ser
1 5

<210> SEQ ID NO 227
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 227

Thr Ala Ser Ile Leu Gln Asn
1 5

<210> SEQ ID NO 228
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 228

Ala Ala Ser Thr Leu Gln Ser
1 5

<210> SEQ ID NO 229
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 229

Asp Ala Ser Thr Arg Ala Thr
1 5

<210> SEQ ID NO 230
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 230

Asp Ala Ser Thr Leu Glu Asp
1 5

<210> SEQ ID NO 231
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 231

Asp Ala Ser Ser Leu Glu Ser
1 5

<210> SEQ ID NO 232
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 232

Trp Ala Ser Thr Arg Lys Ser
1 5

<210> SEQ ID NO 233
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 233

Thr Ala Ser Ile Leu Gln Asn
1 5

<210> SEQ ID NO 234
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 234

Lys Ala Ser Thr Leu Glu Ser
1 5

<210> SEQ ID NO 235
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 235

Gly Ala Ser Thr Arg Ala Thr
1 5

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 236

Lys Ser Ser Ser Leu Ala Ser
1 5

<210> SEQ ID NO 237
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 237

Gly Lys Asn Asn Arg Pro Ser
1 5

<210> SEQ ID NO 238
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 238

Gly Arg Ser Arg Arg Pro Ser
1 5

<210> SEQ ID NO 239
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 239

Gly Lys Asn Asn Arg Pro Ser
1 5

<210> SEQ ID NO 240
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 240

Asp Val Ser Thr Arg Ala Thr
1 5

<210> SEQ ID NO 241
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 241

Asp Ala Ser Thr Arg Ala Thr
1 5

<210> SEQ ID NO 242
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 242

Ala Ala Ser Ser Leu Gln Ser
1 5

<210> SEQ ID NO 243
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 243

Lys Ala Ser Ser Leu Glu Ser
1 5

<210> SEQ ID NO 244
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 244

Ala Ala Ser Thr Leu Gln Ser
1 5

<210> SEQ ID NO 245
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 245

Lys Ser Ser Ser Leu Ala Ser
1               5

<210> SEQ ID NO 246
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Asp Ala Ser Ser Leu Glu Ser
1               5

<210> SEQ ID NO 247
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

His Gln Arg Ser Asn Trp Leu Tyr Thr
1               5

<210> SEQ ID NO 248
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Gln Gln His Asp Asn Leu Pro Leu Thr
1               5

<210> SEQ ID NO 249
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Gln Gln Ser Phe Ser Pro Leu Thr
1               5

<210> SEQ ID NO 250
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Gln Gln Tyr Gly His Leu Pro Met Tyr Thr 1 5 10

<210> SEQ ID NO 251
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 251

Leu Gln Thr Tyr Thr Thr Pro Asp
1 5

<210> SEQ ID NO 252
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 252

Gln Gln Ala Asn Ser Phe Pro Leu Thr
1 5

<210> SEQ ID NO 253
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 253

Gln His Tyr Gly Gly Ser Pro Leu Ile Thr
1 5 10

<210> SEQ ID NO 254
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 254

Gln Gln Tyr Asn Ser Tyr Pro Leu Thr
1 5

<210> SEQ ID NO 255
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 255

Gln Gln Phe Ser Ser Tyr Pro Leu Thr
1 5

<210> SEQ ID NO 256

<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 256

Gln Gln Thr Gln Thr Phe Pro Leu Thr
1 5

<210> SEQ ID NO 257
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 257

Leu Gln Thr Tyr Thr Thr Pro Asp
1 5

<210> SEQ ID NO 258
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 258

Gln Gln Tyr Asn Thr Tyr Ser Pro Tyr Thr
1 5 10

<210> SEQ ID NO 259
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 259

Gln Gln Tyr Gly Ser Ala Pro Val Thr
1 5

<210> SEQ ID NO 260
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 260

Gln Gln Tyr Gln Ser Tyr Pro Leu Thr
1 5

<210> SEQ ID NO 261
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 261

Asn Ser Arg Asp Ser Ser Gly Tyr Pro Val
1               5                   10

<210> SEQ ID NO 262
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Asn Ser Arg Asp Asn Thr Ala Asn His Tyr Val
1               5                   10

<210> SEQ ID NO 263
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Asn Ser Arg Gly Ser Ser Gly Asn His Tyr Val
1               5                   10

<210> SEQ ID NO 264
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Gln Gln Arg Ser Asn Trp Pro Pro Trp Thr
1               5                   10

<210> SEQ ID NO 265
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Gln His Tyr Gly Gly Ser Pro Leu Ile Thr
1               5                   10

<210> SEQ ID NO 266
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Gln Gln Ser Tyr Ser Ile Pro Leu Thr
1 5

<210> SEQ ID NO 267
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 267

Gln Gln Tyr Ser Ser Tyr Pro Leu Thr
1 5

<210> SEQ ID NO 268
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 268

Gln Gln Tyr Tyr Ser Tyr Pro Leu Thr
1 5

<210> SEQ ID NO 269
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 269

Gln Gln Tyr Gln Ser Tyr Pro Leu Thr
1 5

<210> SEQ ID NO 270
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 270

Gln Gln Ser Tyr Ser Thr Pro Trp Thr
1 5

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 274

Val Ile Ser Tyr Asp Gly Ser Asn Lys Tyr Tyr Ala Asp Ser Val Lys
1 5 10 15

Gly

<210> SEQ ID NO 275
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 275

Gln Val Gln Leu Gln Gln Ser Gly Pro Glu Leu Glu Lys Pro Gly Ala
1 5 10 15

Ser Val Lys Ile Ser Cys Lys Ala Ser Gly Tyr Ser Phe Thr Gly Tyr
20 25 30

Thr Met Asn Trp Val Lys Gln Ser His Gly Lys Ser Leu Glu Trp Ile
35 40 45

Gly Leu Ile Thr Pro Tyr Asn Gly Ala Ser Ser Tyr Asn Gln Lys Phe
50 55 60

Arg Gly Lys Ala Thr Leu Thr Val Asp Lys Ser Ser Ser Thr Ala Tyr
65 70 75 80

Met Asp Leu Leu Ser Leu Thr Ser Glu Asp Ser Ala Val Tyr Phe Cys
85 90 95

Ala Arg Gly Gly Tyr Asp Gly Arg Gly Phe Asp Tyr Trp Gly Gln Gly
100 105 110

Thr Thr Val Thr Val Ser Ser Gly Gly Gly Gly Ser Gly Gly Gly Gly
115 120 125

Ser Gly Gly Gly Gly Ser Asp Ile Glu Leu Thr Gln Ser Pro Ala Ile
130 135 140

Met Ser Ala Ser Pro Gly Glu Lys Val Thr Met Thr Cys Ser Ala Ser
145 150 155 160

Ser Ser Val Ser Tyr Met His Trp Tyr Gln Gln Lys Ser Gly Thr Ser
165 170 175

Pro Lys Arg Trp Ile Tyr Asp Thr Ser Lys Leu Ala Ser Gly Val Pro
180 185 190

Gly Arg Phe Ser Gly Ser Gly Ser Gly Asn Ser Tyr Ser Leu Thr Ile
195 200 205

Ser Ser Val Glu Ala Glu Asp Asp Ala Thr Tyr Tyr Cys Gln Gln Trp
210 215 220

Ser Gly Tyr Pro Leu Thr Phe Gly Ala Gly Thr Lys Leu Glu Ile 225 230 235

<210> SEQ ID NO 276

<400> SEQUENCE: 276

000

<210> SEQ ID NO 277

<400> SEQUENCE: 277

000

<210> SEQ ID NO 278
<211> LENGTH: 383
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 278

Met Ala Leu Pro Val Thr Ala Leu Leu Leu Pro Leu Ala Leu Leu Leu
1 5 10 15

His Ala Ala Arg Pro Gln Val Gln Leu Gln Gln Ser Gly Pro Glu Leu
20 25 30

Glu Lys Pro Gly Ala Ser Val Lys Ile Ser Cys Lys Ala Ser Gly Tyr
35 40 45

Ser Phe Thr Gly Tyr Thr Met Asn Trp Val Lys Gln Ser His Gly Lys
50 55 60

Ser Leu Glu Trp Ile Gly Leu Ile Thr Pro Tyr Asn Gly Ala Ser Ser
65 70 75 80

Tyr Asn Gln Lys Phe Arg Gly Lys Ala Thr Leu Thr Val Asp Lys Ser
85 90 95

Ser Ser Thr Ala Tyr Met Asp Leu Leu Ser Leu Thr Ser Glu Asp Ser
100 105 110

Ala Val Tyr Phe Cys Ala Arg Gly Gly Tyr Asp Gly Arg Gly Phe Asp
115 120 125

Tyr Trp Gly Gln Gly Thr Thr Val Thr Val Ser Ser Gly Gly Gly Gly
130 135 140

Ser Gly Gly Gly Gly Ser Gly Gly Gly Gly Ser Asp Ile Glu Leu Thr
145 150 155 160

Gln Ser Pro Ala Ile Met Ser Ala Ser Pro Gly Glu Lys Val Thr Met
165 170 175

Thr Cys Ser Ala Ser Ser Ser Val Ser Tyr Met His Trp Tyr Gln Gln
180 185 190

Lys Ser Gly Thr Ser Pro Lys Arg Trp Ile Tyr Asp Thr Ser Lys Leu
195 200 205

Ala Ser Gly Val Pro Gly Arg Phe Ser Gly Ser Gly Ser Gly Asn Ser
210 215 220

Tyr Ser Leu Thr Ile Ser Ser Val Glu Ala Glu Asp Asp Ala Thr Tyr
225 230 235 240

Tyr Cys Gln Gln Trp Ser Gly Tyr Pro Leu Thr Phe Gly Ala Gly Thr
245 250 255

Lys Leu Glu Ile Thr Thr Thr Pro Ala Pro Arg Pro Pro Thr Pro Ala
260 265 270

```
Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala
    370                 375                 380
```

<210> SEQ ID NO 279
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 279

```
caagtccagc tccagcagtc gggcccagag ttggagaagc ctggggcgag cgtgaagatc     60

tcatgcaaag cctcaggcta ctcctttact ggatacacga tgaattgggt gaaacagtcg    120

catggaaagt cactggaatg gatcggtctg attacgccct acaacggcgc ctccagctac    180

aaccagaagt tcaggggaaa ggcgaccctt actgtcgaca agtcgtcaag caccgcctac    240

atggacctcc tgtccctgac ctccgaagat agcgcggtct acttttgtgc acgcggaggt    300

tacgatggac ggggattcga ctactggggc cagggaacca ctgtcaccgt gtcgagcgga    360

ggcggaggga gcggaggagg aggcagcgga ggtggagggt cggatatcga actcactcag    420

tccccagcaa tcatgtccgc ttcaccggga gaaaaggtga ccatgacttg ctcggcctcc    480

tcgtccgtgt catacatgca ctggtaccaa caaaaatcgg ggacctcccc taagagatgg    540

atctacgata ccagcaaact ggcttcaggc gtgccgggac gcttctcggg ttcggggagc    600

ggaaattcgt attcgttgac catttcgtcc gtggaagccg aggacgacgc aacttattac    660

tgccaacagt ggtcaggcta cccgctcact ttcggagccg gcactaagct ggagatc       717
```

<210> SEQ ID NO 280
<211> LENGTH: 1149
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 280

```
atggccctcc ctgtcaccgc cctgctgctt ccgctggctc ttctgctcca cgccgctcgg     60

ccccaagtcc agctccagca gtcgggccca gagttggaga agcctggggc gagcgtgaag    120

atctcatgca aagcctcagg ctactccttt actggataca cgatgaattg ggtgaaacag    180

tcgcatggaa agtcactgga atggatcggt ctgattacgc cctacaacgg cgcctccagc    240

tacaaccaga agttcagggg aaaggcgacc cttactgtcg acaagtcgtc aagcaccgcc    300
```

```
tacatggacc tcctgtccct gacctccgaa gatagcgcgg tctacttttg tgcacgcgga    360

ggttacgatg gacggggatt cgactactgg ggccagggaa ccactgtcac cgtgtcgagc    420

ggaggcggag ggagcggagg aggaggcagc ggaggtggag ggtcggatat cgaactcact    480

cagtccccag caatcatgtc cgcttcaccg ggagaaaagg tgaccatgac ttgctcggcc    540

tcctcgtccg tgtcatacat gcactggtac caacaaaaat cggggacctc ccctaagaga    600

tggatctacg ataccagcaa actggcttca ggcgtgccgg gacgcttctc gggttcgggg    660

agcggaaatt cgtattcgtt gaccatttcg tccgtggaag ccgaggacga cgcaacttat    720

tactgccaac agtggtcagg ctacccgctc actttcggag ccggcactaa gctggagatc    780

accactaccc cagcaccgag gccacccacc ccggctccta ccatcgcctc ccagcctctg    840

tccctgcgtc cggaggcatg tagacccgca gctggtgggg ccgtgcatac ccggggtctt    900

gacttcgcct gcgatatcta catttgggcc cctctggctg gtacttgcgg ggtcctgctg    960

ctttcactcg tgatcactct ttactgtaag cgcggtcgga agaagctgct gtacatcttt   1020

aagcaaccct tcatgaggcc tgtgcagact actcaagagg aggacggctg ttcatgccgg   1080

ttcccagagg aggaggaagg cggctgcgaa ctgcgcgtga aattcagccg cagcgcagat   1140

gctccagcc                                                           1149


<210> SEQ ID NO 281
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Gly Tyr Ser Phe Thr Gly Tyr Thr Met Asn
1               5                   10


<210> SEQ ID NO 282
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Leu Ile Thr Pro Tyr Asn Gly Ala Ser Ser Tyr Asn Gln Lys Phe Arg
1               5                   10                  15

Gly


<210> SEQ ID NO 283
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Gly Gly Tyr Asp Gly Arg Gly Phe Asp Tyr
1               5                   10


<210> SEQ ID NO 284
```

<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 284

Ser Ala Ser Ser Ser Val Ser Tyr Met His
1 5 10

<210> SEQ ID NO 285
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 285

Asp Thr Ser Lys Leu Ala Ser
1 5

<210> SEQ ID NO 286
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 286

Gln Gln Trp Ser Gly Tyr Pro Leu Thr
1 5

<210> SEQ ID NO 287
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 287

Ser Tyr Trp Met Tyr
1 5

<210> SEQ ID NO 288
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 288

Arg Ile Asp Pro Asn Ser Gly Ser Thr Lys Tyr Asn Glu Lys Phe Lys
1 5 10 15

Asn

<210> SEQ ID NO 289
<211> LENGTH: 11
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 289

Asp Tyr Arg Lys Gly Leu Tyr Ala Met Asp Tyr
1 5 10

<210> SEQ ID NO 290
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 290

Gly Tyr Thr Phe Thr Ser Tyr
1 5

<210> SEQ ID NO 291
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 291

Asp Pro Asn Ser Gly Ser
1 5

<210> SEQ ID NO 292
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 292

Gln Val His Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Trp Met Tyr Trp Val Lys Gln Gly Pro Gly Arg Gly Leu Glu Trp Ile
35 40 45

Gly Arg Ile Asp Pro Asn Ser Gly Ser Thr Lys Tyr Asn Glu Lys Phe
50 55 60

Lys Asn Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Asp Tyr Arg Lys Gly Leu Tyr Ala Met Asp Tyr Trp Gly Gln
100 105 110

Gly Thr Ser Val Thr Val Ser Ser
115 120

<210> SEQ ID NO 293

<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 293

```
caggtccacc tgcagcagcc tggggctgag cttgtgaagc ctggggcttc agtgaagctg     60
tcctgcaagg cttctggcta caccttcacc agttactgga tgtactgggt gaaacagggg    120
cctggacgag gccttgagtg gattggaagg attgatccta atagtgggag tactaagtac    180
aatgagaagt tcaagaacaa ggccacactg actgtagaca aatcctccag cacagcctac    240
atgcagctca gcagcctgac atctgaggac tctgcggtct attattgtgc aagggactat    300
agaaaggggc tctatgctat ggactactgg ggtcaaggaa cctcagtcac cgtctcctca    360
```

<210> SEQ ID NO 294
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 294

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Ser Lys Leu Glu Leu Lys
            100                 105
```

<210> SEQ ID NO 295
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 295

```
Lys Ala Ser Gln Asp Val Gly Thr Ala Val Ala
1               5                   10
```

<210> SEQ ID NO 296
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 296

Trp Ala Ser Thr Arg His Thr
1               5

<210> SEQ ID NO 297
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 297

Gln Gln Tyr Asn Ser Tyr Pro Leu Thr
1               5

<210> SEQ ID NO 298
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 298

Ser Gln Asp Val Gly Thr Ala
1               5

<210> SEQ ID NO 299
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 299

Trp Ala Ser
1

<210> SEQ ID NO 300
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 300

Tyr Asn Ser Tyr Pro Leu
1               5

<210> SEQ ID NO 301
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 301
gacattgtga tgacccagtc tcacaaattc atgtccacat cagtaggaga cagggtcagc     60

```
atcacctgca aggccagtca ggatgtgggt actgctgtag cctggtatca acagaaacca    120

gggcaatctc ctaaactact gatttactgg gcatccaccc ggcacactgg agtccctgat    180

cgcttcacag gcagtggatc tgggacagat ttcactctca ccattagcaa tgtgcagtct    240

gaagacttgg cagattattt ctgtcagcag tataacagct atcctctcac gttcggtgct    300

gggtccaagc tggagctgaa a                                              321


<210> SEQ ID NO 302
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 302

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Tyr Trp Val Lys Gln Gly Pro Gly Arg Gly Leu Glu Trp Ile
        35                  40                  45

Gly Arg Ile Asp Pro Asn Ser Gly Ser Thr Lys Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120


<210> SEQ ID NO 303
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 303

Asp Ile Met Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 304
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 304

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

<210> SEQ ID NO 305
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 305

```
caggttcagc tggtgcagtc tggagctgag gtgaagaagc ctggggcctc agtgaaggtc      60

tcctgcaagg cttctggcta caccttcacc agttactgga tgtactgggt gcgacaggcc     120

actggacaag ggcttgagtg gatgggtagg attgatccta atagtgggag tactaagtac     180

aatgagaagt tcaagaacag attcaccatc tccagagatg attcaaagaa cacggcgtat     240

ctgcaaatga acagcctgaa aaccgaggac acggccgtgt attactgtgc aagggactat     300

agaaaggggc tctatgctat ggactactgg ggccagggca ccaccgtgac cgtgtcctcc     360
```

<210> SEQ ID NO 306
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 306

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

-continued

```
Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 307
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 307
caggttcagc tggtgcagtc tggagctgag gtgaagaagc ctggggcctc agtgaaggtc 60
tcctgcaagg cttctggcta caccttcacc agttactgga tgtactgggt gcgacaggcc 120
actggacaag ggcttgagtg gatgggtagg attgatccta atagtgggag tactaagtac 180
aatgagaagt tcaagaacag attcaccatc tccagagatg attcaaagaa cacggcgtat 240
ctgcaaatga acagcctgaa aaccgaggac acggccgtgt attactgtgc aagggactat 300
agaaaggggc tctatgctat ggactactgg ggccagggca ccaccgtgac cgtgtcctcc 360
gcttccacca agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accgtgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtgt ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 308
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 308

Asp Ile Val Met Thr Gln Thr Pro Leu Ser Leu Pro Val Thr Pro Gly
1               5                   10                  15

Glu Pro Ala Ser Ile Ser Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Ile Pro Ala Arg Phe Ser Gly

```
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 309
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 309

```
gatattgtga tgacccagac tccactctcc ctgcccgtca cccctggaga gccggcctcc     60

atctcctgca aggccagtca ggatgtgggt actgctgtag cctggtacct gcagaagcca    120

gggcagtctc cacagctcct gatctattgg gcatccaccc ggcacactgg gatcccagcc    180

aggttcagtg gcagtgggtc tgggacagag ttcactctca ccatcagcag cctgcagtct    240

gaagattttg cagtttatta ctgtcagcag tataacagct atcctctcac gttcggccaa    300

gggaccaagg tggaaatcaa a                                              321
```

<210> SEQ ID NO 310
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 310

```
Asp Ile Val Met Thr Gln Thr Pro Leu Ser Leu Pro Val Thr Pro Gly
1               5                   10                  15

Glu Pro Ala Ser Ile Ser Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 311
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 311
gatattgtga tgacccagac tccactctcc ctgcccgtca cccctggaga gccggcctcc 60
atctcctgca aggccagtca ggatgtgggt actgctgtag cctggtacct gcagaagcca 120
gggcagtctc cacagctcct gatctattgg gcatccaccc ggcacactgg gatcccagcc 180
aggttcagtg gcagtgggtc tgggacagag ttcactctca ccatcagcag cctgcagtct 240
gaagattttg cagtttatta ctgtcagcag tataacagct atcctctcac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 312
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 312

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gln Gly Thr Lys Val Glu Ile Lys
100 105

<210> SEQ ID NO 313

<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 313

```
gacatccaga tgacccagtc tccatcctcc ctgtctgcat ctgtaggaga cagagtcacc     60

atcacttgca aggccagtca ggatgtgggt actgctgtag cctggtacct gcagaagcca    120

gggcagtctc cacagctcct gatctattgg gcatccaccc ggcacactgg ggtcccatca    180

aggttcagcg gcagtggatc tgggacagat ttcactctca ccatcagcag cctgcagcct    240

gaagattttg caacttatta ctgtcagcag tataacagct atcctctcac gttcggccaa    300

gggaccaagg tggaaatcaa a                                              321
```

<210> SEQ ID NO 314
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 314

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 315
<211> LENGTH: 642

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 315
gacatccaga tgacccagtc tccatcctcc ctgtctgcat ctgtaggaga cagagtcacc 60
atcacttgca aggccagtca ggatgtgggt actgctgtag cctggtacct gcagaagcca 120
gggcagtctc cacagctcct gatctattgg gcatccaccc ggcacactgg ggtcccatca 180
aggttcagcg gcagtggatc tgggacagat ttcactctca ccatcagcag cctgcagcct 240
gaagattttg caacttatta ctgtcagcag tataacagct atcctctcac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 316
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 316

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 317
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 317
gaggtccagc tggtacagtc tggggctgag gtgaagaagc ctggggctac agtgaaaatc 60
tcctgcaagg tttctggcta caccttcacc agttactgga tgtactgggt gcgacaggcc 120
actggacaag ggcttgagtg gatgggtagg attgatccta atagtgggag tactaagtac 180
aatgagaagt tcaagaacag agtcacgatt accgcggaca aatccacgag cacagcctac 240
atggagctga gcagcctgag atctgaggac acggccgtgt attactgtgc aagggactat 300
agaaaggggc tctatgctat ggactactgg ggccagggca ccaccgtgac cgtgtcctcc 360

<210> SEQ ID NO 318
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 318

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Thr Gly Gln Gly Leu Glu Trp Met
35 40 45

Gly Arg Ile Asp Pro Asn Ser Gly Ser Thr Lys Tyr Asn Glu Lys Phe
50 55 60

Lys Asn Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser 290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 319
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 319
gaggtccagc tggtacagtc tggggctgag gtgaagaagc ctggggctac agtgaaaatc 60
tcctgcaagg tttctggcta caccttcacc agttactgga tgtactgggt gcgacaggcc 120
actggacaag ggcttgagtg gatgggtagg attgatccta atagtgggag tactaagtac 180
aatgagaagt tcaagaacag agtcacgatt accgcggaca aatccacgag cacagcctac 240
atggagctga gcagcctgag atctgaggac acggccgtgt attactgtgc aagggactat 300
agaaaggggc tctatgctat ggactactgg ggccagggca ccaccgtgac cgtgtcctcc 360
gcttccacca agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accgtgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtgt ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 320
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 320

Glu Ile Val Leu Thr Gln Ser Pro Asp Phe Gln Ser Val Thr Pro Lys
1 5 10 15

Glu Lys Val Thr Ile Thr Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Val Pro Asp Arg Phe Ser Gly
50 55 60

Ser Gly Ser Gly Thr Asp Phe Thr Leu Lys Ile Ser Arg Val Glu Ala
65 70 75 80

Glu Asp Val Gly Val Tyr Tyr Cys Gln Gln Tyr Asn Ser Tyr Pro Leu
85 90 95

Thr Phe Gly Gln Gly Thr Lys Val Glu Ile Lys
100 105

<210> SEQ ID NO 321
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 321
gaaattgtgc tgactcagtc tccagacttt cagtctgtga ctccaaagga gaaagtcacc 60
atcacctgca aggccagtca ggatgtgggt actgctgtag cctggtacct gcagaagcca 120
gggcagtctc cacagctcct gatctattgg gcatccaccc ggcacactgg ggtcccagac 180
aggttcagtg gcagtgggtc aggcactgat ttcacactga aaatcagcag ggtggaggct 240
gaggatgttg gagtttatta ctgtcagcag tataacagct atcctctcac gttcggccaa 300
gggaccaagg tggaaatcaa a 321

<210> SEQ ID NO 322
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 322

Glu Ile Val Leu Thr Gln Ser Pro Asp Phe Gln Ser Val Thr Pro Lys
1 5 10 15

```
Glu Lys Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 323
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 323

```
gaaattgtgc tgactcagtc tccagacttt cagtctgtga ctccaaagga gaaagtcacc     60

atcacctgca aggccagtca ggatgtgggt actgctgtag cctggtacct gcagaagcca    120

gggcagtctc cacagctcct gatctattgg gcatccaccc ggcacactgg ggtcccagac    180

aggttcagtg gcagtgggtc aggcactgat ttcacactga aaatcagcag ggtggaggct    240

gaggatgttg gagtttatta ctgtcagcag tataacagct atcctctcac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 324
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 325
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 325
gaagtgcagc tggtgcagtc tggagcagag gtgaaaaagc ccggggagtc tctgaggatc     60
tcctgtaagg gttctggcta caccttcacc agttactgga tgtactgggt gcgacaggcc    120
cctggacaag ggcttgagtg gatgggtagg attgatccta atagtgggag tactaagtac    180
aatgagaagt tcaagaacag agtcaccata tcagtagaca cgtccaagaa ccagttctcc    240
ctgaagctga gctctgtgac cgccgcggac acggctgtgt attactgtgc aagggactat    300
agaaaggggc tctatgctat ggactactgg ggccagggca ccaccgtgac cgtgtcctcc    360

<210> SEQ ID NO 326
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 326

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Arg Ile Asp Pro Asn Ser Gly Ser Thr Lys Tyr Asn Glu Lys Phe
    50                  55                  60

```
Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 327
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 327

```
gaagtgcagc tggtgcagtc tggagcagag gtgaaaaagc ccggggagtc tctgaggatc     60

tcctgtaagg gttctggcta caccttcacc agttactgga tgtactgggt gcgacaggcc    120

cctggacaag ggcttgagtg gatgggtagg attgatccta atagtgggag tactaagtac    180

aatgagaagt tcaagaacag agtcaccata tcagtagaca cgtccaagaa ccagttctcc    240

ctgaagctga gctctgtgac cgccgcggac acggctgtgt attactgtgc aagggactat    300

agaaaggggc tctatgctat ggactactgg ggccagggca ccaccgtgac cgtgtcctcc    360

gcttccacca agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accgtgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtgt ccaacaaagg cctcccgtcc tccatcgaga aaaccatctc caaagccaaa   1020

gggcagcccc gagagccaca ggtgtacacc ctgcccccat cccaggagga gatgaccaag   1080

aaccaggtca gcctgacctg cctggtcaaa ggcttctacc ccagcgacat cgccgtggag   1140

tgggagagca atgggcagcc ggagaacaac tacaagacca cgcctcccgt gctggactcc   1200

gacggctcct tcttcctcta cagcaggcta accgtggaca agagcaggtg gcaggagggg   1260

aatgtcttct catgctccgt gatgcatgag gctctgcaca accactacac acagaagagc   1320

ctctccctgt ctctgggtaa a                                             1341
```

<210> SEQ ID NO 328
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 328

```
Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
```

```
                85                  90                  95

Thr Phe Gly Gln Gly Thr Lys Val Glu Ile Lys
            100                 105


<210> SEQ ID NO 329
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 329

gaaattgtgc tgactcagtc tccagacttt cagtctgtga ctccaaagga gaaagtcacc      60

atcacctgca aggccagtca ggatgtgggt actgctgtag cctggtacct gcagaagcca     120

gggcagtctc cacagctcct gatctattgg gcatccaccc ggcacactgg ggtcccatca     180

aggttcagtg gaagtggatc tgggacagat tttactttca ccatcagcag cctgcagcct     240

gaagatattg caacatatta ctgtcagcag tataacagct atcctctcac gttcggccaa     300

gggaccaagg tggaaatcaa a                                               321


<210> SEQ ID NO 330
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 330

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
210

<210> SEQ ID NO 331
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 331
gaaattgtgc tgactcagtc tccagacttt cagtctgtga ctccaaagga gaaagtcacc 60
atcacctgca aggccagtca ggatgtgggt actgctgtag cctggtacct gcagaagcca 120
gggcagtctc cacagctcct gatctattgg gcatccaccc ggcacactgg ggtcccatca 180
aggttcagtg gaagtggatc tgggacagat tttactttca ccatcagcag cctgcagcct 240
gaagatattg caacatatta ctgtcagcag tataacagct atcctctcac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 332
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 332

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Ile Arg Gln Ser Pro Ser Arg Gly Leu Glu Trp Leu
35 40 45

Gly Arg Ile Asp Pro Asn Ser Gly Ser Thr Lys Tyr Asn Glu Lys Phe
50 55 60

Lys Asn Arg Leu Thr Ile Ser Lys Asp Thr Ser Lys Asn Gln Val Val
65 70 75 80

Leu Thr Met Thr Asn Met Asp Pro Val Asp Thr Ala Thr Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser
115 120

<210> SEQ ID NO 333
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 333
gaggtccagc tggtacagtc tggggctgag gtgaagaagc ctggggctac agtgaaaatc 60
tcctgcaagg tttctggcta caccttcacc agttactgga tgtactggat caggcagtcc 120
ccatcgagag gccttgagtg gctgggtagg attgatccta atagtgggag tactaagtac 180
aatgagaagt tcaagaacag actcaccatc tccaaggaca cctccaaaaa ccaggtggtc 240
cttacaatga ccaacatgga ccctgtggac acagccacgt attactgtgc aagggactat 300
agaaaggggc tctatgctat ggactactgg ggccagggca ccaccgtgac cgtgtcctcc 360

<210> SEQ ID NO 334
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 334

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Ile Arg Gln Ser Pro Ser Arg Gly Leu Glu Trp Leu
35 40 45

Gly Arg Ile Asp Pro Asn Ser Gly Ser Thr Lys Tyr Asn Glu Lys Phe
50 55 60

Lys Asn Arg Leu Thr Ile Ser Lys Asp Thr Ser Lys Asn Gln Val Val
65 70 75 80

Leu Thr Met Thr Asn Met Asp Pro Val Asp Thr Ala Thr Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

-continued

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

```
<210> SEQ ID NO 335
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 335

gaggtccagc tggtacagtc tggggctgag gtgaagaagc ctggggctac agtgaaaatc     60

tcctgcaagg tttctggcta caccttcacc agttactgga tgtactggat caggcagtcc    120

ccatcgagag gccttgagtg gctgggtagg attgatccta atagtgggag tactaagtac    180

aatgagaagt tcaagaacag actcaccatc tccaaggaca cctccaaaaa ccaggtggtc    240

cttacaatga ccaacatgga ccctgtggac acagccacgt attactgtgc aagggactat    300

agaaaggggc tctatgctat ggactactgg ggccagggca ccaccgtgac cgtgtcctcc    360

gcttccacca agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accgtgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960
```

tgcaaggtgt ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 336
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 336

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Ser Tyr
20 25 30

Trp Met Tyr Trp Ile Arg Gln Pro Pro Gly Lys Gly Leu Glu Trp Ile
35 40 45

Gly Arg Ile Asp Pro Asn Ser Gly Ser Thr Lys Tyr Asn Glu Lys Phe
50 55 60

Lys Asn Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser
115 120

<210> SEQ ID NO 337
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 337
gaagtgcagc tggtgcagtc tggagcagag gtgaaaaagc ccggggagtc tctgaggatc 60
tcctgtaagg gttctggcta caccttcacc agttactgga tgtactggat ccgccagccc 120
ccagggaagg ggctggagtg gattggtagg attgatccta atagtgggag tactaagtac 180
aatgagaagt tcaagaacag agtcacgatt accgcggaca aatccacgag cacagcctac 240
atggagctga gcagcctgag atctgaggac acggccgtgt attactgtgc aagggactat 300
agaaaggggc tctatgctat ggactactgg ggccagggca ccaccgtgac cgtgtcctcc 360

<210> SEQ ID NO 338
<211> LENGTH: 447
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 338

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Ile Arg Gln Pro Pro Gly Lys Gly Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 339
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 339
gaagtgcagc tggtgcagtc tggagcagag gtgaaaaagc ccggggagtc tctgaggatc 60
tcctgtaagg gttctggcta caccttcacc agttactgga tgtactggat ccgccagccc 120
ccagggaagg ggctggagtg gattggtagg attgatccta atagtgggag tactaagtac 180
aatgagaagt tcaagaacag agtcacgatt accgcggaca aatccacgag cacagcctac 240
atggagctga gcagcctgag atctgaggac acggccgtgt attactgtgc aagggactat 300
agaaaggggc tctatgctat ggactactgg ggccagggca ccaccgtgac cgtgtcctcc 360
gcttccacca agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accgtgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtgt ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 340
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 340

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 341
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 341
caggttcagc tggtgcagtc tggagctgag gtgaagaagc ctggggcctc agtgaaggtc      60
tcctgcaagg cttctggcta caccttcacc agttactgga tgtactggat caggcagtcc     120
ccatcgagag gccttgagtg gctgggtagg attgatccta atagtgggag tactaagtac     180
aatgagaagt tcaagaacag attcaccatc tccagagatg attcaaagaa cacggcgtat     240
ctgcaaatga acagcctgaa aaccgaggac acggccgtgt attactgtgc aagggactat     300
agaaaggggc tctatgctat ggactactgg ggccagggca ccaccgtgac cgtgtcctcc     360

<210> SEQ ID NO 342
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 342

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

-continued

```
Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 343
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 343
caggttcagc tggtgcagtc tggagctgag gtgaagaagc ctggggcctc agtgaaggtc 60
tcctgcaagg cttctggcta caccttcacc agttactgga tgtactggat caggcagtcc 120
ccatcgagag gccttgagtg gctgggtagg attgatccta atagtgggag tactaagtac 180
aatgagaagt tcaagaacag attcaccatc tccagagatg attcaaagaa cacggcgtat 240
ctgcaaatga acagcctgaa aaccgaggac acggccgtgt attactgtgc aagggactat 300
agaaaggggc tctatgctat ggactactgg ggccagggca ccaccgtgac cgtgtcctcc 360
gcttccacca agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accgtgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtgt ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 344
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 344

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Asn Ser Tyr Pro Leu
                85                  90                  95

Thr Phe Gly Gln Gly Thr Lys Val Glu Ile Lys 100 105

<210> SEQ ID NO 345
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 345
gaaattgtgt tgacacagtc tccagccacc ctgtctttgt ctccagggga aagagccacc 60
ctctcctgca aggccagtca ggatgtgggt actgctgtag cctggtacct gcagaagcca 120
gggcagtctc cacagctcct gatctattgg gcatccaccc ggcacactgg gatcccacct 180
cgattcagtg gcagcgggta tggaacagat tttaccctca caattaataa catagaatct 240
gaggatgctg catattactt ctgtcagcag tataacagct atcctctcac gttcggccaa 300
gggaccaagg tggaaatcaa a 321

<210> SEQ ID NO 346
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 346

Glu Ile Val Leu Thr Gln Ser Pro Ala Thr Leu Ser Leu Ser Pro Gly
1 5 10 15

Glu Arg Ala Thr Leu Ser Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln Tyr Asn Ser Tyr Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 347
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 347
gaaattgtgt tgacacagtc tccagccacc ctgtctttgt ctccagggga aagagccacc 60
ctctcctgca aggccagtca ggatgtgggt actgctgtag cctggtacct gcagaagcca 120
gggcagtctc cacagctcct gatctattgg gcatccaccc ggcacactgg gatcccacct 180
cgattcagtg gcagcgggta tggaacagat tttaccctca caattaataa catagaatct 240
gaggatgctg catattactt ctgtcagcag tataacagct atcctctcac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 348
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 348

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

<210> SEQ ID NO 349
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 349
gaagtgcagc tggtgcagtc tggagcagag gtgaaaaagc ccggggagtc tctgaggatc 60
tcctgtaagg gttctggcta caccttcacc agttactgga tgtactgggt gcgacaggct 120
cgtggacaac gccttgagtg gataggtagg attgatccta atagtgggag tactaagtac 180
aatgagaagt tcaagaacag actcaccatc tccaaggaca cctccaaaaa ccaggtggtc 240
cttacaatga ccaacatgga ccctgtggac acagccacgt attactgtgc aagggactat 300
agaaaggggc tctatgctat ggactactgg ggccagggca ccaccgtgac cgtgtcctcc 360

<210> SEQ ID NO 350
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 350

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Ser Tyr
20 25 30

Trp Met Tyr Trp Val Arg Gln Ala Arg Gly Gln Arg Leu Glu Trp Ile
35 40 45

Gly Arg Ile Asp Pro Asn Ser Gly Ser Thr Lys Tyr Asn Glu Lys Phe
50 55 60

Lys Asn Arg Leu Thr Ile Ser Lys Asp Thr Ser Lys Asn Gln Val Val
65 70 75 80

Leu Thr Met Thr Asn Met Asp Pro Val Asp Thr Ala Thr Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

```
Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 351
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 351

```
gaagtgcagc tggtgcagtc tggagcagag gtgaaaaagc ccggggagtc tctgaggatc     60

tcctgtaagg gttctggcta caccttcacc agttactgga tgtactgggt gcgacaggct    120

cgtggacaac gccttgagtg gataggtagg attgatccta atagtgggag tactaagtac    180

aatgagaagt tcaagaacag actcaccatc tccaaggaca cctccaaaaa ccaggtggtc    240

cttacaatga ccaacatgga ccctgtggac acagccacgt attactgtgc aagggactat    300

agaaaggggc tctatgctat ggactactgg ggccagggca ccaccgtgac cgtgtcctcc    360

gcttccacca agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accgtgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840

ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtgt ccaacaaagg cctcccgtcc tccatcgaga aaaccatctc caaagccaaa   1020
```

gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 352
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 352

Asp Val Val Met Thr Gln Ser Pro Leu Ser Leu Pro Val Thr Leu Gly
1 5 10 15

Gln Pro Ala Ser Ile Ser Cys Lys Ala Ser Gln Asp Val Gly Thr Ala
20 25 30

Val Ala Trp Tyr Gln Gln Lys Pro Gly Gln Ala Pro Arg Leu Leu Ile
35 40 45

Tyr Trp Ala Ser Thr Arg His Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Pro Leu
85 90 95

Thr Phe Gly Gln Gly Thr Lys Val Glu Ile Lys
100 105

<210> SEQ ID NO 353
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 353
gatgttgtga tgactcagtc tccactctcc ctgcccgtca cccttggaca gccggcctcc 60
atctcctgca aggccagtca ggatgtgggt actgctgtag cctggtacca gcagaaacct 120
ggccaggctc ccaggctcct catctattgg gcatccaccc ggcacactgg ggtcccatca 180
aggttcagcg gcagtggatc tgggacagaa ttcactctca ccatcagcag cctgcagcct 240
gatgattttg caacttatta ctgtcagcag tataacagct atcctctcac gttcggccaa 300
gggaccaagg tggaaatcaa a 321

<210> SEQ ID NO 354
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 354

Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 355
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 355
gatgttgtga tgactcagtc tccactctcc ctgcccgtca cccttggaca gccggcctcc     60
atctcctgca aggccagtca ggatgtgggt actgctgtag cctggtacca gcagaaacct    120
ggccaggctc ccaggctcct catctattgg gcatccaccc ggcacactgg ggtcccatca    180
aggttcagcg gcagtggatc tgggacagaa ttcactctca ccatcagcag cctgcagcct    240
gatgattttg caacttatta ctgtcagcag tataacagct atcctctcac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 356
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 356

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Ser Tyr
            20                  25                  30

Trp Met Tyr Trp Val Arg Gln Ala Pro Gly Lys Gly Leu Glu Trp Val
        35                  40                  45

Ser Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

<210> SEQ ID NO 357
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 357

```
cagatcacct tgaaggagtc tggtcctacg ctggtgaaac ccacacagac cctcacgctg      60

acctgcacct tctctggcta caccttcacc agttactgga tgtactgggt ccgccaggct     120

ccagggaagg ggctggagtg ggtcagtagg attgatccta atagtgggag tactaagtac     180

aatgagaagt tcaagaacag agtcacgatt accgcggaca aatccacgag cacagcctac     240

atggagctga gcagcctgag atctgaggac acggccgtgt attactgtgc aagggactat     300

agaaaggggc tctatgctat ggactactgg ggccagggca ccaccgtgac cgtgtcctcc     360
```

<210> SEQ ID NO 358
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 358

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Ser Tyr
            20                  25                  30

Trp Met Tyr Trp Val Arg Gln Ala Pro Gly Lys Gly Leu Glu Trp Val
        35                  40                  45
```

```
Ser Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 359
<211> LENGTH: 1341

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 359
cagatcacct tgaaggagtc tggtcctacg ctggtgaaac ccacacagac cctcacgctg 60
acctgcacct tctctggcta caccttcacc agttactgga tgtactgggt ccgccaggct 120
ccagggaagg ggctggagtg ggtcagtagg attgatccta atagtgggag tactaagtac 180
aatgagaagt tcaagaacag agtcacgatt accgcggaca aatccacgag cacagcctac 240
atggagctga gcagcctgag atctgaggac acggccgtgt attactgtgc aagggactat 300
agaaaggggc tctatgctat ggactactgg ggccagggca ccaccgtgac cgtgtcctcc 360
gcttccacca agggcccatc cgtcttcccc ctggcgccct gctccaggag cacctccgag 420
agcacagccg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacgaagacc 600
tacacctgca acgtagatca caagcccagc aacaccaagg tggacaagag agttgagtcc 660
aaatatggtc ccccatgccc accgtgccca gcacctgagt tcctgggggg accatcagtc 720
ttcctgttcc ccccaaaacc caaggacact ctcatgatct cccggacccc tgaggtcacg 780
tgcgtggtgg tggacgtgag ccaggaagac cccgaggtcc agttcaactg gtacgtggat 840
ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtgt ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 360
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

```
Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105


<210> SEQ ID NO 361
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 361

gacatccaga tgacccagtc tccatcctcc ctgtctgcat ctgtaggaga cagagtcacc      60

atcacttgca aggccagtca ggatgtgggt actgctgtag cctggtacca gcagaaacct     120

ggccaggctc ccaggctcct catctattgg gcatccaccc ggcacactgg ggtcccatca     180

aggttcagtg gaagtggatc tgggacagat tttactttca ccatcagcag cctgcagcct     240

gaagatattg caacatatta ctgtcagcag tataacagct atcctctcac gttcggccaa     300

gggaccaagg tggaaatcaa a                                               321


<210> SEQ ID NO 362
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 362

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 363
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 363

```
gacatccaga tgacccagtc tccatcctcc ctgtctgcat ctgtaggaga cagagtcacc     60

atcacttgca aggccagtca ggatgtgggt actgctgtag cctggtacca gcagaaacct    120

ggccaggctc ccaggctcct catctattgg gcatccaccc ggcacactgg ggtcccatca    180

aggttcagtg gaagtggatc tgggacagat tttactttca ccatcagcag cctgcagcct    240

gaagatattg caacatatta ctgtcagcag tataacagct atcctctcac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 364
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 364

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

<210> SEQ ID NO 365
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 365
gaggtccagc tggtacagtc tggggctgag gtgaagaagc ctggggctac agtgaaaatc 60
tcctgcaagg tttctggcta caccttcacc agttactgga tgtactgggt gcgacaggct 120
cgtggacaac gccttgagtg gataggtagg attgatccta atagtgggag tactaagtac 180
aatgagaagt tcaagaacag attcaccatc tccagagaca attccaagaa cacgctgtat 240
cttcaaatga acagcctgag agccgaggac acggccgtgt attactgtgc aagggactat 300
agaaaggggc tctatgctat ggactactgg ggccagggca ccaccgtgac cgtgtcctcc 360

<210> SEQ ID NO 366
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 366

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Arg Gly Gln Arg Leu Glu Trp Ile
35 40 45

Gly Arg Ile Asp Pro Asn Ser Gly Ser Thr Lys Tyr Asn Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 367
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 367

```
gaggtccagc tggtacagtc tggggctgag gtgaagaagc ctggggctac agtgaaaatc     60

tcctgcaagg tttctggcta caccttcacc agttactgga tgtactgggt gcgacaggct    120

cgtggacaac gccttgagtg gataggtagg attgatccta atagtgggag tactaagtac    180

aatgagaagt tcaagaacag attcaccatc tccagagaca attccaagaa cacgctgtat    240

cttcaaatga acagcctgag agccgaggac acggccgtgt attactgtgc aagggactat    300

agaaaggggc tctatgctat ggactactgg ggccagggca ccaccgtgac cgtgtcctcc    360

gcttccacca agggcccatc cgtcttcccc ctggcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accgtgccca gcacctgagt tcctgggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtacgtggat    840
```

ggcgtggagg tgcataatgc caagacaaag ccgcgggagg agcagttcaa cagcacgtac 900
cgtgtggtca gcgtcctcac cgtcctgcac caggactggc tgaacggcaa ggagtacaag 960
tgcaaggtgt ccaacaaagg cctcccgtcc tccatcgaga aaaccatctc caaagccaaa 1020
gggcagcccc gagagccaca ggtgtacacc ctgcccccat cccaggagga gatgaccaag 1080
aaccaggtca gcctgacctg cctggtcaaa ggcttctacc ccagcgacat cgccgtggag 1140
tgggagagca atgggcagcc ggagaacaac tacaagacca cgcctcccgt gctggactcc 1200
gacggctcct tcttcctcta cagcaggcta accgtggaca agagcaggtg gcaggagggg 1260
aatgtcttct catgctccgt gatgcatgag gctctgcaca accactacac acagaagagc 1320
ctctccctgt ctctgggtaa a 1341

<210> SEQ ID NO 368
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 368

Ala Ile Gln Leu Thr Gln Ser Pro Ser Ser Leu Ser Ala Ser Val Gly
1 5 10 15

Asp Arg Val Thr Ile Thr Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Phe Thr Ile Ser Ser Leu Glu Ala
65 70 75 80

Glu Asp Ala Ala Thr Tyr Tyr Cys Gln Gln Tyr Asn Ser Tyr Pro Leu
85 90 95

Thr Phe Gly Gln Gly Thr Lys Val Glu Ile Lys
100 105

<210> SEQ ID NO 369
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 369
gccatccagt tgacccagtc tccatcctcc ctgtctgcat ctgtaggaga cagagtcacc 60
atcacttgca aggccagtca ggatgtgggt actgctgtag cctggtacct gcagaagcca 120
gggcagtctc cacagctcct gatctattgg gcatccaccc ggcacactgg ggtcccctcg 180
aggttcagtg gcagtggatc tgggacagat ttcaccttta ccatcagtag cctggaagct 240
gaagatgctg caacatatta ctgtcagcag tataacagct atcctctcac gttcggccaa 300
gggaccaagg tggaaatcaa a 321

<210> SEQ ID NO 370
<211> LENGTH: 214

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 370

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 371
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 371

gccatccagt tgacccagtc tccatcctcc ctgtctgcat ctgtaggaga cagagtcacc      60

atcacttgca aggccagtca ggatgtgggt actgctgtag cctggtacct gcagaagcca     120

gggcagtctc cacagctcct gatctattgg gcatccaccc ggcacactgg ggtcccctcg     180

aggttcagtg gcagtggatc tgggacagat ttcaccttta ccatcagtag cctggaagct     240

gaagatgctg caacatatta ctgtcagcag tataacagct atcctctcac gttcggccaa     300

gggaccaagg tggaaatcaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480
```

```
gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 372
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 372

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105


<210> SEQ ID NO 373
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 373

gaaattgtgc tgactcagtc tccagacttt cagtctgtga ctccaaagga gaaagtcacc     60

atcacctgca aggccagtca ggatgtgggt actgctgtag cctggtacca gcagaaacct    120

ggccaggctc ccaggctcct catctattgg gcatccaccc ggcacactgg ggtcccatca    180

aggttcagcg gcagtggatc tgggacagaa ttcactctca ccatcagcag cctgcagcct    240

gatgattttg caacttatta ctgtcagcag tataacagct atcctctcac gttcggccaa    300

gggaccaagg tggaaatcaa a                                              321


<210> SEQ ID NO 374
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 374

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
```

20 25 30

Val Ala Trp Tyr Gln Gln Lys Pro Gly Gln Ala Pro Arg Leu Leu Ile
35 40 45

Tyr Trp Ala Ser Thr Arg His Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 375
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 375
gaaattgtgc tgactcagtc tccagacttt cagtctgtga ctccaaagga gaaagtcacc 60
atcacctgca aggccagtca ggatgtgggt actgctgtag cctggtacca gcagaaacct 120
ggccaggctc ccaggctcct catctattgg gcatccaccc ggcacactgg ggtcccatca 180
aggttcagcg gcagtggatc tgggacagaa ttcactctca ccatcagcag cctgcagcct 240
gatgattttg caacttatta ctgtcagcag tataacagct atcctctcac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 376
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 376
gaagtgcagc tggtgcagtc aggcgccgaa gtgaagaagc ccggcgagtc actgagaatt 60
agctgtaaag gttcaggcta caccttcact agctactgga tgtactgggt ccgacaggcc 120
ccagggcaag gcctggagtg gatgggtaga atcgacccta atagcggctc tactaagtat 180
aacgagaagt ttaagaatag agtgactatt agcgtggaca cctctaagaa tcagtttagc 240
ctgaagctgt ctagcgtgac cgccgctgac accgccgtct actactgcgc tagagactat 300
agaaagggcc tgtacgctat ggactactgg ggtcaaggca ctaccgtgac cgtgtcttca 360

<210> SEQ ID NO 377
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 377

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Ser Tyr
20 25 30

Trp Met Tyr Trp Val Arg Gln Ala Pro Gly Gln Gly Leu Glu Trp Met
35 40 45

Gly Arg Ile Asp Pro Asn Ser Gly Ser Thr Lys Tyr Asn Glu Lys Phe
50 55 60

Lys Asn Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 378
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 378
gaagtgcagc tggtgcagtc aggcgccgaa gtgaagaagc ccggcgagtc actgagaatt 60
agctgtaaag gttcaggcta caccttcact agctactgga tgtactgggt ccgacaggcc 120
ccagggcaag gcctggagtg gatgggtaga atcgacccta atagcggctc tactaagtat 180
aacgagaagt ttaagaatag agtgactatt agcgtggaca cctctaagaa tcagtttagc 240
ctgaagctgt ctagcgtgac cgccgctgac accgccgtct actactgcgc tagagactat 300
agaaagggcc tgtacgctat ggactactgg ggtcaaggca ctaccgtgac cgtgtcttca 360
gctagcacta agggcccgtc cgtgttcccc ctggcacctt gtagccggag cactagcgaa 420
tccaccgctg ccctcggctg cctggtcaag gattacttcc cggagcccgt gaccgtgtcc 480
tggaacagcg gagccctgac ctccggagtg cacaccttcc ccgctgtgct gcagagctcc 540
gggctgtact cgctgtcgtc ggtggtcacg gtgccttcat ctagcctggg taccaagacc 600
tacacttgca acgtggacca caagccttcc aacactaagg tggacaagcg cgtcgaatcg 660
aagtacggcc caccgtgccc gccttgtccc gcgccggagt tcctcggcgg tccctcggtc 720
tttctgttcc caccgaagcc caaggacact ttgatgattt cccgcacccc tgaagtgaca 780
tgcgtggtcg tggacgtgtc acaggaagat ccggaggtgc agttcaattg gtacgtggat 840
ggcgtcgagg tgcacaacgc caaaaccaag ccgagggagg agcagttcaa ctccacttac 900
cgcgtcgtgt ccgtgctgac ggtgctgcat caggactggc tgaacgggaa ggagtacaag 960
tgcaaagtgt ccaacaaggg acttcctagc tcaatcgaaa agaccatctc gaaagccaag 1020
ggacagcccc gggaacccca agtgtatacc ctgccaccga gccaggaaga aatgactaag 1080
aaccaagtct cattgacttg ccttgtgaag ggcttctacc catcggatat cgccgtggaa 1140
tgggagtcca acggccagcc ggaaaacaac tacaagacca cccctccggt gctggactca 1200
gacggatcct tcttcctcta ctcgcggctg accgtggata agagcagatg gcaggaggga 1260
aatgtgttca gctgttctgt gatgcatgaa gccctgcaca accactacac tcagaagtcc 1320
ctgtccctct ccctggga 1338

<210> SEQ ID NO 379
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 379
gagatcgtcc tgactcagtc acccgacttt cagtcagtga cccctaaaga gaaagtcact 60
atcacctgta aagcctctca ggacgtgggc accgccgtgg cctggtatct gcagaagcct 120
ggtcaatcac ctcagctgct gatctactgg gcctctacta gacacaccgg cgtgccctct 180
aggtttagcg gtagcggtag tggcaccgac ttcaccttca ctatctcttc actgcagccc 240
gaggatatcg ctacctacta ctgtcagcag tataatagct accccctgac cttcggtcaa 300
ggcactaagg tcgagattaa g 321

<210> SEQ ID NO 380
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 380
gagatcgtcc tgactcagtc acccgacttt cagtcagtga cccctaaaga gaaagtcact 60
atcacctgta aagcctctca ggacgtgggc accgccgtgg cctggtatct gcagaagcct 120
ggtcaatcac ctcagctgct gatctactgg gcctctacta gacacaccgg cgtgccctct 180
aggtttagcg gtagcggtag tggcaccgac ttcaccttca ctatctcttc actgcagccc 240
gaggatatcg ctacctacta ctgtcagcag tataatagct accccctgac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 381
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 381
gaagtgcagc tggtgcagtc aggcgccgaa gtgaagaaac ccggcgctac cgtgaagatt 60
agctgtaaag tctcaggcta caccttcact agctactgga tgtactgggt ccgacaggct 120
accggtcaag gcctggagtg gatgggtaga atcgacccta atagcggctc tactaagtat 180
aacgagaagt ttaagaatag agtgactatc accgccgata agtctactag caccgcctat 240
atggaactgt ctagcctgag atcagaggac accgccgtct actactgcgc tagagactat 300
agaaagggcc tgtacgctat ggactactgg ggtcaaggca ctaccgtgac cgtgtcttca 360

<210> SEQ ID NO 382
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 382

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Thr Gly Gln Gly Leu Glu Trp Met
35 40 45

Gly Arg Ile Asp Pro Asn Ser Gly Ser Thr Lys Tyr Asn Glu Lys Phe
50 55 60

Lys Asn Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

-continued

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 383
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 383
gaagtgcagc tggtgcagtc aggcgccgaa gtgaagaaac ccggcgctac cgtgaagatt 60
agctgtaaag tctcaggcta caccttcact agctactgga tgtactgggt ccgacaggct 120
accggtcaag gcctggagtg gatgggtaga atcgacccta atagcggctc tactaagtat 180
aacgagaagt ttaagaatag agtgactatc accgccgata agtctactag caccgcctat 240
atggaactgt ctagcctgag atcagaggac accgccgtct actactgcgc tagagactat 300
agaaagggcc tgtacgctat ggactactgg ggtcaaggca ctaccgtgac cgtgtcttca 360
gctagcacta agggcccgtc cgtgttcccc ctggcacctt gtagccggag cactagcgaa 420
tccaccgctg ccctcggctg cctggtcaag gattacttcc cggagcccgt gaccgtgtcc 480
tggaacagcg gagccctgac ctccggagtg cacaccttcc ccgctgtgct gcagagctcc 540
gggctgtact cgctgtcgtc ggtggtcacg gtgccttcat ctagcctggg taccaagacc 600
tacacttgca acgtggacca caagccttcc aacactaagg tggacaagcg cgtcgaatcg 660
aagtacggcc caccgtgccc gccttgtccc gcgccggagt tcctcggcgg tccctcggtc 720
tttctgttcc caccgaagcc caaggacact ttgatgattt cccgcacccc tgaagtgaca 780
tgcgtggtcg tggacgtgtc acaggaagat ccggaggtgc agttcaattg gtacgtggat 840
ggcgtcgagg tgcacaacgc caaaaccaag ccgagggagg agcagttcaa ctccacttac 900
cgcgtcgtgt ccgtgctgac ggtgctgcat caggactggc tgaacgggaa ggagtacaag 960
tgcaaagtgt ccaacaaggg acttcctagc tcaatcgaaa agaccatctc gaaagccaag 1020
ggacagcccc gggaacccca agtgtatacc ctgccaccga gccaggaaga aatgactaag 1080
aaccaagtct cattgacttg ccttgtgaag ggcttctacc catcggatat cgccgtggaa 1140
tgggagtcca acggccagcc ggaaaacaac tacaagacca cccctccggt gctggactca 1200
gacggatcct tcttcctcta ctcgcggctg accgtggata agagcagatg gcaggaggga 1260
aatgtgttca gctgttctgt gatgcatgaa gccctgcaca accactacac tcagaagtcc 1320
ctgtccctct ccctggga 1338

<210> SEQ ID NO 384
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 384
gacgtcgtga tgactcagtc acccctgagc ctgcccgtga ccctggggca gcccgcctct 60
attagctgta aagcctctca ggacgtgggc accgccgtgg cctggtatca gcagaagcca 120
gggcaagccc ctagactgct gatctactgg gcctctacta gacacaccgg cgtgccctct 180
aggtttagcg gtagcggtag tggcaccgag ttcaccctga ctatctcttc actgcagccc 240
gacgacttcg ctacctacta ctgtcagcag tataatagct accccctgac cttcggtcaa 300
ggcactaagg tcgagattaa g 321

<210> SEQ ID NO 385
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 385
gacgtcgtga tgactcagtc acccctgagc ctgcccgtga ccctggggca gcccgcctct 60
attagctgta aagcctctca ggacgtgggc accgccgtgg cctggtatca gcagaagcca 120
gggcaagccc ctagactgct gatctactgg gcctctacta gacacaccgg cgtgccctct 180
aggtttagcg gtagcggtag tggcaccgag ttcaccctga ctatctcttc actgcagccc 240
gacgacttcg ctacctacta ctgtcagcag tataatagct accccctgac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 386
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 386
gaagtgcagc tggtgcagtc aggcgccgaa gtgaagaaac ccggcgctac cgtgaagatt 60
agctgtaaag tctcaggcta caccttcact agctactgga tgtactgggt ccgacaggct 120
agagggcaaa gactggagtg gatcggtaga atcgacccta atagcggctc tactaagtat 180
aacgagaagt ttaagaatag gttcactatt agtagggata actctaagaa caccctgtac 240
ctgcagatga atagcctgag agccgaggac accgccgtct actactgcgc tagagactat 300
agaaagggcc tgtacgctat ggactactgg ggtcaaggca ctaccgtgac cgtgtcttca 360

<210> SEQ ID NO 387
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 387
gaagtgcagc tggtgcagtc aggcgccgaa gtgaagaaac ccggcgctac cgtgaagatt 60
agctgtaaag tctcaggcta caccttcact agctactgga tgtactgggt ccgacaggct 120
agagggcaaa gactggagtg gatcggtaga atcgacccta atagcggctc tactaagtat 180
aacgagaagt ttaagaatag gttcactatt agtagggata actctaagaa caccctgtac 240
ctgcagatga atagcctgag agccgaggac accgccgtct actactgcgc tagagactat 300
agaaagggcc tgtacgctat ggactactgg ggtcaaggca ctaccgtgac cgtgtcttca 360
gctagcacta agggcccgtc cgtgttcccc ctggcacctt gtagccggag cactagcgaa 420
tccaccgctg ccctcggctg cctggtcaag gattacttcc cggagcccgt gaccgtgtcc 480
tggaacagcg gagccctgac ctccggagtg cacaccttcc ccgctgtgct gcagagctcc 540
gggctgtact cgctgtcgtc ggtggtcacg gtgccttcat ctagcctggg taccaagacc 600
tacacttgca acgtggacca caagccttcc aacactaagg tggacaagcg cgtcgaatcg 660
aagtacggcc caccgtgccc gccttgtccc gcgccggagt tcctcggcgg tccctcggtc 720
tttctgttcc caccgaagcc caaggacact ttgatgattt cccgcacccc tgaagtgaca 780
tgcgtggtcg tggacgtgtc acaggaagat ccggaggtgc agttcaattg gtacgtggat 840
ggcgtcgagg tgcacaacgc caaaaccaag ccgagggagg agcagttcaa ctccacttac 900
cgcgtcgtgt ccgtgctgac ggtgctgcat caggactggc tgaacgggaa ggagtacaag 960
tgcaaagtgt ccaacaaggg acttcctagc tcaatcgaaa agaccatctc gaaagccaag 1020
ggacagcccc gggaacccca agtgtatacc ctgccaccga gccaggaaga aatgactaag 1080
aaccaagtct cattgacttg ccttgtgaag ggcttctacc catcggatat cgccgtggaa 1140
tgggagtcca acggccagcc ggaaaacaac tacaagacca cccctccggt gctggactca 1200
gacggatcct tcttcctcta ctcgcggctg accgtggata agagcagatg gcaggaggga 1260
aatgtgttca gctgttctgt gatgcatgaa gccctgcaca accactacac tcagaagtcc 1320
ctgtccctct ccctggga 1338

<210> SEQ ID NO 388
<211> LENGTH: 321
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 388
gctattcagc tgactcagtc acctagtagc ctgagcgcta gtgtgggcga tagagtgact 60
atcacctgta aagcctctca ggacgtgggc accgccgtgg cctggtatct gcagaagcct 120
ggtcaatcac ctcagctgct gatctactgg gcctctacta gacacaccgg cgtgccctct 180
aggtttagcg gtagcggtag tggcaccgac ttcaccttca ctatctcttc actggaagcc 240
gaggacgccg ctacctacta ctgtcagcag tataatagct accccctgac cttcggtcaa 300
ggcactaagg tcgagattaa g 321

<210> SEQ ID NO 389
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 389
gctattcagc tgactcagtc acctagtagc ctgagcgcta gtgtgggcga tagagtgact 60
atcacctgta aagcctctca ggacgtgggc accgccgtgg cctggtatct gcagaagcct 120
ggtcaatcac ctcagctgct gatctactgg gcctctacta gacacaccgg cgtgccctct 180
aggtttagcg gtagcggtag tggcaccgac ttcaccttca ctatctcttc actggaagcc 240
gaggacgccg ctacctacta ctgtcagcag tataatagct accccctgac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 390

<400> SEQUENCE: 390

000

<210> SEQ ID NO 391
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 391

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Arg Gly Gln Arg Leu Glu Trp Ile
35 40 45

```
Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 392
<211> LENGTH: 360

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 392
gaagtgcagc tggtgcagtc tggcgccgaa gtgaagaaac ccggcgctac cgtgaagatc 60
tcctgcaagg tgtccggcta caccttcacc agctactgga tgtactgggt gcgacaggct 120
accggccagg gcctggaatg gatgggcaga atcgacccca actccggctc caccaagtac 180
aacgagaagt tcaagaaccg cgtgaccatc accgccgaca agtccacctc caccgcctac 240
atggaactgt cctccctgcg gagcgaggac accgccgtgt actactgcgc cagagactac 300
cggaagggcc tgtacgccat ggactattgg ggccagggca ccaccgtgac cgtgtcctct 360

<210> SEQ ID NO 393
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 393

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Thr Gly Gln Gly Leu Glu Trp Met
35 40 45

Gly Arg Ile Asp Pro Asn Ser Gly Ser Thr Lys Tyr Asn Glu Lys Phe
50 55 60

Lys Asn Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr

```
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 394
<211> LENGTH: 1348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 394

gaagtgcagc tggtgcagtc tggcgccgaa gtgaagaaac ccggcgctac cgtgaagatc     60

tcctgcaagg tgtccggcta caccttcacc agctactgga tgtactgggt gcgacaggct    120

accggccagg gcctggaatg gatgggcaga atcgacccca actccggctc caccaagtac    180

aacgagaagt tcaagaaccg cgtgaccatc accgccgaca agtccacctc caccgcctac    240

atggaactgt cctccctgcg gagcgaggac accgccgtgt actactgcgc cagagactac    300

cggaagggcc tgtacgccat ggactattgg ggccagggca ccaccgtgac cgtgtcctct    360

gcttccacca agggcccaag cgtgttcccc ctggccccct gctccagaag caccagcgag    420

agcacagccg ccctgggctg cctggtgaag gactacttcc ccgagcccgt gaccgtgtcc    480

tggaacagcg gagccctgac cagcggcgtg cacaccttcc ccgccgtgct gcagagcagc    540

ggcctgtaca gcctgagcag cgtggtgacc gtgcccagca gcagcctggg caccaagacc    600

tacacctgta acgtggacca caagcccagc aacaccaagg tggacaagag ggtggagagc    660

aagtacggcc caccctgccc cccctgccca gcccccgagt tcctgggcgg acccagcgtg    720

ttcctgttcc cccccaagcc caaggacacc ctgatgatca gcagaacccc cgaggtgacc    780

tgtgtggtgg tggacgtgtc ccaggaggac cccgaggtcc agttcaactg gtacgtggac    840

ggcgtggagg tgcacaacgc caagaccaag cccagagagg agcagtttaa cagcacctac    900
```

```
cgggtggtgt ccgtgctgac cgtgctgcac caggactggc tgaacggcaa agagtacaag    960

tgtaaggtct ccaacaaggg cctgccaagc agcatcgaaa agaccatcag caaggccaag   1020

ggccagccta gagagcccca ggtctacacc ctgccaccca gccaagagga gatgaccaag   1080

aaccaggtgt ccctgacctg tctggtgaag ggcttctacc caagcgacat cgccgtggag   1140

tgggagagca acggccagcc cgagaacaac tacaagacca cccccccagt gctggacagc   1200

gacggcagct tcttcctgta cagcaggctg accgtggaca agtccagatg gcaggagggc   1260

aacgtcttta gctgctccgt gatgcacgag gccctgcaca accactacac ccagaagagc   1320

ctgagcctgt ccctgggctg atgaattc                                      1348
```

```
<210> SEQ ID NO 395
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 395

gagatcgtgc tgacccagtc ccccgacttc cagtccgtga cccccaaaga aaaagtgacc     60

atcacatgca aggcctccca ggacgtgggc accgccgtgg cttggtatct gcagaagcct    120

ggccagtccc ctcagctgct gatctactgg gcctctacca gacacaccgg cgtgcccgac    180

agattctccg gctctggctc tggcaccgac ttcaccctga agatctcccg ggtggaagcc    240

gaggatgtgg gcgtgtacta ctgccagcag tacaactcct accccctgac cttcggccag    300

ggcaccaagg tggaaatcaa g                                              321
```

```
<210> SEQ ID NO 396
<211> LENGTH: 652
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 396

gagatcgtgc tgacccagtc ccccgacttc cagtccgtga cccccaaaga aaaagtgacc     60

atcacatgca aggcctccca ggacgtgggc accgccgtgg cttggtatct gcagaagcct    120

ggccagtccc ctcagctgct gatctactgg gcctctacca gacacaccgg cgtgcccgac    180

agattctccg gctctggctc tggcaccgac ttcaccctga agatctcccg ggtggaagcc    240

gaggatgtgg gcgtgtacta ctgccagcag tacaactcct accccctgac cttcggccag    300

ggcaccaagg tggaaatcaa gcgtacggtg gccgctccca gcgtgttcat cttcccccca    360

agcgacgagc agctgaagag cggcaccgcc agcgtggtgt gtctgctgaa caacttctac    420

cccagggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac aggggcgagt gctgatgaat tc            652
```

```
<210> SEQ ID NO 397
<211> LENGTH: 360
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 397

gaagtgcagc tggtgcagtc tggcgccgaa gtgaagaagc ctggcgagtc cctgcggatc     60

tcctgcaagg gctccggcta caccttcacc agctactgga tgtactggat ccggcagccc    120

cctggcaagg gcctggaatg gatcggcaga atcgacccca actccggctc caccaagtac    180

aacgagaagt tcaagaaccg cgtgaccatc accgccgaca agtccacctc caccgcctac    240

atggaactgt cctccctgag atccgaggac accgccgtgt actactgcgc cagagactac    300

cggaagggcc tgtacgccat ggactattgg ggccagggca ccaccgtgac cgtgtcctct    360


<210> SEQ ID NO 398
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 398

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Ile Arg Gln Pro Pro Gly Lys Gly Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

-continued

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 399
<211> LENGTH: 1348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 399
gaagtgcagc tggtgcagtc tggcgccgaa gtgaagaagc ctggcgagtc cctgcggatc 60
tcctgcaagg gctccggcta caccttcacc agctactgga tgtactggat ccggcagccc 120
cctggcaagg gcctggaatg gatcggcaga atcgacccca actccggctc caccaagtac 180
aacgagaagt tcaagaaccg cgtgaccatc accgccgaca agtccacctc caccgcctac 240
atggaactgt cctccctgag atccgaggac accgccgtgt actactgcgc cagagactac 300
cggaagggcc tgtacgccat ggactattgg ggccagggca ccaccgtgac cgtgtcctct 360
gcttctacca agggcccaag cgtgttcccc ctggcccct gctccagaag caccagcgag 420
agcacagccg ccctgggctg cctggtgaag gactacttcc ccgagcccgt gaccgtgtcc 480
tggaacagcg gagccctgac cagcggcgtg cacaccttcc ccgccgtgct gcagagcagc 540
ggcctgtaca gcctgagcag cgtggtgacc gtgcccagca gcagcctggg caccaagacc 600
tacacctgta acgtggacca caagcccagc aacaccaagg tggacaagag ggtggagagc 660
aagtacggcc caccctgccc cccctgccca gcccccgagt tcctgggcgg acccagcgtg 720
ttcctgttcc cccccaagcc caaggacacc ctgatgatca gcagaacccc cgaggtgacc 780
tgtgtggtgg tggacgtgtc ccaggaggac cccgaggtcc agttcaactg gtacgtggac 840
ggcgtggagg tgcacaacgc caagaccaag cccagagagg agcagtttaa cagcacctac 900

-continued

```
cgggtggtgt ccgtgctgac cgtgctgcac caggactggc tgaacggcaa agagtacaag    960

tgtaaggtct ccaacaaggg cctgccaagc agcatcgaaa agaccatcag caaggccaag   1020

ggccagccta gagagcccca ggtctacacc ctgccaccca gccaagagga gatgaccaag   1080

aaccaggtgt ccctgacctg tctggtgaag ggcttctacc caagcgacat cgccgtggag   1140

tgggagagca acggccagcc cgagaacaac tacaagacca ccccccccagt gctggacagc   1200

gacggcagct tcttcctgta cagcaggctg accgtggaca agtccagatg gcaggagggc   1260

aacgtcttta gctgctccgt gatgcacgag gccctgcaca accactacac ccagaagagc   1320

ctgagcctgt ccctgggctg atgaattc                                      1348
```

<210> SEQ ID NO 400
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 400

```
gagatcgtgc tgacccagtc ccccgacttc cagtccgtga cccccaaaga aaaagtgacc     60

atcacatgca aggcctccca ggacgtgggc accgccgtgg cttggtatct gcagaagcct    120

ggccagtccc ctcagctgct gatctactgg gcctctacca gacacaccgg cgtgccctcc    180

agattctccg gctctggctc tggcaccgac tttaccttca ccatctccag cctgcagccc    240

gaggatatcg ccacctacta ctgccagcag tacaactcct acccccctgac cttcggccag    300

ggcaccaagg tggaaatcaa g                                              321
```

<210> SEQ ID NO 401
<211> LENGTH: 652
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 401

```
gagatcgtgc tgacccagtc ccccgacttc cagtccgtga cccccaaaga aaaagtgacc     60

atcacatgca aggcctccca ggacgtgggc accgccgtgg cttggtatct gcagaagcct    120

ggccagtccc ctcagctgct gatctactgg gcctctacca gacacaccgg cgtgccctcc    180

agattctccg gctctggctc tggcaccgac tttaccttca ccatctccag cctgcagccc    240

gaggatatcg ccacctacta ctgccagcag tacaactcct acccccctgac cttcggccag    300

ggcaccaagg tggaaatcaa gcgtacggtg gccgctccca gcgtgttcat cttcccccca    360

agcgacgagc agctgaagag cggcaccgcc agcgtggtgt gtctgctgaa caacttctac    420

cccagggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac aggggcgagt gctgatgaat tc            652
```

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437
<400> SEQUENCE: 437
000

<210> SEQ ID NO 438
<400> SEQUENCE: 438
000

<210> SEQ ID NO 439
<400> SEQUENCE: 439
000

<210> SEQ ID NO 440
<400> SEQUENCE: 440
000

<210> SEQ ID NO 441
<400> SEQUENCE: 441
000

<210> SEQ ID NO 442
<400> SEQUENCE: 442
000

<210> SEQ ID NO 443
<400> SEQUENCE: 443
000

<210> SEQ ID NO 444
<400> SEQUENCE: 444
000

<210> SEQ ID NO 445
<400> SEQUENCE: 445
000

<210> SEQ ID NO 446
<400> SEQUENCE: 446
000

<210> SEQ ID NO 447
<400> SEQUENCE: 447
000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516
<400> SEQUENCE: 516
000

<210> SEQ ID NO 517
<400> SEQUENCE: 517
000

<210> SEQ ID NO 518
<400> SEQUENCE: 518
000

<210> SEQ ID NO 519
<400> SEQUENCE: 519
000

<210> SEQ ID NO 520
<400> SEQUENCE: 520
000

<210> SEQ ID NO 521
<400> SEQUENCE: 521
000

<210> SEQ ID NO 522
<400> SEQUENCE: 522
000

<210> SEQ ID NO 523
<400> SEQUENCE: 523
000

<210> SEQ ID NO 524
<400> SEQUENCE: 524
000

<210> SEQ ID NO 525
<400> SEQUENCE: 525
000

<210> SEQ ID NO 526
<400> SEQUENCE: 526
000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597
<211> LENGTH: 521
<212> TYPE: DNA
<213> ORGANISM: Unknown
<220> FEATURE:
<221> NAME/KEY: source
<223> OTHER INFORMATION: /note="Description of Unknown:
Wild-type PGK promoter sequence"

<400> SEQUENCE: 597
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggccccccgg gtgttcccat 360
cgccgcttct aggcccactg cgacgcttgc ctgcacttct tacacgctct gggtcccagc 420
cgcggcgacg caaagggcct tggtgcgggt ctcgtcggcg cagggacgcg tttgggtccc 480
gacggaacct tttccgcgtt ggggttgggg caccataagc t 521

<210> SEQ ID NO 598
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 598
acccctctct ccagccacta agccagttgc tccctcggct gacggctgca cgcgaggcct 60
ccgaacgtct tacgccttgt ggcgcgcccg tccttgtccc gggtgtgatg gcggggtg 118

<210> SEQ ID NO 599
<211> LENGTH: 221
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 599
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac g 221

<210> SEQ ID NO 600
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 600
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccg 324

<210> SEQ ID NO 601
<211> LENGTH: 422
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 601
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggccccccgg gtgttcccat 360
cgccgcttct aggcccactg cgacgcttgc ctgcacttct tacacgctct gggtcccagc 420
cg 422

<210> SEQ ID NO 602
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: misc_feature
<222> LOCATION: (1)..(21)
<223> OTHER INFORMATION: /note="Variant residues given in the sequence have no preference with respect to those in the annotations for variant positions"

<400> SEQUENCE: 602

Gly Ser Gly Glu Gly Arg Gly Ser Leu Leu Thr Cys Gly Asp Val Glu 1 5 10 15

Glu Asn Pro Gly Pro
20

<210> SEQ ID NO 603
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: misc_feature
<222> LOCATION: (1)..(22)
<223> OTHER INFORMATION: /note="Variant residues given in the sequence have no preference with respect to those in the annotations for variant positions"

<400> SEQUENCE: 603

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 604
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: misc_feature
<222> LOCATION: (1)..(23)
<223> OTHER INFORMATION: /note="Variant residues given in the sequence have no preference with respect to those in the annotations for variant positions"

<400> SEQUENCE: 604

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 605
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: misc_feature
<222> LOCATION: (1)..(25)
<223> OTHER INFORMATION: /note="Variant residues given in the sequence have no preference with respect to those in the annotations for variant positions"

<400> SEQUENCE: 605

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 606
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MISC_FEATURE
<222> LOCATION: (1)..(40)
<223> OTHER INFORMATION: /note="This sequence may encompass 1-10 "Gly Gly Gly Ser" repeating units"

<400> SEQUENCE: 606

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser Gly Gly Gly Ser
35 40

<210> SEQ ID NO 607
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 607
acaaaaaaga agtattcatc cagtgtgcac gaccctaacg gtgaatacat gttcatgaga 60
gcagtgaaca cagccaaaaa atccagactc acagatgtga cccta 105

<210> SEQ ID NO 608
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 608
ggtggcggag gttctggagg tgggggttcc 30

<210> SEQ ID NO 609
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 609

Gly Gly Gly Ser

1

<210> SEQ ID NO 610
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 610

Gly Ser Thr Ser Gly Ser Gly Lys Pro Gly Ser Gly Glu Gly Ser Thr
1 5 10 15

Lys Gly

<210> SEQ ID NO 611
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 611

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ile Met Met Trp Val Arg Gln Ala Pro Gly Lys Gly Leu Glu Trp Val
35 40 45

Ser Ser Ile Tyr Pro Ser Gly Gly Ile Thr Phe Tyr Ala Asp Lys Gly
50 55 60

Arg Phe Thr Ile Ser Arg Asp Asn Ser Lys Asn Thr Leu Tyr Leu Gln
65 70 75 80

Met Asn Ser Leu Arg Ala Glu Asp Thr Ala Val Tyr Tyr Cys Ala Arg
85 90 95

Ile Lys Leu Gly Thr Val Thr Thr Val Asp Tyr Trp Gly Gln Gly Thr
100 105 110

Leu Val Thr Val Ser Ser
115

<210> SEQ ID NO 612
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 612

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

-continued

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110


<210> SEQ ID NO 613
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 613

Arg Gly Asp Ser
1
```

MESOTHELIN CHIMERIC ANTIGEN RECEPTOR (CAR) AND ANTIBODY AGAINST PD-L1 INHIBITOR FOR COMBINED USE IN ANTICANCER THERAPY

RELATED APPLICATIONS

This application is a U.S. national phase application and claims the benefit of priority under 35 U.S.C. § 371 of International Application No. PCT/US2016/067957, filed Dec. 21, 2016, which claims priority to U.S. Ser. No. 62/270,780 filed Dec. 22, 2015, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 20, 2016, is named N2067-7099WO_SL.txt and is 520,028 bytes in size.

FIELD OF THE INVENTION

The present invention relates generally to the use of cells, e.g., immune effector cells, engineered to express a Chimeric Antigen Receptor (CAR) that targets mesothelin in combination with PD-L1 inhibitors to treat a disease.

BACKGROUND OF THE INVENTION

Mesothelin was originally identified by Pastan and colleagues as a tumor associated antigen due to its limited expression by normal tissues and overexpression on tumors. Chang K, et al., *Cancer Res.* 1992; 52(1):181-186 and Chang K, et al. *ProcNatlAcadSciUSA.* 1996; 93(1):136-140. The mesothelin gene encodes a precursor 71-kDa protein that is processed to yield the 40-kDa protein, mesothelin, which is anchored at the cell membrane by a glycosylphosphatidyl inositol (GPI) linkage and an amino-terminal 31-kDa shed fragment, called megkaryocyte potentiating factor (MPF). Both fragments contain N-glycosylation sites. A soluble splice variant of the 40-kDa carboxyl-terminal fragment called "soluble mesothelin/MPF-related" has been found in the sera of patients with pancreatic ductal adenocarcinoma (PDA). Johnston, F, et al. *Clinical Cancer Research.* 2009; 15(21):6511. Mesothelin is currently being explored both as a therapeutic target as well as a bio-marker for disease activity and therapeutic response. Argani P, et al. *Clin Cancer Res.* 2001; 7(12):3862-3868.

Mesothelin is a differentiation antigen that is also present on normal tissues. Using the mouse anti-human mesothelin antibody K1 that was developed by the Pastan group, strong K1 reactivity has been demonstrated within mesothelial cells that line the peritoneal, pleural, and pericardial cavities, although at lower levels than usually seen for malignant tissues. Chang K, et al., *Cancer Res.* 1992; 52(1):181-186. Weak K1 reactivity has been detected within the Fallopian tube epithelium, tracheal basal epithelium and tonsils epithelium. Mesothelin has also been found on all layers of the cornea. Jirsova K, et al. *Experimental eye research.* 2010; 91(5):623-629. However, K1 reactivity has not been detected in the majority of normal tissues including the liver, kidneys, spleen, bone marrow, lymph nodes, thymus, cardiac muscle, tongue, skeletal muscle, skin, cerebral cortex, cerebellum, spinal cord, peripheral nerve, pituitary, adrenal, salivary gland, mammary gland, thyroid, parathyroid, testis, prostate, epididymis, cervical epithelium, lung parenchyma, esophagus, small-bowel epithelium, colon epithelium, bladder epithelium, gall-bladder epithelium. Chang K, et al., *Cancer Res.* 1992; 52(1):181-186.

Mesothelin is overexpressed in the vast majority of primary pancreatic adenocarcinomas with rare and weak expression seen in benign pancreatic tissue. Argani P, et al. *Clin Cancer Res.* 2001; 7(12):3862-3868. Epithelial malignant pleural mesothelioma (MPM) universally expresses mesothelin while sarcomatoid MPM does not express mesothelin. Most serous epithelial ovarian carcinomas, and the related primary peritoneal carcinomas, express mesothelin.

Mesothelin is a target of a natural immune response in ovarian cancer, and has been proposed to be a target for cancer immunotherapy. Bracci L, et al. *Clin Cancer Res.* 2007; 13(2 Pt 1):644-653; Moschella F, et al. *Cancer Res.* 2011; 71(10):3528-3539; Gross G, et al. *FASEB J.* 1992; 6(15):3370-3378; Sadelain M, et al. *NatRevCancer.* 2003; 3(1):35-45; Muul L M, et al. *Blood.* 2003; 101(7):2563-2569; Yee C, et al. *Proc Natl Acad Sci USA.* 2002; 99(25):16168-16173. The presence of mesothelin-specific CTLs in patients with pancreatic cancer correlates with overall survival. Thomas A M, et al. *J Exp Med.* 2004; 200:297-306. In addition, Pastan and coworkers have used soluble antibody fragments of an anti-mesothelin antibody conjugated to immunotoxins to treat cancer patients with mesothelin-positive tumors. This approach has demonstrated adequate safety and some clinical activity in pancreatic cancer. Hassan R, et al. *Cancer Immun.* 2007; 7:20 and Hassan R, et al. *Clin Cancer Res.* 2007; 13(17):5144-5149. In ovarian cancer, this therapeutic strategy produced one minor response by RECIST criteria and stable disease in a second patient who also had complete resolution of their ascites.

SUMMARY OF THE INVENTION

The present disclosure features, at least in part, methods and compositions for treating a disease associated with the expression of mesothelin, e.g., a cancer, in a subject by using a combination therapy that includes a cell, e.g., an immune effector cell, expressing a chimeric antigen receptor (CAR) that specifically binds to mesothelin (also referred to herein as a "mesothelin CAR-expressing cell") and an inhibitor of Programmed Death-Ligand 1 (also referred to herein as a "PD-L1 inhibitor"). In some embodiments, the CAR that specifically binds to mesothelin includes an antigen binding domain, e.g., a mesothelin binding domain, a transmembrane domain, and an intracellular signaling domain, e.g., as described herein. In some embodiments, the PD-L1 inhibitor is an antibody molecule, a polypeptide, a small molecule, or a polynucleotide, e.g., an inhibitory nucleic acid. In one embodiment, the PD-L1 inhibitor is an antibody molecule, e.g., an antibody molecule described herein. Without wishing to be bound by theory, treating a subject having a disease associated with mesothelin expression, e.g., a cancer described herein, with a combination therapy that includes a mesothelin CAR-expressing cell and a PD-L1 inhibitor is believed to result in improved inhibition or reduction of tumor progression in the subject, e.g., as compared to treating a subject having the disease with a mesothelin CAR-expressing cell or a PD-L1 inhibitor alone.

Accordingly, in one aspect, the disclosure features a method of treating a subect having a disease associated with expression of mesothelin e.g., a cancer as described herein. The method includes administering to the subject a cell, e.g., a population of cells, comprising, e.g., expressing a CAR that specifically binds to mesothelin, and a PD-L1 inhibitor. In one embodiment, the CAR-expressing cell and the PD-L1 inhibitor is administered sequentially. In one embodiment, the PD-L1 inhibitor is administered prior to administration of the mesothelin CAR-expressing cell. In one embodiment, the PD-L1 inhibitor is administered after the administration of the mesothelin CAR-expressing cell. In one embodiment, the PD-L1 inhibitor and mesothelin CAR-expressing cell are administered simultaneously or concurrently.

In embodiments, the CAR-expressing cell e.g., mesothelin CAR-expressing cell described herein, and the PD-L1 inhibitor is administered in a treatment interval. In one embodiment, the treatment interval comprises a single dose of the PD-L1 inhibitor and a single dose of the CAR-expressing cell. In another embodiment, the treatment interval comprises a first and second dose of the PD-L1 inhibitor and a dose of the CAR-expressing cell.

In embodiments where the treatment interval comprises a single dose of the PD-L1 inhibitor and a single dose of the CAR-expressing cell, the dose of PD-L1 inhibitor is administered prior to the dose of the CAR-expressing cell, and the treatment interval is initiated upon administration of the dose of the PD-L1 inhibitor and completed upon administration of the dose of the CAR-expressing cell. In one embodiment, the treatment interval further comprises one or more, e.g., 1, 2, 3, 4, or 5 or more, subsequent doses of the PD-L1 inhibitor. In such embodiments, the treatment interval comprises two, three, four, five, six, or more, doses of PD-L1 inhibitor and one dose of the CAR-expressing cell. In one embodiment, the dose of the CAR-expressing cell is administered at least 2 days, 3 days, 4 days, 5 days, 6 days, 7 days, or 2 weeks after a dose of PD-L1 inhibitor is administered. In embodiments where more than one dose of PD-L1 inhibitor is administered, the dose of the CAR-expressing cell is administered at least 2 days, 3 days, 4 days, 5, days, 6 days, 7 days, or 2 weeks after the first dose of PD-L1 inhibitor is administered or after the initiation of the treatment interval. In one embodiment, the dose of the CAR-expressing cell is administered about 2 days after the dose of the PD-L1 inhibitor is administered.

In embodiments where the treatment interval comprises a first and second dose of a PD-L1 inhibitor and a dose of a CAR-expressing cell, the dose of the CAR-expressing cell is administered after administration of the first dose of the PD-L1 inhibitor but before the administration of the second dose of the PD-L1 inhibitor. In such embodiments, the treatment interval is initiated upon administration of the first dose of the PD-L1 inhibitor and completed upon administration of the second dose of the PD-L1 inhibitor. In one embodiment, the second dose of the PD-L1 inhibitor is administered at least 5 days, 7 days, 1 week, 2 weeks, 3 weeks, or 4 weeks after administration of the first dose of the PD-L1 inhibitor. In one embodiment, the dose of the CAR-expressing cell is administered at least 2 days, 3 days, 4 days, 5 days, 6 days, 7 days, or 2 weeks after administration of the first dose of the PD-L1 inhibitor. In one embodiment, the second dose of the PD-L1 inhibitor is administered at least 2 days, 3 days, 4 days, 5 days, 6 days, 7 days, 2 weeks, or 3 weeks after administration of the dose of the CAR-expressing cell.

In one embodiment, any of the treatment intervals described herein can be repeated one or more times, e.g., 1, 2, 3, 4, or 5 more times. In one embodiment, the treatment interval is repeated once, resulting in a treatment regimen comprising two treatment intervals. In an embodiment, the repeated treatment interval is administered at least 1 day, e.g., 1 day, 2 days, 3 days, 4 days, 5 days, 6 days, 7 days, or 2 weeks, after the completion of the first or previous treatment interval. In an embodiment, the repeated treatment interval is administered at least 3 days after the completion of the first or previous treatment interval.

In one embodiment, any of the treatment intervals described herein can be followed by one or more, e.g., 1, 2, 3, 4, or 5, subsequent treatment intervals. The one or more subsequent treatment interval is different from the first or previous treatment interval. By way of example, a first treatment interval consisting of a single dose of a PD-L1 inhibitor and a single dose of a CAR-expressing cell is followed by a second treatment interval consisting of two doses of a PD-L1 inhibitor and a single dose of a CAR-expressing cell. In one embodiment, the one or more subsequent treatment intervals is administered at least 1 day, e.g., 1 day, 2 days, 3 days, 4 days, 5 days, 6 days, 7 days, or 2 weeks, after the completion of the first or previous treatment interval.

In any of the methods described herein, one or more subsequent doses, e.g., 1, 2, 3, 4, or 5 or more doses, of the PD-L1 inhibitor is administered after the completion of one or more treatment intervals. In embodiments where the treatment intervals are repeated or two or more treatment intervals are administered, one or more subsequent doses, e.g., 1, 2, 3, 4, or 5, of the PD-L1 inhibitor is administered after the completion of one treatment interval and before the initiation of another treatment interval. In one embodiment, a dose of the PD-L1 inhibitor is administered every 5 days, 7 days, 2 weeks, 3 weeks, or 4 days after the completion of one or more, or each, treatment intervals.

In any of the methods described herein, one or more, e.g., 1, 2, 3, 4, or 5 or more, subsequent doses of the CAR-expressing cell are administered after the completion of one or more treatment intervals. In embodiments where the treatment intervals are repeated or two or more treatment intervals are administered, one or more subsequent doses, e.g., 1, 2, 3, 4, or 5, or more doses, of the CAR-expressing cell is administered after the completion of one treatment interval and before the initiation of another treatment interval. In one embodiment, a dose of the CAR-expressing cell is administered every 2 days, 3 days, 4 days, 5 days, 7 days, 2 weeks, 3 weeks, or 4 days after the completion of one or more, or each, treatment intervals.

In one embodiment, the treatment interval comprises a single dose of a PD-L1 inhibitor that is administered prior to a single dose of a CAR-expressing cell. In this embodiment, the dose of the CAR-expressing cell is administered 2 days after the administration of the dose of the PD-L1 inhibitor. The treatment interval is repeated one time, and the second treatment interval is initiated 3 days after the completion of the first treatment interval, e.g., after the administration of the single dose of the CAR-expressing cell. In one embodiment, the PD-L1 inhibitor is administered every 5 days after the completion of the second treatment interval, e.g., one or more doses of the PD-L1 inhibitor is administered every 5 days, 7 days, 2 weeks, 3 weeks, or 4 weeks, after the second treatment interval.

In any of the methods described herein, the subject is administered a single dose of a CAR-expressing cell and a single dose of a PD-L1 inhibitor. In one embodiment, the single dose of the CAR-expressing cell is administered at least 2 days, e.g., 2, 3, 4, 5, 6, 7 days, or 2 weeks, after administration of the single dose of the PD-L1 inhibitor.

In one embodiment, one or more, e.g., 1, 2, 3, 4, or 5, subsequent doses of a CAR-expressing cell are administered to the subject after the initial dose of the CAR-expressing cell. In one embodiment, the one or more subsequent doses of the CAR-expressing cell are administered at least 2 days, e.g., 2, 3, 4, 5, 6, 7 days or 2 weeks, after the previous dose of the CAR-expressing cell. In one embodiment, the one or more subsequent doses of the CAR-expressing cell are administered at least 5 days after the previous dose of the CAR-expressing cell. In one embodiment, the subject is administered three doses of the CAR-expressing cell per week or one dose every 2 days.

In one embodiment, one or more, e.g., 1, 2, 3, 4, or 5, subsequent doses of PD-L1 inhibitor are administered after administration of the single dose of the PD-L1 inhibitor. In one embodiment, the one or more subsequent doses of the PD-L1 inhibitor are administered at least 5 days, 7 days, 2 weeks, 3 weeks or 4 weeks, after the previous dose of PD-L1 inhibitor.

In one embodiment, the one or more subsequent doses of the PD-L1 inhibitor are administered at least 1, 2, 3, 4, 5, 6, or 7 days, after a dose of the CAR-expressing cell, e.g., the initial dose of the CAR-expressing cell.

In one embodiment, one or more, e.g., 1, 2, 3, 4, or 5, doses of the PD-L1 inhibitor is administered prior to the first dose of the CAR-expressing cell.

In one embodiment, the administration of the one or more doses of the CAR-expressing cell and the one or more doses of PD-L1 inhibitor is repeated, e.g., 1, 2, 3, 4, or 5 more times.

In any of the administration regimens or treatment intervals described herein, a dose of mesothelin CAR-expressing cells comprises at least about $1\times10^7$, $1.5\times10^7$, $2\times10^7$, $2.5\times10^7$, $3\times10^7$, $3.5\times10^7$, $4\times10^7$, $5\times10^7$, $1\times10^8$, $1.5\times10^8$, $2\times10^8$, $2.5\times10^8$, $3\times10^8$, $3.5\times10^8$, $4\times10^8$, $5\times10^8$, $1\times10^9$, $2\times10^9$, or $5\times10^9$ cells. In some embodiments, a dose of mesothelin CAR-expressing cells comprises at least about $1\text{-}3\times10^7$ to $1\text{-}3\times10^8$. In some embodiments, the subject is administered about $1\text{-}3\times10^7$ mesothelin CAR-expressing cells. In other embodiments, the subject is administered about $1\text{-}3\times10^8$ mesothelin CAR-expressing cells.

In any of the administration regimens described herein, a dose of a PD-L1 inhibitor, e.g., an anti-PD-L1 antibody molecule described herein, comprises about 1 to 30 mg/kg, e.g., about 5 to 25 mg/kg, about 10 to 20 mg/kg, about 1 to 5 mg/kg, or about 3 mg/kg. In one embodiment, the dose is about 10 to 20 mg/kg. In one embodiment, the dose is about 1 to 5 mg/kg. In one embodiment, the dose is less than 5 mg/kg, less than 4 mg/kg, less than 3 mg/kg, less than 2 mg/kg, or less than 1 mg/kg.

In another aspect, the disclosure features a composition (e.g., one or more dosage formulations, combinations, or one or more pharmaceutical compositions) comprising a cell expressing a mesothelin CAR described herein and a PD-L1 inhibitor described herein. In one embodiment, the mesothelin CAR comprises a mesothelin antigen binding domain, a transmembrane domain, and an intracellular signaling domain, as described herein. In one embodiment, the mesothelin CAR comprises a mesothelin antigen binding domain listed in Table 2. In one embodiment, the PD-L1 inhibitor comprises an antibody molecule, a small molecule, a polypeptide, e.g., a fusion protein, or an inhibitory nucleic acid, e.g., a siRNA or shRNA. In one embodiment, the PD-L1 inhibitor comprises an antibody molecule, e.g., an antibody molecule listed in Table 6. The CAR-expressing cell and the PD-L1 inhibitor can be in the same or different formulation or pharmaceutical composition.

In another aspect, the disclosure features a composition (e.g., one or more dosage formulations, combinations, or one or more pharmaceutical compositions) comprising a cell expressing a mesothelin CAR described herein and a PD-L1 inhibitor described herein, for use in a method of treating a disease associated with expression of mesothelin, e.g., a cancer described herein. In one embodiment, the mesothelin CAR comprises a mesothelin antigen binding domain, a transmembrane domain, and an intracellular signaling domain, as described herein. In one embodiment, the mesothelin CAR comprises a mesothelin antigen binding domain listed in Table 2. In one embodiment, the PD-L1 inhibitor comprises an antibody molecule, a small molecule, a polypeptide, e.g., a fusion protein, or an inhibitory nucleic acid, e.g., a siRNA or shRNA. In one embodiment, the PD-L1 inhibitor comprises an antibody molecule, e.g., an antibody molecule listed in Table 6. The CAR-expressing cell and the PD-L1 inhibitor can be in the same or different formulation or pharmaceutical composition.

PD-L1 Inhibitors

Provided herein are PD-L1 inhibitors for use in any of the methods or compositions described herein. In any of the methods or compositions described herein, the PD-L1 inhibitor comprises an antibody molecule, a small molecule, a polypeptide, e.g., a fusion protein, or an inhibitory nucleic acid, e.g., a siRNA or shRNA.

In one embodiment, the PD-L1 inhibitor is characterized by one or more of the following: inhibits or reduces PD-L1 expression, e.g., transcription or translation of PD-L1; inhibits or reduces PD-L1 activity, e.g., inhibits or reduces binding of PD-L1 to its receptor, e.g., PD-1 or CD80 (B7-1) or both; or binds to PD-L1 or its receptor, e.g., PD-1.

In one embodiment, the PD-L1 inhibitor is an antibody molecule. In one embodiment, the PD-L1 inhibitor is selected from the group consisting of YW243.55.S70, MPDL3280A (atezolizumab), MEDI-4736, MSB-0010718C (avelumab), MDX-1105, and any anti-PD-L1 antibody molecules listed in Table 6.

In one embodiment, the PD-L1 inhibitor comprises an anti-PD-L1 antibody molecule comprising a heavy chain complementary determining region 1 (HC CDR1), a heavy chain complementary determining region 2 (HC CDR2), and a heavy chain complementary determining region 3 (HC CDR3) of any PD-L1 antibody molecule amino acid sequence listed in Table 6; and a light chain complementary determining region 1 (LC CDR1), a light chain complementary determining region 2 (LC CDR2), and a light chain complementary determining region 3 (LC CDR3) of any PD-L1 antibody molecule amino acid sequence listed in Table 6. In one embodiment, the anti-PD-L1 antibody molecule comprises a HC CDR1 amino acid sequence chosen from SEQ ID NO: 287, 290, or 195, a HC CDR2 amino acid sequence of SEQ ID NO: 288, and a HC CDR3 amino acid sequence of SEQ ID NO: 289; and a LC CDR1 amino acid sequence of SEQ ID NO: 295, a LC CDR2 amino acid sequence of SEQ ID NO: 296, and a LC CDR3 amino acid sequence of SEQ ID NO: 297. In one embodiment, the anti-PD-L1 antibody comprises a HC CDR1 amino acid sequence chosen from SEQ ID NO: 287, 290, or 195, a HC CDR2 amino acid sequence of SEQ ID NO: 291, and a HC CDR3 amino acid sequence of SEQ ID NO: 292; and a LC CDR1 amino acid sequence of SEQ ID NO: 298, a LC CDR2 amino acid sequence of SEQ ID NO: 299, and a LC CDR3 amino acid sequence of SEQ ID NO: 300.

In one embodiment, the anti-PD-L1 antibody molecule comprises a heavy chain variable region comprising the amino acid sequence of any heavy chain variable region listed in Table 6, e.g., SEQ ID NOs: 304, 316, 324, 332, 336, 340, 348, 356, or 364. In one embodiment, the anti-PD-L1 antibody molecule comprises a heavy chain variable region comprising the amino acid sequence having at least one, two or three modifications but not more than 30, 20 or 10 modifications to the amino acid sequence of any heavy chain variable region provided in Table 6, e.g., SEQ ID NOs: 304, 316, 324, 332, 336, 340, 348, 356, or 364. In one embodiment, the anti-PD-L1 antibody molecule comprises a heavy chain variable region comprising an amino acid sequence with 95-99% identity to the amino acid sequence of any heavy chain variable region provided in Table 6, e.g., SEQ ID NOs: 304, 316, 324, 332, 336, 340, 348, 356, or 364.

In one embodiment, the anti-PD-L1 antibody molecule comprises a heavy chain comprising the amino acid sequence of any heavy chain listed in Table 6, e.g., SEQ ID NOs: 306, 318, 326, 334, 338, 342, 350, 358, 366, 393, 377, or 382. In one embodiment, the anti-PD-L1 antibody molecule comprises a heavy chain comprising the amino acid sequence having at least one, two or three modifications but not more than 30, 20 or 10 modifications to any heavy chain listed in Table 6, e.g., SEQ ID NOs: 306, 318, 326, 334, 338, 342, 350, 358, 366, 393, 377, or 382. In one embodiment, the anti-PD-L1 antibody molecule comprises a heavy chain comprising an amino acid sequence with 95-99% identity to the amino acid sequence of any heavy chain listed in Table 6, e.g., SEQ ID NOs: 306, 318, 326, 334, 338, 342, 350, 358, 366, 393, 377, or 382.

In one embodiment, the anti-PD-L1 antibody molecule comprises a light chain variable region comprising the amino acid sequence of any light chain variable region listed in Table 6, e.g., SEQ ID NOs: 308, 312, 320, 328, 344, 352, 360, 368, or 372. In one embodiment, the anti-PD-L1 antibody molecule comprises a light chain variable region comprising the amino acid sequence having at least one, two or three modifications but not more than 30, 20 or 10 modifications to the amino acid sequence of any light chain variable region provided in Table 6, e.g., SEQ ID NOs: 308, 312, 320, 328, 344, 352, 360, 368, or 372. In one embodiment, the anti-PD-L1 antibody molecule comprises a light chain variable region comprising an amino acid sequence with 95-99% identity to the amino acid sequence of any light chain variable region provided in Table 6, e.g., SEQ ID NOs: 308, 312, 320, 328, 344, 352, 360, 368, or 372.

In one embodiment, the anti-PD-L1 antibody molecule comprises a light chain comprising the amino acid sequence of any light chain listed in Table 6, e.g., SEQ ID NOs: 310, 314, 322, 330, 346, 354, 362, 370, or 374. In one embodiment, the anti-PD-L1 antibody molecule comprises a light chain comprising the amino acid sequence having at least one, two or three modifications but not more than 30, 20 or 10 modifications to any light chain listed in Table 6, e.g., SEQ ID NOs: 310, 314, 322, 330, 346, 354, 362, 370, or 374. In one embodiment, the anti-PD-L1 antibody molecule comprises a light chain comprising an amino acid sequence with 95-99% identity to the amino acid sequence to any any light chain listed in Table 6, e.g., SEQ ID NOs: 310, 314, 322, 330, 346, 354, 362, 370, or 374.

In one embodiment, the anti-PD-L1 antibody molecule comprises:

i) a heavy chain variable domain comprising the amino acid sequence of SEQ ID NO: 304 and a light chain variable domain comprising the amino acid sequence of SEQ ID NO: 308;

ii) a heavy chain variable domain comprising the amino acid sequence of SEQ ID NO: 304 and a light chain variable domain comprising the amino acid sequence of SEQ ID NO: 312;

iii) a heavy chain variable domain comprising the amino acid sequence of SEQ ID NO: 304 and a light chain variable domain comprising the amino acid sequence of SEQ ID NO: 372.

iv) a heavy chain variable domain comprising the amino acid sequence of SEQ ID NO: 316 and a light chain variable domain comprising the amino acid sequence of SEQ ID NO: 320;

v) a heavy chain variable domain comprising the amino acid sequence of SEQ ID NO: 316 and a light chain variable domain comprising the amino acid sequence of SEQ ID NO: 352;

vi) a heavy chain variable domain comprising the amino acid sequence of SEQ ID NO: 324 and a light chain variable domain comprising the amino acid sequence of SEQ ID NO: 328;

vii) a heavy chain variable domain comprising the amino acid sequence of SEQ ID NO: 324 and a light chain variable domain comprising the amino acid sequence of SEQ ID NO: 360;

viii) a heavy chain variable domain comprising the amino acid sequence of SEQ ID NO: 332 and a light chain variable domain comprising the amino acid sequence of SEQ ID NO: 328;

ix) a heavy chain variable domain comprising the amino acid sequence of SEQ ID NO: 336 and a light chain variable domain comprising the amino acid sequence of SEQ ID NO: 328;

x) a heavy chain variable domain comprising the amino acid sequence of SEQ ID NO: 336 and a light chain variable domain comprising the amino acid sequence of SEQ ID NO: 308;

xi) a heavy chain variable domain comprising the amino acid sequence of SEQ ID NO: 336 and a light chain variable domain comprising the amino acid sequence of SEQ ID NO: 372;

xii) a heavy chain variable domain comprising the amino acid sequence of SEQ ID NO: 340 and a light chain variable domain comprising the amino acid sequence of SEQ ID NO: 344;

xiii) a heavy chain variable domain comprising the amino acid sequence of SEQ ID NO: 340 and a light chain variable domain comprising the amino acid sequence of SEQ ID NO: 372;

xiv) a heavy chain variable domain comprising the amino acid sequence of SEQ ID NO: 348 and a light chain variable domain comprising the amino acid sequence of SEQ ID NO: 352;

xv) a heavy chain variable domain comprising the amino acid sequence of SEQ ID NO: 348 and a light chain variable domain comprising the amino acid sequence of SEQ ID NO: 386;

xvi) a heavy chain variable domain comprising the amino acid sequence of SEQ ID NO: 356 and a light chain variable domain comprising the amino acid sequence of SEQ ID NO: 352; or xvii) a heavy chain variable domain comprising the amino acid sequence of SEQ ID NO: 78 and a light chain variable domain comprising the amino acid sequence of SEQ ID NO: 368.

In one embodiment, the anti-PD-L1 antibody molecule comprises:

i) a heavy chain comprising the amino acid sequence of SEQ ID NO: 306 and a light chain comprising the amino acid sequence of SEQ ID NO: 310;

ii) a heavy chain comprising the amino acid sequence of SEQ ID NO: 306 and a light chain comprising the amino acid sequence of SEQ ID NO: 214;
iii) a heavy chain comprising the amino acid sequence of SEQ ID NO: 306 and a light chain comprising the amino acid sequence of SEQ ID NO: 374;
iv) a heavy chain comprising the amino acid sequence of SEQ ID NO: 318 and a light chain comprising the amino acid sequence of SEQ ID NO: 322;
v) a heavy chain comprising the amino acid sequence of SEQ ID NO: 318 and a light chain comprising the amino acid sequence of SEQ ID NO: 354;
vi) a heavy chain comprising the amino acid sequence of SEQ ID NO: 326 and a light chain comprising the amino acid sequence of SEQ ID NO: 330;
vii) a heavy chain comprising the amino acid sequence of SEQ ID NO: 326 and a light chain comprising the amino acid sequence of SEQ ID NO: 362;
viii) a heavy chain comprising the amino acid sequence of SEQ ID NO: 334 and a light chain comprising the amino acid sequence of SEQ ID NO: 330;
ix) a heavy chain comprising the amino acid sequence of SEQ ID NO: 338 and a light chain comprising the amino acid sequence of SEQ ID NO: 330;
x) a heavy chain comprising the amino acid sequence of SEQ ID NO: 338 and a light chain comprising the amino acid sequence of SEQ ID NO: 310;
xi) a heavy chain comprising the amino acid sequence of SEQ ID NO: 338 and a light chain comprising the amino acid sequence of SEQ ID NO: 374;
xii) a heavy chain comprising the amino acid sequence of SEQ ID NO: 342 and a light chain comprising the amino acid sequence of SEQ ID NO: 346;
xiii) a heavy chain comprising the amino acid sequence of SEQ ID NO: 342 and a light chain comprising the amino acid sequence of SEQ ID NO: 374;
xiv) a heavy chain comprising the amino acid sequence of SEQ ID NO: 350 and a light chain comprising the amino acid sequence of SEQ ID NO: 354;
xv) a heavy chain comprising the amino acid sequence of SEQ ID NO: 350 and a light chain comprising the amino acid sequence of SEQ ID NO: 374;
xvi) a heavy chain comprising the amino acid sequence of SEQ ID NO: 358 and a light chain comprising the amino acid sequence of SEQ ID NO: 354;
xvii) a heavy chain comprising the amino acid sequence of SEQ ID NO: 366 and a light chain comprising the amino acid sequence of SEQ ID NO: 370;
xviii) a heavy chain comprising the amino acid sequence of SEQ ID NO: 393 and a light chain comprising the amino acid sequence of SEQ ID NO: 322;
xix) a heavy chain comprising the amino acid sequence of SEQ ID NO: 91 and a light chain comprising the amino acid sequence of SEQ ID NO: 330; or
xx) a heavy chain comprising the amino acid sequence of SEQ ID NO: 382 and a light chain comprising the amino acid sequence of SEQ ID NO: 354.

Mesothelin CAR-Expressing Cells

Provided herein are cells, e.g., immune effector cells, that express a chimeric antigen receptor (CAR) that targets, e.g., specifically binds to, mesothelin for use in any of the methods or compositions described herein. The CAR that specifically binds to mesothelin also referred to herein as "a mesothelin CAR or a mesoCAR". The mesothelin CAR expressed by the mesothelin CAR-expressing cell described herein includes a mesothelin binding domain, a transmembrane domain, and an intracellular signaling domain. In one embodiment, the intracellular signaling domain comprises a costimulatory domain and/or a primary signaling domain.

In one embodiment, the mesothelin binding domain comprises a heavy chain complementary determining region 1 (HC CDR1), a heavy chain complementary determining region 2 (HC CDR2), and a heavy chain complementary determining region 3 (HC CDR3) of any mesothelin heavy chain binding domain amino acid sequence listed in Table 2; and a light chain complementary determining region 1 (LC CDR1), a light chain complementary determining region 2 (LC CDR2), and a light chain complementary determining region 3 (LC CDR3) of any mesothelin light chain binding domain amino acid sequence listed in Table 2. In one embodiment, the mesothelin binding domain comprises a HC CDR1, a HC CDR2, and a HC CDR3 according to the HC CDR amino acid sequences in Table 4, and a LC CDR1, a LC CDR2, and a LC CDR3 according to the LC CDR amino acid sequences in Table 5.

In one embodiment, the mesothelin binding domain comprises (e.g., consists of) the amino acid sequence selected from the group consisting of SEQ ID NO: 43, SEQ ID NO: 49, SEQ ID NO: 275, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62. In one embodiment, the mesothelin binding domain comprises (e.g., consists of) an amino acid sequence having at least one, two or three modifications but not more than 30, 20 or 10 modifications (e.g., substitutions, e.g., conservative substitutions) to any of SEQ ID NO: 43, SEQ ID NO: 49, SEQ ID NO: 275, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62. In one embodiment, the mesothelin binding domain comprises (e.g., consists of) an amino acid sequence with 95-99% identity to the amino acid sequence to any of SEQ ID NO: 43, SEQ ID NO: 49, SEQ ID NO: 275, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62.

In one embodiment, the mesothelin CAR includes a transmembrane domain that comprises a transmembrane domain of a protein, e.g., a protein described herein, e.g., selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises the sequence of SEQ ID NO: 6. In one embodiment, the transmembrane domain comprises an amino acid sequence comprising at least one, two or three modifications but not more than 20, 10 or 5 modifications of the amino acid sequence of SEQ ID NO:6, or a sequence with 95-99% identity to an amino acid sequence of SEQ ID NO:6. In one embodiment, the nucleic acid sequence encoding the transmembrane domain comprises a nucleotide sequence of SEQ ID NO: 17, or a sequence with 95-99% identity thereof.

In one embodiment, the mesothelin binding domain is connected to the transmembrane domain by a hinge region, e.g., a hinge region described herein. In one embodiment, the encoded hinge region comprises SEQ ID NO:2, or a sequence with 95-99% identity thereof. In one embodiment, the nucleic acid sequence encoding the hinge region comprises a nucleotide sequence of SEQ ID NO: 13, or a sequence with 95-99% identity thereof.

In one embodiment, the isolated nucleic acid molecule further comprises a sequence encoding a costimulatory domain, e.g., a costimulatory domain described herein. In embodiments, the intracellular signaling domain comprises a costimulatory domain. In embodiments, the intracellular signaling domain comprises a primary signaling domain. In embodiments, the intracellular signaling domain comprises a costimulatory domain and a primary signaling domain.

In one embodiment, the costimulatory domain is a functional signaling domain from a protein, e.g., described herein, e.g., selected from the group consisting of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one embodiment, the costimulatory domain of 4-1BB comprises the amino acid sequence of SEQ ID NO:7. In one embodiment, the encoded costimulatory domain comprises an amino acid sequence having at least one, two or three modifications but not more than 20, 10 or 5 modifications of an amino acid sequence of SEQ ID NO:7, or a sequence with 95-99% identity to the amino acid sequence of SEQ ID NO:7. In one embodiment, the nucleic acid sequence encoding the costimulatory domain comprises the nucleotide sequence of SEQ ID NO:18, or a sequence with 95-99% identity thereof. In another embodiment, the costimulatory domain of CD28 comprises the amino acid sequence of SEQ ID NO:43. In one embodiment, the costimulatory domain comprises an amino acid sequence having at least one, two or three modifications but not more than 20, 10 or 5 modifications of an amino acid sequence of SEQ ID NO:43, or a sequence with 95-99% identity to an amino acid sequence of SEQ ID NO:43. In one embodiment, the nucleic acid sequence encoding the costimulatory domain of CD28 comprises the nucleotide sequence of SEQ ID NO:44, or a sequence with 95-99% identity thereof. In another embodiment, the costimulatory domain of CD27 comprises the amino acid sequence of SEQ ID NO:8. In one embodiment, the costimulatory domain comprises an amino acid sequence having at least one, two or three modifications but not more than 20, 10 or 5 modifications of an amino acid sequence of SEQ ID NO:8, or a sequence with 95-99% identity to an amino acid sequence of SEQ ID NO:8. In one embodiment, the nucleic acid sequence encoding the costimulatory domain of CD27 comprises the nucleotide sequence of SEQ ID NO:19, or a sequence with 95-99% identity thereof. In another embodiment, the costimulatory domain of ICOS comprises the amino acid sequence of SEQ ID NO:45. In one embodiment, the costimulatory domain of ICOS comprises an amino acid sequence having at least one, two or three modifications but not more than 20, 10 or 5 modifications of an amino acid sequence of SEQ ID NO:45, or a sequence with 95-99% identity to an amino acid sequence of SEQ ID NO:45. In one embodiment, the nucleic acid sequence encoding the costimulatory domain of ICOS comprises the nucleotide sequence of SEQ ID NO:46, or a sequence with 95-99% identity thereof.

In some embodiments, the primary signaling domain comprises a functional signaling domain of CD3 zeta. In embodiments, the functional signaling domain of CD3 zeta comprises the amino acid sequence of SEQ ID NO:9 (mutant CD3 zeta) or SEQ ID NO:10 (wild type human CD3 zeta), or a sequence with 95-99% identity thereof.

In one embodiment, the intracellular signaling domain comprises a functional signaling domain of 4-1BB and/or a functional signaling domain of CD3 zeta. In one embodiment, the intracellular signaling domain of 4-1BB comprises the sequence of SEQ ID NO: 7 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:7 and/or an amino acid sequence of SEQ ID NO:9 or SEQ ID NO:10, or a sequence with 95-99% identity to an amino acid sequence of SEQ ID NO:7 and/or an amino acid sequence of SEQ ID NO:9 or SEQ ID NO:10. In one embodiment, the intracellular signaling domain comprises the sequence of SEQ ID NO:7 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain comprises the nucleotide sequence of SEQ ID NO:18, or a sequence with 95-99% identity thereof, and/or the CD3 zeta nucleotide sequence of SEQ ID NO:20 or SEQ ID NO:21, or a sequence with 95-99% identity thereof.

In one embodiment, the intracellular signaling domain comprises a functional signaling domain of CD27 and/or a functional signaling domain of CD3 zeta. In one embodiment, the encoded intracellular signaling domain of CD27 comprises the amino acid sequence of SEQ ID NO:8 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:8 and/or an amino acid sequence of SEQ ID NO:9 or SEQ ID NO:10, or a sequence with 95-99% identity to an amino acid sequence of SEQ ID NO:8 and/or an amino acid sequence of SEQ ID NO:9 or SEQ ID NO:10. In one embodiment, the intracellular signaling domain comprises the sequence of SEQ ID NO:8 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of CD27 comprises the nucleotide sequence of SEQ ID NO:19, or a sequence with 95-99% identity thereof, and/or the CD3 zeta nucleotide sequence of SEQ ID NO:20 or SEQ ID NO:21, or a sequence with 95-99% identity thereof.

In one embodiment, the intracellular signaling domain comprises a functional signaling domain of CD28 and/or a functional signaling domain of CD3 zeta. In one embodiment, the intracellular signaling domain of CD28 comprises the amino acid sequence of SEQ ID NO:43 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:43 and/or an amino acid sequence of SEQ ID NO:9 or SEQ ID NO:10, or a sequence with 95-99% identity to an amino acid sequence of SEQ ID NO:43 and/or an amino acid sequence of SEQ ID NO:9 or SEQ ID NO:10. In one embodiment, the intracellular signaling domain comprises the sequence of SEQ ID NO:43 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of CD28 comprises the nucleotide sequence of SEQ ID NO:44, or a sequence with 95-99% identity thereof, and/or the CD3 zeta nucleotide sequence of SEQ ID NO:20 or SEQ ID NO:21, or a sequence with 95-99% identity thereof.

In one embodiment, the intracellular signaling domain comprises a functional signaling domain of ICOS and/or a functional signaling domain of CD3 zeta. In one embodiment, the intracellular signaling domain of ICOS comprises the amino acid sequence of SEQ ID NO:45 and/or the CD3 zeta amino acid sequence of SEQ ID NO:9 or SEQ ID NO:10. In one embodiment, the intracellular signaling domain comprises an amino acid sequence having at least one, two or three modifications but not more than 20, 10 or 5 modifications of an amino acid sequence of SEQ ID NO:45 and/or an amino acid sequence of SEQ ID NO:9 or SEQ ID NO:10, or a sequence with 95-99% identity to an amino acid sequence of SEQ ID NO:45 and/or an amino acid sequence of SEQ ID NO:9 or SEQ ID NO:10. In one embodiment, the intracellular signaling domain comprises the sequence of SEQ ID NO:45 and the sequence of SEQ ID NO:9 or SEQ ID NO:10, wherein the sequences comprising the intracellular signaling domain are expressed in the same frame and as a single polypeptide chain. In one embodiment, the nucleic acid sequence encoding the intracellular signaling domain of ICOS comprises the nucleotide sequence of SEQ ID NO:46, or a sequence with 95-99% identity thereof, and/or the CD3 zeta nucleotide sequence of SEQ ID NO:20 or SEQ ID NO:21, or a sequence with 95-99% identity thereof.

In one embodiment, the mesothelin CAR further comprises a leader sequence comprising the amino acid sequence of SEQ ID NO: 1.

In one embodiment, the mesothelin CAR comprises the amino acid sequence of any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86. In one embodiment, the mesothelin CAR comprises an amino acid sequence having at least one, two or three modifications but not more than 30, 20 or 10 modifications to any of SEQ ID NO: 67, SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86. In one embodiment, the mesothelin CAR comprises an amino acid sequence with 95-99% identity to any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86.

In embodiments of any of the methods and compositions described herein, the cell comprising a CAR comprises a nucleic acid encoding the CAR.

In one embodiment, the nucleic acid encoding the CAR is a lentiviral vector. In one embodiment, the nucleic acid encoding the CAR is introduced into the cells by lentiviral transduction. In one embodiment, the nucleic acid encoding the CAR is an RNA, e.g., an in vitro transcribed RNA. In one embodiment, the nucleic acid encoding the CAR is introduced into the cells by electroporation.

In embodiments of any of the methods and compositions described herein, the cell is a T cell or an NK cell. In one embodiment, the T cell is an autologous or allogeneic T cell.

In one embodiment, the method further comprises administering an additional therapeutic agent for treating a disease described herein, e.g., an anti-cancer therapeutic agent.

In embodiments of any of the methods and compositions described herein, the disease associated with mesothelin expression is a cancer. In one embodiment, the cancer is chosen from one or more of mesothelioma, malignant pleural mesothelioma, non-small cell lung cancer, small cell lung cancer, squamous cell lung cancer, or large cell lung cancer, pancreatic cancer, pancreatic ductal adenocarcinoma, pancreatic metatstatic, ovarian cancer, or colorectal cancer and bladder cancer, or a metastasis thereof.

In embodiments of any of the methods and compositions described herein, the subject is a mammal, e.g., a human. In one embodiment, the subject expresses PD-L1 and/or PD-L2. In one embodiment, the cancer cell or a cell in close proximity to a cancer cell, e.g., a cancer-associated cell, in the subject expresses PD-L1 and/or PD-L2. In an embodiment, the cancer-associated cell is a anti-tumor immune cell, e.g., a tumor infiltrating lymphocyte (TIL).

In one embodiment, the cell expressing a CAR, e.g., a mesothelin CAR-expressing cell described herein, expresses PD-1 and/or PD-L1.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIG. 8, comprising FIG. 8A shows day 0 PK following the first dose of RAD001. FIG. 8B shows Day 14 PK following the final RAD001 dose. Diamonds denote the 10 mg/kg dose of RAD001; squares denote the 1 mg/kg dose of RAD001; triangles denote the 3 mg/kg dose of RAD001; and x's denote the 10 mg/kg dose of RAD001.

FIG. 9, comprising FIG. 9A shows $CD4^+$ CAR T cells; FIG. 9B shows $CD8^+$ CAR T cells. Circles denote PBS; squares denote huCTL019; triangles denote huCTL019 with 3 mg/kg RAD001; inverted triangles denote huCTL019 with 0.3 mg/kg RAD001; diamonds denote huCTL019 with 0.03 mg/kg RAD001; and circles denote huCTL019 with 0.003 mg/kg RAD001.

DETAILED DESCRIPTION

Definitions

Figure 1A:
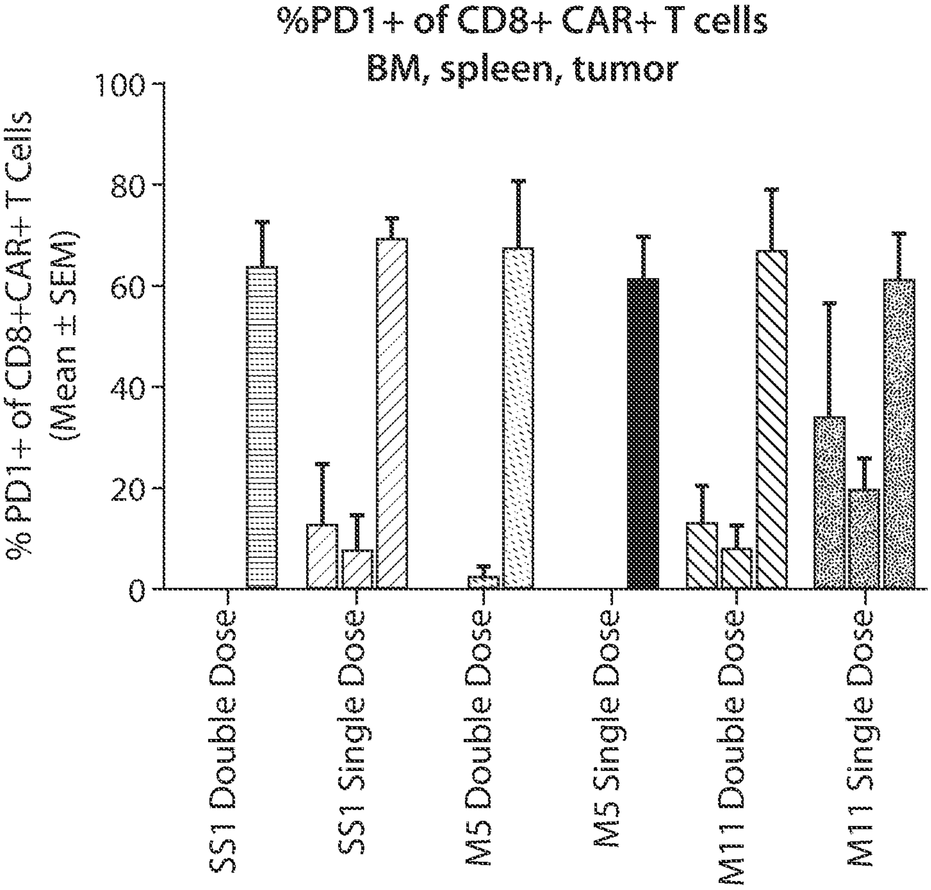
FIG. 1A shows flow cytometric analysis of the expression of PD1 on CAR T cells. Shown is the percentage of CD8+ CAR+ cells expressing PD1. Bone marrow, spleen and tumor were analyzed 30 days after adoptive transfer into Panc02.03 tumor bearing NSG mice. CAR T cells taken from the tumors, but not the other organs were largely positive for PD1 expression (more than 60%). CARTs were stained with anti-CD8a (BioLegend, RPAT8), anti-PD1 (BD Bioscience, EH12.1), anti-PDL1 (BD Bioscience, M1H1), ProteinL-Biotin, and Streptavidin-PE.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein.

In one aspect, the stimulatory molecule is the zeta chain associated with the T cell receptor complex. In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27, ICOS, and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen recognition domain (e.g., a scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers. In some aspects, the signaling domain of the CAR described herein is derived from a stimulatory molecule or co-stimulatory molecule described herein, or is a synthesized or engineered signaling domain.

As used herein, the term "mesothelin" refers to the 40-kDa protein, mesothelin, which is anchored at the cell membrane by a glycosylphosphatidyl inositol (GPI) linkage and an amino-terminal 31-kDa shed fragment, called megkaryocyte potentiating factor (MPF). Both fragments contain N-glycosylation sites. The term also refers to a soluble splice variant of the 40-kDa carboxyl-terminal fragment also called "soluble mesothelin/MPF-related". Preferably, the term refers to a human mesothelin of GenBank accession number AAH03512.1, and naturally cleaved portions thereof, e.g., as expressed on a cell membrane, e.g., a cancer cell membrane.

The term "antibody" or "antibody molecule" as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules. In one embodiment, the antibody or antibody molecule comprises, e.g., consists of, an antibody fragment.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', $F(ab')_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The portion of the CAR of the invention comprising an antibody or antibody fragment thereof may exist in a variety of forms where the antigen binding domain is expressed as part of a contiguous polypeptide chain including, for example, scFv antibody fragments, linear antibodies, single domain antibodies such as sdAb (either VL or VH), camelid VHH domains, a humanized antibody, a bispecific antibody, an antibody conjugate (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR of the invention comprises an antibody fragment. In a further aspect, the CAR comprises an antibody fragment that comprises a scFv.

As used herein, the term "antibody molecule" refers to a protein, e.g., an immunoglobulin chain or fragment thereof, comprising at least one immunoglobulin variable domain sequence. The term antibody molecule encompasses antibodies and antibody fragments. In one embodiment, an antibody molecule encompasses a "binding domain" (also referred to herein as "anti-target (e.g., mesothelin) binding domain"). In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" refers to a disease characterized by the uncontrolled growth of aberrant cells. Cancer includes all types of cancerous growths or oncogenic processes, metastatic tissues or malignantly transformed cells, tissues or organs irrespective of the histopathologic type or stage of invasiveness. Cancer cells can spread locally or through the bloodstream and lymphatic system to other parts of the body. Examples of various cancers are described herein and include, but are not limited to, mesothelioma, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "disease associated with expression of mesothelin" includes, but is not limited to, a disease associated with expression of mesothelin or condition associated with cells which express mesothelin including, e.g., proliferative diseases such as a cancer or malignancy or a precancerous condition such as a mesothelial hyperplasia; or a noncancer related indication associated with cells which express mesothelin. Examples of various cancers that express mesothelin include but are not limited to, mesothelioma, lung cancer, ovarian cancer, pancreatic cancer, and the like.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested, e.g., for the ability to bind mesothelin using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules, such as downregulation of TGF-β, and/or reorganization of cytoskeletal structures, and the like.

The term "stimulatory molecule," refers to a molecule expressed by an immune effector cell (e.g., a T cell, NK cell, B cell) that provides the cytoplasmic signaling sequence(s) that regulate activation of the immune effector cell in a stimulatory way for at least some aspect of the immune effector cell signaling pathway, e.g., the T cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from CD3 zeta, common FcR gamma (FCER1G), Fc gamma RIIa, FcR beta (Fc epsilon Rib), CD3 gamma, CD3 delta, CD3 epsilon, CD5, CD22, CD79a, CD79b, CD278 (also known as "ICOS"), FcεRI, DAP10, DAP12, and CD66d. In a specific CAR of the invention, the intracellular signaling domain in any one or more CARs of the invention comprises an intracellular signaling sequence, e.g., a primary signaling sequence of CD3-zeta. In a specific CAR of the invention, the primary signaling sequence of CD3-zeta is the sequence provided as SEQ ID NO:18, or the equivalent residues from a non-human species, e.g., mouse, rodent, monkey, ape and the like. In a specific CAR of the invention, the primary signaling sequence of CD3-zeta is the sequence as provided in SEQ ID NO:20, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR-expressing-cell, e.g., a CART cell or CAR-expressing NK cell. Examples of immune effector function, e.g., in a CART cell or CAR-expressing NK cell, include cytolytic activity and helper activity, including the secretion of cytokines. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. In an embodiment, the intracellular signaling domain is synthesized or engineered. For example, in the case of a CAR-expressing immune effector cell, e.g., CART cell or CAR-expressing NK cell, a primary intracellular signaling domain can comprise a cytoplasmic sequence of a T cell receptor, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta, CD3 gamma, CD3 delta, CD3 epsilon, CD5, CD22, CD79a, CD79b, CD278 ("ICOS"), FccRI CD66d, DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:18. In one aspect, the "zeta stimulatory domain" or a "CD3-zeta stimulatory domain" is the sequence provided as SEQ ID NO:20. Also encompassed herein are CD3 zeta domains comprising one or more mutations to the amino acid sequences described herein, e.g., SEQ ID NO: 20.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:14 or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" is used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by its promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "humanized" refers to those forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise a significant portion of at least one, and typically two, variable domains, in which all or substantially all of the CDR regions correspond to those of a non-human immunoglobulin and all or substantially all of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The term "fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(Gly-Gly-Gly-Ser)_n$, where n is a positive integer equal to or greater than 1 (SEQ ID NO: 609). For example, n=1, n=2, n=3, n=4, n=5 and n=6, n=7, n=8, n=9 and n=10 (SEQ ID NO: 606). In one embodiment, the flexible polypeptide linkers include, but are not limited to, $(Gly_4\ Ser)_4$ (SEQ ID NO: 27) or $(Gly_4\ Ser)_3$ (SEQ ID NO: 28). In another embodiment, the linkers include multiple repeats of $(Gly_2Ser)$, (GlySer) or $(Gly_3Ser)$ (SEQ ID NO: 29). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 30), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a binding partner (e.g., tumor antigen) protein present in a sample, but which antibody or ligand does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with regulatable intracellular signal generation. In some embodiments, an RCAR comprises at least an extracellular antigen binding domain, a transmembrane and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as "RCARX cell"). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjuction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^{+}$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^{+}$, decreased KLRG1, and increased BCL2;

wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or "relapse" as used herein refers to the return or reappearance of a disease (e.g., cancer) or the signs and symptoms of a disease such as cancer after a period of improvement or responsiveness, e.g., after prior treatment of a therapy, e.g., cancer therapy. The initial period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%. For example, e.g., in the context of B-ALL, the reappearance may involve, e.g., a reappearance of blasts in the blood, bone marrow (>5%), or any extramedullary site, after a complete response. A complete response, in this context, may involve <5% BM blast. More generally, in an embodiment, a response (e.g., complete response or partial response) can involve the absence of detectable MRD (minimal residual disease). In an embodiment, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98%, or 99% identity, and includes subranges such as 96-99%, 96-98%, 96-97%, 97-99%, 97-98%, and 98-99% identity. This applies regardless of the breadth of the range.

Description

Provided herein are compositions and methods for treating a disease such as cancer, by administering a cell comprising a chimeric antigen receptor that targets mesothelin, e.g., mesothelin CAR, in combination with a PD-L1 inhibitor. Exemplary components to generate a mesothelin CAR and a mesothelin CAR-expressing cell are disclosure herein. Exemplary PD-L1 inhibitors are also described herein.

In embodiments, the combination therapy of a mesothelin CAR-expressing cell described herein and a PD-L1 inhibitor described herein results in one or more of the following: improved or increased anti-tumor activity of the mesothelin CAR-expressing cell; increased proliferation or persistence of the mesothelin CAR-expressing cell; improved or increased infiltration of the mesothelin CAR-expressing cell; improved inhibition of tumor progression; delay of tumor progression; inhibition or reduction in cancer cell proliferation; and/or reduction in tumor burden, e.g., tumor volume, or size.

As demonstrated in the examples provided herein, in some embodiments, administration of the PD-L1 inhibitor prior to administration of a mesothelin CAR-expressing cell results in increased therapeutic efficacy, e.g., increased inhibition of tumor progression and/or tumor growth, in some cancers, e.g., as compared to administration of the PD-L1 inhibitor after administration of a mesothelin CAR-expressing cell or administration fo the PD-L1 inhibitor or mesothelin CAR-expressing cell alone.

PD-L1 is known to downregulate the immune response, e.g., anti-tumor immune response. PD-L1 can also be expressed by cancer cells or cancer associated cells, e.g., tumor infiltrating lymphocytes (TILs). Without wishing to be bound by theory, in some embodiments, a subject that is administered the combination therapy described herein, e.g., a mesothelin CAR-expressing cell and a PD-L1 inhibitor, is more likely to have increased anti-tumor activity if the subject has one or more of: a cancer that expresses, e.g., highly expresses, PD-L1; a cancer that is infiltrated by anti-tumor immune cells, e.g., tumor infiltrating lymphocytes (TILs); and/or cancer-associated cells that express, e.g., highly express, PD-L1, as compared to a subject that is not administered the combination therapy, or is administered a mesothelin CAR-expressing cell or PD-L1 inhibitor alone. For example, without wishing to be bound by theory, treatment with a PD-L1 inhibitor prevents or reduces the down-regulation of the anti-tumor immune response, e.g., exhaustion of anti-tumor immune cells, e.g., TILs or mesothelin CAR expressing immune cells, thereby increasing the anti-tumor efficacy.

Mesothelin Chimeric Antigen Receptor (CAR)

The present disclosure encompasses immune effector cells (e.g., T cells or NK cells) comprising a CAR molecule that targets, e.g., specifically binds, to mesothelin (mesothelin CAR). In one embodiment, the immune effector cells are engineered to express the mesothelin CAR. In one embodiment, the immune effector cells comprise a recombinant nucleic acid construct comprising nucleic acid sequences encoding the mesothelin CAR.

In embodiments, the mesothelin CAR comprises an antigen binding domain that specifically binds to mesothelin, e.g., mesothelin binding domain, a transmembrane domain, and an intracellular signaling domain. In one embodiment, the sequence of the antigen binding domain is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

Sequences of non-limiting examples of various components that can be part of a mesothelin CAR molecule described herein, are listed in Table 1, where "aa" stands for amino acids, and "na" stands for nucleic acids that encode the corresponding peptide.

TABLE 1

Sequences of various components of CAR (aa-amino acid sequence, na-nucleic acid sequence)

| SEQ ID NO | Descrip. | Sequence |
|---|---|---|
| 11 | EF-1 promoter (na) | CGTGAGGCTCCGGTGCCCGTCAGTGGGCAGAGCGCACATCGCCCAC AGTCCCCGAGAAGTTGGGGGGAGGGGTCGGCAATTGAACCGGTGCC TAGAGAAGGTGGCGCGGGGTAAACTGGGAAAGTGATGTCGTGTACT GGCTCCGCCTTTTTCCCGAGGGTGGGGGAGAACCGTATATAAGTGC AGTAGTCGCCGTGAACGTTCTTTTTCGCAACGGGTTTGCCGCCAGA ACACAGGTAAGTGCCGTGTGTGGTTCCCGCGGGCCTGGCCTCTTTA CGGGTTATGGCCCTTGCGTGCCTTGAATTACTTCCACCTGGCTGCA GTACGTGATTCTTGATCCCGAGCTTCGGGTTGGAAGTGGGTGGGAG AGTTCGAGGCCTTGCGCTTAAGGAGCCCCTTCGCCTCGTGCTTGAG TTGAGGCCTGGCCTGGGCGCTGGGGCCGCCGCGTGCGAATCTGGTG GCACCTTCGCGCCTGTCTCGCTGCTTTCGATAAGTCTCTAGCCATT TAAAATTTTTGATGACCTGCTGCGACGCTTTTTTTCTGGCAAGATA GTCTTGTAAATGCGGGCCAAGATCTGCACACTGGTATTTCGGTTTT TGGGGCCGCGGGCGGCGACGGGGCCCGTGCGTCCCAGCGCACATGT TCGGCGAGGCGGGGCCTGCGAGCGCGGCCACCGAGAATCGGACGGG GGTAGTCTCAAGCTGGCCGGCCTGCTCTGGTGCCTGGCCTCGCGCC GCCGTGTATCGCCCCGCCCTGGGCGGCAAGGCTGGCCCGGTCGGCA CCAGTTGCGTGAGCGGAAAGATGGCCGCTTCCCGGCCCTGCTGCAG GGAGCTCAAAATGGAGGACGCGGCGCTCGGGAGAGCGGGCGGGTGA GTCACCCACACAAAGGAAAAGGGCCTTTCCGTCCTCAGCCGTCGCT TCATGTGACTCCACGGAGTACCGGGCGCCGTCCAGGCACCTCGATT AGTTCTCGAGCTTTTGGAGTACGTCGTCTTTAGGTTGGGGGGAGGG GTTTTATGCGATGGAGTTTCCCCACACTGAGTGGGTGGAGACTGAA GTTAGGCCAGCTTGGCACTTGATGTAATTCTCCTTGGAATTTGCCC TTTTTGAGTTTGGATCTTGGTTCATTCTCAAGCCTCAGACAGTGGT TCAAAGTTTTTTTCTTCCATTTCAGGTGTCGTGA |

TABLE 1-continued

Sequences of various components of CAR
(aa-amino acid sequence, na-nucleic acid sequence)

| SEQ ID NO | Descrip. | Sequence |
|---|---|---|
| 1 | Leader (aa) | MALPVTALLLPLALLLHAARP |
| 12 | Leader (na) | ATGGCCCTGCCTGTGACAGCCCTGCTGCTGCCTCTGGCTCTGCTGC TGCATGCCGCTAGACCC |
| 2 | CD 8 hinge (aa) | TTTPAPRPPTPAPTIASQPLSLRPEACRPAAGGAVHTRGLDFACD |
| 13 | CD8 hinge (na) | ACCACGACGCCAGCGCCGCGACCACCAACACCGGCGCCCACCATCG CGTCGCAGCCCCTGTCCCTGCGCCCAGAGGCGTGCCGGCCAGCGGC GGGGGGCGCAGTGCACACGAGGGGGCTGGACTTCGCCTGTGAT |
| 3 | Ig4 hinge (aa) | ESKYGPPCPPCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGKM |
| 14 | Ig4 hinge (na) | GAGAGCAAGTACGGCCCTCCCTGCCCCCCTTGCCCTGCCCCCGAGT TCCTGGGCGGACCCAGCGTGTTCCTGTTCCCCCCCAAGCCCAAGGA CACCCTGATGATCAGCCGGACCCCCGAGGTGACCTGTGTGGTGGTG GACGTGTCCCAGGAGGACCCCGAGGTCCAGTTCAACTGGTACGTGG ACGGCGTGGAGGTGCACAACGCCAAGACCAAGCCCCGGGAGGAGCA GTTCAATAGCACCTACCGGGTGGTGTCCGTGCTGACCGTGCTGCAC CAGGACTGGCTGAACGGCAAGGAATACAAGTGTAAGGTGTCCAACA AGGGCCTGCCCAGCAGCATCGAGAAAACCATCAGCAAGGCCAAGGG CCAGCCTCGGGAGCCCCAGGTGTACACCCTGCCCCCTAGCCAAGAG GAGATGACCAAGAACCAGGTGTCCCTGACCTGCCTGGTGAAGGGCT TCTACCCCAGCGACATCGCCGTGGAGTGGGAGAGCAACGGCCAGCC CGAGAACAACTACAAGACCACCCCCCCTGTGCTGGACAGCGACGGC AGCTTCTTCCTGTACAGCCGGCTGACCGTGGACAAGAGCCGGTGGC AGGAGGGCAACGTCTTTAGCTGCTCCGTGATGCACGAGGCCCTGCA CAACCACTACACCCAGAAGAGCCTGAGCCTGTCCCTGGGCAAGATG |
| 4 | IgD hinge (aa) | RWPESPKAQASSVPTAQPQAEGSLAKATTAPATTRNTGRGGEEKKK EKEKEEQEERETKTPECPSHTQPLGVYLLTPAVQDLWLRDKATFTC FVVGSDLKDAHLTWEVAGKVPTGGVEEGLLERHSNGSQSQHSRLTL PRSLWNAGTSVTCTLNHPSLPPQRLMALREPAAQAPVKLSLNLLAS SDPPEAASWLLCEVSGFSPPNILLMWLEDQREVNTSGFAPARPPPQ PGSTTFWAWSVLRVPAPPSPQPATYTCVVSHEDSRTLLNASRSLEV SYVTDH |
| 15 | IgD hinge (na) | AGGTGGCCCGAAAGTCCCAAGGCCCAGGCATCTAGTGTTCCTACTG CACAGCCCCAGGCAGAAGGCAGCCTAGCCAAAGCTACTACTGCACC TGCCACTACGCGCAATACTGGCCGTGGCGGGGAGGAGAAGAAAAAG GAGAAAGAGAAAGAAGAACAGGAAGAGAGGGAGACCAAGACCCCTG AATGTCCATCCCATACCCAGCCGCTGGGCGTCTATCTCTTGACTCC CGCAGTACAGGACTTGTGGCTTAGAGATAAGGCCACCTTTACATGT TTCGTCGTGGGCTCTGACCTGAAGGATGCCCATTTGACTTGGGAGG TTGCCGGAAAGGTACCCACAGGGGGGGTTGAGGAAGGGTTGCTGGA GCGCCATTCCAATGGCTCTCAGAGCCAGCACTCAAGACTCACCCTT CCGAGATCCCTGTGGAACGCCGGGACCTCTGTCACATGTACTCTAA ATCATCCTAGCCTGCCCCCACAGCGTCTGATGGCCCTTAGAGAGCC AGCCGCCCAGGCACCAGTTAAGCTTAGCCTGAATCTGCTCGCCAGT AGTGATCCCCCAGAGGCCGCCAGCTGGCTCTTATGCGAAGTGTCCG GCTTTAGCCCGCCCAACATCTTGCTCATGTGGCTGGAGGACCAGCG AGAAGTGAACACCAGCGGCTTCGCTCCAGCCCGGCCCCCACCCCAG CCGGGTTCTACCACATTCTGGGCCTGGAGTGTCTTAAGGGTCCCAG CACCACCTAGCCCCCAGCCAGCCACATACACCTGTGTTGTGTCCCA TGAAGATAGCAGGACCCTGCTAAATGCTTCTAGGAGTCTGGAGGTT TCCTACGTGACTGACCATT |
| 6 | CD8 Transmembrane (aa) | IYIWAPLAGTCGVLLLSLVITLYC |
| 17 | CD8 Transmembrane (na) | ATCTACATCTGGGCGCCCTTGGCCGGGACTTGTGGGGTCCTTCTCC TGTCACTGGTTATCACCCTTTACTGC |
| 7 | 4-1BB intracellular domain (aa) | KRGRKKLLYIFKQPFMRPVQTTQEEDGCSCRFPEEEEGGCEL |

TABLE 1-continued

| Sequences of various components of CAR (aa-amino acid sequence, na-nucleic acid sequence) | | |
|---|---|---|
| SEQ ID NO | Descrip. | Sequence |
| 18 | 4-1BB intracellular domain (na) | AAACGGGGCAGAAAGAAACTCCTGTATATATTCAAACAACCATTTA TGAGACCAGTACAAACTACTCAAGAGGAAGATGGCTGTAGCTGCCG ATTTCCAGAAGAAGAAGAAGGAGGATGTGAACTG |
| 8 | CD27 (aa) | QRRKYRSNKGESPVEPAEPCRYSCPREEEGSTIPIQEDYRKPEPAC SP |
| 19 | CD27 (na) | AGGAGTAAGAGGAGCAGGCTCCTGCACAGTGACTACATGAACATGA CTCCCCGCCGCCCCGGGCCCACCCGCAAGCATTACCAGCCCTATGC CCCACCACGCGACTTCGCAGCCTATCGCTCC |
| 9 | CD3-zeta (aa) (Q/K mutant) | RVKFSRSADAPAYKQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR |
| 20 | CD3-zeta (na) (Q/K mutant) | AGAGTGAAGTTCAGCAGGAGCGCAGACGCCCCCGCGTACAAGCAGG GCCAGAACCAGCTCTATAACGAGCTCAATCTAGGACGAAGAGAGGA GTACGATGTTTTGGACAAGAGACGTGGCCGGGACCCTGAGATGGGG GGAAAGCCGAGAAGGAAGAACCCTCAGGAAGGCCTGTACAATGAAC TGCAGAAAGATAAGATGGCGGAGGCCTACAGTGAGATTGGGATGAA AGGCGAGCGCCGGAGGGGCAAGGGGCACGATGGCCTTTACCAGGGT CTCAGTACAGCCACCAAGGACACCTACGACGCCCTTCACATGCAGG CCCTGCCCCCTCGC |
| 10 | CD3-zeta (aa) (NCBI Reference Sequence NM_000734.3) | RVKFSRSADAPAYQQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR |
| 21 | CD3-zeta (na) (NCBI Reference Sequence NM_000734.3) | AGAGTGAAGTTCAGCAGGAGCGCAGACGCCCCCGCGTACCAGCAGG GCCAGAACCAGCTCTATAACGAGCTCAATCTAGGACGAAGAGAGGA GTACGATGTTTTGGACAAGAGACGTGGCCGGGACCCTGAGATGGGG GGAAAGCCGAGAAGGAAGAACCCTCAGGAAGGCCTGTACAATGAAC TGCAGAAAGATAAGATGGCGGAGGCCTACAGTGAGATTGGGATGAA AGGCGAGCGCCGGAGGGGCAAGGGGCACGATGGCCTTTACCAGGGT CTCAGTACAGCCACCAAGGACACCTACGACGCCCTTCACATGCAGG CCCTGCCCCCTCGC |
| 36 | CD28 Intracellular domain (amino acid sequence) | RSKRSRLLHSDYMNMTPRRPGPTRKHYQPYAPPRDFAAYRS |
| 37 | CD28 Intracellular domain (nucleotide sequence) | AGGAGTAAGAGGAGCAGGCTCCTGCACAGTGACTACATGAACATGA CTCCCCGCCGCCCCGGGCCCACCCGCAAGCATTACCAGCCCTATGC CCCACCACGCGACTTCGCAGCCTATCGCTCC |
| 38 | ICOS Intracellular domain (amino acid sequence) | TKKKYSSSVHDPNGEYMFMRAVNTAKKSRLTDVTL |
| 607 | ICOS Intracellular domain (nucleotide sequence) | ACAAAAAAGAAGTATTCATCCAGTGTGCACGACCCTAACGGTGAAT ACATGTTCATGAGAGCAGTGAACACAGCCAAAAAATCCAGACTCAC AGATGTGACCCTA |
| 5 | GS hinge/linker (aa) | GGGGSGGGGS |
| 16 | GS hinge/linker (na) | GGTGGCGGAGGTTCTGGAGGTGGAGGTTCC |

TABLE 1-continued

Sequences of various components of CAR (aa-amino acid sequence, na-nucleic acid sequence)

| SEQ ID NO | Descrip. | Sequence |
|---|---|---|
| 608 | GS hinge/linker (na) | GGTGGCGGAGGTTCTGGAGGTGGGGGTTCC |
| 25 | linker | GGGGS |
| 26 | linker | (Gly-Gly-Gly-Gly-Ser)n, where n = 1-6, e.g.,<br>GGGGSGGGGSGGGGSGGGGSGGGGSGGGGS |
| 27 | linker | (Gly4 Ser)4 |
| 28 | linker | (Gly4 Ser)3 |
| 29 | linker | (Gly3Ser) |
| 609 | linker | (Gly-Gly-Gly-Ser)n where n is a positive integer equal to or greater than 1 |
| 606 | linker | (Gly-Gly-Gly-Ser)n, where n =1-10, e.g.,<br>GGGSGGGSGG GSGGGSGGGSGGGSGGGSGG GSGGGSGGGS |
| 610 | linker | GSTSGSGKPGSGEGSTKG |
| 30 | polyA | (A)$_{5000}$<br>This sequence may encompass 50-5000 adenines. |
| 31 | polyT | (T)$_{100}$ |
| 32 | polyT | (T)$_{5000}$<br>This sequence may encompass 50-5000 thymines. |
| 33 | polyA | (A)$_{5000}$<br>This sequence may encompass 100-5000 adenines. |
| 34 | polyA | (A)$_{400}$<br>This sequence may encompass 100-400 adenines. |
| 35 | polyA | (A)$_{2000}$<br>This sequence may encompass 50-2000 adenines. |
| 22 | PD1 CAR (aa) | pgwfldspdrpwnpptfspallvvtegdnatftcsfsntsesfvln<br>wyrmspsnqtdklaafpedrsqpgqdcrfrvtqlpngrdfhmsvvr<br>arrndsgtylcgaislapkaqikeslraelrvterraevptahpsp<br>sprpagqfqtlvtttpaprpptpaptiasqplslrpeacrpaagga<br>vhtrgldfacdiyiwaplagtcgvlllslvitlyckrgrkkllyif<br>kqpfmrpvqttqeedgcscrfpeeeeggcelrvkfsrsadapaykq<br>gqnqlynelnlgrreeydvldkrrgrdpemggkprrknpqeglyne<br>lqkdkmaeayseigmkgerrrgkghdglyqglstatkdtydalhmq<br>alppr |
| 23 | PD-1 CAR (na) (PD1 ECD underlined) | atggccctccctgtcactgccctgcttctccccctcgcactcctgc<br>tccacgccgctagaccacccggatggtttctggactctccggatcg<br>cccgtggaatcccccaaccactcaccggcactcaggttgtgactga<br>gggcgataatgcgaccttcacgtgctcgttctccaacacctccgaa<br>tcattcgtgctgaactggtaccgcatgagcccgtcaaaccagaccg<br>acaagctcgccgcgtttccggaagatcggtcgcaaccgggacagga<br>ttgtcggttccgcgtgactcaactgccgaatggcagagacttccac<br>atgagcgtggtccgcgctaggcgaaacgactccgggacctacctgt<br>gcggagccatctcgctggcgcctaaggcccaaatcaaagagagctt<br>gagggccgaactgagagtgaccgagcgcagagctgaggtgccaact<br>gcacatccatccccatcgcctcggcctgcggggcagtttcagaccc<br>tggtcacgaccactccggcgccgcgcccaccgactccggccccaac<br>tatcgcgagccagcccctgtcgctgaggccggaagcatgccgccct<br>gccgccggaggtgctgtgcatacccggggattggacttcgcatgcg<br>acatctacatttgggctcctctcgccggaacttgtggcgtgctcct<br>tctgtccctggtcatcaccctgtactgcaagcggggtcggaaaaag<br>cttctgtacattttcaagcagcccttcatgaggcccgtgcaaacca<br>cccaggaggaggacggttgctcctgccggttccccgaagaggaaga<br>aggaggttgcgagctgcgcgtgaagttctcccggagcgccgacgcc<br>cccgcctataagcagggccagaaccagctgtacaacgaactgaacc<br>tgggacggcgggaagagtacgatgtgctggacaagcggcgcggccg<br>ggaccccgaaatgggcgggaagcctagaagaaagaaccctcaggaa |

TABLE 1-continued

Sequences of various components of CAR
(aa-amino acid sequence, na-nucleic acid sequence)

| SEQ ID NO | Descrip. | Sequence |
|---|---|---|
| | | ggcctgtataacgagctgcagaaggacaagatggccgaggcctact ccgaaattgggatgaagggagagcggcggaggggaaaggggcacga cggcctgtaccaaggactgtccaccgccaccaaggacacatacgat gccctgcacatgcaggcccttccccctcgc |
| 24 | PD-1 CAR (aa) with signal (PD1 ECD underlined) | Malpvtalllplalllhaarppgwfldspdrpwnpptfspallvvt egdnatftcsfsntsesfvlnwyrmspsnqtdklaafpedrsqpgq dcrfrvtqlpngrdfhmsvvrarrndsgtylcgaislapkaqikes lraelrvterraevptahpspsprpagqfqtlvtttpaprpptpap tiasqplslrpeacrpaaggavhtrgldfacdiyiwaplagtcgvl llslvitlyckrgrkkllyiflcqpfmrpvqttqeedgcscrfpee eeggcelrvkfsrsadapaykqgqnqlynelnlgrreeydvldkag rdpemggkprrknpqeglynelqkdkmaeayseigmkgeragkghd glyqglstatkdtydalhmqalppr |

In one aspect, an exemplary CAR constructs comprise an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

In one aspect, the mesothelin CARs of the invention comprise at least one intracellular signaling domain selected from the group of a CD137 (4-1BB) signaling domain, a CD28 signaling domain, a CD27 signaling domain, an ICOS signaling domain, a CD3zeta signal domain, and any combination thereof. In one aspect, the CARs of the invention comprise at least one intracellular signaling domain is from one or more costimulatory molecule(s) selected from CD137 (4-1BB), CD28, CD27, or ICOS.

Antigen Binding Domain

In one aspect, the CAR of the invention comprises a target-specific binding element otherwise referred to as an antigen binding domain. In one embodiment, the portion of the CAR comprising the antigen binding domain comprises an antigen binding domain that targets, e.g., specifically binds to, mesothelin. In one embodiment, the antigen binding domain targets, e.g., specifically binds to, human mesothelin.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as an antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. Thus, in one aspect, the antigen binding domain comprises a human antibody or an antibody fragment.

In one embodiment, the mesothelin binding domain comprises one or more (e.g., all three) light chain complementary determining region 1 (LC CDR1), light chain complementary determining region 2 (LC CDR2), and light chain complementary determining region 3 (LC CDR3) of a mesothelin binding domain selected from SEQ ID NOS: 39-62 and one or more (e.g., all three) heavy chain complementary determining region 1 (HC CDR1), heavy chain complementary determining region 2 (HC CDR2), and heavy chain complementary determining region 3 (HC CDR3) of a mesothelin binding domain selected from SEQ ID NOS: 39-62. In one embodiment, the mesothelin binding domain comprises a light chain variable region described herein (e.g., in Table 2) and/or a heavy chain variable region described herein (e.g., in Table 2). In one embodiment, the mesothelin binding domain is a scFv comprising a light chain variable region and a heavy chain variable region of an amino acid sequence of Table 2. In an embodiment, the mesothelin binding domain (e.g., an scFV) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 2, or a sequence with 95-99% identity to an amino acid sequence of Table 2; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 2, or a sequence with 95-99% identity to an amino acid sequence of Table 2.

In one embodiment, the mesothelin binding domain comprises a light chain variable region comprising an amino acid sequence described herein, e.g., in Table 2 or 3, is attached to a heavy chain variable region comprising an amino acid sequence described herein, e.g., in Table 2 or 3, via a linker, e.g., a linker described herein. In one embodiment, the humanized anti-mesothelin binding domain includes a (Gly4-Ser)n linker (SEQ ID NO: 26), wherein n is 1, 2, 3, 4, 5, or 6, preferably 3 or 4. The light chain variable region and heavy chain variable region of a scFv can be, e.g., in any of the following orientations: light chain variable region-linker-heavy chain variable region or heavy chain variable region-linker-light chain variable region.

In another embodiment, the mesothelin binding domain comprises any antibody or antibody fragment thereof known in the art that binds to mesothelin. Examples of other anti-mesothelin antibodies or antibody fragment thereof known in the art include those described in WO2009/120769 (e.g., antibody m912, whose light and heavy chain amino acid sequences are SEQ ID NO: 1 and SEQ ID NO: 2 of WO2009/120769); U.S. Pat. No. 6,083,502, US Patent Publication No. US2008/0261245, WO2009/068204, WO2010/111282, WO2014/004549, and U.S. Patent Publication No. US2015/0274836.

In one aspect, the antibodies of the invention may exist in a variety of other forms including, for example, Fab, Fab', $F(ab')_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide brudge at the hinge region, and an isolated CDR or other epitope binding fragments of an antibody. In one aspect, the antibody fragment provided herein is a scFv. In some instances, a human scFv may also be derived from a yeast display library.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together, e.g., using flexible polypeptide linkers. The scFv molecules can comprise a linker (e.g., a Ser-Gly linker) with an optimized length and/or amino acid composition. The linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_n$, where n is a positive integer equal to or greater than 1. (SEQ ID NO: 135) In one embodiment, the linker can be $(Gly_4Ser)_4$ (SEQ ID NO: 27) or $(Gly_4Ser)_3$ (SEQ ID NO: 28). Variation in the linker length may retain or enhance activity, giving rise to superior efficacy in activity studies.

Exemplary Mesothelin Antigen Binding Domains and CAR Constructs

Exemplary mesothelin CAR constructs disclosed herein comprise a scFv (e.g., a human scFv) as disclosed in Table 2 or 3 herein, optionally preceded with an optional leader sequence (e.g., SEQ ID NO:1 and SEQ ID NO:12 for exemplary leader amino acid and nucleotide sequences, respectively). The sequences of the scFv fragments (amino acid sequences of SEQ ID NOs: 39-62) are provided herein in Table 2. The mesothelin CAR construct can further include an optional hinge domain, e.g., a CD8 hinge domain (e.g., including the amino acid sequence of SEQ ID NO: 2 or encoded by a nucleic acid sequence of SEQ ID NO:13); a transmembrane domain, e.g., a CD8 transmembrane domain (e.g., including the amino acid sequence of SEQ ID NO: 6 or encoded by the nucleotide sequence of SEQ ID NO: 17); an intracellular domain, e.g., a 4-1BB intracellular domain (e.g., including the amino acid sequence of SEQ ID NO: 7 or encoded by the nucleotide sequence of SEQ ID NO: 18; and a functional signaling domain, e.g., a CD3 zeta domain (e.g., including amino acid sequence of SEQ ID NO: 9 or 10, or encoded by the nucleotide sequence of SEQ ID NO: 20 or 21). In certain embodiments, the domains are contiguous with and in the same reading frame to form a single fusion protein. In other embodiments, the domain are in separate polypeptides, e.g., as in an RCAR molecule as described herein.

In certain embodiments, the full length mesothelin CAR molecule includes the amino acid sequence of, or is encoded by the nucleotide sequence of, M1, M2, M3, M4, M5, M6, M7, M8, M9, M10, M11, M12, M13, M14, M15, M16, M17, M18, M19, M20, M21, M22, M23, M24, or ss1, provided in Table 2 or 3, or a sequence substantially identical (e.g., 95-99% identical thereto, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes the scFv amino acid sequence of, or is encoded by the nucleotide sequence of, M1, M2, M3, M4, M5, M6, M7, M8, M9, M10, M11, M12, M13, M14, M15, M16, M17, M18, M19, M20, M21, M22, M23, M24, or ss1, provided in Table 2 or 3, or a sequence substantially identical (e.g., 95-99% identical thereto, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes the heavy chain variable region and/or the light chain variable region of M1, M2, M3, M4, M5, M6, M7, M8, M9, M10, M11, M12, M13, M14, M15, M16, M17, M18, M19, M20, M21, M22, M23, M24, or ss1, provided in Table 2, or a sequence substantially identical (e.g., 95-99% identical, or up to 20, 15, 10, 8, 6, 5, 4, 3, 2, or 1 amino acid changes) to any of the aforesaid sequences.

In certain embodiments, the mesothelin CAR molecule, or the mesothelin antigen binding domain, includes one, two or three CDRs from the heavy chain variable region (e.g., HCDR1, HCDR2 and/or HCDR3) of M1, M2, M3, M4, M5, M6, M7, M8, M9, M10, M11, M12, M13, M14, M15, M16, M17, M18, M19, M20, M21, M22, M23, M24, or ss1, provided in Table 4; and/or one, two or three CDRs from the light chain variable region (e.g., LCDR1, LCDR2 and/or LCDR3) of M1, M2, M3, M4, M5, M6, M7, M8, M9, M10, M11, M12, M13, M14, M15, M16, M17, M18, M19, M20, M21, M22, M23, M24, or ss1, provided in Table 5; or a sequence substantially identical (e.g., 95-99% identical, or up to 5, 4, 3, 2, or 1 amino acid changes) to any of the aforesaid sequences.

The sequences of CDR sequences of the scFv domains are shown in Table 4 for the heavy chain variable domains and in Table 5 for the light chain variable domains.

TABLE 4

Amino acid sequences for the heavy chain (HC) CDR1, CDR2, and CDR3 regions of human anti-mesothelin scFvs

| Descrip. | HC-CDR1 | SEQ ID NO: | HC-CDR2 | SEQ ID NO: | HC-CDR3 | SEQ ID NO: |
|---|---|---|---|---|---|---|
| M1 | GYTFTGYYMH | 136 | RINPNSGGTNYAQKFQG | 155 | GRYYGMDV | 175 |
| M2 | GYTFTGYYMH | 136 | WINPNSGGTNYAQKFQG | 156 | DLRRTVVTPRAYYGMDV | 176 |
| M3 | GYTFTGYYMH | 136 | WINPNSGGTNYAQKFQG | 156 | GEWDGSYYYDY | 177 |
| M4 | GFTFSSYWMH | 137 | RINTDGSTTTYADSVEG | 157 | GHWAV | 178 |
| M5 | GYTFTDYYMH | 138 | WINPNSGGTNYAQKFQG | 156 | GWDFDY | 179 |
| M6 | GYTFTSYYMH | 139 | IINPSGGSTSYAQKFQ | 158 | YRLIAVAGDYYYYGMDV | 180 |
| M7 | GFTFSSYAMH | 140 | VISYDGSNKYYADSVKG | 274 | WKVSSSSPAFDY | 181 |
| M8 | GYPFTGYSLH | 141 | WINPNSGGTNYAQKFQG | 159 | DHYGGNSLFY | 182 |
| M9 | GYTFTSYYMH | 142 | IINPSGGSTGYAQKFQG | 160 | GGYSSSSDAFDI | 183 |
| M10 | GYTFTSYGIS | 143 | WISAYNGNTNYAQKLQ | 161 | VAGGIYYYYGMDV | 184 |
| M11 | GYTFTGYYMH | 144 | WINPNSGGTNYAQNFQG | 162 | GWDFDY | 185 |
| M12 | GYTFTGYYMH | 144 | RINPNSGGTNYAQKFQG | 163 | TTTSYAFDI | 186 |
| M13 | GFIFSDYYMG | 145 | YIGRSGSSMYYADSVKG | 164 | SPVVAATEDFQH | 187 |
| M14 | GFTFRGYYIH | 146 | IINPSGGSRAYAQKFQG | 165 | TASCGGDCYYLDY | 188 |
| M15 | GFTFDDYAMH | 147 | GISWNSGSIGYADSVK | 166 | DGSSSWSWGYFDY | 189 |
| M16 | GFTFDDYAMH | 147 | GISWNSGSTGYADSVKG | 167 | DSSSWYGGGSAFDI | 190 |
| M17 | GFTFDDYAMH | 147 | GISWNSGSTGYADSVKG | 167 | DSSSWYGGGSAFDI | 191 |
| M18 | GFTFSSYWMH | 148 | RINSDGSSTSYADSVKG | 168 | TGWVGSYYYYMDV | 192 |
| M19 | GFTFSSYGMH | 149 | VISYDGSNKYYADSVKG | 169 | GYSRYYYYGMDV | 193 |
| M20 | GFTFSSYAMS | 150 | AISGSGGSTYYADSVKG | 170 | REAAAGHDWYFDL | 194 |
| M21 | GYTFTSYYMH | 151 | IINPSGGSTSYAQKFQG | 171 | SPRVTTGYFDY | 195 |
| M22 | GDTSTRHYIH | 152 | VINPTTGPATGSPAYAQMLQG | 172 | SVVGRSAPYYFDY | 196 |
| M23 | GYTFTNYYMH | 153 | IINPSGGYTTYAQKFQG | 173 | IRSCGGDCYYFDN | 197 |
| M24 | GFSLSTAGVHVG | 154 | LISWADDKRYRPSLRS | 174 | QGFDGYEAN | 198 |
| Ss1 | GYSFTGYTMN | 281 | LITPYNGASSYNQKFRG | 282 | GGYDGRGFDY | 283 |

TABLE 5

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M1 | RASQSVSSNFA | 199 | DASNRAT | 223 | HQRSNWLYT | 247 |
| M2 | QASQDISNSLN | 200 | DASTLET | 224 | QQHDNLPLT | 248 |
| M3 | RASQSINTYLN | 201 | AASSLQS | 225 | QQSFSPLT | 249 |
| M4 | RASQSISDRLA | 202 | KASSLES | 226 | QQYGHLPMYT | 250 |
| M5 | RASQSIRYYLS | 203 | TASILQN | 227 | LQTYTTPD | 251 |
| M6 | RASQGVGRWLA | 204 | AASTLQS | 228 | QQANSFPLT | 252 |
| M7 | RASQSVYTKYLG | 205 | DASTRAT | 229 | QHYGGSPLIT | 253 |

TABLE 5-continued

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M8 | RASQDSGTWLA | 206 | DASTLED | 230 | QQYNSYPLT | 254 |
| M9 | RASQDISSALA | 207 | DASSLES | 231 | QQFSSYPLT | 255 |
| M10 | KSSHSVLYNRNNKNYLA | 208 | WASTRKS | 232 | QQTQTFPLT | 256 |
| M11 | RASQSIRYYLS | 209 | TASILQN | 233 | LQTYTTPD | 257 |
| M12 | RASQSISTWLA | 210 | KASTLES | 234 | QQYNTYSPYT | 258 |
| M13 | RASQSVTSNYLA | 211 | GASTRAT | 235 | QQYGSAPVT | 259 |
| M14 | RASENVNIWLA | 212 | KSSSLAS | 236 | QQYQSYPLT | 260 |
| M15 | QGDALRSYYAS | 213 | GKNNRPS | 237 | NSRDSSGYPV | 261 |
| M16 | QGDSLRSYYAS | 214 | GRSRRPS | 238 | NSRDNTANHYV | 262 |
| M17 | QGDSLRSYYAS | 215 | GKNNRPS | 239 | NSRGSSGNHYV | 263 |
| M18 | RASQSVSSNYLA | 216 | DVSTRAT | 240 | QQRSNWPPWT | 264 |
| M19 | RASQSVYTKYLG | 217 | DASTRAT | 241 | QHYGGSPLIT | 265 |
| M20 | RASQSISSYLN | 218 | AASSLQS | 242 | QQSYSIPLT | 266 |
| M21 | RASQSISSWLA | 219 | KASSLES | 243 | QQYSSYPLT | 267 |
| M22 | RASQGISDYS | 220 | AASTLQS | 244 | QQYYSYPLT | 268 |
| M23 | RASENVNIWLA | 221 | KSSSLAS | 245 | QQYQSYPLT | 269 |
| M24 | RASRGISSALA | 222 | DASSLES | 246 | QQSYSTPWT | 270 |
| Ssl | SASSSVSYMH | 284 | DTSKLAS | 285 | QQWSGYPLT | 286 |

The amino acid and nucleic acid sequences of the mesothelin scFv domains and mesothelin CAR molecules are provided in Table 2 (amino acid sequences) and Table 3 (nucleic acid sequences). In one embodiment, the mesothelin CAR molecule includes a leader sequence described herein, e.g., as underlined in the sequences provided in Table 2. In one embodiment, the mesothelin CAR molecule does not include a leader sequence.

TABLE 2

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LCCDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| 39 | M1 (ScFv domain) | QVQLQQSGAEVKKPGASVKVSCKASGYTFTGYYMHWVRQ APGQGLEWMGRINPNSGGTNYAQKFQGRVTMTRDTSISTAYMELSRLRSEDTAVYYCARG RYYGMDVWGQGTMVTVSSGGGGSGGGGSGGGGSGGGGSEIVLTQSPATLSLSPGERATIS CRASQSVSSNFAWYQQRPGQAPRLLIYDASNRATGIPPRFSGSGSGTDFTLTISSLEPED FAAYYCHQRSNWLYTFGQGTKVDIK |
| 63 | M1 (full) >ZA53-27BC (M1 ZA53-27BC R001-A11 126161) | **MALPVTALLLPLALLLHAARP**QVQLQQSGAEVKKPGASVKVSCKASGYTFTGYYMHWVRQ APGQGLEWMGRINPNSGGTNYAQKFQGRVTMTRDTSISTAYMELSRLRSEDTAVYYCARG RYYGMDVWGQGTMVTVSSGGGGSGGGGSGGGGSGGGGSEIVLTQSPATLSLSPGERATIS CRASQSVSSNFAWYQQRPGQAPRLLIYDASNRATGIPPRFSGSGSGTDFTLTISSLEPED FAAYYCHQRSNWLYTFGQGTKVDIKTTTPAPRPPTPAPTIASQPLSLRPEACRPAAGGAV HTRGLDFACDIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVLDKRRGRDPE MGGKPRRKNPQEGLYNELQKDKMAEAYSEIGMKGERRRGKGHDGLYQGLSTATKDTYDAL HMQALPPR |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LCCDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| 40 | M2 (ScFv domain) | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDLRRTVVTPRAYYGMDVWGQGTTVTVSSGGGGSGGGGSGGGGSGGGGSDIQLTQSPSTLSASVGDRVTITCQASQDISNSLNWYQQKAGKAPKLLIYDASTLETGVPSRFSGSGSGTDFSFTISSLQPEDIATYYCQQHDNLPLTFGQGTKVEIK |
| 64 | M2 (full) >FA56-26RC (M2 FA56-26RC R001-A10 126162) | **MALPVTALLLPLALLLHAARP**QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDLRRTVVTPRAYYGMDVWGQGTTVTVSSGGGGSGGGGSGGGGSGGGGSDIQLTQSPSTLSASVGDRVTITCQASQDISNSLNWYQQKAGKAPKLLIYDASTLETGVPSRFSGSGSGTDFSFTISSLQPEDIATYYCQQHDNLPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCREPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 41 | M3 (ScFv domain) | QVQLVQSGAEVKKPGAPVKVSCKASGYTFTGYYMHWVRQAPGQGLEWMGWINPNSGGTNYAQKFQGRVTMTRDTSISTAYMELSRLRSDDTAVYYCARGEWDGSYYYDYWGQGTLVTVSSGGGGSGGGGSGGGGSGGGGSDIVLTQTPSSLSASVGDRVTITCRASQSINTYLNWYQHKPGKAPKLLIYAASSLQSGVPSRFSGSGSGTDFTLTISSLQPEDFATYYCQQSFSPLTFGGGTKLEIK |
| 65 | M3 >VA58-21LC (M3 VA58-21LC R001-A1 126163) | **MALPVTALLLPLALLLHAARP**QVQLVQSGAEVKKPGAPVKVSCKASGYTFTGYYMHWVRQAPGQGLEWMGWINPNSGGTNYAQKFQGRVTMTRDTSISTAYMELSRLRSDDTAVYYCARGEWDGSYYYDYWGQGTLVTVSSGGGGSGGGGSGGGGSGGGGSDIVLTQTPSSLSASVGDRVTITCRASQSINTYLNWYQHKPGKAPKLLIYAASSLQSGVPSRFSGSGSGTDFTLTISSLQPEDFATYYCQQSFSPLTFGGGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCREPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 42 | M4 (ScFv domain) | QVQLVESGGGLVQPGGSLRLSCAASGFTFSSYWMHWVRQVPGKGLVWVSRINTDGSTTTYADSVEGRFTISRDNAKNTLYLQMNSLRDDDTAVYYCVGGHWAVWGQGTTVTVSSGGGGSGGGGSGGGGSGGGGSDIQMTQSPSTLSASVGDRVTITCRASQSISDRLAWYQQKPGKAPKLLIYKASSLESGVPSRFSGSGSGTEFTLTISSLQPDDFAVYYCQQYGHLPMYTFGQGTKVEIK |
| 66 | M4 >DP37-07IC (M4 DP37-07IC R001-C6 126164) | **MALPVTALLLPLALLLHAARP**QVQLVESGGGLVQPGGSLRLSCAASGFTFSSYWMHWVRQVPGKGLVWVSRINTDGSTTTYADSVEGRFTISRDNAKNTLYLQMNSLRDDDTAVYYCVGGHWAVWGQGTTVTVSSGGGGSGGGGSGGGGSGGGGSDIQMTQSPSTLSASVGDRVTITCRASQSISDRLAWYQQKPGKAPKLLIYKASSLESGVPSRFSGSGSGTEFTLTISSLQPDDFAVYYCQQYGHLPMYTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCREPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 43 | M5 (ScFv domain) | QVQLVQSGAEVEKPGASVKVSCKASGYTFTDYYMHWVRQAPGQGLEWMGWINPNSGGTNYAQKFQGRVTMTRDTSISTAYMELSRLRSDDTAVYYCASGWDFDYWGQGTLVTVSSGGGGSGGGGSGGGGSGGGGSDIVMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIK |
| 67 | M5 >XP31-20LC (M5 XP31-20LC R001-B4 126165) | **MALPVTALLLPLALLLHAARP**QVQLVQSGAEVEKPGASVKVSCKASGYTFTDYYMHWVRQAPGQGLEWMGWINPNSGGTNYAQKFQGRVTMTRDTSISTAYMELSRLRSDDTAVYYCASGWDFDYWGQGTLVTVSSGGGGSGGGGSGGGGSGGGGSDIVMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCREPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 44 | M6 (ScFv domain) | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARYRLIAVAGDYYYYGMDVWGQGTMVTVSSGGGGSGGGGSGGGGSGGGGSDIQMTQSPSSVSASVGDRVTITCRASQGVGRWLAWYQQKPGTAPKLLIYAASTLQSGVPSRFSGSGSGTDFTLTINNLQPEDFATYYCQQANSFPLTFGGGTRLEIK |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LCCDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| 68 | M6 >FE10-06ID (M6 46FE10-06ID R001-A4 126166) | **MALPVTALLLPLALLLHAARP**QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARYRLIAVAGDYYYYGMDVWGQGTMVTVSSGGGGSGGGGSGGGGSGGGGSDIQMTQSPSSVSASVGDRVTITCRASQGVGRWLAWYQQKPGTAPKLLIYAASTLQSGVPSRFSGSGSGTDFTLTINNLQPEDFATYYCQQANSFPLTFGGGTRLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 45 | M7 (ScFv domain) | QVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARWKVSSSSPAFDYWGQGTLVTVSSGGGGSGGGGSGGGGSGGGGSEIVLTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTRLEIK |
| 69 | M7 >VE12-01CD (M7 VE12-01CD R001-A5 126167) | **MALPVTALLLPLALLLHAARP**QVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARWKVSSSSPAFDYWGQGTLVTVSSGGGGSGGGGSGGGGSGGGGSEIVLTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTRLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 46 | M8 (ScFv domain) | QVQLQQSGAEVKKPGASVKVSCKTSGYPFTGYSLHWVRQAPGQGLEWMGWINPNSGGTNYAQKFQGRVTMTRDTSISTAYMELSRLRSDDTAVYYCARDHYGGNSLFYWGQGTLVTVSSGGGGSGGGGSGGGGSGGGGSDIQLTQSPSSISASVGDTVSITCRASQDSGTWLAWYQQKPGKAPNLLMYDASTLEDGVPSRFSGSASGTEFTLTVNRLQPEDSATYYCQQYNSYPLTFGGGTKVDIK |
| 70 | M8 >LE13-05XD (M8 LE13-05XD R001-E5 126168) | **MALPVTALLLPLALLLHAARP**QVQLQQSGAEVKKPGASVKVSCKTSGYPFTGYSLHWVRQAPGQGLEWMGWINPNSGGTNYAQKFQGRVTMTRDTSISTAYMELSRLRSDDTAVYYCARDHYGGNSLFYWGQGTLVTVSSGGGGSGGGGSGGGGSGGGGSDIQLTQSPSSISASVGDTVSITCRASQDSGTWLAWYQQKPGKAPNLLMYDASTLEDGVPSRFSGSASGTEFTLTVNRLQPEDSATYYCQQYNSYPLTFGGGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 47 | M9 (ScFv domain) | QVQLVQSGAEVKKPGASVEVSCKASGYTFTSYYMHWVRQAPGQGLEWMGIINPSGGSTGYAQKFQGRVTMTRDTSTSTVHMELSSLRSEDTAVYYCARGGYSSSSDAFDIWGQGTMVTVSSGGGGSGGGGSGGGGSGGGGSDIQMTQSPPSLSASVGDRVTITCRASQDISSALAWYQQKPGTPPKLLIYDASSLESGVPSRFSGSGSGTDFTLTISSLQPEDFATYYCQQFSSYPLTFGGGTRLEIK |
| 71 | M9 >BE15-00SD (M9 BE15-00SD R001-A3 126169) | **MALPVTALLLPLALLLHAARP**QVQLVQSGAEVKKPGASVEVSCKASGYTFTSYYMHWVRQAPGQGLEWMGIINPSGGSTGYAQKFQGRVTMTRDTSTSTVHMELSSLRSEDTAVYYCARGGYSSSSDAFDIWGQGTMVTVSSGGGGSGGGGSGGGGSGGGGSDIQMTQSPPSLSASVGDRVTITCRASQDISSALAWYQQKPGTPPKLLIYDASSLESGVPSRFSGSGSGTDFTLTISSLQPEDFATYYCQQFSSYPLTFGGGTRLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 48 | M10 (ScFv domain) | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARVAGGIYYYYGMDVWGQGTTITVSSGGGGSGGGGSGGGGSGGGGSDIVMTQTPDSLAVSLGERATISCKSSHSVLYNRNNKNYLAWYQQKPGQPPKLLFYWASTRKSGVPDRFSGSGSGTDFTLTISSLQPEDFATYFCQQTQTFPLTFGQGTRLEIN |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LCCDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| 72 | M10 >RE16-05MD (M10 RE16-05MD R001-D10 126170) | **MALPVTALLLPLALLLHAARP**QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARVAGGIYYYYGMDVWGQGTTITVSSGGGGSGGGGSGGGGSGGGGSDIVMTQTPDSLAVSLGERATISCKSSHSVLYNRNNKNYLAWYQQKPGQPPKLLFYWASTRKSGVPDRFSGSGSGTDFTLTISSLQPEDFATYFCQQTQTFPLTFGQGTRLEINTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 49 | M11 (ScFv domain) | QVQLQQSGAEVKKPGASVKVSCKASGYTFTGYYMHWVRQAPGQGLEWMGWINPNSGGTNYAQNFQGRVTMTRDTSISTAYMELRRLRSDDTAVYYCASGWDFDYWGQGTLVTVSSGGGGSGGGGSGGGGSGGGGSDIRMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIK |
| 73 | M11 >NE10-19WD (M11 NE10-19WD R001-G2 126171) | **MALPVTALLLPLALLLHAARP**QVQLQQSGAEVKKPGASVKVSCKASGYTFTGYYMHWVRQAPGQGLEWMGWINPNSGGTNYAQNFQGRVTMTRDTSISTAYMELRRLRSDDTAVYYCASGWDFDYWGQGTLVTVSSGGGGSGGGGSGGGGSGGGGSDIRMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 50 | M12 (ScFv domain) | QVQLVQSGAEVKKPGASVKVSCKASGYTFTGYYMHWVRQAPGQGLEWMGRINPNSGGTNYAQKFQGRVTMTTDTSTSTAYMELRSLRSDDTAVYYCARTTTSYAFDIWGQGTMVTVSSGGGGSGGGGSGGGGSGGGGSDIQLTQSPSTLSASVGDRVTITCRASQSISTWLAWYQQKPGKAPNLLIYKASTLESGVPSRFSGSGSGTEFTLTISSLQPDDFATYYCQQYNTYSPYTFGQGTKLEIK |
| 74 | M12 >DE12-14RD (M12 DE12-14RD R001-G9 126172) | **MALPVTALLLPLALLLHAARP**QVQLVQSGAEVKKPGASVKVSCKASGYTFTGYYMHWVRQAPGQGLEWMGRINPNSGGTNYAQKFQGRVTMTTDTSTSTAYMELRSLRSDDTAVYYCARTTTSYAFDIWGQGTMVTVSSGGGGSGGGGSGGGGSGGGGSDIQLTQSPSTLSASVGDRVTITCRASQSISTWLAWYQQKPGKAPNLLIYKASTLESGVPSRFSGSGSGTEFTLTISSLQPDDFATYYCQQYNTYSPYTFGQGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 51 | M13 (ScFv domain) | QVQLVQSGGGLVKPGGSLRLSCEASGFIFSDYYMGWIRQAPGKGLEWVSYIGRSGSSMYYADSVKGRFTFSRDNAKNSLYLQMNSLRAEDTAVYYCAASPVVAATEDFQHWGQGTLVTVSSGGGGSGGGGSGGGGSGGGGSDIVMTQTPATLSLSPGERATLSCRASQSVTSNYLAWYQQKPGQAPRLLLFGASTRATGIPDRFSGSGSGTDFTLTINRLEPEDFAMYYCQQYGSAPVTFGQGTKLEIK |
| 75 | M13 >TE13-19LD (M13 TE13-19LD R002-C3 126173) | **MALPVTALLLPLALLLHAARP**QVQLVQSGGGLVKPGGSLRLSCEASGFIFSDYYMGWIRQAPGKGLEWVSYIGRSGSSMYYADSVKGRFTFSRDNAKNSLYLQMNSLRAEDTAVYYCAASPVVAATEDFQHWGQGTLVTVSSGGGGSGGGGSGGGGSGGGGSDIVMTQTPATLSLSPGERATLSCRASQSVTSNYLAWYQQKPGQAPRLLLFGASTRATGIPDRFSGSGSGTDFTLTINRLEPEDFAMYYCQQYGSAPVTFGQGTKLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 52 | M14 (ScFv domain) | QVQLVQSGAEVRAPGASVKISCKASGFTFRGYYIHWVRQAPGQGLEWMGIINPSGGSRAYAQKFQGRVTMTRDTSTSTVYMELSSLRSDDTAMYYCARTASCGGDCYYLDYWGQGTLVTVSSGGGGSGGGGSGGGGSGGGGSDIQMTQSPPTLSASVGDRVTITCRASENVNIWLAWYQQKPGKAPKLLIYKSSSLASGVPSRFSGSGSGAEFTLTISSLQPDDFATYYCQQYQSYPLTFGGGTKVDIK |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LCCDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| 76 | M14 >BS83-95ID (M14 BS83-95ID R001-E8 126174) | **MALPVTALLLPLALLLHAARP**QVQLVQSGAEVRAPGASVKISCKASGFTFRGYYIHWVRQ APGQGLEWMGIINPSGGSRAYAQKFQGRVTMTRDTSTSTVYMELSSLRSDDTAMYYCART ASCGGDCYYLDYWGQGTLVTVSSGGGGSGGGGSGGGGSGGGGSDIQMTQSPPTLSASVGD RVTITCRASENVNIWLAWYQQKPGKAPKLLIYKSSSLASGVPSRFSGSGSGAEFTLTISS LQPDDFATYYCQQYQSYPLTFGGGTKVDIKTTTPAPRPPTPAPTIASQPLSLRPEACRPA AGGAVHTRGLDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRREEYDVLDKRR GRDPEMGGKPRRKNPQEGLYNELQKDKMAEAYSEIGMKGERRRGKGHDGLYQGLSTATKD TYDALHMQALPPR |
| 53 | M15 (ScFv domain) | QVQLVQSGGGLVQPGRSLRLSCAASGFTFDDYAMHWVRQ APGKGLEWVSGISWNSGSIGYADSVKGRFTISRDNAKNSLYLQMNSLRAEDTAVYYCAKD GSSSWSWGYFDYWGQGTLVTVSSGGGGSGGGGSGGGGSSSELTQDPAVSVALGQTVRTTC QGDALRSYYASWYQQKPGQAPMLVIYGKNNRPSGIPDRFSGSDSGDTASLTITGAQAEDE ADYYCNSRDSSGYPVFGTGTKVTVL |
| 77 | M15 >HS86-94XD (M15 HS86-94XD NT 127553) | **MALPVTALLLPLALLLHAARP**QVQLVQSGGGLVQPGRSLRLSCAASGFTFDDYAMHWVRQ APGKGLEWVSGISWNSGSIGYADSVKGRFTISRDNAKNSLYLQMNSLRAEDTAVYYCAKD GSSSWSWGYFDYWGQGTLVTVSSGGGGSGGGGSGGGGSSSELTQDPAVSVALGQTVRTTC QGDALRSYYASWYQQKPGQAPMLVIYGKNNRPSGIPDRFSGSDSGDTASLTITGAQAEDE ADYYCNSRDSSGYPVFGTGTKVTVLTTTPAPRPPTPAPTIASQPLSLRPEACRPAAGGAV HTRGLDFACDIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVLDKRRGRDPE MGGKPRRKNPQEGLYNELQKDKMAEAYSEIGMKGERRRGKGHDGLYQGLSTATKDTYDAL HMQALPPR |
| 54 | M16 (ScFv domain) | EVQLVESGGGLVQPGRSLRLSCAASGFTFDDYAMHWVRQ APGKGLEWVSGISWNSGSTGYADSVKGRFTISRDNAKNSLYLQMNSLRAEDTALYYCAKD SSSWYGGGSAFDIWGQGTMVTVSSGGGGSGGGGSGGGGSSSELTQEPAVSVALGQTVRIT CQGDSLRSYYASWYQQKPGQAPVLVIFGRSRRPSGIPDRFSGSSSGNTASLIITGAQAED EADYYCNSRDNTANHYVFGTGTKLTVL |
| 78 | M16 >XS87-99RD (M16 XS87-99RD NT 127554) | **MALPVTALLLPLALLLHAARP**EVQLVESGGGLVQPGRSLRLSCAASGFTFDDYAMHWVRQ APGKGLEWVSGISWNSGSTGYADSVKGRFTISRDNAKNSLYLQMNSLRAEDTALYYCAKD SSSWYGGGSAFDIWGQGTMVTVSSGGGGSGGGGSGGGGSSSELTQEPAVSVALGQTVRIT CQGDSLRSYYASWYQQKPGQAPVLVIFGRSRRPSGIPDRFSGSSSGNTASLIITGAQAED EADYYCNSRDNTANHYVFGTGTKLTVLTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 55 | M17 (ScFv domain) | EVQLVESGGGLVQPGRSLRLSCAASGFTFDDYAMHWVRQ APGKGLEWVSGISWNSGSTGYADSVKGRFTISRDNAKNSLYLQMNSLRAEDTALYYCAKD SSSWYGGGSAFDIWGQGTMVTVSSGGGGSGGGGSGGGGSSSELTQDPAVSVALGQTVRIT CQGDSLRSYYASWYQQKPGQAPVLVIYGKNNRPSGIPDRFSGSSSGNTASLTITGAQAED EADYYCNSRGSSGNHYVFGTGTKVTVL |
| 79 | M17 >NS89-94MD (M17 N589-94MD NT 127555) | **MALPVTALLLPLALLLHAARP**EVQLVESGGGLVQPGRSLRLSCAASGFTFDDYAMHWVRQ APGKGLEWVSGISWNSGSTGYADSVKGRFTISRDNAKNSLYLQMNSLRAEDTALYYCAKD SSSWYGGGSAFDIWGQGTMVTVSSGGGGSGGGGSGGGGSSSELTQDPAVSVALGQTVRIT CQGDSLRSYYASWYQQKPGQAPVLVIYGKNNRPSGIPDRFSGSSSGNTASLTITGAQAED EADYYCNSRGSSGNHYVFGTGTKVTVLTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 56 | M18 (ScFv domain) | QVQLVQSGGGLVQPGGSLRLSCAASGFTFSSYWMHWVRQ APGKGLVWVSRINSDGSSTSYADSVKGRFTISRDNAKNTLYLQMNSLRAEDTAVYYCVRT GWVGSYYYYMDVWGKGTTVTVSSGGGGSGGGGSGGGGSGGGGSEIVLTQSPGTLSLSPGE RATLSCRASQSVSSNYLAWYQQKPGQPPRLLIYDVSTRATGIPARFSGGGSGTDFTLTIS SLEPEDFAVYYCQQRSNWPPWTFGQGTKVEIK |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LCCDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
| --- | --- | --- |
| 80 | M18 >DS90-09HD (M18 DS90-09HD R003-A05 127556) | **MALPVTALLLPLALLLHAARP**QVQLVQSGGGLVQPGGSLRLSCAASGFTFSSYWMHWVRQAPGKGLVWVSRINSDGSSTSYADSVKGRFTISRDNAKNTLYLQMNSLRAEDTAVYYCVRTGWVGSYYYYMDVWGKGTTVTVSSGGGGSGGGGSGGGGSGGGGSEIVLTQSPGTLSLSPGERATLSCRASQSVSSNYLAWYQQKPGQPPRLLIYDVSTRATGIPARFSGGGSGTDFTLTISSLEPEDFAVYYCQQRSNWPPWTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 57 | M19 (ScFv domain) | QVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKGYSRYYYYGMDVWGQGTTVTVSSGGGGSGGGGSGGGGSGGGGSEIVMTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTKVDIK |
| 81 | M19 >TS92-04BD (M19 TS92-04BD R003-C06 127557) | **MALPVTALLLPLALLLHAARP**QVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKGYSRYYYYGMDVWGQGTTVTVSSGGGGSGGGGSGGGGSGGGGSEIVMTQSPATLSLSPGERAILSCRASQSVYTKYLGWYQQKPGQAPRLLIYDASTRATGIPDRFSGSGSGTDFTLTINRLEPEDFAVYYCQHYGGSPLITFGQGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 58 | M20 (ScFv domain) | QVQLVQSGGGLVQPGGSLRLSCAASGFTFSSYAMSWVRQAPGKGLEWVSAISGSGGSTYYADSVKGRFTISRDNSKNTLYLQMNSLRAEDTAVYYCAKREAAAGHDWYFDLWGRGTLVTVSSGGGGSGGGGSGGGGSGGGGSDIRVTQSPSSLSASVGDRVTITCRASQSISSYLNWYQQKPGKAPKLLIYAASSLQSGVPSRFSGSGSGTDFTLTISSLQPEDFATYYCQQSYSIPLTFGQGTKVEIK |
| 82 | M20 (full) >JS93-08WD (M20 JS93-08WD R003-E07 127558) | **MALPVTALLLPLALLLHAARP**QVQLVQSGGGLVQPGGSLRLSCAASGFTFSSYAMSWVRQAPGKGLEWVSAISGSGGSTYYADSVKGRFTISRDNSKNTLYLQMNSLRAEDTAVYYCAKREAAAGHDWYFDLWGRGTLVTVSSGGGGSGGGGSGGGGSGGGGSDIRVTQSPSSLSASVGDRVTITCRASQSISSYLNWYQQKPGKAPKLLIYAASSLQSGVPSRFSGSGSGTDFTLTISSLQPEDFATYYCQQSYSIPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 59 | M21 (ScFv domain) | QVQLVQSWAEVKKPGASVKVSCKASGYTFTSYYMHWVRQAPGQGLEWMGIINPSGGSTSYAQKFQGRVTMTRDTSTSTVYMELSNLRSEDTAVYYCARSPRVTTGYFDYWGQGTLVTVSSGGGGSGGGGSGGGGSGGGGSDIQLTQSPSTLSASVGDRVTITCRASQSISSWLAWYQQKPGKAPKLLIYKASSLESGVPSRFSGSGSGTEFTLTISSLQPDDFATYYCQQYSSYPLTFGGGTRLEIK |
| 83 | M21 (full CAR) | **MALPVTALLLPLALLLHAARP**QVQLVQSWAEVKKPGASVKVSCKASGYTFTSYYMHWVRQAPGQGLEWMGIINPSGGSTSYAQKFQGRVTMTRDTSTSTVYMELSNLRSEDTAVYYCARSPRVTTGYFDYWGQGTLVTVSSGGGGSGGGGSGGGGSGGGGSDIQLTQSPSTLSASVGDRVTITCRASQSISSWLAWYQQKPGKAPKLLIYKASSLESGVPSRFSGSGSGTEFTLTISSLQPDDFATYYCQQYSSYPLTFGGGTRLEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 60 | M22 (ScFv domain) | QVQLVQSGAEVRRPGASVKISCRASGDTSTRHYIHWLRQAPGQGPEWMGVINPTTGPATGSPAYAQMLQGRVTMTRDTSTRTVYMELRSLRFEDTAVYYCARSVVGRSAPYYFDYWGQGTLVTVSSGGGGSGGGGSGGGGSGGGGSDIQMTQSPSSLSASVGDRVTITCRASQGISDYSAWYQQKPGKAPKLLIYAASTLQSGVPSRFSGSGSGTDFTLTISYLQSEDFATYYCQQYYSYPLTFGGGTKVDIK |
| 84 | M22 (full CAR) | **MALPVTALLLPLALLLHAARP**QVQLVQSGAEVRRPGASVKISCRASGDTSTRHYIHWLRQAPGQGPEWMGVINPTTGPATGSPAYAQMLQGRVTMTRDTSTRTVYMELRSLRFEDTAVYYCARSVVGRSAPYYFDYWGQGTLVTVSSGGGGSGGGGSGGGGSGGGGSDIQMTQSPSSLSASVGDRVTITCRASQGISDYSAWYQQKPGKAPKLLIYAASTLQSGVPSRFSGSGSGTDFTL |

TABLE 2-continued

Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LCCDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| | | TISYLQSEDFATYYCQQYYSYPLTFGGGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 61 | M23 (ScFv domain) | QVQLQQSGAEVKKPGASVKVSCKASGYTFTNYYMHWVRQAPGQGLEWMGIINPSGGYTTYAQKFQGRLTMTRDTSTSTVYMELSSLRSEDTAVYYCARIRSCGGDCYYFDNWGQGTLVTVSSGGGGSGGGGSGGGGSGGGGSDIQLTQSPSTLSASVGDRVTITCRASENVNIWLAWYQQKPGKAPKLLIYKSSSLASGVPSRFSGSGSGAEFTLTISSLQPDDFATYYCQQYQSYPLTFGGGTKVDIK |
| 85 | M23 (full CAR) | **MALPVTALLLPLALLLHAARP**QVQLQQSGAEVKKPGASVKVSCKASGYTFTNYYMHWVRQAPGQGLEWMGIINPSGGYTTYAQKFQGRLTMTRDTSTSTVYMELSSLRSEDTAVYYCARIRSCGGDCYYFDNWGQGTLVTVSSGGGGSGGGGSGGGGSGGGGSDIQLTQSPSTLSASVGDRVTITCRASENVNIWLAWYQQKPGKAPKLLIYKSSSLASGVPSRFSGSGSGAEFTLTISSLQPDDFATYYCQQYQSYPLTFGGGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 62 | M24 (ScFv domain) | QITLKESGPALVKPTQTLTLTCTFSGFSLSTAGVHVGWIRQPPGKALEWLALISWADDKRYRPSLRSRLDITRVTSKDQVVLSMTNMQPEDTATYYCALQGFDGYEANWGPGTLVTVSSGGGGSGGGGSGGGGSGGGGSDIVMTQSPSSLSASAGDRVTITCRASRGISSALAWYQQKPGKPPKLLIYDASSLESGVPSRFSGSGSGTDFTLTIDSLEPEDFATYYCQQSYSTPWTFGQGTKVDIK |
| 86 | M24 (full CAR) | **MALPVTALLLPLALLLHAARP**QITLKESGPALVKPTQTLTLTCTFSGFSLSTAGVHVGWIRQPPGKALEWLALISWADDKRYRPSLRSRLDITRVTSKDQVVLSMTNMQPEDTATYYCALQGFDGYEANWGPGTLVTVSSGGGGSGGGGSGGGGSGGGGSDIVMTQSPSSLSASAGDRVTITCRASRGISSALAWYQQKPGKPPKLLIYDASSLESGVPSRFSGSGSGTDFTLTIDSLEPEDFATYYCQQSYSTPWTFGQGTKVDIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 275 | Ss1 (scFv domain) | QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVTVSSGGGGSGGGGSGGGGSDIELTQSPAIMSASPGEKVTMTCSASSSVSYMHWYQQKSGTSPKRWIYDTSKLASGVPGRFSGSGSGNSYSLTISSVEAEDDATYYCQQWSGYPLTFGAGTKLEI |
| 278 | Ss1 (full CAR) | **MALPVTALLLPLALLLHAARP**QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVTVSSGGGGSGGGGSGGGGSDIELTQSPAIMSASPGEKVTMTCSASSSVSYMHWYQQKSGTSPKRWIYDTSKLASGVPGRFSGSGSGNSYSLTISSVEAEDDATYYCQQWSGYPLTFGAGTKLEITTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPA |

TABLE 3

Nucleic Acid Sequences encoding CAR molecules (the leader sequence is underlined)

| SEQ ID NO: | Desc. | Nucleic Acid Sequence |
|---|---|---|
| 87 | M1 (ScFv domain) >ZA53-27BC (M1) | CAAGTCCAACTGCAGCAGTCAGGAGCGGAAGTGAAGAAACCAGGAGCGTCAGTCAAAGTGTCGTGCAAGGCTAGCGGCTACACCTTCACCGGCTACTACATGCACTGGGTTCGACAGGCTCCAGGGCAGGGTCTGGAGTGGATGGGCCGCATCAACCCGAATTCCGGTGGGACTAACTACGCCCAGAAGTTCCAGGGAAGAGTGACCATGACTAGGGACACGTCGATCAGCACTGCGTACATGGAACTGAGCCGCCTGCGGTCCGAGGATACTGCCGTCTACTACTGCGCACGCGGAAGGTACTATGGAATGGACGTGTGGGGCCAAGGGACTATGGTGACTGTGAGCTCGGGAGGGGGAGGCTCCGGTGGCGGGGGATCAGGAGGAGGAGGATCAGGGGGAGGAGGTTCCGAAATTG |

TABLE 3-continued

Nucleic Acid Sequences encoding CAR molecules (the leader sequence is underlined)

| SEQ ID NO: | Desc. | Nucleic Acid Sequence |
|---|---|---|
| | | TCCTCACCCAGAGCCCGGCAACCCTCTCACTTTCCCCGGGAGAGCGCGCAACCATCTCTTGCCGGGCTAGCCAATCCGTG<br>TCGTCCAATTTCGCCTGGTACCAGCAACGGCCGGGACAAGCCCCTAGACTCCTGATCTACGACGCCAGCAACAGAGCGAC<br>TGGAATTCCTCCACGCTTTTCGGGATCAGGCTCCGGTACCGACTTCACCCTGACTATCTCGTCGCTCGAACCCGAGGATT<br>TCGCCGCCTACTACTGTCATCAGCGGTCGAACTGGTTGTATACGTTTGGCCAGGGCACCAAGGTGGATATCAAG |
| 111 | M1 (Full) >ZA53-27BC (M1) | ATGGCCCTCCCTGTCACCGCCCTGCTGCTTCCGCTGGCTCTTCTGCTCCACGCCGCTCGGCCCCAAGTCCAACTGCAGCAG<br>TCAGGAGCGGAAGTGAAGAAACCAGGAGCGTCAGTCAAAGTGTCGTGCAAGGCTAGCGGCTACACCTTCACCGGCTACTA<br>CATGCACTGGGTTCGACAGGCTCCAGGGCAGGGTCTGGAGTGGATGGGCCGCATCAACCCGAATTCCGGTGGGACTAACT<br>ACGCCCAGAAGTTCCAGGGAAGAGTGACCATGACTAGGGACACGTCGATCAGCACTGCGTACATGGAACTGAGCCGCCTG<br>CGGTCCGAGGATACTGCCGTCTACTACTGCGCACGCGGAAGGTACTATGGAATGGACGTGTGGGGCCAAGGGACTATGGT<br>GACTGTGAGCTCGGGAGGGGGAGGCTCCGGTGGCGGGGGATCAGGAGGAGGAGGATCAGGGGGAGGAGGTTCCGAAATTG<br>TCCTCACCCAGAGCCCGGCAACCCTCTCACTTTCCCCGGGAGAGCGCGCAACCATCTCTTGCCGGGCTAGCCAATCCGTG<br>TCGTCCAATTTCGCCTGGTACCAGCAACGGCCGGGACAAGCCCCTAGACTCCTGATCTACGACGCCAGCAACAGAGCGAC<br>TGGAATTCCTCCACGCTTTTCGGGATCAGGCTCCGGTACCGACTTCACCCTGACTATCTCGTCGCTCGAACCCGAGGATT<br>TCGCCGCCTACTACTGTCATCAGCGGTCGAACTGGTTGTATACGTTTGGCCAGGGCACCAAGGTGGATATCAAGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGGCCGTGCATACCCGGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 88 | M2 (ScFv domain) >FA56-26RC (M2) | CAAGTCCAACTCGTCCAGTCAGGAGCAGAAGTCAAGAAACCAGGTGCTAGCGTGAAAGTGTCGTGCAAGGCGTCGGGATAC<br>ACTTTCACCGGATACTAC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATTATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAG |
| 112 | M2 (Full) >FA56-26RC (M2) | ATGGCCCTCCCTGTCACCGCCCTGCTGCTTCCGCTGGCTCTTCTGCTCCACGCCGCTCGGCCCCAAGTCCAACTCGTCCAG<br>TCAGGAGCAGAAGTCAAGAAACCAGGTGCTAGCGTGAAAGTGTCGTGCAAGGCGTCGGGATACACTTTCACCGGATACTAC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATTATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 89 | M3 (ScFv domain) >VA58-21LC (M3) | CAAGTCCAACTCGTCCAA<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGGCAGGCCCCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGGAGGATCTGGAGGAGGAGGGT<br>CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGGAAAGCACCAAAGCTGCTGATCTACGCCGCCTCATC<br>CTTGCAGAGCGGTGTGCCTTCACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCGGGACCAAGCTGGAAATCAAG |
| 113 | M3 (Full) >VA58-21LC (M3) | ATGGCCCTCCCTGTCACCGCCCTGCTGCTTCCGCTGGCTCTTCTGCTCCACGCCGCTCGGCCCCAAGTCCAACTCGTCCAA<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGGCAGGCCCCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGGAGGATCTGGAGGAGGAGGGT |

TABLE 3-continued

Nucleic Acid Sequences encoding CAR molecules (the leader sequence is underlined)

| SEQ ID NO: | Desc. | Nucleic Acid Sequence |
|---|---|---|
| | | CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGGAAAGCACCAAAGCTGCTGATCTACGCCGCCTCATC<br>CTTGCAGAGCGGTGTGCCTTCACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCGGGACCAAGCTGGAAATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 90 | M4<br>(ScFv<br>domain)<br>>DP37-<br>07IC<br>(M4) | CAAGTGCAACTCGTTGAA<br>TCAGGTGGAGGTTTGGTGCAACCCGGAGGATCTCTCAGACTGTCGTGTGCGGCGTCCGGGTTCACCTTTTCGTCCTACTG<br>GATGCACTGGGTGCGCCAGGTGCCGGGAAAAGGACTGGTGTGGGTGTCCAGAATCAACACCGACGGGTCAACGACTACCT<br>ACGCAGATAGCGTGGAAGGTCGGTTCACCATTTCGCGGGACAACGCTAAAAACACTCTGTACCTTCAGATGAATTCACTG<br>CGCGATGACGACACCGCAGTCTACTACTGCGTCGGTGGACACTGGGCGGTCTGGGGACAGGGAACTACGGTGACTGTGTC<br>CAGCGGCGGGGGAGGAAGCGGCGGAGGGGGGAGCGGAGGCGGAGGATCAGGAGGAGGCGGCTCCGATATCCAGATGACCC<br>AGTCGCCATCGACCCTCTCCGCTAGCGTGGGGGATAGGGTCACTATCACTTGCCGAGCCAGCCAATCCATTAGCGACCGG<br>CTTGCCTGGTACCAACAGAAACCTGGAAAGGCCCCGAAGCTGCTCATCTACAAGGCCTCGTCACTGGAGTCGGGAGTCCC<br>GTCCCGCTTTTCCGGCTCGGGCTCAGGCACCGAGTTCACTCTGACCATCTCGAGCCTGCAGCCGGACGATTTCGCCGTGT<br>ATTACTGCCAGCAATACGGACATCTCCCAATGTACACGTTCGGTCAGGGCACCAAGGTCGAAATCAAG |
| 114 | M4<br>>DP37-<br>07IC<br>(M4) | ATGGCCCTCCCTGTCACCGCCCTGCTGCTTCCGCTGGCTCTTCTGCTCCACGCCGCTCGGCCCCAAGTGCAACTCGTTGAA<br>TCAGGTGGAGGTTTGGTGCAACCCGGAGGATCTCTCAGACTGTCGTGTGCGGCGTCCGGGTTCACCTTTTCGTCCTACTG<br>GATGCACTGGGTGCGCCAGGTGCCGGGAAAAGGACTGGTGTGGGTGTCCAGAATCAACACCGACGGGTCAACGACTACCT<br>ACGCAGATAGCGTGGAAGGTCGGTTCACCATTTCGCGGGACAACGCTAAAAACACTCTGTACCTTCAGATGAATTCACTG<br>CGCGATGACGACACCGCAGTCTACTACTGCGTCGGTGGACACTGGGCGGTCTGGGGACAGGGAACTACGGTGACTGTGTC<br>CAGCGGCGGGGGAGGAAGCGGCGGAGGGGGGAGCGGAGGCGGAGGATCAGGAGGAGGCGGCTCCGATATCCAGATGACCC<br>AGTCGCCATCGACCCTCTCCGCTAGCGTGGGGGATAGGGTCACTATCACTTGCCGAGCCAGCCAATCCATTAGCGACCGG<br>CTTGCCTGGTACCAACAGAAACCTGGAAAGGCCCCGAAGCTGCTCATCTACAAGGCCTCGTCACTGGAGTCGGGAGTCCC<br>GTCCCGCTTTTCCGGCTCGGGCTCAGGCACCGAGTTCACTCTGACCATCTCGAGCCTGCAGCCGGACGATTTCGCCGTGT<br>ATTACTGCCAGCAATACGGACATCTCCCAATGTACACGTTCGGTCAGGGCACCAAGGTCGAAATCAAG**ACCACTACC**CCA<br>GCACCGAGGCCACCCACCCCGGCTCCTACCATCGCCTCCCAGCCTCTGTCCCTGCGTCCGGAGGCATGTAGACCCGCAGC<br>TGGTGGGGCCGTGCATACCCGGGGTCTTGACTTCGCCTGCGATATCTACATTTGGGCCCCTCTGGCTGGTACTTGCGGGG<br>TCCTGCTGCTTTCACTCGTGATCACTCTTTACTGTAAGCGCGGTCGGAAGAAGCTGCTGTACATCTTTAAGCAACCCTTC<br>ATGAGGCCTGTGCAGACTACTCAAGAGGAGGACGGCTGTTCATGCCGGTTCCCAGAGGAGGAGGAAGGCGGCTGCGAACT<br>GCGCGTGAAATTCAGCCGCAGCGCAGATGCTCCAGCCTACAAGCAGGGGCAGAACCAGCTCTACAACGAACTCAATCTTG<br>GTCGGAGAGAGGAGTACGACGTGCTGGACAAGCGGAGAGGACGGGACCCAGAAATGGGCGGGAAGCCGCGCAGAAAGAAT<br>CCCCAAGAGGGCCTGTACAACGAGCTCCAAAAGGATAAGATGGCAGAAGCCTATAGCGAGATTGGTATGAAAGGGGAACG<br>CAGAAGAGGCAAAGGCCACGACGGACTGTACCAGGGACTCAGCACCGCCACAAGGACACCTATGACGCTCTTCACATGC<br>AGGCCCTGCCGCCTCGG |
| 91 | M5<br>(ScFv<br>domain)<br>>XP31-<br>20LC<br>(M5) | CAAGTCCAACTCGTTCAATCAGGCGCAGAAGTCGAAAAGCCCGGAGCATCAGTCAAAGTCTCTTGCAAGGCTTCCGGCTAC<br>ACCTTCACGGACTACTAC<br>ATGCACTGGGTGCGCCAGGCTCCAGGCCAGGGACTGGAGTGGATGGGATGGATCAACCCGAATTCCGGGGGAACTAACTA<br>CGCCCAGAAGTTTCAGGGCCGGGTGACTATGACTCGCGATACCTCGATCTCGACTGCGTACATGGAGCTCAGCCGCCTCC<br>GGTCGGACGATACCGCCGTGTACTATTGTGCGTCGGGATGGGACTTCGACTACTGGGGGCAGGGCACTCTGGTCACTGTG<br>TCAAGCGGAGGAGGTGGATCAGGTGGAGGTGGAAGCGGGGGAGGAGGTTCCGGCGGCGGAGGATCAGATATCGTGATGAC<br>GCAATCGCCTTCCTCGTTGTCCGCATCCGTGGGAGACAGGGTGACCATTACTTGCAGAGCGTCCCAGTCCATTCGGTACT<br>ACCTGTCGTGGTACCAGCAGAAGCCGGGGAAAGCCCCAAAACTGCTTATCTATACTGCCTCGATCCTCCAAAACGGCGTG<br>CCATCAAGATTCAGCGGTTCGGGCAGCGGGACCGACTTTACCCTGACTATCAGCAGCCTGCAGCCGGAAGATTTCGCCAC<br>GTACTACTGCCTGCAAACCTACACCACCCCGGACTTCGGACCTGGAACCAAGGTGGAGATCAAG |
| 115 | M5<br>(Full)<br>>XP31-<br>20LC<br>(M5) | ATGGCCCTCCCTGTCACCGCCCTGCTGCTTCCGCTGGCTCTTCTGCTCCACGCCGCTCGGCCCCAAGTCCAACTCGTTCAA<br>TCAGGCGCAGAAGTCGAAAAGCCCGGAGCATCAGTCAAAGTCTCTTGCAAGGCTTCCGGCTACACCTTCACGGACTACTAC<br>ATGCACTGGGTGCGCCAGGCTCCAGGCCAGGGACTGGAGTGGATGGGATGGATCAACCCGAATTCCGGGGGAACTAACTA<br>CGCCCAGAAGTTTCAGGGCCGGGTGACTATGACTCGCGATACCTCGATCTCGACTGCGTACATGGAGCTCAGCCGCCTCC<br>GGTCGGACGATACCGCCGTGTACTATTGTGCGTCGGGATGGGACTTCGACTACTGGGGGCAGGGCACTCTGGTCACTGTG<br>TCAAGCGGAGGAGGTGGATCAGGTGGAGGTGGAAGCGGGGGAGGAGGTTCCGGCGGCGGAGGATCAGATATCGTGATGAC<br>GCAATCGCCTTCCTCGTTGTCCGCATCCGTGGGAGACAGGGTGACCATTACTTGCAGAGCGTCCCAGTCCATTCGGTACT<br>ACCTGTCGTGGTACCAGCAGAAGCCGGGGAAAGCCCCAAAACTGCTTATCTATACTGCCTCGATCCTCCAAAACGGCGTG<br>CCATCAAGATTCAGCGGTTCGGGCAGCGGGACCGACTTTACCCTGACTATCAGCAGCCTGCAGCCGGAAGATTTCGCCAC<br>GTACTACTGCCTGCAAACCTACACCACCCCGGACTTCGGACCTGGAACCAAGGTGGAGATCAAG**ACCACTACC**CCAGCAC<br>CGAGGCCACCCACCCCGGCTCCTACCATCGCCTCCCAGCCTCTGTCCCTGCGTCCGGAGGCATGTAGACCCGCAGCTGGT<br>GGGGCCGTGCATACCCGGGGTCTTGACTTCGCCTGCGATATCTACATTTGGGCCCCTCTGGCTGGTACTTGCGGGGTCCT<br>GCTGCTTTCACTCGTGATCACTCTTTACTGTAAGCGCGGTCGGAAGAAGCTGCTGTACATCTTTAAGCAACCCTTCATGA<br>GGCCTGTGCAGACTACTCAAGAGGAGGACGGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAACCAGCTCTACAACGAACTCAATCTTGGTCG<br>GAGAGAGGAGTACGACGTGCTGGACAAGCGGAGAGGACGGGACCCAGAAATGGGCGGGAAGCCGCGCAGAAAGAATCCCC |

TABLE 3-continued

Nucleic Acid Sequences encoding CAR molecules (the leader sequence is underlined)

| SEQ ID NO: | Desc. | Nucleic Acid Sequence |
|---|---|---|
| | | AAGAGGGCCTGTACAACGAGCTCCAAAAGGATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAGGACACCTATGACGCTCTTCACATGCAGGC<br>CCTGCCGCCTCGG |
| 92 | M6<br>(ScFv<br>domain)<br>>FE10-<br>06ID<br>(M6) | CAAGTGCAACTCGTCCAGTCAGGTGCAGAAGTGAAGAAACCCGGAGCGTCAGTCAAAGTGTCATGCAAGGCGTCAGGCTAC<br>ACCTTCACCAGCTACTAC<br>ATGCACTGGGTGCGGCAGGCCCCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAG |
| 116 | M6<br>(Full)<br>>FE10-<br>06ID<br>(M6) | ATGGCCCTCCCTGTCACCGCCCTGCTGCTTCCGCTGGCTCTTCTGCTCCACGCCGCTCGGCCCCAAGTGCAACTCGTCCAG<br>TCAGGTGCAGAAGTGAAGAAACCCGGAGCGTCAGTCAAAGTGTCATGCAAGGCGTCAGGCTACACCTTCACCAGCTACTAC<br>ATGCACTGGGTGCGGCAGGCCCCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 93 | M7<br>(ScFv<br>domain)<br>>VE12-<br>01CD<br>(M7) | CAAGTGCAATTGGTTCAA<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAGAGAGCGATCCTGTCCTGCCGCGCC<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAG |
| 117 | M7<br>(Full)<br>>VE12-<br>01CD<br>(M7) | ATGGCCCTCCCTGTCACCGCCCTGCTGCTTCCGCTGGCTCTTCTGCTCCACGCCGCTCGGCCCCAAGTGCAATTGGTTCAA<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAGAGAGCGATCCTGTCCTGCCGCGCC<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAG**ACCACTACC**CCAGCACCGAGGCCACCCACCCCGGCTCCTACCATCGCCTCCCAGCCTCTGTCCCTGCG<br>TCCGGAGGCATGTAGACCCGCAGCTGGTGGGGCCGTGCATACCCGGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGGCAGAACC<br>AGCTCTACAACGAACTCAATCTTGGTCGGAGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |
| 94 | M8<br><br>(ScFv<br>domain)<br>>LE13-<br>05XD<br>(M8) | CAAGTCCAACTCCAGCAG<br><br>TCAGGTGCAGAAGTCAAAAAGCCAGGAGCATCCGTGAAGGTTTCGTGCAAGACTTCCGGCTACCCTTTTACCGGGTACTC<br>CCTCCATTGGGTGAGACAAGCACCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG<br>AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG |

TABLE 3-continued

Nucleic Acid Sequences encoding CAR molecules (the leader sequence is underlined)

| SEQ ID NO: | Desc. | Nucleic Acid Sequence |
|---|---|---|
| | | ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG |
| 118 | M8 (Full) >LE13-05XD (M8) | ATGGCCCTCCCTGTCACCGCCCTGCTGCTTCCGCTGGCTCTTCTGCTCCACGCCGCTCGGCCCCAAGTCCAACTCCAGCAG<br>TCAGGTGCAGAAGTCAAAAAGCCAGGAGCATCCGTGAAGGTTTCGTGCAAGACTTCCGGCTACCCTTTTACCGGGTACTC<br>CCTCCATTGGGTGAGACAAGCACCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG<br>AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 95 | M9 (ScFv domain) >BE15-00SD (M9) | CAAGTGCAACTCGTCCAG<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAG |
| 119 | M9 (Full) >BE15-00SD (M9) | ATGGCCCTCCCTGTCACCGCCCTGCTGCTTCCGCTGGCTCTTCTGCTCCACGCCGCTCGGCCCCAAGTGCAACTCGTCCAG<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAG**ACCACTACC**CCAGCACCGAGGCCACCCACCCCGGCTCCTACCATCGCCTCCCAGCCTCTGTCCCTGCGTCCGGA<br>GGCATGTAGACCCGCAGCTGGTGGGGCCGTGCATACCCGGGGTCTTGACTTCGCCTGCGATATCTACATTTGGGCCCCTCT<br>GGCTGGTACTTGCGGGGTCCTGCTGCTTTCACTCGTGATCACTCTTTACTGTAAGCGCGGTCGGAAGAAGCTGCTGTAC<br>ATCTTTAAGCAACCCTTCATGAGGCCTGTGCAGACTACTCAAGAGGAGGACGGCTGTTCATGCCGGTTCCCAGAGGAGGA<br>GGAAGGCGGCTGCGAACTGCGCGTGAAATTCAGCCGCAGCGCAGATGCTCCAGCCTACAAGCAGGGGCAGAACCAGCTCT<br>ACAACGAACTCAATCTTGGTCGGAGAGAGGAGTACGACGTGCTGGACAAGCGGAGAGGACGGGACCCAGAAATGGGCGGG<br>AAGCCGCGCAGAAAGAATCCCCAAGAGGGCCTGTACAACGAGCTCCAAAAGGATAAGATGGCAGAAGCCTATAGCGAGAT<br>TGGTATGAAAGGGGAACGCAGAAGAGGCAAAGGCCACGACGGACTGTACCAGGGACTCAGCACCGCCACCAAGGACACCT<br>ATGACGCTCTTCACATGCAGGCCCTGCCGCCTCGG |
| 96 | M10 (ScFv domain) >RE16-05MD (M10) | CAAGTGCAACTCGTCCAGAGCGGAGCAGAAGTCAAGAAGCCAGGAGCGTCAGTGAAAGTGTCATGCAAGGCCAGCGGCTAT<br>ACCTTTACTTCGTATGGG<br>ATCTCCTGGGTGCGGCAGGCACCGGGCCAAGGACTGGAGTGGATGGGATGGATCTCAGCCTACAACGGTAACACCAACTA<br>CGCCCAGAAGCTGCAAGGACGCGTGACCATGACTACTGATACGAGCACCTCCACTGCCTACATGGAATTGCGGTCCCTTC<br>GGTCGGACGATACTGCTGTGTACTACTGCGCAAGAGTCGCCGGAGGGATCTACTACTACTACGGCATGGACGTCTGGGGA<br>CAGGGAACCACCATTACGGTGTCGAGCGGAGGGGGAGGCTCGGGGGGAGGAGGAAGCGGAGGTGGCGGCTCCGGGGGCGG<br>CGGATCGGACATTGTGATGACCCAGACTCCTGACTCCCTGGCTGTTTCGTTGGGAGAGCGCGCGACTATCTCGTGTAAGT<br>CCAGCCACTCAGTCCTGTACAATCGCAATAACAAGAACTACCTCGCGTGGTACCAGCAAAAACCGGGTCAGCCGCCTAAA<br>CTCCTGTTCTACTGGGCCTCCACCAGAAAGAGCGGGGTGCCAGATCGATTCTCTGGATCAGGATCAGGTACCGACTTTAC<br>GCTGACCATCTCGTCCCTGCAGCCGGAGGATTTCGCGACTTACTTCTGCCAGCAGACTCAGACTTTCCCCCTCACCTTCG<br>GTCAAGGCACCAGGCTGGAAATCAAT |
| 120 | M10 (Full) >RE16-05MD (M10) | ATGGCCCTCCCTGTCACCGCCCTGCTGCTTCCGCTGGCTCTTCTGCTCCACGCCGCTCGGCCCCAAGTGCAACTCGTCCAG<br>AGCGGAGCAGAAGTCAAGAAGCCAGGAGCGTCAGTGAAAGTGTCATGCAAGGCCAGCGGCTATACCTTTACTTCGTATGGG<br>ATCTCCTGGGTGCGGCAGGCACCGGGCCAAGGACTGGAGTGGATGGGATGGATCTCAGCCTACAACGGTAACACCAACTA<br>CGCCCAGAAGCTGCAAGGACGCGTGACCATGACTACTGATACGAGCACCTCCACTGCCTACATGGAATTGCGGTCCCTTC<br>GGTCGGACGATACTGCTGTGTACTACTGCGCAAGAGTCGCCGGAGGGATCTACTACTACTACGGCATGGACGTCTGGGGA |

TABLE 3-continued

Nucleic Acid Sequences encoding CAR molecules (the leader sequence is underlined)

| SEQ ID NO: | Desc. | Nucleic Acid Sequence |
|---|---|---|
| | | CAGGGAACCACCATTACGGTGTCGAGCGGAGGGGGAGGCTCGGGGGGAGGAGGAAGCGGAGGTGGCGGCTCCGGGGGCGG<br>CGGATCGGACATTGTGATGACCCAGACTCCTGACTCCCTGGCTGTTTCGTTGGGAGAGCGCGACTATCTCGTGTAAGT<br>CCAGCCACTCAGTCCTGTACAATCGCAATAACAAGAACTACCTCGCGTGGTACCAGCAAAAACCGGGTCAGCCGCCTAAA<br>CTCCTGTTCTACTGGGCCTCCACCAGAAAGAGCGGGGTGCCAGATCGATTCTCTGGATCAGGATCAGGTACCGACTTTAC<br>GCTGACCATCTCGTCCCTGCAGCCGGAGGATTTCGCGACTTACTTCTGCCAGCAGACTCAGACTTTCCCCCTCACCTTCG<br>GTCAAGGCACCAGGCTGGAAATCAAT**ACCACTACC**CCAGCACCGAGGCCACCCACCCCGGCTCCTACCATCGCCTCCCAG<br>CCTCTGTCCCTGCGTCCGGAGGCATGTAGACCCGCAGCTGGTGGGGCCGTGCATACCCGGGGTCTTGACTTCGCCTGCGA<br>TATCTACATTTGGGCCCCTCTGGCTGGTACTTGCGGGGTCCTGCTGCTTTCACTCGTGATCACTCTTTACTGTAAGCGCG<br>GTCGGAAGAAGCTGCTGTACATCTTTAAGCAACCCTTCATGAGGCCTGTGCAGACTACTCAAGAGGAGGACGGCTGTTCA<br>TGCCGGTTCCCAGAGGAGGAGGAAGGCGGCTGCGAACTGCGCGTGAAATTCAGCCGCAGCGCAGATGCTCCAGCCTACAA<br>GCAGGGGCAGAACCAGCTCTACAACGAACTCAATCTTGGTCGGAGAGAGGAGTACGACGTGCTGGACAAGCGGAGAGGAC<br>GGGACCCAGAAATGGGCGGGAAGCCGCGCAGAAAGAATCCCCAAGAGGGCCTGTACAACGAGCTCCAAAAGGATAAGATG<br>GCAGAAGCCTATAGCGAGATTGGTATGAAAGGGGAACGCAGAAGAGGCAAAGGCCACGACGGACTGTACCAGGGACTCAG<br>CACCGCCACCAAGGACACCTATGACGCTCTTCACATGCAGGCCCTGCCGCCTCGG |
| 97 | M11 (ScFv domain) >NE10-19WD (M11) | CAAGTCCAATTGCAGCAGAGCGGAGCAGAAGTGAAGAAGCCAGGAGCGTCAGTCAAAGTGTCGTGTAAGGCGTCAGGATAC<br>ACCTTCACGGGATACTAC<br>ATGCACTGGGTGCGCCAGGCCCCGGGCCAAGGACTCGAGTGGATGGGCTGGATCAACCCTAACTCTGGAGGCACCAACTA<br>CGCCCAGAATTTCCAAGGCAGAGTGACCATGACCCGGGACACCTCCATCTCGACTGCCTATATGGAACTGCGGCGGCTGC<br>GCTCGGACGATACTGCTGTGTATTACTGCGCCAGCGGCTGGGACTTTGACTACTGGGGACAGGGTACTCTGGTGACTGTT<br>TCCTCGGGAGGAGGCGGATCGGGTGGAGGAGGTAGCGGGGGAGGGGGGTCGGGAGGCGGAGGCAGCGATATTCGCATGAC<br>TCAATCGCCGTCCTCCCTGAGCGCTAGCGTGGGAGATCGAGTCACCATCACTTGCAGAGCGTCACAGTCGATTCGCTACT<br>ACCTGTCCTGGTACCAGCAGAAACCGGGAAAGGCACCAAAGCTTCTGATCTACACGGCCTCCATCCTGCAAAATGGTGTC<br>CCATCAAGGTTCTCCGGGTCAGGGAGCGGCACTGACTTCACTCTCACCATCTCCTCACTCCAGCCCGAGGACTTTGCAAC<br>CTACTACTGCCTCCAGACGTACACCACCCCGGATTTCGGTCCTGGAACCAAGGTGGAAATCAAA |
| 121 | M11 (Full) >NE10-19WD (M11) | ATGGCCCTCCCTGTCACCGCCCTGCTGCTTCCGCTGGCTCTTCTGCTCCACGCCGCTCGGCCCCAAGTCCAATTGCAGCAG<br>AGCGGAGCAGAAGTGAAGAAGCCAGGAGCGTCAGTCAAAGTGTCGTGTAAGGCGTCAGGATACACCTTCACGGGATACTAC<br>ATGCACTGGGTGCGCCAGGCCCCGGGCCAAGGACTCGAGTGGATGGGCTGGATCAACCCTAACTCTGGAGGCACCAACTA<br>CGCCCAGAATTTCCAAGGCAGAGTGACCATGACCCGGGACACCTCCATCTCGACTGCCTATATGGAACTGCGGCGGCTGC<br>GCTCGGACGATACTGCTGTGTATTACTGCGCCAGCGGCTGGGACTTTGACTACTGGGGACAGGGTACTCTGGTGACTGTT<br>TCCTCGGGAGGAGGCGGATCGGGTGGAGGAGGTAGCGGGGGAGGGGGGTCGGGAGGCGGAGGCAGCGATATTCGCATGAC<br>TCAATCGCCGTCCTCCCTGAGCGCTAGCGTGGGAGATCGAGTCACCATCACTTGCAGAGCGTCACAGTCGATTCGCTACT<br>ACCTGTCCTGGTACCAGCAGAAACCGGGAAAGGCACCAAAGCTTCTGATCTACACGGCCTCCATCCTGCAAAATGGTGTC<br>CCATCAAGGTTCTCCGGGTCAGGGAGCGGCACTGACTTCACTCTCACCATCTCCTCACTCCAGCCCGAGGACTTTGCAAC<br>CTACTACTGCCTCCAGACGTACACCACCCCGGATTTCGGTCCTGGAACCAAGGTGGAAATCAAA**ACCACTACC**CCAGCAC<br>CGAGGCCACCCACCCCGGCTCCTACCATCGCCTCCCAGCCTCTGTCCCTGCGTCCGGAGGCATGTAGACCCGCAGCTGGT<br>GGGGCCGTGCATACCCGGGGTCTTGACTTCGCCTGCGATATCTACATTTGGGCCCCTCTGGCTGGTACTTGCGGGGTCCT<br>GCTGCTTTCACTCGTGATCACTCTTTACTGTAAGCGCGGTCGGAAGAAGCTGCTGTACATCTTTAAGCAACCCTTCATGA<br>GGCCTGTGCAGACTACTCAAGAGGAGGACGGCTGTTCATGCCGGTTCCCAGAGGAGGAGGAAGGCGGCTGCGAACTGCGC<br>GTGAAATTCAGCCGCAGCGCAGATGCTCCAGCCTACAAGCAGGGGCAGAACCAGCTCTACAACGAACTCAATCTTGGTCG<br>GAGAGAGGAGTACGACGTGCTGGACAAGCGGAGAGGACGGGACCCAGAAATGGGCGGGAAGCCGCGCAGAAAGAATCCCC<br>AAGAGGGCCTGTACAACGAGCTCCAAAAGGATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAGGACACCTATGACGCTCTTCACATGCAGGC<br>CCTGCCGCCTCGG |
| 98 | M12 (ScFv domain) >DE12-14RD (M12) | CAAGTCCAACTCGTCCAA<br>AGCGGAGCAGAAGTCAAAAAGCCAGGAGCGTCGGTGAAAGTGTCTTGCAAAGCCAGCGGCTACACCTTCACGGGTTACTA<br>CATGCACTGGGTGCGCCAGGCGCCGGGCCAGGGGCTGGAGTGGATGGGCCGGATTAACCCTAACAGCGGGGGAACTAATT<br>ACGCTCAGAAGTTCCAGGGTAGAGTCACCATGACTACGGACACTTCCACTTCCACCGCCTATATGGAACTGCGCTCCCTC<br>CGCTCAGATGATACTGCCGTGTATTACTGCGCGCGGACTACCACGTCATACGCATTTGACATCTGGGGCCAGGGAACTAT<br>GGTGACCGTGAGCTCGGGCGGAGGCGGTTCAGGGGGAGGAGGAAGCGGAGGAGGAGGATCGGGAGGAGGTGGCTCCGATA<br>TCCAGCTGACTCAGTCCCCGAGCACCCTGTCGGCGTCGGTGGGGGACAGGGTTACCATCACCTGTAGAGCTTCCCAATCC<br>ATTTCGACTTGGCTGGCCTGGTACCAGCAAAAGCCGGGAAAGGCCCCTAATTTGCTTATCTACAAGGCATCGACCCTCGA<br>AAGCGGTGTGCCCTCCCGGTTTTCGGGATCAGGATCAGGGACCGAGTTCACCCTGACCATCTCATCCCTCCAGCCGGACG<br>ACTTCGCCACTTACTACTGCCAGCAGTACAACACCTACTCGCCATACACTTTCGGCCAAGGCACCAAGCTGGAGATCAAG |
| 122 | M12 (Full) >DE12-14RD (M12) | ATGGCCCTCCCTGTCACCGCCCTGCTGCTTCCGCTGGCTCTTCTGCTCCACGCCGCTCGGCCCCAAGTCCAACTCGTCCAA<br>AGCGGAGCAGAAGTCAAAAAGCCAGGAGCGTCGGTGAAAGTGTCTTGCAAAGCCAGCGGCTACACCTTCACGGGTTACTA<br>CATGCACTGGGTGCGCCAGGCGCCGGGCCAGGGGCTGGAGTGGATGGGCCGGATTAACCCTAACAGCGGGGGAACTAATT<br>ACGCTCAGAAGTTCCAGGGTAGAGTCACCATGACTACGGACACTTCCACTTCCACCGCCTATATGGAACTGCGCTCCCTC<br>CGCTCAGATGATACTGCCGTGTATTACTGCGCGCGGACTACCACGTCATACGCATTTGACATCTGGGGCCAGGGAACTAT<br>GGTGACCGTGAGCTCGGGCGGAGGCGGTTCAGGGGGAGGAGGAAGCGGAGGAGGAGGATCGGGAGGAGGTGGCTCCGATA<br>TCCAGCTGACTCAGTCCCCGAGCACCCTGTCGGCGTCGGTGGGGGACAGGGTTACCATCACCTGTAGAGCTTCCCAATCC<br>ATTTCGACTTGGCTGGCCTGGTACCAGCAAAAGCCGGGAAAGGCCCCTAATTTGCTTATCTACAAGGCATCGACCCTCGA<br>AAGCGGTGTGCCCTCCCGGTTTTCGGGATCAGGATCAGGGACCGAGTTCACCCTGACCATCTCATCCCTCCAGCCGGACG<br>ACTTCGCCACTTACTACTGCCAGCAGTACAACACCTACTCGCCATACACTTTCGGCCAAGGCACCAAGCTGGAGATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT |

TABLE 3-continued

| Nucleic Acid Sequences encoding CAR molecules (the leader sequence is underlined) | | |
|---|---|---|
| SEQ ID NO: | Desc. | Nucleic Acid Sequence |
| | | GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 99 | M13<br>(ScFv<br>domain)<br>>TE13-<br>19LD<br>(M13) | CAAGTTCAACTCGTGCAATCAGGTGGAGGACTCGTCAAACCCGGAGGATCATTGAGACTGTCATGCGAAGCGAGCGGTTTT<br>ATCTTCTCCGATTACTAT<br>ATGGGATGGATTCGGCAGGCCCCGGGAAAGGGACTCGAATGGGTGTCATACATCGGAAGGTCAGGCTCGTCCATGTACTA<br>CGCAGACTCGGTGAAAGGCAGATTCACCTTTAGCCGGGACAACGCCAAGAATTCCCTCTACTTGCAGATGAACAGCCTGC<br>GAGCCGAGGATACTGCTGTCTACTACTGTGCCGCGTCGCCGGTGGTGGCAGCTACTGAAGATTTCCAGCACTGGGGACAG<br>GGAACTCTGGTCACGGTGTCGAGCGGTGGGGGCGGAAGCGGAGGCGGAGGATCGGGCGGCGGAGGTTCGGGGGGGGGAGG<br>GTCTGACATCGTGATGACCCAAACCCCAGCCACCCTGAGCCTCTCCCCTGGAGAGCGCGCGACTCTTTCGTGCCGCGCTT<br>CCCAGTCAGTGACCAGCAATTACTTGGCTTGGTACCAACAGAAGCCGGGACAGGCGCCACGGCTGCTGCTTTTTGGTGCC<br>AGCACTCGCGCCACCGGAATCCCGGATCGCTTCTCGGGCTCAGGGTCCGGGACGGACTTCACCCTGACTATCAACCGGCT<br>GGAACCTGAGGACTTCGCGATGTACTACTGCCAGCAGTACGGCTCCGCACCAGTCACTTTCGGACAAGGCACCAAGCTGG<br>AGATCAAG |
| 123 | m13<br>(Full)<br>>TE13-<br>19LD<br>(M13) | ATGGCCCTCCCTGTCACCGCCCTGCTGCTTCCGCTGGCTCTTCTGCTCCACGCCGCTCGGCCCCAAGTTCAACTCGTGCAA<br>TCAGGTGGAGGACTCGTCAAACCCGGAGGATCATTGAGACTGTCATGCGAAGCGAGCGGTTTTATCTTCTCCGATTACTAT<br>ATGGGATGGATTCGGCAGGCCCCGGGAAAGGGACTCGAATGGGTGTCATACATCGGAAGGTCAGGCTCGTCCATGTACTA<br>CGCAGACTCGGTGAAAGGCAGATTCACCTTTAGCCGGGACAACGCCAAGAATTCCCTCTACTTGCAGATGAACAGCCTGC<br>GAGCCGAGGATACTGCTGTCTACTACTGTGCCGCGTCGCCGGTGGTGGCAGCTACTGAAGATTTCCAGCACTGGGGACAG<br>GGAACTCTGGTCACGGTGTCGAGCGGTGGGGGCGGAAGCGGAGGCGGAGGATCGGGCGGCGGAGGTTCGGGGGGGGGAGG<br>GTCTGACATCGTGATGACCCAAACCCCAGCCACCCTGAGCCTCTCCCCTGGAGAGCGCGCGACTCTTTCGTGCCGCGCTT<br>CCCAGTCAGTGACCAGCAATTACTTGGCTTGGTACCAACAGAAGCCGGGACAGGCGCCACGGCTGCTGCTTTTTGGTGCC<br>AGCACTCGCGCCACCGGAATCCCGGATCGCTTCTCGGGCTCAGGGTCCGGGACGGACTTCACCCTGACTATCAACCGGCT<br>GGAACCTGAGGACTTCGCGATGTACTACTGCCAGCAGTACGGCTCCGCACCAGTCACTTTCGGACAAGGCACCAAGCTGG<br>AGATCAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 100 | M14<br>(ScFv<br>domain)<br>>BS83-<br>95ID<br>(M14) | CAAGTCCAACTCGTCCAGTCGGGAGCAGAAGTTAGAGCACCAGGAGCGTCAGTGAAAATCTCATGCAAGGCCTCGGGCTTC<br>ACGTTCCGCGGATACTAC<br>ATCCACTGGGTGCGCCAAGCCCCGGGTCAGGGATTGGAGTGGATGGGAATCATTAACCCATCAGGAGGGAGCCGGGCTTA<br>CGCGCAGAAGTTCCAGGGACGCGTCACTATGACCCGAGATACTTCCACCTCGACTGTGTACATGGAACTCTCGTCCCTGA<br>GGTCCGACGACACTGCGATGTATTACTGTGCTCGGACTGCCAGCTGCGGTGGGGACTGTTACTACCTCGATTACTGGGGC<br>CAGGGAACTCTGGTGACCGTGTCCAGCGGAGGTGGCGGGTCAGGGGGTGGCGGAAGCGGAGGCGGCGGTTCAGGCGGAGG<br>AGGCTCGGACATCCAAATGACGCAATCGCCGCCTACCCTGAGCGCTTCCGTGGGAGATCGGGTGACCATTACTTGCAGAG<br>CATCCGAGAACGTCAATATCTGGCTGGCCTGGTACCAACAGAAGCCGGGGAAGGCCCCTAAACTGCTGATCTACAAGTCG<br>AGCAGCCTTGCCTCTGGAGTGCCCTCCCGCTTCTCGGGCTCGGGATCAGGAGCGGAATTCACCCTCACCATCTCCTCCCT<br>GCAGCCAGATGACTTTGCCACCTACTACTGCCAGCAGTACCAGAGCTATCCGTTGACCTTTGGGGGAGGCACTAAAGTGG<br>ACATCAAG |
| 124 | M14<br>(Full)<br>>BS83-<br>95ID<br>(M14) | ATGGCCCTCCCTGTCACCGCCCTGCTGCTTCCGCTGGCTCTTCTGCTCCACGCCGCTCGGCCCCAAGTCCAACTCGTCCAG<br>TCGGGAGCAGAAGTTAGAGCACCAGGAGCGTCAGTGAAAATCTCATGCAAGGCCTCGGGCTTCACGTTCCGCGGATACTAC<br>ATCCACTGGGTGCGCCAAGCCCCGGGTCAGGGATTGGAGTGGATGGGAATCATTAACCCATCAGGAGGGAGCCGGGCTTA<br>CGCGCAGAAGTTCCAGGGACGCGTCACTATGACCCGAGATACTTCCACCTCGACTGTGTACATGGAACTCTCGTCCCTGA<br>GGTCCGACGACACTGCGATGTATTACTGTGCTCGGACTGCCAGCTGCGGTGGGGACTGTTACTACCTCGATTACTGGGGC<br>CAGGGAACTCTGGTGACCGTGTCCAGCGGAGGTGGCGGGTCAGGGGGTGGCGGAAGCGGAGGCGGCGGTTCAGGCGGAGG<br>AGGCTCGGACATCCAAATGACGCAATCGCCGCCTACCCTGAGCGCTTCCGTGGGAGATCGGGTGACCATTACTTGCAGAG<br>CATCCGAGAACGTCAATATCTGGCTGGCCTGGTACCAACAGAAGCCGGGGAAGGCCCCTAAACTGCTGATCTACAAGTCG<br>AGCAGCCTTGCCTCTGGAGTGCCCTCCCGCTTCTCGGGCTCGGGATCAGGAGCGGAATTCACCCTCACCATCTCCTCCCT<br>GCAGCCAGATGACTTTGCCACCTACTACTGCCAGCAGTACCAGAGCTATCCGTTGACCTTTGGGGGAGGCACTAAAGTGG<br>ACATCAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 101 | M15<br>(ScFv<br>domain)<br>>HS86-<br>94XD<br>(M15) | CAAGTTCAACTCGTTCAA<br>TCAGGTGGAGGACTCGTGCAACCAGGAAGATCACTCAGACTCAGCTGCGCCGCGTCGGGATTCACTTTCGATGACTACGC<br>AATGCACTGGGTGCGGCAGGCCCCGGGCAAAGGACTGGAATGGGTGAGCGGAATTAGCTGGAACTCGGGGTCCATCGGGT<br>ACGCCGACTCGGTGAAGGGACGCTTTACGATCTCCCGGGACAATGCCAAGAACTCCCTGTATTTGCAGATGAACTCCTTG<br>AGGGCTGAGGACACCGCCGTGTACTACTGCGCTAAAGATGGATCATCGTCCTGGTCCTGGGGATACTTCGATTACTGGGG<br>CCAGGGCACTCTGGTGACCGTGTCGTCAGGCGGTGGAGGGTCGGGCGGAGGAGGTAGCGGAGGCGGAGGGAGCAGCTCTG<br>AACTGACCCAAGACCCGGCGGTGTCGGTCGCCCTTGGTCAGACTGTGCGGACTACCTGTCAGGGGGACGCGCTGCGCTCG |

TABLE 3-continued

Nucleic Acid Sequences encoding CAR molecules (the leader sequence is underlined)

| SEQ ID NO: | Desc. | Nucleic Acid Sequence |
|---|---|---|
| | | TACTACGCTTCATGGTACCAGCAGAAGCCCGGACAGGCACCTATGCTGGTCATCTACGGAAAGAATAACCGCCCATCCGG<br>CATCCCGGATCGCTTCTCGGGTTCGGACAGCGGCGACACCGCATCCCTGACGATCACTGGAGCGCAGGCCGAGGATGAAG<br>CCGACTACTACTGCAATTCCCGAGATTCAAGCGGCTACCCTGTGTTTGGGACCGGAACTAAGGTCACCGTCCTG |
| 125 | m15 (Full) >HS86-94XD (M15) | ATGGCCCTCCCTGTCACCGCCCTGCTGCTTCCGCTGGCTCTTCTGCTCCACGCCGCTCGGCCCCAAGTTCAACTCGTTCAA<br>TCAGGTGGAGGACTCGTGCAACCAGGAAGATCACTCAGACTCAGCTGCGCCGCGTCGGGATTCACTTTCGATGACTACGC<br>AATGCACTGGGTGCGGCAGGCCCCGGGCAAAGGACTGGAATGGGTGAGCGGAATTAGCTGGAACTCGGGGTCCATCGGGT<br>ACGCCGACTCGGTGAAGGGACGCTTTACGATCTCCCGGGACAATGCCAAGAACTCCCTGTATTTGCAGATGAACTCCTTG<br>AGGGCTGAGGACACCGCCGTGTACTACTGCGCTAAAGATGGATCATCGTCCTGGTCCTGGGGATACTTCGATTACTGGGG<br>CCAGGGCACTCTGGTGACCGTGTCGTCAGGCGGTGGAGGGTCGGGCGGAGGAGGTAGCGGAGGCGGAGGGAGCAGCTCTG<br>AACTGACCCAAGACCCGGCGGTGTCGGTCGCCCTTGGTCAGACTGTGCGGACTACCTGTCAGGGGGACGCGCTGCGCTCG<br>TACTACGCTTCATGGTACCAGCAGAAGCCCGGACAGGCACCTATGCTGGTCATCTACGGAAAGAATAACCGCCCATCCGG<br>CATCCCGGATCGCTTCTCGGGTTCGGACAGCGGCGACACCGCATCCCTGACGATCACTGGAGCGCAGGCCGAGGATGAAG<br>CCGACTACTACTGCAATTCCCGAGATTCAAGCGGCTACCCTGTGTTTGGGACCGGAACTAAGGTCACCGTCCTGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGGCCGTGCATACCCGGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 102 | M16 (ScFv domain) >XS87-99RD (M16) | GAAGTGCAACTCGTGGAA<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG |
| 126 | M16 (Full) >XS87-99RD (M16) | ATGGCCCTCCCTGTCACCGCCCTGCTGCTTCCGCTGGCTCTTCTGCTCCACGCCGCTCGGCCCGAAGTGCAACTCGTGGAA<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 103 | M17 (ScFv domain) >NS89-94MD (M17) | GAAGTTCAATTGGTGGAA<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCCTGGAAAAGGACTGGAGTGGGTGTCAGGCATCTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTCTACTACTGCGCCAAAGACAGCTCGTCATGGTATGGCGGAGGGTCGGCATTTGACATCTG<br>GGGACAGGGAACTATGGTGACTGTGTCATCAGGAGGCGGCGGAAGCGGCGGCGGCGGGTCCGGCGGAGGAGGGTCGTCCA<br>GCGAACTCACCCAAGATCCAGCAGTGAGCGTCGCGCTGGGCCAGACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC<br>GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG |
| 127 | M17 (Full) >NS89-94MD (M17) | ATGGCCCTCCCTGTCACCGCCCTGCTGCTTCCGCTGGCTCTTCTGCTCCACGCCGCTCGGCCCGAAGTTCAATTGGTGGAA<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCCTGGAAAAGGACTGGAGTGGGTGTCAGGCATCTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTCTACTACTGCGCCAAAGACAGCTCGTCATGGTATGGCGGAGGGTCGGCATTTGACATCTG<br>GGGACAGGGAACTATGGTGACTGTGTCATCAGGAGGCGGCGGAAGCGGCGGCGGCGGGTCCGGCGGAGGAGGGTCGTCCA<br>GCGAACTCACCCAAGATCCAGCAGTGAGCGTCGCGCTGGGCCAGACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC |

TABLE 3-continued

Nucleic Acid Sequences encoding CAR molecules (the leader sequence is underlined)

| SEQ ID NO: | Desc. | Nucleic Acid Sequence |
|---|---|---|
| | | GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 104 | M18 (ScFv-domain) >DS90-09HD (M18) | CAAGTGCAGCTCGTTCAATCAGGCGGAGGACTCGTTCAACCAGGAGGATCATTGCGACTCTCATGTGCGGCCTCTGGATTC<br>ACGTTTAGCTCATATTGG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACTACATGGACGTGTGGGGC<br>AAAGGAACTACTGTCACCGTGTCAAGCGGCGGTGGAGGTTCCGGCGGGGGAGGATCGGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACAGAAGCCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAG |
| 128 | M18 (Full) >DS90-09HD (M18) | ATGGCCCTCCCTGTCACCGCCCTGCTGCTTCCGCTGGCTCTTCTGCTCCACGCCGCTCGGCCCCAAGTGCAGCTCGTTCAA<br>TCAGGCGGAGGACTCGTTCAACCAGGAGGATCATTGCGACTCTCATGTGCGGCCTCTGGATTCACGTTTAGCTCATATTGG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACTACATGGACGTGTGGGGC<br>AAAGGAACTACTGTCACCGTGTCAAGCGGCGGTGGAGGTTCCGGCGGGGGAGGATCGGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACAGAAGCCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAG**ACCACTACC**CCAGCACCGAGGCCACCCACCCCGGCTCCTACCATCGCCTCCCAGCCTCTGTCCCTG<br>CGTCCGGAGGCATGTAGACCCGCAGCTGGTGGGGCCGTGCATACCCGGGGTCTTGACTTCGCCTGCGATATCTACATTTG<br>GGCCCCTCTGGCTGGTACTTGCGGGGTCCTGCTGCTTTCACTCGTGATCACTCTTTACTGTAAGCGCGGTCGGAAGAAGC<br>TGCTGTACATCTTTAAGCAACCCTTCATGAGGCCTGTGCAGACTACTCAAGAGGAGGACGGCTGTTCATGCCGGTTCCCA<br>GAGGAGGAGGAAGGCGGCTGCGAACTGCGCGTGAAATTCAGCCGCAGCGCAGATGCTCCAGCCTACAAGCAGGGGCAGAA<br>CCAGCTCTACAACGAACTCAATCTTGGTCGGAGAGAGGAGTACGACGTGCTGGACAAGCGGAGAGGACGGGACCCAGAAA<br>TGGGCGGGAAGCCGCGCAGAAAGAATCCCCAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGACTGTACCAGGGACTCAGCACCGCCACCAA<br>GGACACCTATGACGCTCTTCACATGCAGGCCCTGCCGCCTCGG |
| 105 | M19 (ScFv domain) >TS92-04BD (M19) | CAAGTGCAATTGGTTCAA<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGCTAAGGGATACTCGCGCTACTACTACTATGGAATGGATGTGTGGGGCCA<br>GGGAACTACCGTGACGGTGTCGTCCGGCGGCGGTGGGTCGGGCGGAGGCGGATCAGGTGGAGGTGGAAGCGGAGGAGGAG<br>GGAGCGAAATCGTCATGACTCAGTCCCCTGCTACCCTTTCTCTGTCGCCGGGAGAAAGAGCCATCCTGAGCTGCCGGGCC<br>TCCCAGAGCGTGTACACCAAATACCTGGGATGGTACCAGCAGAAGCCGGGGCAGGCACCAAGGCTCCTGATCTACGATGC<br>GTCCACCCGCGCGACTGGTATCCCAGACCGCTTTTCCGGCTCGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA<br>GTGGACATCAAG |
| 129 | m19 (Full) >TS92-04BD (M19) | ATGGCCCTCCCTGTCACCGCCCTGCTGCTTCCGCTGGCTCTTCTGCTCCACGCCGCTCGGCCCCAAGTGCAATTGGTTCAA<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGCTAAGGGATACTCGCGCTACTACTACTATGGAATGGATGTGTGGGGCCA<br>GGGAACTACCGTGACGGTGTCGTCCGGCGGCGGTGGGTCGGGCGGAGGCGGATCAGGTGGAGGTGGAAGCGGAGGAGGAG<br>GGAGCGAAATCGTCATGACTCAGTCCCCTGCTACCCTTTCTCTGTCGCCGGGAGAAAGAGCCATCCTGAGCTGCCGGGCC<br>TCCCAGAGCGTGTACACCAAATACCTGGGATGGTACCAGCAGAAGCCGGGGCAGGCACCAAGGCTCCTGATCTACGATGC<br>GTCCACCCGCGCGACTGGTATCCCAGACCGCTTTTCCGGCTCGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA<br>GTGGACATCAAG**ACCACTACC**CCAGCACCGAGGCCACCCACCCCGGCTCCTACCATCGCCTCCCAGCCTCTGTCCCTGCG<br>TCCGGAGGCATGTAGACCCGCAGCTGGTGGGGCCGTGCATACCCGGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGGCAGAACC |

TABLE 3-continued

Nucleic Acid Sequences encoding CAR molecules (the leader sequence is underlined)

| SEQ ID NO: | Desc. | Nucleic Acid Sequence |
|---|---|---|
| | | AGCTCTACAACGAACTCAATCTTGGTCGGAGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |
| 106 | M20 (ScFv domain) >JS93-08WD (M20) | CAAGTGCAACTTGTTCAATCAGGAGGAGGACTCGTTCAACCCGGAGGATCACTGCGACTCTCATGTGCAGCGTCGGGGTTC<br>ACCTTCTCCAGCTACGCA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGAAGAGAGAAGCTGCCGCAGGGCACGATTGGTACTTCGACTTGTGGGGC<br>AGGGGCACCCTTGTGACCGTGTCCTCCGGTGGAGGCGGATCAGGAGGTGGGGGATCGGGTGGAGGAGGAAGCGGAGGCGG<br>CGGTTCGGACATTCGCGTCACCCAGTCACCGAGCTCCCTCAGCGCATCGGTGGGCGACCGGGTCACTATCACTTGCCGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAG |
| 130 | M20 (Full) >JS93-08WD (M20) | ATGGCCCTCCCTGTCACCGCCCTGCTGCTTCCGCTGGCTCTTCTGCTCCACGCCGCTCGGCCCCAAGTGCAACTTGTTCAA<br>TCAGGAGGAGGACTCGTTCAACCCGGAGGATCACTGCGACTCTCATGTGCAGCGTCGGGGTTCACCTTCTCCAGCTACGCA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGAAGAGAGAAGCTGCCGCAGGGCACGATTGGTACTTCGACTTGTGGGGC<br>AGGGGCACCCTTGTGACCGTGTCCTCCGGTGGAGGCGGATCAGGAGGTGGGGGATCGGGTGGAGGAGGAAGCGGAGGCGG<br>CGGTTCGGACATTCGCGTCACCCAGTCACCGAGCTCCCTCAGCGCATCGGTGGGCGACCGGGTCACTATCACTTGCCGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 107 | M21 (ScFv domain) >ZS95-03QD (M21) | CAAGTCCAACTCGTTCAGTCATGGGCAGAAGTCAAGAAACCCGGTGCAAGCGTCAAAGTGTCGTGTAAGGCCTCCGGCTAC<br>ACTTTCACTTCCTACTAC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAGGG<br>ACCCTGGTGACCGTCAGCTCGGGAGGCGGAGGATCGGGAGGTGGAGGGTCCGGTGGAGGCGGCTCTGGAGGAGGCGGGTC<br>GGACATTCAATTGACCCAGAGCCCATCCACCCTCTCAGCCTCGGTGGGGGATAGGGTGACTATCACTTGCCGGGCCTCCC<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AA |
| 131 | M21 (Full) >ZS95-03QD (M21) | ATGGCCCTCCCTGTCACCGCCCTGCTGCTTCCGCTGGCTCTTCTGCTCCACGCCGCTCGGCCCCAAGTCCAACTCGTTCAG<br>TCATGGGCAGAAGTCAAGAAACCCGGTGCAAGCGTCAAAGTGTCGTGTAAGGCCTCCGGCTACACTTTCACTTCCTACTAC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAGGG<br>ACCCTGGTGACCGTCAGCTCGGGAGGCGGAGGATCGGGAGGTGGAGGGTCCGGTGGAGGCGGCTCTGGAGGAGGCGGGTC<br>GGACATTCAATTGACCCAGAGCCCATCCACCCTCTCAGCCTCGGTGGGGGATAGGGTGACTATCACTTGCCGGGCCTCCC<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AA**ACCACTACC**CCAGCACCGAGGCCACCCACCCCGGCTCCTACCATCGCCTCCCAGCCTCTGTCCCTGCGTCCGGAGGCA<br>TGTAGACCCGCAGCTGGTGGGGCCGTGCATACCCGGGGTCTTGACTTCGCCTGCGATATCTACATTTGGGCCCCTCTGGC<br>TGGTACTTGCGGGGTCCTGCTGCTTTCACTCGTGATCACTCTTTACTGTAAGCGCGGTCGGAAGAAGCTGCTGTACATCT<br>TTAAGCAACCCTTCATGAGGCCTGTGCAGACTACTCAAGAGGAGGACGGCTGTTCATGCCGGTTCCCAGAGGAGGAGGAA<br>GGCGGCTGCGAACTGCGCGTGAAATTCAGCCGCAGCGCAGATGCTCCAGCCTACAAGCAGGGGCAGAACCAGCTCTACAA<br>CGAACTCAATCTTGGTCGGAGAGAGGAGTACGACGTGCTGGACAAGCGGAGAGGACGGGACCCAGAAATGGGCGGGAAGC<br>CGCGCAGAAAGAATCCCCAAGAGGGCCTGTACAACGAGCTCCAAAAGGATAAGATGGCAGAAGCCTATAGCGAGATTGGT<br>ATGAAAGGGGAACGCAGAAGAGGCAAAGGCCACGACGGACTGTACCAGGGACTCAGCACCGCCACCAAGGACACCTATGA<br>CGCTCTTCACATGCAGGCCCTGCCGCCTCGG |

TABLE 3-continued

Nucleic Acid Sequences encoding CAR molecules (the leader sequence is underlined)

| SEQ ID NO: | Desc. | Nucleic Acid Sequence |
|---|---|---|
| 108 | M22 (ScFv domain) >PS96-08LD (M22) | CAAGTCCAACTCGTCCAGTCCGGTGCAGAAGTCAGAAGGCCAGGAGCAAGCGTGAAGATCTCGTGTAGAGCGTCAGGAGAC<br>ACCAGCACTCGCCATTAC<br>ATCCACTGGCTGCGCCAGGCTCCGGGCCAAGGGCCGGAGTGGATGGGTGTGATCAACCCGACTACGGGACCGGCTACCGG<br>AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAG |
| 132 | M22 (Full) >PS96-08LD (M22) | ATGGCCCTCCCTGTCACCGCCCTGCTGCTTCCGCTGGCTCTTCTGCTCCACGCCGCTCGGCCCCAAGTCCAACTCGTCCAG<br>TCCGGTGCAGAAGTCAGAAGGCCAGGAGCAAGCGTGAAGATCTCGTGTAGAGCGTCAGGAGACACCAGCACTCGCCATTAC<br>ATCCACTGGCTGCGCCAGGCTCCGGGCCAAGGGCCGGAGTGGATGGGTGTGATCAACCCGACTACGGGACCGGCTACCGG<br>AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAG**ACCACTACC**CCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 109 | M23 (ScFv domain) >XH66-84HE (M23) | CAAGTCCAACTCCAGCAATCGGGAGCAGAAGTCAAGAAACCAGGCGCATCGGTGAAAGTGTCGTGTAAGGCGTCAGGGTAC<br>ACCTTCACCAACTACTAT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAG |
| 133 | M23 (Full) >XH66-84HE (M23) | ATGGCCCTCCCTGTCACCGCCCTGCTGCTTCCGCTGGCTCTTCTGCTCCACGCCGCTCGGCCCCAAGTCCAACTCCAGCAA<br>TCGGGAGCAGAAGTCAAGAAACCAGGCGCATCGGTGAAAGTGTCGTGTAAGGCGTCAGGGTACACCTTCACCAACTACTAT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAG**ACCACTACC**CCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 110 | M24 (ScFv domain) >NH67-89CE (M24) | CAAATCACTCTGAAAGAA<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTATCACTTGCCGGGCCAGCCGC |

TABLE 3-continued

| Nucleic Acid Sequences encoding CAR molecules (the leader sequence is underlined) | | |
|---|---|---|
| SEQ ID NO: | Desc. | Nucleic Acid Sequence |
| | | GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG |
| 134 | M24 (Full) >NH67-89CE (M24) | ATGGCCCTCCCTGTCACCGCCCTGCTGCTTCCGCTGGCTCTTCTGCTCCACGCCGCTCGGCCCCAAATCACTCTGAAAGAA<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTATCACTTGCCGGGCCAGCCGC<br>GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG<br>**ACCACTACC**CCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 279 | Ss1 (scFV domain) | CAAGTCCAGCTCCAGCAGTCGGGCCCAGAGTTGGAGAAGCCTGGGGCGAGCGTGAAGAT<br>CTCATGCAAAGCCTCAGGCTACTCCTTTACTGGATACACGATGAATTGGGTGAAACAGT<br>CGCATGGAAAGTCACTGGAATGGATCGGTCTGATTACGCCCTACAACGGCGCCTCCAGC<br>TACAACCAGAAGTTCAGGGGAAAGGCGACCCTTACTGTCGACAAGTCGTCAAGCACCGC<br>CTACATGGACCTCCTGTCCCTGACCTCCGAAGATAGCGCGGTCTACTTTTGTGCACGCG<br>GAGGTTACGATGGACGGGGATTCGACTACTGGGGCCAGGGAACCACTGTCACCGTGTCG<br>AGCGGAGGCGGAGGGAGCGGAGGAGGAGGCAGCGGAGGTGGAGGGTCGGATATCGAACT<br>CACTCAGTCCCCAGCAATCATGTCCGCTTCACCGGGAGAAAAGGTGACCATGACTTGCT<br>CGGCCTCCTCGTCCGTGTCATACATGCACTGGTACCAACAAAAATCGGGGACCTCCCCT<br>AAGAGATGGATCTACGATACCAGCAAACTGGCTTCAGGCGTGCCGGGACGCTTCTCGGG<br>TTCGGGGAGCGGAAATTCGTATTCGTTGACCATTTCGTCCGTGGAAGCCGAGGACGACG<br>CAACTTATTACTGCCAACAGTGGTCAGGCTACCCGCTCACTTTCGGAGCCGGCACTAAG<br>CTGGAGATC |
| 280 | Ss1 (full) | ATGGCCCTCCCTGTCACCGCCCTGCTGCTTCCGCTGGCTCTTCTGCTCCACGCCGCTCG<br>GCCCCAAGTCCAGCTCCAGCAGTCGGGCCCAGAGTTGGAGAAGCCTGGGGCGAGCGTGA<br>AGATCTCATGCAAAGCCTCAGGCTACTCCTTTACTGGATACACGATGAATTGGGTGAAA<br>CAGTCGCATGGAAAGTCACTGGAATGGATCGGTCTGATTACGCCCTACAACGGCGCCTC<br>CAGCTACAACCAGAAGTTCAGGGGAAAGGCGACCCTTACTGTCGACAAGTCGTCAAGCA<br>CCGCCTACATGGACCTCCTGTCCCTGACCTCCGAAGATAGCGCGGTCTACTTTTGTGCA<br>CGCGGAGGTTACGATGGACGGGGATTCGACTACTGGGGCCAGGGAACCACTGTCACCGT<br>GTCGAGCGGAGGCGGAGGGAGCGGAGGAGGAGGCAGCGGAGGTGGAGGGTCGGATATCG<br>AACTCACTCAGTCCCCAGCAATCATGTCCGCTTCACCGGGAGAAAAGGTGACCATGACT<br>TGCTCGGCCTCCTCGTCCGTGTCATACATGCACTGGTACCAACAAAAATCGGGGACCTC<br>CCCTAAGAGATGGATCTACGATACCAGCAAACTGGCTTCAGGCGTGCCGGGACGCTTCT<br>CGGGTTCGGGGAGCGGAAATTCGTATTCGTTGACCATTTCGTCCGTGGAAGCCGAGGAC<br>GACGCAACTTATTACTGCCAACAGTGGTCAGGCTACCCGCTCACTTTCGGAGCCGGCAC<br>TAAGCTGGAGATCACCACTACCCCAGCACCGAGGCCACCCACCCCGGCTCCTACCATCG<br>CCTCCCAGCCTCTGTCCCTGCGTCCGGAGGCATGTAGACCCGCAGCTGGTGGGGCCGTG<br>CATACCCGGGGTCTTGACTTCGCCTGCGATATCTACATTTGGGCCCCTCTGGCTGGTAC<br>TTGCGGGGTCCTGCTGCTTTCACTCGTGATCACTCTTTACTGTAAGCGCGGTCGGAAGA<br>AGCTGCTGTACATCTTTAAGCAACCCTTCATGAGGCCTGTGCAGACTACTCAAGAGGAG<br>GACGGCTGTTCATGCCGGTTCCCAGAGGAGGAGGAAGGCGGCTGCGAACTGCGCGTGAA<br>ATTCAGCCGCAGCGCAGATGCTCCAGCC |

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus futher associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$—$VH_2$—$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$—$VH_2$—$VL_2$. The linker may be a linker as described herein, e.g., a ($Gly_4$-Ser)n linker, wherein n is 1, 2, 3, 4, 5, or 6, preferably 4 (SEQ ID NO: 26). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for mesothelin, e.g., comprises a scFv as described herein, e.g., as described in Table 2 or 3, or comprises the light chain CDRs and/or heavy chain CDRs from a mesothelin scFv described herein, and a second immunoglobulin variable domain sequence that has binding specificity for a second epitope on a different antigen. In some aspects the second immunoglobulin variable domain sequence has binding specificity for an antigen other than mesothelin, e.g., an antigen expressed by a cancer or tumor cell. In some aspects, the second immunoglobulin variable domain sequence has binding specificity for an antigen selected from a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HERS, IGF-1R, EGFR, DLL4, or Trop-2.

Chimeric TCR

In one aspect, the mesothelin antibodies and antibody fragments of the present invention (for example, those disclosed in Tables 2 or 3) can be grafted to one or more constant domain of a T cell receptor ("TCR") chain, for example, a TCR alpha or TCR beta chain, to create an chimeric TCR that binds specificity to mesothelin. Without being bound by theory, it is believed that chimeric TCRs will signal through the TCR complex upon antigen binding. For example, a mesothelin scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, a mesothelin antibody fragment, for example a VL domain as described herein, can be grafted to the constant domain of a TCR alpha chain, and a mesothelin antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of a mesothelin antibody or antibody fragment, e.g., the CDRs of a mesothelin antibody or antibody fragment as described in Tables 4 or 5 may be grafted into a TCR alpha and/or beta chain to create a chimeric TCR that binds specifically to mesothelin. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used, e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect, the transmembrane domain is capable of signaling to the intracellular domain(s) whenever the CAR has bound to a target. A transmembrane domain of particular use in this invention may include at least the transmembrane domain(s) of, e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:2. In one aspect, the transmembrane domain comprises (e.g., consists of) a transmembrane domain of SEQ ID NO: 6.

In one aspect, the hinge or spacer comprises an IgG4 hinge. For example, in one embodiment, the hinge or spacer comprises a hinge of the amino acid sequence SEQ ID NO:3.

In some embodiments, the hinge or spacer comprises a hinge encoded by a nucleotide sequence SEQ ID NO:14.

In one aspect, the hinge or spacer comprises an IgD hinge. For example, in one embodiment, the hinge or spacer comprises a hinge of the amino acid sequence SEQ ID NO:4.

In some embodiments, the hinge or spacer comprises a hinge encoded by a nucleotide sequence of SEQ ID NO:15.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic signaling region of the CAR. A glycine-serine doublet provides a particularly suitable linker. For example, in one aspect, the linker comprises the amino acid sequence of GGGGSGGGGS (SEQ ID NO:5). In some embodiments, the linker is encoded by a nucleotide sequence of GGTGGCGGAGGTTCTGGAGGTGGAGGTTCC (SEQ ID NO:16).

In one aspect, the hinge or spacer comprises a KIR2DS2 hinge and portions thereof.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introducede. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary cytoplasmic signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon R1b), CD3 gamma, CD3 delta, CD3 epsilon, CD5, CD22, CD79a, CD79b, CD278 (also known as "ICOS"), FccRI, CD66d, DAP10, and DAP12. In one embodiment, a CAR of the invention comprises an intracellular signaling domain, e.g., a primary signaling domain of CD3-zeta, e.g., a CD3-zeta sequence described herein.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

The intracellular domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1 (also known as PD1), ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9

(CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. For example, CD27 costimulation has been demonstrated to enhance expansion, effector function, and survival of human CART cells in vitro and augments human T cell persistence and antitumor activity in vivo (Song et al. Blood. 2012; 119(3): 696-706).

The intracellular signaling domains within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling domains. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 7. In one aspect, the signaling domain of CD3-zeta is a signaling domain of SEQ ID NO: 9 (mutant CD3-zeta) or SEQ ID NO: 10 (wild type human CD3-zeta).

In one aspect, the intracellular is designed to comprise the signaling domain of CD3-zeta and the signaling domain of 4-1BB. In one aspect, the signaling domain of 4-1BB comprises an amino acid sequence of SEQ ID NO: 7. In one aspect, the signaling domain of 4-1BB is encoded by a nucleic acid sequence of SEQ ID NO: 18.

In one aspect, the intracellular signaling domain is designed to comprise the signaling domain of CD3-zeta and the signaling domain of CD27. In one aspect, the signaling domain of CD27 comprises an amino acid sequence of SEQ ID NO:8. In one aspect, the signalling domain of CD27 is encoded by a nucleic acid sequence of SEQ ID NO:19.

In one aspect, the intracellular is designed to comprise the signaling domain of CD3-zeta and the signaling domain of CD28. In one aspect, the signaling domain of CD28 comprises an amino acid sequence of SEQ ID NO: 44. In one aspect, the signaling domain of CD28 is encoded by a nucleic acid sequence of SEQ ID NO: 45.

In one aspect, the intracellular is designed to comprise the signaling domain of CD3-zeta and the signaling domain of ICOS. In one aspect, the signaling domain of ICOS comprises an amino acid sequence of SEQ ID NO: 42. In one aspect, the signaling domain of ICOS is encoded by a nucleic acid sequence of SEQ ID NO: 43.

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cyotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Split CAR

In some embodiments, the CAR-expressing cell described herein, uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes the tumor antigen or B cell antigen described herein, e.g., comprises an antigen binding domain described herein, and the second antigen binding domain recognizes a second antigen, e.g., a second tumor antigen or a second B cell antigen described herein.

Co-Expression of CAR with Other Molecules or Agents

Co-Expression of a Second CAR

In one aspect, the CAR-expressing cell described herein can further comprise a second CAR, e.g., a second CAR that includes a different antigen binding domain, e.g., to the same target (mesothelin) or a different target (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HERS, IGF-1R, EGFR, DLL4, or Trop-2). In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. Placement of a costimulatory signaling domain, e.g., 4-1BB, CD28, CD27, OX-40 or ICOS, onto the first CAR, and the primary signaling domain, e.g., CD3 zeta, on the second CAR can limit the CAR activity to cells where both targets are expressed. In one embodiment, the CAR expressing cell comprises a first mesothelin CAR that includes a mesothelin binding domain, a transmembrane domain and a costimulatory domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain, a transmembrane domain and a primary signaling domain. In another embodiment, the CAR expressing cell comprises a first mesothelin CAR that includes a mesothelin binding domain, a transmembrane domain and a primary signaling domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain to the antigen, a transmembrane domain and a costimulatory signaling domain.

In one embodiment, the CAR-expressing cell comprises a mesothelin CAR described herein and an inhibitory CAR. In one embodiment, the inhibitory CAR comprises an antigen binding domain that binds an antigen found on normal cells but not cancer cells, e.g., normal cells that also express mesothelin. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising an antigen binding domains that minimize such interactions, as well as methods of making and using such cells and nucleic acids. In an embodiment the antigen binding domain of one of the first and the second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of the first and the second CAR does not comprise a variable light domain and a variable heavy domain. In some embodiments, the antigen binding domain of one of the first and the second CAR is an scFv, and the other is not an scFv. In some embodiments, the antigen binding domain of one of the first and the second CAR comprises a single VH domain, e.g., a camelid, shark, or lamprey single VH domain, or a single VH domain derived from a human or mouse sequence. In some embodiments, the antigen binding domain of one of the first and the second CAR comprises a nanobody. In some embodiments, the antigen binding domain of one of the first and the second CAR comprises a camelid VHH domain.

In some embodiments, the antigen binding domain of one of the first and the second CAR comprises an scFv, and the other comprises a single VH domain, e.g., a camelid, shark, or lamprey single VH domain, or a single VH domain derived from a human or mouse sequence. In some embodiments, the antigen binding domain of one of the first and the second CAR comprises an scFv, and the other comprises a nanobody. In some embodiments, the antigen binding domain of one of the first and the second CAR comprises comprises an scFv, and the other comprises a camelid VHH domain.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first and the second CAR, associate with one another less than if both were scFv antigen binding domains. In some embodiments, the antigen binding domains of the first and the second CAR, associate with one another 85%, 90%, 95%, 96%, 97%, 98% or 99% less than if both were scFv antigen binding domains.

Co-Expression of an Agent that Enhances CAR Activity

In another aspect, the CAR-expressing cell described herein can further express another agent, e.g., an agent that enhances the activity or fitness of a CAR-expressing cell.

For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, or TGFR beta.

In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In an embodiment, the agent that modulates or regulates, e.g., inhibits, T-cell function is inhibited within a CAR-expressing cell. For example, a dsRNA molecule that inhibits expression of a molecule that modulates or regulates, e.g., inhibits, T-cell function is linked to the nucleic acid that encodes a component, e.g., all of the components, of the CAR.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a mesothelin CAR described herein, improves the persistence of the T cell. In one embodiment, the CAR is a PD1 CAR comprising the extracellular domain of PD1 indicated as underlined in SEQ ID NO: 24 and a signal sequence at amino acids 1-21 of SEQ ID NO:24. In one embodiment, the PD1 CAR comprises the amino acid sequence of SEQ ID NO:24.

In one embodiment, the PD1 CAR without the N-terminal signal sequence comprises the amino acid sequence provided of SEQ ID NO:22.

In one embodiment, the agent comprises a nucleic acid sequence encoding the PD1 CAR with the N-terminal signal sequence, e.g., the PD1 CAR described herein. In one embodiment, the nucleic acid sequence for the PD1 CAR is shown in Table 1, with the PD1 ECD underlined in SEQ ID NO: 23.

In another example, in one embodiment, the agent which enhances the activity of a CAR-expressing cell can be a costimulatory molecule or costimulatory molecule ligand. Examples of costimulatory molecules include MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, e.g., as described herein. Examples of costimulatory molecule ligands include CD80, CD86, CD40L, ICOSL, CD70, OX40L, 4-1BBL, GITRL, and LIGHT. In embodiments, the costimulatory molecule ligand is a ligand for a costimulatory molecule different from the costimulatory molecule domain of the CAR. In embodiments, the costimulatory molecule ligand is a ligand for a costimulatory molecule that is the same as the costimulatory molecule domain of the CAR. In an embodiment, the costimulatory molecule ligand is 4-1BBL. In an embodiment, the costimulatory ligand is CD80 or CD86. In an embodiment, the costimulatory molecule ligand is CD70. In embodiments, a CAR-expressing immune effector cell described herein can be further engineered to express one or more additional costimulatory molecules or costimulatory molecule ligands.

Co-Expression of CAR with a Chemokine Receptor

In embodiments, the CAR-expressing cell described herein, e.g., mesothelin CAR-expressing cell, further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., J Immunother. 2010 October; 33(8):780-8 and Kershaw et al., Hum Gene Ther. 2002 Nov. 1; 13(16):1971-80). Thus, without wishing to be bound by theory, it is believed that chemokine receptors expressed in CAR-expressing cells that recognize chemokines secreted by tumors, e.g., solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell (e.g., CAR-Tx) described herein include a CXC chemokine receptor (e.g., CXCR1, CXCR2, CXCR3, CXCR4, CXCR5, CXCR6, or CXCR7), a CC chemokine receptor (e.g., CCR1, CCR2, CCR3, CCR4, CCR5, CCR6, CCR7, CCR8, CCR9, CCR10, or CCR11), a CX3C chemokine receptor (e.g., CX3CR1), a XC chemokine receptor (e.g., XCR1), or a chemokine-binding fragment thereof. In one embodiment, the chemokine receptor molecule to be expressed with a CAR described herein is selected based on the chemokine(s) secreted by the tumor. In one embodiment, the CAR-expressing cell described herein further comprises, e.g., expresses, a CCR2b receptor or a CXCR2 receptor. In an embodiment, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

Nucleic Acid Constructs Encoding a CAR

The present invention provides CAR transgenes comprising nucleic acid sequences encoding one or more CAR constructs of the invention. In one aspect, the CAR transgene is provided as a messenger RNA transcript. In one aspect, the CAR transgene is provided as a DNA construct.

Accordingly, in one aspect, the invention pertains to an isolated nucleic acid molecule encoding a chimeric antigen receptor (CAR), wherein the CAR comprises an anti-mesothelin binding domain (e.g., a human anti-mesothelin binding domain), a transmembrane domain, and an intracellular signaling domain comprising a stimulatory domain. In one embodiment, the anti-mesothelin binding domain is an anti-mesothelin binding domain described herein, e.g., an anti-mesothelin binding domain which comprises a sequence selected from a group consisting of SEQ ID NO: 87-111, or a sequence with 95-99% identify thereof. In one embodiment, the isolated nucleic acid molecule further comprises a sequence encoding a costimulatory domain. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 6, or a sequence with 95-99% identity thereof. In one embodiment, the anti-mesothelin binding domain is connected to the transmembrane domain by a hinge region, e.g., a hinge described herein. In one embodiment, the hinge region comprises SEQ ID NO:2 or SEQ ID NO:3 or SEQ ID NO:4 or SEQ ID NO:5, or a sequence with 95-99% identity thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp. In one embodiment, the costimulatory domain comprises a sequence of SEQ ID NO:7, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 7 or SEQ ID NO: 8, or a sequence with 95-99% identity thereof, and the sequence of SEQ ID NO: 9 or SEQ ID NO: 10, or a sequence with 95-99% identity thereof, wherein the sequences comprising the intracellular signaling domain are expressed in the same frame and as a single polypeptide chain. In another aspect, the invention pertains to an isolated nucleic acid molecule encoding a CAR construct comprising a leader sequence of SEQ ID NO: 1, a scFv domain having a sequence selected from the group consisting of SEQ ID NO: 39; SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62, (or a sequence with 95-99% identify thereof), a hinge region of SEQ ID NO: 2 or SEQ ID NO:3 or SEQ ID NO:4 or SEQ ID NO:5 (or a sequence with 95-99% identity thereof), a transmembrane domain having a sequence of SEQ ID NO: 6 (or a sequence with 95-99% identity thereof), a 4-1BB costimulatory domain having a sequence of SEQ ID NO:7 (or a sequence with 95-99% identity thereof) or a CD27 costimulatory domain having a sequence of SEQ ID NO: 8 (or a sequence with 95-99% identity thereof), and a CD3 zeta stimulatory domain having a sequence of SEQ ID NO:9 or SEQ ID NO: 10 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO: 63; SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, and SEQ ID NO: 86, or a sequence with 95-99% identity thereof.

In another aspect, the invention pertains to an isolated nucleic acid molecule encoding a chimeric antigen receptor (CAR) molecule that comprises an anti-mesothelin binding domain, a transmembrane domain, and an intracellular signaling domain comprising a stimulatory domain, and wherein the nucleic acid encoding the anti-mesothelin binding domain comprises a sequence selected from the group consisting of SEQ ID NO: 111; SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO:134, or a sequence with 95-99% identify thereof.

In one embodiment, the encoded CAR molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18) and 4-1BB (CD137). In one embodiment, the costimulatory domain comprises a sequence of SEQ ID NO:7. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:6. In one embodiment, the intracellular signaling domain comprises a functional signaling domain of 4-1BB and a functional signaling domain of zeta. In one embodiment, the intracellular signaling domain comprises the sequence of SEQ ID NO: 7 and the sequence of SEQ ID NO: 9, wherein the sequences comprising the intracellular signaling domain are expressed in the same frame and as a single polypeptide chain. In one embodiment, the anti-mesothelin binding domain is connected to the transmembrane domain by a hinge region. In one embodiment, the hinge region comprises SEQ ID NO:2. In one embodiment, the hinge region comprises SEQ ID NO: 3, SEQ ID NO: 4, or SEQ ID NO: 5.

In another aspect, the invention pertains to an isolated CAR molecule comprising a leader sequence of SEQ ID NO: 1, a scFv domain having a sequence selected from the group consisting of SEQ ID NOS: 39-62, or a sequence with 95-99% identify thereof, a hinge region of SEQ ID NO:2 or SEQ ID NO: 3 or SEQ ID NO: 4 or SEQ ID NO: 5, a transmembrane domain having a sequence of SEQ ID NO: 6, a 4-1BB costimulatory domain having a sequence of SEQ ID NO:7 or a CD27 costimulatory domain having a sequence of SEQ ID NO: 8, and a CD3 zeta stimulatory domain having a sequence of SEQ ID NO:9 or SEQ ID NO: 10. In one embodiment, the encoded CAR molecule comprises a sequence selected from the group consisting of SEQ ID NOS: 63-86, or a sequence with 95-99% identify thereof.

The present invention further provides vectors comprising CAR transgenes. In one aspect, a CAR vectors can be directly transduced into a cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells or NK cells. In one aspect, the mammalian T cell is a human T cell or a human NK cell.

The present invention also includes a CAR encoding RNA construct that can be directly transfected into a cell, e.g., a T cell or a NK cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one aspect, the template includes sequences for the CAR.

In one aspect the mesothelin CAR transgene is encoded by a messenger RNA (mRNA). In one aspect the mRNA encoding the mesothelin CAR transgene is introduced into a T cell for production of a CART cell, or a NK cell.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In one embodiment, the vector comprising the nucleic acid encoding the desired CAR of the invention is a DNA, a RNA, a plasmid, an adenoviral vector, a lentivirus vector, or a retrovirus vector. A retroviral vector may also be, e.g., a gammaretroviral vector. A gammaretroviral vector may include, e.g., a promoter, a packaging signal (w), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, CRISPR, CAS9, and zinc finger nucleases. See, e.g., June et al. 2009 *Nature Reviews Immunology* 9.10: 704-716, incorporated herein by reference in its entirety.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR transgene in a mammalian T cell is the EF1alpha promoter (EF1a or EF1α). The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO:11.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below.

```
WT PGK Promoter
                                        (SEQ ID NO: 597)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT
```

-continued

Exemplary truncated PGK Promoters:
PGK 100:

(SEQ ID NO: 598)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

PGK 200:

(SEQ ID NO: 599)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK 300:

(SEQ ID NO: 600)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG

PGK 400:

(SEQ ID NO: 601)

ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCG

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the vector can further comprise a nucleic acid encoding a second CAR. In one embodiment, the second CAR includes an antigen binding domain to, e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2. In one embodiment, the vector comprises a nucleic acid sequence encoding a first CAR that targets a first antigen and includes an intracellular signaling domain having a costimulatory signaling domain but not a primary signaling domain, and a nucleic acid encoding a second CAR that targets a second, different, antigen and includes an intracellular signaling domain having a primary signaling domain but not a costimulatory signaling domain. In one embodiment, the vector comprises a nucleic acid encoding a first mesothelin CAR that includes a mesothelin binding domain, a transmembrane domain and a costimulatory domain and a nucleic acid encoding a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2) and includes an antigen binding domain, a transmembrane domain and a primary signaling domain. In another embodiment, the vector comprises a nucleic acid encoding a first mesothelin CAR that includes a mesothelin binding domain, a transmembrane domain and a primary signaling domain and a nucleic acid encoding a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2) and includes an antigen binding domain to the antigen, a transmembrane domain and a costimulatory signaling domain.

In one embodiment, the vector comprises a nucleic acid encoding a mesothelin CAR described herein and a nucleic acid encoding an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, CEACAM (e.g., CEACAM-1, CEACAM-3 and/or CEACAM-5), LAGS, VISTA, BTLA, TIGIT, LAIR1, CD160, 2B4 and TGFR beta.

In embodiments, the vector may comprise two or more nucleic acid sequences, wherein one of the nucleic acid sequences encodes a CAR described herein, e.g., a mesothelin CAR described herein. In on emebodiment, the other nucleic acid can encode a second CAR, e.g., an inhibitory CAR or a specifically binds to an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2), or a polypeptide that can regulate activity of the mesothelin CAR described herein. In such embodiments, the two or more nucleic acid sequences, e.g., encoding a mesothelin CAR described herein and a second CAR or other polypeptide, are encoded by a single nucleic molecule in the same frame and as a single polypeptide chain. In one embodiment, the two or more polypeptides can be separated by one or more peptide cleavage sites (e.g., an auto-cleavage site or a substrate for an intracellular protease). Examples of peptide cleavage sites include the following, wherein the GSG residues are optional:

```
                                  (SEQ ID NO: 602)
T2A: (GSG)E G R G S L L T C G D V E E N P G P

                                  (SEQ ID NO: 603)
P2A: (GSG)A T N F S L L K Q A G D V E E N P G P

                                  (SEQ ID NO: 604)
E2A: (GSG)Q C T N Y A L L K L A G D V E S N P G P

                                  (SEQ ID NO: 605)
F2A: (GSG)V K Q T L N F D L L K L A G D V E S N P

G P
```

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is lipofection, e.g., using Lipofectamine (Life Technologies).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or a NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell. In one aspect, the mammalian cell is a human NK cell.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:35). RNA so produced can efficiently transfect different kinds of cells. In one aspect, the template includes sequences for the CAR.

In one aspect the mesothelin CAR is encoded by a messenger RNA (mRNA). In one aspect the mRNA encoding the mesothelin CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. The term "substantially complementary" refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. The term "upstream" refers to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. The term "downstream" refers to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 33).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1(2011):R14-20; Singh et al. Cancer Res. 15(2008):2961-2971; Huang et al. Mol. Ther. 16(2008):580-589; Grabundzija et al. Mol. Ther. 18(2010):1200-1209; Kebriaei et al. Blood. 122.21(2013): 166; Williams. Molecular Therapy 16.9(2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3(2013): 1829-47; and Singh et al. Cancer Res. 68.8(2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Sources of Cells

Prior to expansion and genetic modification, e.g., to express a CAR described herein, a source of cells, e.g., T cell or NK cells, can be obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present disclosure, any number of T cell lines available in the art, may be used. In certain aspects of the present disclosure, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells.

In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In one embodiment, a T cell population can be selected that expresses one or more of IFN-7, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present disclosure.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present disclosure, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR Immune Effector Cells

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class I and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell. Expression systems for siRNA and shRNAs, and exemplary shRNAs, are described, e.g., in paragraphs 649 and 650 of International Publication WO2015/142675, filed Mar. 13, 2015, which is incorporated by reference in its entirety.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein.

A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

The CRISPR/Cas system, and uses thereof, are described, e.g., in paragraphs 651-658 of International Publication WO2015/142675, filed Mar. 13, 2015, which is incorporated by reference in its entirety.

TALEN to Inhibit TCR and/or HLA

TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

TALENs, and uses thereof, are described, e.g., in paragraphs 659-665 of International Publication WO2015/142675, filed Mar. 13, 2015, which is incorporated by reference in its entirety.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

ZFNs, and uses thereof, are described, e.g., in paragraphs 666-671 of International Publication WO2015/142675, filed Mar. 13, 2015, which is incorporated by reference in its entirety.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as set out in SEQ ID NO: 110 herein.

In an embodiment, the hTERT has a sequence at least 80%, 85%, 90%, 95%, 96^, 97%, 98%, or 99% identical to the sequence of SEQ ID NO: 110. In an embodiment, the hTERT has a sequence of SEQ ID NO: 110. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as set out in SEQ ID NO: 111 herein.

In an embodiment, the hTERT is encoded by a nucleic acid having a sequence at least 80%, 85%, 90%, 95%, 96, 97%, 98%, or 99% identical to the sequence of SEQ ID NO: 111. In an embodiment, the hTERT is encoded by a nucleic acid of SEQ ID NO: 111.

Activation and Expansion of Immune Effector Cells (e.g., T Cells)

Immune effector cells, such as T cells, may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells, e.g., T cells may be expanded by contact with a surface having attached thereto an agent that stimulates a CD3/TCR complex associated signal and a ligand that stimulates a costimulatory molecule on the surface of the immune effector cells, e.g., T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present disclosure.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present disclosure, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type. In one aspect, the most typical ratios for use are in the neighborhood of 1:1, 2:1 and 3:1 on the first day.

In further aspects of the present disclosure, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CAR-expressing cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CAR-expressing cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CAR-expressing cell described herein, expanded for 5 days show at least a one, two, three, four, five, tenfold or more increase in pg/ml of proinflammatory cytokine production, e.g., IFN-γ and/or GM-CSF levels, as compared to the same cells expanded in culture for 9 days under the same culture conditions.

In one aspect of the present disclosure, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

In one embodiment, the cells are cultured (e.g., expanded, simulated, and/or transduced) in media comprising serum. The serum may be, e.g., human AB serum (hAB). In some embodiments, the hAB serum is present at about 2%, about 5%, about 2-3%, about 3-4%, about 4-5%, or about 2-5%. 2% and 5% serum are each suitable levels that allow for many fold expansion of T cells. Furthermore, as shown in Smith et al., "Ex vivo expansion of human T cells for adoptive immunotherapy using the novel Xeno-free CTS Immune Cell Serum Replacement" Clinical & Translational Immunology (2015) 4, e31; doi:10.1038/cti.2014.31, medium containing 2% human AB serum is suitable for ex vivo expansion of T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some embodiments, cells transduced with a nucleic acid encoding a CAR, e.g., a CAR described herein, can be selected for administration based upon, e.g., protein expression levels of one or more of CCL20, GM-CSF, IFNγ, IL-10, IL-13, IL-17a, IL-2, IL-21, IL-4, IL-5, IL-6, IL-9, TNFα and/or combinations thereof. In some embodiments, cells transduced with a nucleic acid encoding a CAR, e.g., a CAR described herein, can be selected for administration based upon, e.g., protein expression levels of CCL20, IL-17a, IL-6 and combinations thereof.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a mesothelin CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a mesothelin CAR are described, e.g., in paragraphs [0417]-[00423] of International Publication WO2015/090230, filed Dec. 19, 2014, which is incorporated by reference in its entirety.

Populations of CAR Cells

In another aspect, the present invention provides a population of CAR-expressing cells, e.g., a population of mesothelin CAR-expressing cells. In some embodiments, the population of CAR-expressing cells comprises a mixture of cells expressing different CARs.

For example, in one embodiment, the population of CAR-expressing cells can include a first cell expressing a CAR having an anti-mesothelin binding domain described herein, and a second cell expressing a CAR having a different anti-mesothelin binding domain, e.g., an anti-mesothelin binding domain described herein that differs from the anti-mesothelin binding domain in the CAR expressed by the first cell.

As another example, the population of CAR-expressing cells can include a first cell expressing a CAR that includes an anti-mesothelin binding domain, e.g., as described herein, and a second cell expressing a CAR that includes an antigen binding domain to a target other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2). In one embodiment, the population of CAR-expressing cells includes, e.g., a first cell expressing a CAR that includes a primary intracellular signaling domain, and a second cell expressing a CAR that includes a secondary signaling domain.

In one embodiment, thepopulation of CAR-expressing cells can include a first cell expressing a CAR that includes an anti-mesothelin binding domain and a second cell expressing a CAR that includes an antigen binding domain that targets, e.g., specifically binds, an antigen expressed on B cells, or a B cell antigen. In one embodiment, the B cell antigen is CD19.

In another aspect, the present invention provides a population of cells wherein at least one cell in the population expresses a CAR having an anti-mesothelin binding domain described herein, and a second cell expressing another agent, e.g., an agent which enhances the activity or function of a CAR-expressing cell. For example, in one embodiment, the agent can be an agent which modulates or regulates, e.g., inhibits, T cell function. In some embodiments, the molecule that modulates or regulates T cell function is an inhibitory molecule, e.g., an agent described herein. Inhibitory molecules, e.g., can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells, e.g., CART cells, e.g., a mixture of cells expressing different CARs, in combination with another agent, e.g., a PD-L1 inhibitor, such as a PD-L1 inhibitor described herein. In another aspect, the present invention provides methods comprising administering a population of cells wherein at least one cell in the population expresses a CAR having an anti-mesoothelinbinding domain as described herein, and a second cell expressing another agent, e.g., an agent which enhances the activity or fitness of a CAR-expressing cell, in combination with another agent, e.g., a PD-L1 inhibitor, such as a PD-L1 inhibitor described herein.

PD-L1 Inhibitors

The immune system has the capability of recognizing and eliminating tumor cells; however, tumors can use multiple strategies to evade immunity. Blockade of immune checkpoints is one of the approaches to activating or reactivating therapeutic antitumor immunity. Programmed Death Ligand 1 (PD-L1) has been described as a ligand for the immuneinhibitory receptor Programmed Death 1 (PD-1). Binding of PD-L1 to PD-1 leads to the inhibition of T cell receptor-mediated lymphocyte proliferation and cytokine secretion (Freeman et al. (2000) *J Exp Med* 192:1027-34). Thus, blocking of PD-L1 can lead to enhancement of antitumor immunity.

Several cell types express PD-L1. For example, PD-L1 is expressed on activated T cells, dendritic cells (DCs), natural killer (NK) cells, macrophages, B cells, monocytes, and vascular endothelium cells. PD-L1 is expressed in many cancers, including human lung, ovarian and colon carcinoma and various myelomas, (Iwai et al. (2002) *PNAS* 99:12293-7; Ohigashi et al. (2005) *Clin Cancer Res* 11:2947-53; Okazaki et al. (2007) *Intern. Immun.* 19:813-24; Thompson et al. (2006) *Cancer Res.* 66:3381-5). PD-L1 expression strongly correlates with unfavorable prognosis in various types of cancer including kidney, ovarian, bladder, breast, gastric and pancreatic cancer.

Many tumor infiltrating T lymphocytes predominantly express PD-1 compared to T lymphocytes in normal tissues and peripheral blood T lymphocytes. This indicates that up-regulation of PD-1 on tumor-reactive T cells can contribute to impaired antitumor immune responses (Ahmadzadeh et al. (2009) *Blood* 114:1537-44). Thus, PD-L1 signaling mediated by PD-L1 expressing tumor cells interacting with PD-1 expressing T cells may lead to attenuation of T cell activation and evasion of immune surveillance (Sharpe et al. (2002) *Nat Rev Immunol.* 2:116-26; Keir et al. (2008) *Annu Rev Immunol.* 26:677-704). PD-1 blockade can inhibit hematogenous spread of poorly immunogenic tumor cells by enhanced recruitment of effector T cells (Iwai et al. (2005) *Int. Immunol.* 17:133-144).

PD-L1 inhibition can enhance T-cell immunity, e.g., through blocking both its inhibitory interactions with PD-1 and B7-1. PD-L1 inhibition can also allow for immune regulation via PD-L2/PD-1. Both PD-1 and B7-1 are expressed on T cells, B cells, DCs, and macrophages, which provides potential for bidirectional interactions between B7-1 and PD-L1 on these cell types. PD-L1 on non-hematopoietic cells may interact with B7-1 as well as PD-1 on T cells.

The term "Programmed Death Ligand 1" or "PD-L1" include isoforms, mammalian, e.g., human PD-L1, species homologs of human PD-1, and analogs comprising at least one common epitope with PD-L1. The amino acid sequence of PD-L1, e.g., human PD-1, is known in the art, e.g., Dong et al. (1999) *Nat Med.* 5(12):1365-9; Freeman et al. (2000) *J Exp Med.* 192(7):1027-34).

The present disclosure provides methods and combinations for treating a disease, e.g., associated with mesothelin expression, that include the administration of a PD-L1 inhibitor. The PD-L1 inhibitor can have one or more of the following properties: inhibits or reduces binding of PD-L1 to a receptor, e.g., PD-1 or CD80 (B7-1), or both; binds to PD-L1 or a PD-L1 binding receptor, e.g., PD-1 or CD80 (B7-1), or both; inhibits or reduces one or more activities of PD-L1, e.g., results in one or more of: an increase in tumor infiltrating lymphocytes, an increase in T-cell receptor mediated proliferation, or a decrease in immune evasion by cancerous cells; or inhibits or reduces PD-L1 expression, e.g., transcription or translation of PD-L1.

In embodiments, the PD-L1 inhibitor reduces binding of PD-L1 to a receptor, e.g., to PD-1 or CD80 (B7-1), or both. For example, the PD-L1 binding to a receptor, e.g., to PD-1 or CD80 (B7-1), or both, is reduced in the presence of the PD-L1 inhibitor by at least 1%, 5%, 10%, 20%, 30%, 40%, 50%, 60%, 70%, 80%, or 90% as compared to binding in the absence of the PD-L1 inhibitor. In one embodiment, PD-L1 binding to a receptor, e.g., to PD-1 or CD80 (B7-1), or both, is negligible, e.g., undetectable, by the standard binding assays known in the art. Ligand-receptor binding assays are well known in the art, and include immunoprecipitation and western blotting assays.

In embodiments, the PD-L1 inhibitor reduces one or more activities of PD-L1. For example, PD-L1 activity is reduced by at least 1%, 5%, 10%, 20%, 30%, 40%, 50%, 60%, 70%, 80%, or 90% as compared to PD-L1 activity in the absence of the PD-L1 inhibitor.

In embodiments, the PD-L1 inhibitor reduces PD-L1 expression, e.g., reduces transcription or translation of PD-L1. For example, PD-L1 transcription is reduced by at least 1%, 5%, 10%, 20%, 30%, 40%, 50%, 60%, 70%, 80%, or 90% as compared to PD-L1 transcription in the absence of the PD-L1 inhibitor. In another example, PD-L1 translation is reduced by at least 1%, 5%, 10%, 20%, 30%, 40%, 50%, 60%, 70%, 80%, or 90% as compared to PD-L1 translation in the absence of the PD-L1 inhibitor. Assays for determining PD-L1 RNA expression are known in the art, and include PCR amplification-based assays, e.g., QPCR, and nucleic acid hybridization-based assays, e.g., Northern blots. Assays for determining PD-L1 protein expression are known in the art, and include western blotting and immunohistochemical analysis. In such embodiments, administration of PD-L1 inhibitor results in reduced levels or amount of PD-L1 expressed in a cell, or reduced numbers of PD-L1 expressing cells.

In one embodiment, the PD-L1 inhibitor can be a small molecule; a polypeptide, e.g., a fusion protein; an antibody molecule; or an inhibitory nucleic acid; e.g., a siRNA or shRNA.

In one embodiment, the PD-L1 inhibitor is a small molecule. In one embodiment, the small molecule inhibitor binds to PD-L1. In another embodiment, the small molecule inhibitor binds to the receptor for PD-L1, e.g., PD-1 or CD80 (B7-1), or both. In yet another embodiment, the small molecule inhibitor prevents or reduces binding of PD-L1 to its receptor, e.g., PD-1 or CD80 (B7-1), or both.

In one embodiment, the PD-L1 inhibitor is a polypeptide or peptide. In one embodiment, the polypeptide or peptide inhibitor of PD-L1 binds to PD-L1 or its receptor, e.g., PD-1 or CD80 (B7-1), or both. In one embodiment, the polypeptide or peptide prevents or reduces binding of PD-L1 to its receptor, e.g., PD-1 or CD80 (B7-1), or both. In one embodiment, the polypeptide comprises a portion of PD-L1, e.g., a receptor binding portion of PD-L1, or a modified portion thereof that may exhibit increased affinity for PD-1 or CD80 (B7-1) as compared to wild-type PD-L1. In such embodiments, the polypeptide inhibits or reduces PD-L1 activity by competing for binding with the receptor.

In one embodiment, the PD-L1 inhibitor is an inhibitory nucleic acid, e.g., an RNA interfering (RNAi) agent. The inhibitory nucleic acid can be a double stranded or single stranded nucleic acid. The inhibitory nucleic acid can be a DNA, a RNA, or a hybrid comprising DNA and RNA. An inhibitory nucleic acid inhibits or reduces the expression, e.g., translation, of PD-L1. An RNA intereference (RNAi) agent typically causes the destruction of target mRNA molecules to inhibit or reduce the expression, e.g., translation, of a target gene, e.g., PD-L1. Examples of RNAi agents include long dsRNA, siRNA, shRNA, and microRNAs. Inhibitory nucleic acids described herein include, but are not limited to, an aptamer, a morpholino, a ribozyme, and a nucleic acid sequences, e.g., plasmids or vectors, that comprise or encode a long dsRNA, siRNA, shRNA, or microRNA.

In one embodiment, the inhibitory nucleic acid is a RNA with at least 75%, 80%, 85%, 90%, 95%, or 99% sequence identity or complementarity to the PD-L1 gene or a fragment thereof.

In one embodiment, the inhibitory nucleic acid is a siRNA or shRNA of about 15 to about 65, about 15 to about 40, or about 15 to about 28 nucleotides in length. In embodiments where the inhibitory nucleic acid is a siRNA, the siRNA has a length of about 19 to 25 nucleotides, e.g., 19, 20, 21, or 22 nucleotides. In embodiments where the inhibitory nucleic acid is a shRNA, the shRNA has a length of about 42 to about 70 nucleotides. In one embodiment, the shRNA comprises paired antisense and sense RNA strands connected by a loop of unpaired nucleotides. In one embodiment, the duplex stem has a length of about 19 to about 29 nuclotides, either fully paired or with internal mismatches and loops. In one embodiment, the loop comprises 4, 5, 6, 7, 8, 9, or 10 nucleotides, e.g., 4 or 7 nucleotides.

The inhibitoy nucleic acid can be synthesized or expressed, e.g., from a plasmid or vector. Synthetic RNAi agents can be generated using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114: 4557-4565; Masters, J. R. et al. (2001) *Proc. Natl. Acad. Sci. USA* 98:8012-8017; and Tuschl, T. et al. (1999) *Genes & Development* 13:3191-3197). Alternatively, several commercial RNA synthesis suppliers are available including, but not limited to, Proligo (Hamburg, Germany), Dharmacon Research (Lafayette, Co., USA), Pierce Chemical (part of *Perbio Science*, Rockford, Ill., USA), Glen Research (Sterling, Va., USA), ChemGenes (Ashland, Mass., USA), and Cruachem (Glasgow, UK).

Assays for assessing expression, e.g., assessing RNA or protein levels, are well known in the art. For example, probes based on the PD-L1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes are used, e.g., in a PCR-based assay, to measure the level of PD-L1 mRNA. Western blotting techniques are well known in the art and are used to measure the level of PD-L1 protein.

In one embodiment, the PD-L1 inhibitor is an antibody molecule. In one embodiment, the antibody molecule binds to a mammalian, e.g., human, PD-L1. For example, the antibody molecule binds specifically to an epitope, e.g., linear or conformational epitope, (e.g., an epitope as described herein) on PD-L1.

In some embodiments, the PD-L1 inhibitor is chosen from YW243.55.570, MPDL3280A, MEDI-4736, MSB-0010718C, or MDX-1105. MEDI4736 (Medimmune) is a human monoclonal antibody that binds to PDL1, and inhibits interaction of the ligand with PD1.

In some embodiments, the anti-PD-L1 antibody is MSB0010718C. MSB0010718C (also referred to as A09-246-2; Merck Serono or avelumab) is a monoclonal antibody that binds to PD-L1. Other anti-PD-L1 antibodies and inhibitors are disclosed in WO2013/079174, WO2001/014557, WO2002/086083, WO2007005874, WO2010036959, WO2010077634 and WO2011066389, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

```
Heavy chain (SEQ ID NO: 24 as disclosed in WO2013/
079174)
                                  (SEQ ID NO: 611)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTVSS

Light chain (SEQ ID NO: 25 as disclosed in WO2013/
079174)
                                  (SEQ ID NO: 612)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL
```

In one embodiment, the PD-L1 inhibitor is YW243.55.S70. The YW243.55.S70 antibody is an anti-PD-L1 antibody described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche) (also known as atezolizumab). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

Exemplary PD-L1 Antibody Molecules

In one embodiment, the PD-L1 inhibitor comprises an antibody molecule (e.g., an isolated or recombinant antibody molecule) having one or more of the following properties:

(i) binds to PD-L1, e.g., human PD-L1, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger;

(ii) does not substantially bind to CD28, CTLA-4, ICOS or BTLA;

(iii) inhibits or reduces binding of PD-L1 to a receptor, e.g., PD-1 or CD80 (B7-1), or both;

(iv) binds specifically to an epitope on PD-L1, e.g., the same or similar epitope as the epitope recognized by murine monoclonal antibody BAP058 or a chimeric antibody BAP058, e.g., BAP058-chi;

(v) shows the same or similar binding affinity or specificity, or both, as any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(vi) shows the same or similar binding affinity or specificity, or both, as an antibody molecule (e.g., an heavy chain variable region and light chain variable region) described in Table 1;

(vii) shows the same or similar binding affinity or specificity, or both, as an antibody molecule (e.g., an heavy chain variable region and light chain variable region) having an amino acid sequence shown in Table 1;

(viii) shows the same or similar binding affinity or specificity, or both, as an antibody molecule (e.g., an heavy chain variable region and light chain variable region) encoded by the nucleotide sequence shown in Table 1;

(ix) inhibits, e.g., competitively inhibits, the binding of a second antibody molecule to PD-L1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(x) binds the same or an overlapping epitope with a second antibody molecule to PD-1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xi) competes for binding, and/or binds the same epitope, with a second antibody molecule to PD-L1, wherein the second antibody molecule is an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xii) has one or more biological properties of an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xiii) has one or more pharmacokinetic properties of an antibody molecule described herein, e.g., an antibody molecule chosen from, e.g., any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O;

(xiv) inhibits one or more activities of PD-L1, e.g., results in one or more of: an increase in tumor infiltrating lymphocytes, an increase in T-cell receptor mediated proliferation, or a decrease in immune evasion by cancerous cells; or (xv) binds human PD-L1 and is cross-reactive with cynomolgus PD-L1.

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0, as provided in Table 6, or encoded by the nucleotide sequence in Table 6; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 6, or encoded by the nucleotide sequence in Table 6; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 6, or encoded by a nucleotide sequence shown in Table 6. In one embodiment, one or more of the CDRs (or collectively all of the CDRs) have one, two, three, four, five, six or more changes, e.g., amino acid substitutions or deletions, relative to the amino acid sequence shown in Table 6, or encoded by a nucleotide sequence shown in Table 6.

In yet another embodiment, the anti-PD-L1 antibody molecule includes at least one, two, or three CDRs (or collectively all of the CDRs) from a light chain variable region comprising an amino acid sequence shown in Table 6, or encoded by a nucleotide sequence shown in Table 6. In one embodiment, one or more of the CDRs (or collectively all of the CDRs) have one, two, three, four, five, six or more changes, e.g., amino acid substitutions or deletions, relative to the amino acid sequence shown in Table 6, or encoded by a nucleotide sequence shown in Table 6. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 6, or encoded by a nucleotide sequence shown in Table 6. In one embodiment, one or more of the CDRs (or collectively all of the CDRs) have one, two, three, four, five, six or more changes, e.g., amino acid substitutions or deletions, relative to the amino acid sequence shown in Table 6, or encoded by a nucleotide sequence shown in Table 6.

In one embodiment, the anti-PD-L1 antibody molecule includes:

(i) a heavy chain variable region (VH) including a VHCDR1 amino acid sequence chosen from SEQ ID NO: 287, SEQ ID NO: 290 or SEQ ID NO: 195; a VHCDR2 amino acid sequence of SEQ ID NO: 288; and a VHCDR3 amino acid sequence of SEQ ID NO: 289, each disclosed in Table 6; and (ii) a light chain variable region (VL) including a VLCDR1 amino acid sequence of SEQ ID NO: 295, a VLCDR2 amino acid sequence of SEQ ID NO: 296, and a VLCDR3 amino acid sequence of SEQ ID NO: 297, each disclosed in Table 6.

In another embodiment, the anti-PD-L1 antibody molecule includes:

(i) a heavy chain variable region (VH) including a VHCDR1 amino acid sequence chosen from SEQ ID NO: 287, SEQ ID NO: 290 or SEQ ID NO: 195; a VHCDR2 amino acid sequence of SEQ ID NO: 291, and a VHCDR3 amino acid sequence of SEQ ID NO: 292, each disclosed in Table 6; and (ii) a light chain variable region (VL) including a VLCDR1 amino acid sequence of SEQ ID NO: 298, a VLCDR2 amino acid sequence of SEQ ID NO: 299, and a VLCDR3 amino acid sequence of SEQ ID NO: 300, each disclosed in Table 6.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 195.

In embodiments, the aforesaid antibody molecules have a heavy chain variable region comprising at least one framework (FW) region comprising the amino acid sequence of any of SEQ ID NOs: 124, 126, 128, 130, 132, 134, 136, 138, 140, 142, 144, 146, 148, 150, 152, or 154, or an amino acid sequence at least 90% identical thereto, or having no more than two amino acid substitutions, insertions or deletions compared to the amino acid sequence of any of SEQ ID NOs: 124, 126, 128, 130, 132, 134, 136, 138, 140, 142, 144, 146, 148, 150, 152, or 154.

In other embodiments, the aforesaid antibody molecules have a heavy chain variable region comprising at least one framework region comprising the amino acid sequence of any of SEQ ID NOs: 124, 126, 128, 130, 132, 134, 136, 138, 140, 142, 144, 146, 148, 150, 152, or 154.

In yet other embodiments, the aforesaid antibody molecules have a heavy chain variable region comprising at least two, three, or four framework regions comprising the amino acid sequences of any of SEQ ID NOs: 124, 126, 128, 130, 132, 134, 136, 138, 140, 142, 144, 146, 148, 150, 152, or 154.

In other embodiments, the aforesaid antibody molecules comprise a VHFW1 amino acid sequence of SEQ ID NO: 124, 126, 128, or 130, a VHFW2 amino acid sequence of SEQ ID NO: 132, 134, 136, 138, 140, or 142, and a VHFW3 amino acid sequence of SEQ ID NO: 144, 146, 148, 150, or 152, and, optionally, further comprising a VHFW4 amino acid sequence of SEQ ID NO: 154.

In other embodiments, the aforesaid antibody molecules have a light chain variable region comprising at least one framework region comprising the amino acid sequence of any of SEQ ID NOs: 156, 158, 160, 162, 164, 166, 168, 170, 172, 174, 176, 178, 180, 182, 184, or 186, or an amino acid sequence at least 90% identical thereto, or having no more than two amino acid substitutions, insertions or deletions compared to the amino acid sequence of any of 156, 158, 160, 162, 164, 166, 168, 170, 172, 174, 176, 178, 180, 182, 184, or 186.

In other embodiments, the aforesaid antibody molecules have a light chain variable region comprising at least one framework region comprising the amino acid sequence of any of SEQ ID NOs: 156, 158, 160, 162, 164, 166, 168, 170, 172, 174, 176, 178, 180, 182, 184, or 186.

In other embodiments, the aforesaid antibody molecules have a light chain variable region comprising at least two, three, or four framework regions comprising the amino acid sequences of any of SEQ ID NOs: 156, 158, 160, 162, 164, 166, 168, 170, 172, 174, 176, 178, 180, 182, 184, or 186.

In other embodiments, the aforesaid antibody molecules comprise a VLFW1 amino acid sequence of SEQ ID NO: 156, 158, 160, 162, 164, or 166, a VLFW2 amino acid sequence of SEQ ID NO: 168 or 170, and a VLFW3 amino acid sequence of SEQ ID NO: 172, 174, 176, 178, 180, 182, or 184, and, optionally, further comprising a VLFW4 amino acid sequence of SEQ ID NO: 186.

In other embodiments, the aforesaid antibody molecules comprise a heavy chain variable domain comprising the amino acid sequence of SEQ ID NO: 18, 30, 38, 46, 50, 54, 62, 70, or 78, or an amino acid sequence that is at least 85% identical to the amino acid sequence of SEQ ID NO: 18, 30, 38, 46, 50, 54, 62, 70, or 78.

In other embodiments, the aforesaid antibody molecules comprise a light chain variable domain comprising an amino acid sequence of SEQ ID NO: 22, 26, 34, 42, 58, 66, 74, 82, or 86 or an amino acid sequence that is at least 85% identical to any of SEQ ID NOs: 22, 26, 34, 42, 58, 66, 74, 82, or 86.

In other embodiments, the aforesaid antibody molecules are chosen from a Fab, F(ab')2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules are capable of binding to human PD-L1 with a dissociation constant ($K_D$) of less than about 0.2 nM.

In some embodiments, the aforesaid antibody molecules bind to human PD-L1 with a $K_D$ of less than about 0.2 nM, 0.15 nM, 0.1 nM, 0.05 nM, or 0.02 nM, e.g., about 0.2 nM to 0.1 nM, e.g., about 0.166 nM to 0.176 nM, e.g., about 0.171 nM, e.g., as measured by a Biacore method.

In other embodiments, the aforesaid antibody molecules are capable of reducing binding of PD-1 or B7-1 to PD-L1 or a cell that expresses PD-L1. In some embodiments, the aforesaid antibody molecules reduce (e.g., block) PD-L1 binding to a cell that expresses PD-L1 with an IC50 of less than about 1.5 nM, 1 nM, 0.8 nM, 0.6 nM, 0.4 nM, 0.2 nM, or 0.1 nM, e.g., between about 0.2 nM and about 0.1 nM, e.g., about 0.15 nM or less, e.g., about 0.145 nM. In some embodiments, the aforesaid antibodies reduce (e.g., block) B7-1 binding to a cell that expresses PD-L1 (e.g., human PD-L1-expressing 300.19 cells) with an IC50 of less than about 2 nM, 1.5 nM, 1 nM, 0.5 nM, or 0.2 nM, e.g., between about 0.5 nM and about 0.01 nM, or about 0.2 nM or less, e.g., about 0.1 nM.

In other embodiments, the aforesaid antibody molecules are capable of enhancing an antigen-specific T cell response.

In some embodiments, the aforesaid antibody molecules bind to PD-L1 with a Kd slower than $5\times10^{-4}$, $1\times10^{-4}$, $5\times10^{-5}$, or $1\times10^{-5}$ $s^{-1}$, e.g., about $6.33\times10^{-5}$ $s^{-1}$, e.g., as measured by a Biacore method. In some embodiments, the aforesaid antibody molecules bind to PD-L1 with a Ka faster than $1\times10^4$, $5\times10^4$, $1\times10^5$, or $5\times10^5$ $M^{-1}s^{-1}$, e.g., about $3.07\times10^4$ $M^{-1}s^{-1}$, e.g., as measured by a Biacore method.

In embodiments, the anti-PD-L1 antibody molecule is a monospecific antibody molecule or a bispecific antibody molecule. In embodiments, the anti-PD-L1 antibody molecule has a first binding specificity for PD-L1 and a second binding specifity for TIM-3, LAG-3, CEACAM (e.g., CEACAM-1, CEACAM-3, and/or CEACAM-5), PD-1 or PD-L2. In embodiments, the antibody molecule comprises an antigen binding fragment of an antibody, e.g., a half antibody or antigen binding fragment of a half antibody.

TABLE 6

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| **BAP058 HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 292 | VH | QVHLQQPGAELVKPGASVKLSCKASGYTFTSYWMYWVKQGPGRGLEWIGRIDPN<br>SGSTKYNEKFKNKATLTVDKSSSTAYMQLSSLTSEDSAVYYCARDYRKGLYAMD<br>YWGQGTSVTVSS |
| SEQ ID NO: 293 | DNA VH | CAGGTCCACCTGCAGCAGCCTGGGGCTGAGCTTGTGAAGCCTGGGGCTTCAGTG<br>AAGCTGTCCTGCAAGGCTTCTGGCTACACCTTCACCAGTTACTGGATGTACTGG<br>GTGAAACAGGGGCCTGGACGAGGCCTTGAGTGGATTGGAAGGATTGATCCTAAT<br>AGTGGGAGTACTAAGTACAATGAGAAGTTCAAGAACAAGGCCACACTGACTGTA<br>GACAAATCCTCCAGCACAGCCTACATGCAGCTCAGCAGCCTGACATCTGAGGAC<br>TCTGCGGTCTATTATTGTGCAAGGGACTATAGAAAGGGGCTCTATGCTATGGAC<br>TACTGGGGTCAAGGAACCTCAGTCACCGTCTCCTCA |
| **BAP058 LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 294 | VL | DIVMTQSHKFMSTSVGDRVSITCKASQDVGTAVAWYQQKPGQSPKLLIYWASTR<br>HTGVPDRFTGSGSGTDFTLTISNVQSEDLADYFCQQYNSYPLTFGAGSKLELK |
| SEQ ID NO: 301 | DNA VL | GACATTGTGATGACCCAGTCTCACAAATTCATGTCCACATCAGTAGGAGACAGG<br>GTCAGCATCACCTGCAAGGCCAGTCAGGATGTGGGTACTGCTGTAGCCTGGTAT<br>CAACAGAAACCAGGGCAATCTCCTAAACTACTGATTTACTGGGCATCCACCCGG<br>CACACTGGAGTCCCTGATCGCTTCACAGGCAGTGGATCTGGGACAGATTTCACT<br>CTCACCATTAGCAATGTGCAGTCTGAAGACTTGGCAGATTATTTCTGTCAGCAG<br>TATAACAGCTATCCTCTCACGTTCGGTGCTGGGTCCAAGCTGGAGCTGAAA |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| **BAP058-chi HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 302 | VH | EVQLQQSGAELVKPGASVKLSCKASGYTFTSYWMYWVKQGPGRGLEWIGRIDPN SGSTKYNEKFKNKATLTVDKSSSTAYMQLSSLTSEDSAVYYCARDYRKGLYAMD YWGQGTTVTVSS |
| **BAP058-chi LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 303 | VL | DIMMTQSHKFMSTSVGDRVSITCKASQDVGTAVAWYQQKPGQSPKLLIYWASTR HTGVPDRFTGSGSGTDFTLTISNVQSEDLADYFCQQYNSYPLTFGQGTKVEIK |
| **BAP058-hum01-HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 304 | VH | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSS |
| SEQ ID NO: 305 | DNA VH | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 306 | Heavy Chain | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 307 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| | | **BAP058-hum01-LC** |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 308 | VL | DIVMTQTPLSLPVTPGEPASISCKASQDVGTAVAWYLQKPGQSPQLLIYWASTR<br>HTGIPARFSGSGSGTEFTLTISSLQSEDFAVYYCQQYNSYPLTFGQGTKVEIK |
| SEQ ID NO: 309 | DNA VL | GATATTGTGATGACCCAGACTCCACTCTCCCTGCCCGTCACCCCTGGAGAGCCG<br>GCCTCCATCTCCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGATCCCAGCCAGGTTCAGTGGCAGTGGGTCTGGGACAGAGTTCACT<br>CTCACCATCAGCAGCCTGCAGTCTGAAGATTTTGCAGTTTATTACTGTCAGCAG<br>TATAACAGCTATCCTCTCACGTTCGGCCAAGGGACCAAGGTGGAAATCAAA |
| SEQ ID NO: 310 | Light Chain | DIVMTQTPLSLPVTPGEPASISCKASQDVGTAVAWYLQKPGQSPQLLIYWASTR<br>HTGIPARFSGSGSGTEFTLTISSLQSEDFAVYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 311 | DNA Light Chain | GATATTGTGATGACCCAGACTCCACTCTCCCTGCCCGTCACCCCTGGAGAGCCG<br>GCCTCCATCTCCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGATCCCAGCCAGGTTCAGTGGCAGTGGGTCTGGGACAGAGTTCACT<br>CTCACCATCAGCAGCCTGCAGTCTGAAGATTTTGCAGTTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| | | **BAP058-hum02-HC** |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 289 (Chothia) | HCDR3 | DYRKGLYAMDY |
| SEQ ID NO: 304 | VH | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSS |
| SEQ ID NO: 305 | DNA VH | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 306 | Heavy Chain | QVQLVQSGAEVKKPGASVKVSCKASGYTFTSYWMYWVRQATGQGLEWMGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 307 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum02-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 312 | VL | DIQMTQSPSSLSASVGDRVTITCKASQDVGTAVAWYLQKPGQSPQLLIYWASTR HTGVPSRFSGSGSGTDFTLTISSLQPEDFATYYCQQYNSYPLTFGQGTKVEIK |
| SEQ ID NO: 313 | DNA VL | GACATCCAGATGACCCAGTCTCCATCCTCCCTGTCTGCATCTGTAGGAGACAGA GTCACCATCACTTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCATCAAGGTTCAGCGGCAGTGGATCTGGGACAGATTTCACT CTCACCATCAGCAGCCTGCAGCCTGAAGATTTTGCAACTTATTACTGTCAGCAG TATAACAGCTATCCTCTCACGTTCGGCCAAGGGACCAAGGTGGAAATCAAA |
| SEQ ID NO: 314 | Light Chain | DIQMTQSPSSLSASVGDRVTITCKASQDVGTAVAWYLQKPGQSPQLLIYWASTR HTGVPSRFSGSGSGTDFTLTISSLQPEDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 315 | DNA Light Chain | GACATCCAGATGACCCAGTCTCCATCCTCCCTGTCTGCATCTGTAGGAGACAGA GTCACCATCACTTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCATCAAGGTTCAGCGGCAGTGGATCTGGGACAGATTTCACT CTCACCATCAGCAGCCTGCAGCCTGAAGATTTTGCAACTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

BAP058-hum03-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSS |
| SEQ ID NO: 317 | DNA VH | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 318 | Heavy Chain | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 319 | DNA Heavy Chain | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

BAP058-hum03-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 320 | VL | EIVLTQSPDFQSVTPKEKVTITCKASQDVGTAVAWYLQKPGQSPQLLIYWASTR HTGVPDRFSGSGSGTDFTLKISRVEAEDVGVYYCQQYNSYPLTFGQGTKVEIK |
| SEQ ID NO: 321 | DNA VL | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCAGACAGGTTCAGTGGCAGTGGGTCAGGCACTGATTTCACA CTGAAAATCAGCAGGGTGGAGGCTGAGGATGTTGGAGTTTATTACTGTCAGCAG TATAACAGCTATCCTCTCACGTTCGGCCAAGGGACCAAGGTGGAAATCAAA |
| SEQ ID NO: 322 | Light Chain | EIVLTQSPDFQSVTPKEKVTITCKASQDVGTAVAWYLQKPGQSPQLLIYWASTR HTGVPDRFSGSGSGTDFTLKISRVEAEDVGVYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 323 | DNA Light Chain | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCAGACAGGTTCAGTGGCAGTGGGTCAGGCACTGATTTCACA CTGAAAATCAGCAGGGTGGAGGCTGAGGATGTTGGAGTTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

BAP058-hum04-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 324 | VH | EVQLVQSGAEVKKPGESLRISCKGSGYTFTSYWMYWVRQAPGQGLEWMGRIDPN SGSTKYNEKFKNRVTISVDTSKNQFSLKLSSVTAADTAVYYCARDYRKGLYAMD YWGQGTTVTVSS |
| SEQ ID NO: 325 | DNA VH | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCCCCTGGACAAGGGCTTGAGTGGATGGGTAGGATTGATCCTAAT AGTGGGAGTACTAAGTACAATGAGAAGTTCAAGAACAGAGTCACCATATCAGTA GACACGTCCAAGAACCAGTTCTCCCTGAAGCTGAGCTCTGTGACCGCCGCGGAC ACGGCTGTGTATTACTGTGCAAGGGACTATAGAAAGGGGCTCTATGCTATGGAC TACTGGGGCCAGGGCACCACCGTGACCGTGTCCTCC |
| SEQ ID NO: 326 | Heavy Chain | EVQLVQSGAEVKKPGESLRISCKGSGYTFTSYWMYWVRQAPGQGLEWMGRIDPN SGSTKYNEKFKNRVTISVDTSKNQFSLKLSSVTAADTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 327 | DNA Heavy Chain | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCCCCTGGACAAGGGCTTGAGTGGATGGGTAGGATTGATCCTAAT AGTGGGAGTACTAAGTACAATGAGAAGTTCAAGAACAGAGTCACCATATCAGTA GACACGTCCAAGAACCAGTTCTCCCTGAAGCTGAGCTCTGTGACCGCCGCGGAC ACGGCTGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum04-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIK |
| SEQ ID NO: 329 | DNA VL | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCATCAAGGTTCAGTGGAAGTGGATCTGGGACAGATTTTACT TTCACCATCAGCAGCCTGCAGCCTGAAGATATTGCAACATATTACTGTCAGCAG TATAACAGCTATCCTCTCACGTTCGGCCAAGGGACCAAGGTGGAAATCAAA |
| SEQ ID NO: 330 | Light Chain | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 331 | DNA Light Chain | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCATCAAGGTTCAGTGGAAGTGGATCTGGGACAGATTTTACT TTCACCATCAGCAGCCTGCAGCCTGAAGATATTGCAACATATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

BAP058-hum05-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 332 | VH | EVQLVQSGAEVKKPGATVKISCKVSGYTFTSYWMYWIRQSPSRGLEWLGRIDPN<br>SGSTKYNEKFKNRLTISKDTSKNQVVLTMTNMDPVDTATYYCARDYRKGLYAMD<br>YWGQGTTVTVSS |
| SEQ ID NO: 333 | DNA VH | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>ATCAGGCAGTCCCCATCGAGAGGCCTTGAGTGGCTGGGTAGGATTGATCCTAAT<br>AGTGGGAGTACTAAGTACAATGAGAAGTTCAAGAACAGACTCACCATCTCCAAG<br>GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCC |
| SEQ ID NO: 334 | Heavy Chain | EVQLVQSGAEVKKPGATVKISCKVSGYTFTSYWMYWIRQSPSRGLEWLGRIDPN<br>SGSTKYNEKFKNRLTISKDTSKNQVVLTMTNMDPVDTATYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 335 | DNA Heavy Chain | GAGGTCCAGCTGGTACAGTCTGGGGCTGAGGTGAAGAAGCCTGGGGCTACAGTG<br>AAAATCTCCTGCAAGGTTTCTGGCTACACCTTCACCAGTTACTGGATGTACTGG<br>ATCAGGCAGTCCCCATCGAGAGGCCTTGAGTGGCTGGGTAGGATTGATCCTAAT<br>AGTGGGAGTACTAAGTACAATGAGAAGTTCAAGAACAGACTCACCATCTCCAAG<br>GACACCTCCAAAAACCAGGTGGTCCTTACAATGACCAACATGGACCCTGTGGAC<br>ACAGCCACGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |

BAP058-hum05-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIK |
| SEQ ID NO: 329 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAA |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 330 | Light Chain | EIVLTQSPDFQSVTPKEKVTITCKASQDVGTAVAWYLQKPGQSPQLLIYWASTR<br>HTGVPSRFSGSGSGTDFTFTISSLQPEDIATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 331 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CTGCAGAAGCCAGGGCAGTCTCCACAGCTCCTGATCTATTGGGCATCCACCCGG<br>CACACTGGGGTCCCATCAAGGTTCAGTGGAAGTGGATCTGGGACAGATTTTACT<br>TTCACCATCAGCAGCCTGCAGCCTGAAGATATTGCAACATATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

BAP058-hum06-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSS |
| SEQ ID NO: 337 | DNA VH | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>ATCCGCCAGCCCCCAGGGAAGGGGCTGGAGTGGATTGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 338 | Heavy Chain | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 339 | DNA Heavy Chain | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>ATCCGCCAGCCCCCAGGGAAGGGGCTGGAGTGGATTGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| BAP058-hum06-LC | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIK |
| SEQ ID NO: 329 | DNA VL | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCATCAAGGTTCAGTGGAAGTGGATCTGGGACAGATTTTACT TTCACCATCAGCAGCCTGCAGCCTGAAGATATTGCAACATATTACTGTCAGCAG TATAACAGCTATCCTCTCACGTTCGGCCAAGGGACCAAGGTGGAAATCAAA |
| SEQ ID NO: 330 | Light Chain | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 331 | DNA Light Chain | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCATCAAGGTTCAGTGGAAGTGGATCTGGGACAGATTTTACT TTCACCATCAGCAGCCTGCAGCCTGAAGATATTGCAACATATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |
| BAP058-hum07-HC | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 340 | VH | QVQLVQSGAEVKKPGASVKVSCKASGYTFTSYWMYWIRQSPSRGLEWLGRIDPN SGSTKYNEKFKNRFTISRDDSKNTAYLQMNSLKTEDTAVYYCARDYRKGLYAMD YWGQGTTVTVSS |
| SEQ ID NO: 341 | DNA VH | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG ATCAGGCAGTCCCCATCGAGAGGCCTTGAGTGGCTGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 342 | Heavy Chain | QVQLVQSGAEVKKPGASVKVSCKASGYTFTSYWMYWIRQSPSRGLEWLGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 343 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG ATCAGGCAGTCCCCATCGAGAGGCCTTGAGTGGCTGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum07-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 344 | VL | EIVLTQSPATLSLSPGERATLSCKASQDVGTAVAWYLQKPGQSPQLLIYWASTR HTGIPPRFSGSGYGTDFTLTINNIESEDAAYYFCQQYNSYPLTFGQGTKVEIK |
| SEQ ID NO: 345 | DNA VL | GAAATTGTGTTGACACAGTCTCCAGCCACCCTGTCTTTGTCTCCAGGGGAAAGA GCCACCCTCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCACCTCGATTCAGTGGCAGCGGGTATGGAACAGATTTTACC CTCACAATTAATAACATAGAATCTGAGGATGCTGCATATTACTTCTGTCAGCAG TATAACAGCTATCCTCTCACGTTCGGCCAAGGGACCAAGGTGGAAATCAAA |
| SEQ ID NO: 346 | Light Chain | EIVLTQSPATLSLSPGERATLSCKASQDVGTAVAWYLQKPGQSPQLLIYWASTR HTGIPPRFSGSGYGTDFTLTINNIESEDAAYYFCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 347 | DNA Light Chain | GAAATTGTGTTGACACAGTCTCCAGCCACCCTGTCTTTGTCTCCAGGGGAAAGA GCCACCCTCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCACCTCGATTCAGTGGCAGCGGGTATGGAACAGATTTTACC CTCACAATTAATAACATAGAATCTGAGGATGCTGCATATTACTTCTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | BAP058-hum08-HC | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 348 | VH | EVQLVQSGAEVKKPGESLRISCKGSGYTFTSYWMYWVRQARGQRLEWIGRIDPN SGSTKYNEKFKNRLTISKDTSKNQVVLTMTNMDPVDTATYYCARDYRKGLYAMD YWGQGTTVTVSS |
| SEQ ID NO: 349 | DNA VH | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCTCGTGGACAACGCCTTGAGTGGATAGGTAGGATTGATCCTAAT AGTGGGAGTACTAAGTACAATGAGAAGTTCAAGAACAGACTCACCATCTCCAAG GACACCTCCAAAAACCAGGTGGTCCTTACAATGACCAACATGGACCCTGTGGAC ACAGCCACGTATTACTGTGCAAGGGACTATAGAAAGGGGCTCTATGCTATGGAC TACTGGGGCCAGGGCACCACCGTGACCGTGTCCTCC |
| SEQ ID NO: 350 | Heavy Chain | EVQLVQSGAEVKKPGESLRISCKGSGYTFTSYWMYWVRQARGQRLEWIGRIDPN SGSTKYNEKFKNRLTISKDTSKNQVVLTMTNMDPVDTATYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 351 | DNA Heavy Chain | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCTCGTGGACAACGCCTTGAGTGGATAGGTAGGATTGATCCTAAT AGTGGGAGTACTAAGTACAATGAGAAGTTCAAGAACAGACTCACCATCTCCAAG GACACCTCCAAAAACCAGGTGGTCCTTACAATGACCAACATGGACCCTGTGGAC ACAGCCACGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| | BAP058-hum08-LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 352 | VL | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 353 | DNA VL | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 354 | Light Chain | DVVMTQSPLSLPVTLGQPASISCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 355 | DNA Light Chain | GATGTTGTGATGACTCAGTCTCCACTCTCCCTGCCCGTCACCCTTGGACAGCCG<br>GCCTCCATCTCCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |

BAP058-hum09-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSS |
| SEQ ID NO: 337 | DNA VH | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>ATCCGCCAGCCCCCAGGGAAGGGGCTGGAGTGGATTGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 338 | Heavy Chain | EVQLVQSGAEVKKPGESLRISCKGSGYTFTSYWMYWIRQPPGKGLEWIGRIDPN<br>SGSTKYNEKFKNRVTITADKSTSTAYMELSSLRSEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 339 | DNA Heavy Chain | GAAGTGCAGCTGGTGCAGTCTGGAGCAGAGGTGAAAAAGCCCGGGGAGTCTCTG<br>AGGATCTCCTGTAAGGGTTCTGGCTACACCTTCACCAGTTACTGGATGTACTGG<br>ATCCGCCAGCCCCCAGGGAAGGGGCTGGAGTGGATTGGTAGGATTGATCCTAAT<br>AGTGGGAGTACTAAGTACAATGAGAAGTTCAAGAACAGAGTCACGATTACCGCG<br>GACAAATCCACGAGCACAGCCTACATGGAGCTGAGCAGCCTGAGATCTGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| | BAP058-hum09-LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 308 | VL | DIVMTQTPLSLPVTPGEPASISCKASQDVGTAVAWYLQKPGQSPQLLIYWASTR HTGIPARFSGSGSGTEFTLTISSLQSEDFAVYYCQQYNSYPLTFGQGTKVEIK |
| SEQ ID NO: 309 | DNA VL | GATATTGTGATGACCCAGACTCCACTCTCCCTGCCCGTCACCCCTGGAGAGCCG GCCTCCATCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCAGCCAGGTTCAGTGGCAGTGGGTCTGGGACAGAGTTCACT CTCACCATCAGCAGCCTGCAGTCTGAAGATTTTGCAGTTTATTACTGTCAGCAG TATAACAGCTATCCTCTCACGTTCGGCCAAGGGACCAAGGTGGAAATCAAA |
| SEQ ID NO: 310 | Light Chain | DIVMTQTPLSLPVTPGEPASISCKASQDVGTAVAWYLQKPGQSPQLLIYWASTR HTGIPARFSGSGSGTEFTLTISSLQSEDFAVYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 311 | DNA Light Chain | GATATTGTGATGACCCAGACTCCACTCTCCCTGCCCGTCACCCCTGGAGAGCCG GCCTCCATCTCCTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGATCCCAGCCAGGTTCAGTGGCAGTGGGTCTGGGACAGAGTTCACT CTCACCATCAGCAGCCTGCAGTCTGAAGATTTTGCAGTTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |
| | BAP058-hum10-HC | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 356 | VH | QITLKESGPTLVKPTQTLTLTCTFSGYTFTSYWMYWVRQAPGKGLEWVSRIDPN SGSTKYNEKFKNRVTITADKSTSTAYMELSSLRSEDTAVYYCARDYRKGLYAMD YWGQGTTVTVSS |
| SEQ ID NO: 357 | DNA VH | CAGATCACCTTGAAGGAGTCTGGTCCTACGCTGGTGAAACCCACACAGACCCTC ACGCTGACCTGCACCTTCTCTGGCTACACCTTCACCAGTTACTGGATGTACTGG GTCCGCCAGGCTCCAGGGAAGGGGCTGGAGTGGGTCAGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 358 | Heavy Chain | QITLKESGPTLVKPTQTLTLTCTFSGYTFTSYWMYWVRQAPGKGLEWVSRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 359 | DNA Heavy Chain | CAGATCACCTTGAAGGAGTCTGGTCCTACGCTGGTGAAACCCACACAGACCCTC ACGCTGACCTGCACCTTCTCTGGCTACACCTTCACCAGTTACTGGATGTACTGG GTCCGCCAGGCTCCAGGGAAGGGGCTGGAGTGGGTCAGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum10-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 352 | VL | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 353 | DNA VL | GATGTTGTGATGACTCAGTCTCCACTCTCCCTGCCCGTCACCCTTGGACAGCCG GCCTCCATCTCCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAA |
| SEQ ID NO: 354 | Light Chain | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 355 | DNA Light Chain | GATGTTGTGATGACTCAGTCTCCACTCTCCCTGCCCGTCACCCTTGGACAGCCG GCCTCCATCTCCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| BAP058-hum11-HC | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSS |
| SEQ ID NO: 317 | DNA VH | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 318 | Heavy Chain | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 319 | DNA Heavy Chain | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCCACTGGACAAGGGCTTGAGTGGATGGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| BAP058-hum11-LC | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 352 | VL | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 353 | DNA VL | GATGTTGTGATGACTCAGTCTCCACTCTCCCTGCCCGTCACCCTTGGACAGCCG GCCTCCATCTCCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAA |
| SEQ ID NO: 354 | Light Chain | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 355 | DNA Light Chain | GATGTTGTGATGACTCAGTCTCCACTCTCCCTGCCCGTCACCCTTGGACAGCCG GCCTCCATCTCCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

BAP058-hum12-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 324 | VH | EVQLVQSGAEVKKPGESLRISCKGSGYTFTSYWMYWVRQAPGQGLEWMGRIDPN SGSTKYNEKFKNRVTISVDTSKNQFSLKLSSVTAADTAVYYCARDYRKGLYAMD YWGQGTTVTVSS |
| SEQ ID NO: 325 | DNA VH | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCCCCTGGACAAGGGCTTGAGTGGATGGGTAGGATTGATCCTAAT AGTGGGAGTACTAAGTACAATGAGAAGTTCAAGAACAGAGTCACCATATCAGTA GACACGTCCAAGAACCAGTTCTCCCTGAAGCTGAGCTCTGTGACCGCCGCGGAC ACGGCTGTGTATTACTGTGCAAGGGACTATAGAAAGGGGCTCTATGCTATGGAC TACTGGGGCCAGGGCACCACCGTGACCGTGTCCTCC |
| SEQ ID NO: 326 | Heavy Chain | EVQLVQSGAEVKKPGESLRISCKGSGYTFTSYWMYWVRQAPGQGLEWMGRIDPN SGSTKYNEKFKNRVTISVDTSKNQFSLKLSSVTAADTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 327 | DNA Heavy Chain | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCCCCTGGACAAGGGCTTGAGTGGATGGGTAGGATTGATCCTAAT AGTGGGAGTACTAAGTACAATGAGAAGTTCAAGAACAGAGTCACCATATCAGTA GACACGTCCAAGAACCAGTTCTCCCTGAAGCTGAGCTCTGTGACCGCCGCGGAC ACGGCTGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| | BAP058-hum12-LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 360 | VL | DIQMTQSPSSLSASVGDRVTITCKASQDVGTAVAWYQQKPGQAPRLLIYWASTR HTGVPSRFSGSGSGTDFTFTISSLQPEDIATYYCQQYNSYPLTFGQGTKVEIK |
| SEQ ID NO: 361 | DNA VL | GACATCCAGATGACCCAGTCTCCATCCTCCCTGTCTGCATCTGTAGGAGACAGA GTCACCATCACTTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGTGGAAGTGGATCTGGGACAGATTTTACT TTCACCATCAGCAGCCTGCAGCCTGAAGATATTGCAACATATTACTGTCAGCAG TATAACAGCTATCCTCTCACGTTCGGCCAAGGGACCAAGGTGGAAATCAAA |
| SEQ ID NO: 362 | Light Chain | DIQMTQSPSSLSASVGDRVTITCKASQDVGTAVAWYQQKPGQAPRLLIYWASTR HTGVPSRFSGSGSGTDFTFTISSLQPEDIATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 363 | DNA Light Chain | GACATCCAGATGACCCAGTCTCCATCCTCCCTGTCTGCATCTGTAGGAGACAGA GTCACCATCACTTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGTGGAAGTGGATCTGGGACAGATTTTACT TTCACCATCAGCAGCCTGCAGCCTGAAGATATTGCAACATATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |
| | BAP058-hum13-HC | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 364 | VH | EVQLVQSGAEVKKPGATVKISCKVSGYTFTSYWMYWVRQARGQRLEWIGRIDPN SGSTKYNEKFKNRFTISRDNSKNTLYLQMNSLRAEDTAVYYCARDYRKGLYAMD YWGQGTTVTVSS |
| SEQ ID NO: 365 | DNA VH | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCTCGTGGACAACGCCTTGAGTGGATAGGTAGGATTGATCCTAAT AGTGGGAGTACTAAGTACAATGAGAAGTTCAAGAACAGATTCACCATCTCCAGA GACAATTCCAAGAACACGCTGTATCTTCAAATGAACAGCCTGAGAGCCGAGGAC ACGGCCGTGTATTACTGTGCAAGGGACTATAGAAAGGGGCTCTATGCTATGGAC TACTGGGGCCAGGGCACCACCGTGACCGTGTCCTCC |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 391 | Heavy Chain | EVQLVQSGAEVKKPGATVKISCKVSGYTFTSYWMYWVRQARGQRLEWIGRIDPN SGSTKYNEKFKNRFTISRDNSKNTLYLQMNSLRAEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 367 | DNA Heavy Chain | GAGGTCCAGCTGGTACAGTCTGGGGCTGAGGTGAAGAAGCCTGGGGCTACAGTG AAAATCTCCTGCAAGGTTTCTGGCTACACCTTCACCAGTTACTGGATGTACTGG GTGCGACAGGCTCGTGGACAACGCCTTGAGTGGATAGGTAGGATTGATCCTAAT AGTGGGAGTACTAAGTACAATGAGAAGTTCAAGAACAGATTCACCATCTCCAGA GACAATTCCAAGAACACGCTGTATCTTCAAATGAACAGCCTGAGAGCCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum13-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 368 | VL | AIQLTQSPSSLSASVGDRVTITCKASQDVGTAVAWYLQKPGQSPQLLIYWASTR HTGVPSRFSGSGSGTDFTFTISSLEAEDAATYYCQQYNSYPLTFGQGTKVEIK |
| SEQ ID NO: 369 | DNA VL | GCCATCCAGTTGACCCAGTCTCCATCCTCCCTGTCTGCATCTGTAGGAGACAGA GTCACCATCACTTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCCTCGAGGTTCAGTGGCAGTGGATCTGGGACAGATTTCACC TTTACCATCAGTAGCCTGGAAGCTGAAGATGCTGCAACATATTACTGTCAGCAG TATAACAGCTATCCTCTCACGTTCGGCCAAGGGACCAAGGTGGAAATCAAA |
| SEQ ID NO: 370 | Light Chain | AIQLTQSPSSLSASVGDRVTITCKASQDVGTAVAWYLQKPGQSPQLLIYWASTR HTGVPSRFSGSGSGTDFTFTISSLEAEDAATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 371 | DNA Light Chain | GCCATCCAGTTGACCCAGTCTCCATCCTCCCTGTCTGCATCTGTAGGAGACAGA GTCACCATCACTTGCAAGGCCAGTCAGGATGTGGGTACTGCTGTAGCCTGGTAC CTGCAGAAGCCAGGGCAGTCTCCACAGCTCCTGATCTATTGGGCATCCACCCGG CACACTGGGGTCCCCTCGAGGTTCAGTGGCAGTGGATCTGGGACAGATTTCACC TTTACCATCAGTAGCCTGGAAGCTGAAGATGCTGCAACATATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| **BAP058-hum14-HC** | | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 304 | VH | QVQLVQSGAEVKKPGASVKVSCKASGYTFTSYWMYWVRQATGQGLEWMGRIDPN<br>SGSTKYNEKEKNRFTISRDDSKNTAYLQMNSLKTEDTAVYYCARDYRKGLYAMD<br>YWGQGTTVTVSS |
| SEQ ID NO: 305 | DNA VH | CAGGTTCAGCTGGTGCAGTCTGGAGCTGAGGTGAAGAAGCCTGGGGCCTCAGTG<br>AAGGTCTCCTGCAAGGCTTCTGGCTACACCTTCACCAGTTACTGGATGTACTGG<br>GTGCGACAGGCCACTGGACAAGGGCTTGAGTGGATGGGTAGGATTGATCCTAAT<br>AGTGGGAGTACTAAGTACAATGAGAAGTTCAAGAACAGATTCACCATCTCCAGA<br>GATGATTCAAAGAACACGGCGTATCTGCAAATGAACAGCCTGAAAACCGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |
| SEQ ID NO: 306 | Heavy Chain | QVQLVQSGAEVKKPGASVKVSCKASGYTFTSYWMYWVRQATGQGLEWMGRIDPN<br>SGSTKYNEKFKNRFTISRDDSKNTAYLQMNSLKTEDTAVYYCARDYRKGLYAMD<br>YWGQGTTVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDK<br>RVESKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFSCSVMHEAL<br>HNHYTQKSLSLSLGK |
| SEQ ID NO: 307 | DNA Heavy Chain | CAGGTTCAGCTGGTGCAGTCTGGAGCTGAGGTGAAGAAGCCTGGGGCCTCAGTG<br>AAGGTCTCCTGCAAGGCTTCTGGCTACACCTTCACCAGTTACTGGATGTACTGG<br>GTGCGACAGGCCACTGGACAAGGGCTTGAGTGGATGGGTAGGATTGATCCTAAT<br>AGTGGGAGTACTAAGTACAATGAGAAGTTCAAGAACAGATTCACCATCTCCAGA<br>GATGATTCAAAGAACACGGCGTATCTGCAAATGAACAGCCTGAAAACCGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCCGCTTCCACCAAGGGCCCA<br>TCCGTCTTCCCCCTGGCGCCCTGCTCCAGGAGCACCTCCGAGAGCACAGCCGCC<br>CTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCA<br>GGACTCTACTCCCTCAGCAGCGTGGTGACCGTGCCCTCCAGCAGCTTGGGCACG<br>AAGACCTACACCTGCAACGTAGATCACAAGCCCAGCAACACCAAGGTGGACAAG<br>AGAGTTGAGTCCAAATATGGTCCCCCATGCCCACCGTGCCCAGCACCTGAGTTC<br>CTGGGGGGACCATCAGTCTTCCTGTTCCCCCCAAAACCCAAGGACACTCTCATG<br>ATCTCCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| **BAP058-hum14-LC** | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 372 | VL | EIVLTQSPDFQSVTPKEKVTITCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAA |
| SEQ ID NO: 374 | Light Chain | EIVLTQSPDFQSVTPKEKVTITCKASQDVGTAVAWYQQKPGQAPRLLIYWASTR HTGVPSRFSGSGSGTEFTLTISSLQPDDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

BAP058-hum15-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN SGSTKYNEKFKNRVTITADKSTSTAYMELSSLRSEDTAVYYCARDYRKGLYAMD YWGQGTTVTVSS |
| SEQ ID NO: 337 | DNA VH | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG ATCCGCCAGCCCCCAGGGAAGGGGCTGGAGTGGATTGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCC |
| SEQ ID NO: 338 | Heavy Chain | EVQLVQSGAEVKKPGESLRISCKGSGYTFTSYWMYWIRQPPGKGLEWIGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 339 | DNA Heavy Chain | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG ATCCGCCAGCCCCCAGGGAAGGGGCTGGAGTGGATTGGTAGGATTGATCCTAAT AGTGGGAGTACTAAGTACAATGAGAAGTTCAAGAACAGAGTCACGATTACCGCG GACAAATCCACGAGCACAGCCTACATGGAGCTGAGCAGCCTGAGATCTGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | ACAAAGCCGCGGGAGGAGCAGTTCAACAGCACGTACCGTGTGGTCAGCGTCCTC<br>ACCGTCCTGCACCAGGACTGGCTGAACGGCAAGGAGTACAAGTGCAAGGTGTCC<br>AACAAAGGCCTCCCGTCCTCCATCGAGAAAACCATCTCCAAAGCCAAAGGGCAG<br>CCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCC<br>GTGGAGTGGGAGAGCAATGGGCAGCCGGAGAACAACTACAAGACCACGCCTCCC<br>GTGCTGGACTCCGACGGCTCCTTCTTCCTCTACAGCAGGCTAACCGTGGACAAG<br>AGCAGGTGGCAGGAGGGGAATGTCTTCTCATGCTCCGTGATGCATGAGGCTCTG<br>CACAACCACTACACACAGAAGAGCCTCTCCCTGTCTCTGGGTAAA |
| | BAP058-hum15-LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 372 | VL | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAA |
| SEQ ID NO: 374 | Light Chain | EIVLTQSPDFQSVTPKEKVTITCKASQDVGTAVAWYQQKPGQAPRLLIYWASTR<br>HTGVPSRFSGSGSGTEFTLTISSLQPDDFATYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA<br>GTCACCATCACCTGCAAGGCCAGTCAGGATGTGGGTACTGCTGTAGCCTGGTAC<br>CAGCAGAAACCTGGCCAGGCTCCCAGGCTCCTCATCTATTGGGCATCCACCCGG<br>CACACTGGGGTCCCATCAAGGTTCAGCGGCAGTGGATCTGGGACAGAATTCACT<br>CTCACCATCAGCAGCCTGCAGCCTGATGATTTTGCAACTTATTACTGTCAGCAG<br>TATAACAGCTATCCTCTCACGTTCGGCCAAGGGACCAAGGTGGAAATCAAACGT<br>ACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT |
| | BAP058-hum16-HC | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 340 | VH | QVQLVQSGAEVKKPGASVKVSCKASGYTFTSYWMYWIRQSPSRGLEWLGRIDPN<br>SGSTKYNEKFKNRFTISRDDSKNTAYLQMNSLKTEDTAVYYCARDYRKGLYAMD<br>YWGQGTTVTVSS |
| SEQ ID NO: 341 | DNA VH | CAGGTTCAGCTGGTGCAGTCTGGAGCTGAGGTGAAGAAGCCTGGGGCCTCAGTG<br>AAGGTCTCCTGCAAGGCTTCTGGCTACACCTTCACCAGTTACTGGATGTACTGG<br>ATCAGGCAGTCCCCATCGAGAGGCCTTGAGTGGCTGGGTAGGATTGATCCTAAT<br>AGTGGGAGTACTAAGTACAATGAGAAGTTCAAGAACAGATTCACCATCTCCAGA<br>GATGATTCAAAGAACACGGCGTATCTGCAAATGAACAGCCTGAAAACCGAGGAC<br>ACGGCCGTGTATTACTGTGCAAGGGACTATAGAAAGGGGCTCTATGCTATGGAC<br>TACTGGGGCCAGGGCACCACCGTGACCGTGTCCTCC |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 342 | Heavy Chain | QVQLVQSGAEVKKPGASVKVSCKASGYTFTSYWMYWIRQSPSRGLEWLGRIDPN SGSTKYNEKFKNRFTISRDDSKNTAYLQMNSLKTEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 343 | DNA Heavy Chain | CAGGTTCAGCTGGTGCAGTCTGGAGCTGAGGTGAAGAAGCCTGGGGCCTCAGTG AAGGTCTCCTGCAAGGCTTCTGGCTACACCTTCACCAGTTACTGGATGTACTGG ATCAGGCAGTCCCCATCGAGAGGCCTTGAGTGGCTGGGTAGGATTGATCCTAAT AGTGGGAGTACTAAGTACAATGAGAAGTTCAAGAACAGATTCACCATCTCCAGA GATGATTCAAAGAACACGGCGTATCTGCAAATGAACAGCCTGAAAACCGAGGAC ACGGCCGTGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |
| BAP058-hum16-LC | | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 372 | VL | EIVLTQSPDFQSVTPKEKVTITCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAA |
| SEQ ID NO: 374 | Light Chain | EIVLTQSPDFQSVTPKEKVTITCKASQDVGTAVAWYQQKPGQAPRLLIYWASTR HTGVPSRFSGSGSGTEFTLTISSLQPDDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

BAP058-hum17-HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 348 | VH | EVQLVQSGAEVKKPGESLRISCKGSGYTFTSYWMYWVRQARGQRLEWIGRIDPN SGSTKYNEKFKNRLTISKDTSKNQVVLTMTNMDPVDTATYYCARDYRKGLYAMD YWGQGTTVTVSS |
| SEQ ID NO: 349 | DNA VH | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCTCGTGGACAACGCCTTGAGTGGATAGGTAGGATTGATCCTAAT AGTGGGAGTACTAAGTACAATGAGAAGTTCAAGAACAGACTCACCATCTCCAAG GACACCTCCAAAAACCAGGTGGTCCTTACAATGACCAACATGGACCCTGTGGAC ACAGCCACGTATTACTGTGCAAGGGACTATAGAAAGGGGCTCTATGCTATGGAC TACTGGGGCCAGGGCACCACCGTGACCGTGTCCTCC |
| SEQ ID NO: 350 | Heavy Chain | EVQLVQSGAEVKKPGESLRISCKGSGYTFTSYWMYWVRQARGQRLEWIGRIDPN SGSTKYNEKFKNRLTISKDTSKNQVVLTMTNMDPVDTATYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLGK |
| SEQ ID NO: 351 | DNA Heavy Chain | GAAGTGCAGCTGGTGCAGTCTGGAGCAGAGGTGAAAAAGCCCGGGGAGTCTCTG AGGATCTCCTGTAAGGGTTCTGGCTACACCTTCACCAGTTACTGGATGTACTGG GTGCGACAGGCTCGTGGACAACGCCTTGAGTGGATAGGTAGGATTGATCCTAAT AGTGGGAGTACTAAGTACAATGAGAAGTTCAAGAACAGACTCACCATCTCCAAG GACACCTCCAAAAACCAGGTGGTCCTTACAATGACCAACATGGACCCTGTGGAC ACAGCCACGTATTACTGTGCAAGGGACTATAGAAAGGGGCTCTATGCTATGGAC TACTGGGGCCAGGGCACCACCGTGACCGTGTCCTCCGCTTCCACCAAGGGCCCA TCCGTCTTCCCCCTGGCGCCCTGCTCCAGGAGCACCTCCGAGAGCACAGCCGCC CTGGGCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTCCTCA GGACTCTACTCCCTCAGCAGCGTGGTGACCGTGCCCTCCAGCAGCTTGGGCACG AAGACCTACACCTGCAACGTAGATCACAAGCCCAGCAACACCAAGGTGGACAAG AGAGTTGAGTCCAAATATGGTCCCCCATGCCCACCGTGCCCAGCACCTGAGTTC CTGGGGGGACCATCAGTCTTCCTGTTCCCCCCAAAACCCAAGGACACTCTCATG ATCTCCCGGACCCCTGAGGTCACGTGCGTGGTGGTGGACGTGAGCCAGGAAGAC CCCGAGGTCCAGTTCAACTGGTACGTGGATGGCGTGGAGGTGCATAATGCCAAG ACAAAGCCGCGGGAGGAGCAGTTCAACAGCACGTACCGTGTGGTCAGCGTCCTC ACCGTCCTGCACCAGGACTGGCTGAACGGCAAGGAGTACAAGTGCAAGGTGTCC AACAAAGGCCTCCCGTCCTCCATCGAGAAAACCATCTCCAAAGCCAAAGGGCAG CCCCGAGAGCCACAGGTGTACACCCTGCCCCCATCCCAGGAGGAGATGACCAAG AACCAGGTCAGCCTGACCTGCCTGGTCAAAGGCTTCTACCCCAGCGACATCGCC GTGGAGTGGGAGAGCAATGGGCAGCCGGAGAACAACTACAAGACCACGCCTCCC GTGCTGGACTCCGACGGCTCCTTCTTCCTCTACAGCAGGCTAACCGTGGACAAG AGCAGGTGGCAGGAGGGGAATGTCTTCTCATGCTCCGTGATGCATGAGGCTCTG CACAACCACTACACACAGAAGAGCCTCTCCCTGTCTCTGGGTAAA |

BAP058-hum17-LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 372 | VL | EIVLTQSPDFQSVTPKEKVTITCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 373 | DNA VL | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAA |
| SEQ ID NO: 374 | Light Chain | EIVLTQSPDFQSVTPKEKVTITCKASQDVGTAVAWYQQKPGQAPRLLIYWASTR HTGVPSRFSGSGSGTEFTLTISSLQPDDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 375 | DNA Light Chain | GAAATTGTGCTGACTCAGTCTCCAGACTTTCAGTCTGTGACTCCAAAGGAGAAA GTCACCATCACCTGCAAGGCCAGTCAGGATGTGGGTACTGCTGTAGCCTGGTAC CAGCAGAAACCTGGCCAGGCTCCCAGGCTCCTCATCTATTGGGCATCCACCCGG CACACTGGGGTCCCATCAAGGTTCAGCGGCAGTGGATCTGGGACAGAATTCACT CTCACCATCAGCAGCCTGCAGCCTGATGATTTTGCAACTTATTACTGTCAGCAG TATAACAGCTATCCTCTCACGTTCGGCCAAGGGACCAAGGTGGAAATCAAACGT ACGGTGGCTGCACCATCTGTCTTCATCTTCCCGCCATCTGATGAGCAGTTGAAA TCTGGAACTGCCTCTGTTGTGTGCCTGCTGAATAACTTCTATCCCAGAGAGGCC AAAGTACAGTGGAAGGTGGATAACGCCCTCCAATCGGGTAACTCCCAGGAGAGT GTCACAGAGCAGGACAGCAAGGACAGCACCTACAGCCTCAGCAGCACCCTGACG CTGAGCAAAGCAGACTACGAGAAACACAAAGTCTACGCCTGCGAAGTCACCCAT CAGGGCCTGAGCTCGCCCGTCACAAAGAGCTTCAACAGGGGAGAGTGT |

BAP058-Clone K HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSS |
| SEQ ID NO: 392 | DNA VH | GAAGTGCAGCTGGTGCAGTCTGGCGCCGAAGTGAAGAAACCCGGCGCTACCGTG AAGATCTCCTGCAAGGTGTCCGGCTACACCTTCACCAGCTACTGGATGTACTGG GTGCGACAGGCTACCGGCCAGGGCCTGGAATGGATGGGCAGAATCGACCCCAAC TCCGGCTCCACCAAGTACAACGAGAAGTTCAAGAACCGCGTGACCATCACCGCC GACAAGTCCACCTCCACCGCCTACATGGAACTGTCCTCCCTGCGGAGCGAGGAC ACCGCCGTGTACTACTGCGCCAGAGACTACCGGAAGGGCCTGTACGCCATGGAC TATTGGGGCCAGGGCACCACCGTGACCGTGTCCTCT |
| SEQ ID NO: 393 | Heavy Chain | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO: 394 | DNA Heavy Chain | GAAGTGCAGCTGGTGCAGTCTGGCGCCGAAGTGAAGAAACCCGGCGCTACCGTG AAGATCTCCTGCAAGGTGTCCGGCTACACCTTCACCAGCTACTGGATGTACTGG GTGCGACAGGCTACCGGCCAGGGCCTGGAATGGATGGGCAGAATCGACCCCAAC TCCGGCTCCACCAAGTACAACGAGAAGTTCAAGAACCGCGTGACCATCACCGCC GACAAGTCCACCTCCACCGCCTACATGGAACTGTCCTCCCTGCGGAGCGAGGAC ACCGCCGTGTACTACTGCGCCAGAGACTACCGGAAGGGCCTGTACGCCATGGAC TATTGGGGCCAGGGCACCACCGTGACCGTGTCCTCTGCTTCCACCAAGGGCCCA AGCGTGTTCCCCCTGGCCCCCTGCTCCAGAAGCACCAGCGAGAGCACAGCCGCC CTGGGCTGCCTGGTGAAGGACTACTTCCCCGAGCCCGTGACCGTGTCCTGGAAC AGCGGAGCCCTGACCAGCGGCGTGCACACCTTCCCCGCCGTGCTGCAGAGCAGC GGCCTGTACAGCCTGAGCAGCGTGGTGACCGTGCCCAGCAGCAGCCTGGGCACC AAGACCTACACCTGTAACGTGGACCACAAGCCCAGCAACACCAAGGTGGACAAG AGGGTGGAGAGCAAGTACGGCCCACCCTGCCCCCCCTGCCCAGCCCCCGAGTTC CTGGGCGGACCCAGCGTGTTCCTGTTCCCCCCCAAGCCCAAGGACACCCTGATG ATCAGCAGAACCCCCGAGGTGACCTGTGTGGTGGTGGACGTGTCCCAGGAGGAC CCCGAGGTCCAGTTCAACTGGTACGTGGACGGCGTGGAGGTGCACAACGCCAAG |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | ACCAAGCCCAGAGAGGAGCAGTTTAACAGCACCTACCGGGTGGTGTCCGTGCTG<br>ACCGTGCTGCACCAGGACTGGCTGAACGGCAAAGAGTACAAGTGTAAGGTCTCC<br>AACAAGGGCCTGCCAAGCAGCATCGAAAAGACCATCAGCAAGGCCAAGGGCCAG<br>CCTAGAGAGCCCCAGGTCTACACCCTGCCACCCAGCCAAGAGGAGATGACCAAG<br>AACCAGGTGTCCCTGACCTGTCTGGTGAAGGGCTTCTACCCAAGCGACATCGCC<br>GTGGAGTGGGAGAGCAACGGCCAGCCCGAGAACAACTACAAGACCACCCCCCCA<br>GTGCTGGACAGCGACGGCAGCTTCTTCCTGTACAGCAGGCTGACCGTGGACAAG<br>TCCAGATGGCAGGAGGGCAACGTCTTTAGCTGCTCCGTGATGCACGAGGCCCTG<br>CACAACCACTACACCCAGAAGAGCCTGAGCCTGTCCCTGGGCTGATGAATTC |
| | BAP058-Clone K LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 320 | VL | EIVLTQSPDFQSVTPKEKVTITCKASQDVGTAVAWYLQKPGQSPQLLIYWASTR<br>HTGVPDRFSGSGSGTDFTLKISRVEAEDVGVYYCQQYNSYPLTFGQGTKVEIK |
| SEQ ID NO: 395 | DNA VL | GAGATCGTGCTGACCCAGTCCCCCGACTTCCAGTCCGTGACCCCCAAAGAAAAA<br>GTGACCATCACATGCAAGGCCTCCCAGGACGTGGGCACCGCCGTGGCTTGGTAT<br>CTGCAGAAGCCTGGCCAGTCCCCTCAGCTGCTGATCTACTGGGCCTCTACCAGA<br>CACACCGGCGTGCCCGACAGATTCTCCGGCTCTGGCTCTGGCACCGACTTCACC<br>CTGAAGATCTCCCGGGTGGAAGCCGAGGATGTGGGCGTGTACTACTGCCAGCAG<br>TACAACTCCTACCCCCTGACCTTCGGCCAGGGCACCAAGGTGGAAATCAAG |
| SEQ ID NO: 322 | Light Chain | EIVLTQSPDFQSVTPKEKVTITCKASQDVGTAVAWYLQKPGQSPQLLIYWASTR<br>HTGVPDRFSGSGSGTDFTLKISRVEAEDVGVYYCQQYNSYPLTFGQGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| SEQ ID NO: 396 | DNA Light Chain | GAGATCGTGCTGACCCAGTCCCCCGACTTCCAGTCCGTGACCCCCAAAGAAAAA<br>GTGACCATCACATGCAAGGCCTCCCAGGACGTGGGCACCGCCGTGGCTTGGTAT<br>CTGCAGAAGCCTGGCCAGTCCCCTCAGCTGCTGATCTACTGGGCCTCTACCAGA<br>CACACCGGCGTGCCCGACAGATTCTCCGGCTCTGGCTCTGGCACCGACTTCACC<br>CTGAAGATCTCCCGGGTGGAAGCCGAGGATGTGGGCGTGTACTACTGCCAGCAG<br>TACAACTCCTACCCCCTGACCTTCGGCCAGGGCACCAAGGTGGAAATCAAGCGT<br>ACGGTGGCCGCTCCCAGCGTGTTCATCTTCCCCCCAAGCGACGAGCAGCTGAAG<br>AGCGGCACCGCCAGCGTGGTGTGTCTGCTGAACAACTTCTACCCCAGGGAGGCC<br>AAGGTGCAGTGGAAGGTGGACAACGCCCTGCAGAGCGGCAACAGCCAGGAGAGC<br>GTCACCGAGCAGGACAGCAAGGACTCCACCTACAGCCTGAGCAGCACCCTGACC<br>CTGAGCAAGGCCGACTACGAGAAGCACAAGGTGTACGCCTGTGAGGTGACCCAC<br>CAGGGCCTGTCCAGCCCCGTGACCAAGAGCTTCAACAGGGGCGAGTGCTGATGA<br>ATTC |
| | BAP058-Clone L HC | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 324 | VH | EVQLVQSGAEVKKPGESLRISCKGSGYTFTSYWMYWVRQAPGQGLEWMGRIDPN<br>SGSTKYNEKFKNRVTISVDTSKNQFSLKLSSVTAADTAVYYCARDYRKGLYAMD<br>YWGQGTTVTVSS |
| SEQ ID NO: 376 | DNA VH | GAAGTGCAGCTGGTGCAGTCAGGCGCCGAAGTGAAGAAGCCCGGCGAGTCACTG<br>AGAATTAGCTGTAAAGGTTCAGGCTACACCTTCACTAGCTACTGGATGTACTGG<br>GTCCGACAGGCCCCAGGGCAAGGCCTGGAGTGGATGGGTAGAATCGACCCTAAT<br>AGCGGCTCTACTAAGTATAACGAGAAGTTTAAGAATAGAGTGACTATTAGCGTG<br>GACACCTCTAAGAATCAGTTTAGCCTGAAGCTGTCTAGCGTGACCGCCGCTGAC<br>ACCGCCGTCTACTACTGCGCTAGAGACTATAGAAAGGGCCTGTACGCTATGGAC<br>TACTGGGGTCAAGGCACTACCGTGACCGTGTCTTCA |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 377 | Heavy Chain | EVQLVQSGAEVKKPGESLRISCKGSGYTFTSYWMYWVRQAPGQGLEWMGRIDPN SGSTKYNEKFKNRVTISVDTSKNQFSLKLSSVTAADTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO: 378 | DNA Heavy Chain | GAAGTGCAGCTGGTGCAGTCAGGCGCCGAAGTGAAGAAGCCCGGCGAGTCACTG AGAATTAGCTGTAAAGGTTCAGGCTACACCTTCACTAGCTACTGGATGTACTGG GTCCGACAGGCCCCAGGGCAAGGCCTGGAGTGGATGGGTAGAATCGACCCTAAT AGCGGCTCTACTAAGTATAACGAGAAGTTTAAGAATAGAGTGACTATTAGCGTG GACACCTCTAAGAATCAGTTTAGCCTGAAGCTGTCTAGCGTGACCGCCGCTGAC ACCGCCGTCTACTACTGCGCTAGAGACTATAGAAAGGGCCTGTACGCTATGGAC TACTGGGGTCAAGGCACTACCGTGACCGTGTCTTCAGCTAGCACTAAGGGCCCG TCCGTGTTCCCCCTGGCACCTTGTAGCCGGAGCACTAGCGAATCCACCGCTGCC CTCGGCTGCCTGGTCAAGGATTACTTCCCGGAGCCCGTGACCGTGTCCTGGAAC AGCGGAGCCCTGACCTCCGGAGTGCACACCTTCCCCGCTGTGCTGCAGAGCTCC GGGCTGTACTCGCTGTCGTCGGTGGTCACGGTGCCTTCATCTAGCCTGGGTACC AAGACCTACACTTGCAACGTGGACCACAAGCCTTCCAACACTAAGGTGGACAAG CGCGTCGAATCGAAGTACGGCCCACCGTGCCCGCCTTGTCCCGCGCCGGAGTTC CTCGGCGGTCCCTCGGTCTTTCTGTTCCCACCGAAGCCCAAGGACACTTTGATG ATTTCCCGCACCCCTGAAGTGACATGCGTGGTCGTGGACGTGTCACAGGAAGAT CCGGAGGTGCAGTTCAATTGGTACGTGGATGGCGTCGAGGTGCACAACGCCAAA ACCAAGCCGAGGGAGGAGCAGTTCAACTCCACTTACCGCGTCGTGTCCGTGCTG ACGGTGCTGCATCAGGACTGGCTGAACGGGAAGGAGTACAAGTGCAAAGTGTCC AACAAGGGACTTCCTAGCTCAATCGAAAAGACCATCTCGAAAGCCAAGGGACAG CCCCGGGAACCCCAAGTGTATACCCTGCCACCGAGCCAGGAAGAAATGACTAAG AACCAAGTCTCATTGACTTGCCTTGTGAAGGGCTTCTACCCATCGGATATCGCC GTGGAATGGGAGTCCAACGGCCAGCCGGAAAACAACTACAAGACCACCCCTCCG GTGCTGGACTCAGACGGATCCTTCTTCCTCTACTCGCGGCTGACCGTGGATAAG AGCAGATGGCAGGAGGGAAATGTGTTCAGCTGTTCTGTGATGCATGAAGCCCTG CACAACCACTACACTCAGAAGTCCCTGTCCCTCTCCCTGGGA |

BAP058-Clone L LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 328 | VL | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIK |
| SEQ ID NO: 379 | DNA VL | GAGATCGTCCTGACTCAGTCACCCGACTTTCAGTCAGTGACCCCTAAAGAGAAA GTCACTATCACCTGTAAAGCCTCTCAGGACGTGGGCACCGCCGTGGCCTGGTAT CTGCAGAAGCCTGGTCAATCACCTCAGCTGCTGATCTACTGGGCCTCTACTAGA CACACCGGCGTGCCCTCTAGGTTTAGCGGTAGCGGTAGTGGCACCGACTTCACC TTCACTATCTCTTCACTGCAGCCCGAGGATATCGCTACCTACTACTGTCAGCAG TATAATAGCTACCCCCTGACCTTCGGTCAAGGCACTAAGGTCGAGATTAAG |
| SEQ ID NO: 330 | Light Chain | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 380 | DNA Light Chain | GAGATCGTCCTGACTCAGTCACCCGACTTTCAGTCAGTGACCCCTAAAGAGAAA GTCACTATCACCTGTAAAGCCTCTCAGGACGTGGGCACCGCCGTGGCCTGGTAT CTGCAGAAGCCTGGTCAATCACCTCAGCTGCTGATCTACTGGGCCTCTACTAGA CACACCGGCGTGCCCTCTAGGTTTAGCGGTAGCGGTAGTGGCACCGACTTCACC TTCACTATCTCTTCACTGCAGCCCGAGGATATCGCTACCTACTACTGTCAGCAG TATAATAGCTACCCCCTGACCTTCGGTCAAGGCACTAAGGTCGAGATTAAGCGT ACGGTGGCCGCTCCCAGCGTGTTCATCTTCCCCCCCAGCGACGAGCAGCTGAAG AGCGGCACCGCCAGCGTGGTGTGCCTGCTGAACAACTTCTACCCCCGGGAGGCC AAGGTGCAGTGGAAGGTGGACAACGCCCTGCAGAGCGGCAACAGCCAGGAGAGC GTCACCGAGCAGGACAGCAAGGACTCCACCTACAGCCTGAGCAGCACCCTGACC CTGAGCAAGGCCGACTACGAGAAGCATAAGGTGTACGCCTGCGAGGTGACCCAC CAGGGCCTGTCCAGCCCCGTGACCAAGAGCTTCAACAGGGGCGAGTGC |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

BAP058-Clone M HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 336 | VH | EVQLVQSGAEVKKPGESLRISCKGSGYTFTSYWMYWIRQPPGKGLEWIGRIDPN SGSTKYNEKFKNRVTITADKSTSTAYMELSSLRSEDTAVYYCARDYRKGLYAMD YWGQGTTVTVSS |
| SEQ ID NO: 397 | DNA VH | GAAGTGCAGCTGGTGCAGTCTGGCGCCGAAGTGAAGAAGCCTGGCGAGTCCCTG CGGATCTCCTGCAAGGGCTCCGGCTACACCTTCACCAGCTACTGGATGTACTGG ATCCGGCAGCCCCCTGGCAAGGGCCTGGAATGGATCGGCAGAATCGACCCCAAC TCCGGCTCCACCAAGTACAACGAGAAGTTCAAGAACCGCGTGACCATCACCGCC GACAAGTCCACCTCCACCGCCTACATGGAACTGTCCTCCCTGAGATCCGAGGAC ACCGCCGTGTACTACTGCGCCAGAGACTACCGGAAGGGCCTGTACGCCATGGAC TATTGGGGCCAGGGCACCACCGTGACCGTGTCCTCT |
| SEQ ID NO: 398 | Heavy Chain | EVQLVQSGAEVKKPGESLRISCKGSGYTFTSYWMYWIRQPPGKGLEWIGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO: 399 | DNA Heavy Chain | GAAGTGCAGCTGGTGCAGTCTGGCGCCGAAGTGAAGAAGCCTGGCGAGTCCCTG CGGATCTCCTGCAAGGGCTCCGGCTACACCTTCACCAGCTACTGGATGTACTGG ATCCGGCAGCCCCCTGGCAAGGGCCTGGAATGGATCGGCAGAATCGACCCCAAC TCCGGCTCCACCAAGTACAACGAGAAGTTCAAGAACCGCGTGACCATCACCGCC GACAAGTCCACCTCCACCGCCTACATGGAACTGTCCTCCCTGAGATCCGAGGAC ACCGCCGTGTACTACTGCGCCAGAGACTACCGGAAGGGCCTGTACGCCATGGAC TATTGGGGCCAGGGCACCACCGTGACCGTGTCCTCTGCTTCTACCAAGGGCCCA AGCGTGTTCCCCCTGGCCCCCTGCTCCAGAAGCACCAGCGAGAGCACAGCCGCC CTGGGCTGCCTGGTGAAGGACTACTTCCCCGAGCCCGTGACCGTGTCCTGGAAC AGCGGAGCCCTGACCAGCGGCGTGCACACCTTCCCCGCCGTGCTGCAGAGCAGC GGCCTGTACAGCCTGAGCAGCGTGGTGACCGTGCCCAGCAGCAGCCTGGGCACC AAGACCTACACCTGTAACGTGGACCACAAGCCCAGCAACACCAAGGTGGACAAG AGGGTGGAGAGCAAGTACGGCCCACCCTGCCCCCCCTGCCCAGCCCCCGAGTTC CTGGGCGGACCCAGCGTGTTCCTGTTCCCCCCCAAGCCCAAGGACACCCTGATG ATCAGCAGAACCCCCGAGGTGACCTGTGTGGTGGTGGACGTGTCCCAGGAGGAC CCCGAGGTCCAGTTCAACTGGTACGTGGACGGCGTGGAGGTGCACAACGCCAAG ACCAAGCCCAGAGAGGAGCAGTTTAACAGCACCTACCGGGTGGTGTCCGTGCTG ACCGTGCTGCACCAGGACTGGCTGAACGGCAAAGAGTACAAGTGTAAGGTCTCC AACAAGGGCCTGCCAAGCAGCATCGAAAAGACCATCAGCAAGGCCAAGGGCCAG CCTAGAGAGCCCCAGGTCTACACCCTGCCACCCAGCCAAGAGGAGATGACCAAG AACCAGGTGTCCCTGACCTGTCTGGTGAAGGGCTTCTACCCAAGCGACATCGCC GTGGAGTGGGAGAGCAACGGCCAGCCCGAGAACAACTACAAGACCACCCCCCCA GTGCTGGACAGCGACGGCAGCTTCTTCCTGTACAGCAGGCTGACCGTGGACAAG TCCAGATGGCAGGAGGGCAACGTCTTTAGCTGCTCCGTGATGCACGAGGCCCTG CACAACCACTACACCCAGAAGAGCCTGAGCCTGTCCCTGGGCTGATGAATTC |

BAP058-Clone M LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 328 | VL | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIK |
| SEQ ID NO: 400 | DNA VL | GAGATCGTGCTGACCCAGTCCCCCGACTTCCAGTCCGTGACCCCCAAAGAAAAA GTGACCATCACATGCAAGGCCTCCCAGGACGTGGGCACCGCCGTGGCTTGGTAT CTGCAGAAGCCTGGCCAGTCCCCTCAGCTGCTGATCTACTGGGCCTCTACCAGA CACACCGGCGTGCCCTCCAGATTCTCCGGCTCTGGCTCTGGCACCGACTTTACC TTCACCATCTCCAGCCTGCAGCCCGAGGATATCGCCACCTACTACTGCCAGCAG TACAACTCCTACCCCCTGACCTTCGGCCAGGGCACCAAGGTGGAAATCAAG |
| SEQ ID NO: 330 | Light Chain | EIVLTQSPDFQSVTPKEKVTITCKASQDVGTAVAWYLQKPGQSPQLLIYWASTR HTGVPSRFSGSGSGTDFTFTISSLQPEDIATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 401 | DNA Light Chain | GAGATCGTGCTGACCCAGTCCCCCGACTTCCAGTCCGTGACCCCCAAAGAAAAA GTGACCATCACATGCAAGGCCTCCCAGGACGTGGGCACCGCCGTGGCTTGGTAT CTGCAGAAGCCTGGCCAGTCCCCTCAGCTGCTGATCTACTGGGCCTCTACCAGA CACACCGGCGTGCCCTCCAGATTCTCCGGCTCTGGCTCTGGCACCGACTTTACC TTCACCATCTCCAGCCTGCAGCCCGAGGATATCGCCACCTACTACTGCCAGCAG TACAACTCCTACCCCCTGACCTTCGGCCAGGGCACCAAGGTGGAAATCAAGCGT ACGGTGGCCGCTCCCAGCGTGTTCATCTTCCCCCCCAAGCGACGAGCAGCTGAAG AGCGGCACCGCCAGCGTGGTGTGTCTGCTGAACAACTTCTACCCCAGGGAGGCC AAGGTGCAGTGGAAGGTGGACAACGCCCTGCAGAGCGGCAACAGCCAGGAGAGC GTCACCGAGCAGGACAGCAAGGACTCCACCTACAGCCTGAGCAGCACCCTGACC CTGAGCAAGGCCGACTACGAGAAGCACAAGGTGTACGCCTGTGAGGTGACCCAC CAGGGCCTGTCCAGCCCCGTGACCAAGAGCTTCAACAGGGGCGAGTGCTGATGA ATTC |

BAP058-Clone N HC

| | | |
|---|---|---|
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 316 | VH | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSS |
| SEQ ID NO: 381 | DNA VH | GAAGTGCAGCTGGTGCAGTCAGGCGCCGAAGTGAAGAAACCCGGCGCTACCGTG AAGATTAGCTGTAAAGTCTCAGGCTACACCTTCACTAGCTACTGGATGTACTGG GTCCGACAGGCTACCGGTCAAGGCCTGGAGTGGATGGGTAGAATCGACCCTAAT AGCGGCTCTACTAAGTATAACGAGAAGTTTAAGAATAGAGTGACTATCACCGCC GATAAGTCTACTAGCACCGCCTATATGGAACTGTCTAGCCTGAGATCAGAGGAC ACCGCCGTCTACTACTGCGCTAGAGACTATAGAAAGGGCCTGTACGCTATGGAC TACTGGGGTCAAGGCACTACCGTGACCGTGTCTTCA |
| SEQ ID NO: 382 | Heavy Chain | EVQLVQSGAEVKKPGATVKISCKVSGYTFTSYWMYWVRQATGQGLEWMGRIDPN SGSTKYNEKFKNRVTITADKSTSTAYMELSSLRSEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO: 383 | DNA Heavy Chain | GAAGTGCAGCTGGTGCAGTCAGGCGCCGAAGTGAAGAAACCCGGCGCTACCGTG AAGATTAGCTGTAAAGTCTCAGGCTACACCTTCACTAGCTACTGGATGTACTGG GTCCGACAGGCTACCGGTCAAGGCCTGGAGTGGATGGGTAGAATCGACCCTAAT AGCGGCTCTACTAAGTATAACGAGAAGTTTAAGAATAGAGTGACTATCACCGCC GATAAGTCTACTAGCACCGCCTATATGGAACTGTCTAGCCTGAGATCAGAGGAC ACCGCCGTCTACTACTGCGCTAGAGACTATAGAAAGGGCCTGTACGCTATGGAC TACTGGGGTCAAGGCACTACCGTGACCGTGTCTTCAGCTAGCACTAAGGGCCCG TCCGTGTTCCCCCTGGCACCTTGTAGCCGGAGCACTAGCGAATCCACCGCTGCC CTCGGCTGCCTGGTCAAGGATTACTTCCCGGAGCCCGTGACCGTGTCCTGGAAC AGCGGAGCCCTGACCTCCGGAGTGCACACCTTCCCCGCTGTGCTGCAGAGCTCC GGGCTGTACTCGCTGTCGTCGGTGGTCACGGTGCCTTCATCTAGCCTGGGTACC AAGACCTACACTTGCAACGTGGACCACAAGCCTTCCAACACTAAGGTGGACAAG CGCGTCGAATCGAAGTACGGCCCACCGTGCCCGCCTTGTCCCGCGCCGGAGTTC CTCGGCGGTCCCTCGGTCTTTCTGTTCCCACCGAAGCCCAAGGACACTTTGATG ATTTCCCGCACCCCTGAAGTGACATGCGTGGTCGTGGACGTGTCACAGGAAGAT |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| | | CCGGAGGTGCAGTTCAATTGGTACGTGGATGGCGTCGAGGTGCACAACGCCAAA ACCAAGCCGAGGGAGGAGCAGTTCAACTCCACTTACCGCGTCGTGTCCGTGCTG ACGGTGCTGCATCAGGACTGGCTGAACGGGAAGGAGTACAAGTGCAAAGTGTCC AACAAGGGACTTCCTAGCTCAATCGAAAAGACCATCTCGAAAGCCAAGGGACAG CCCCGGGAACCCCAAGTGTATACCCTGCCACCGAGCCAGGAAGAAATGACTAAG AACCAAGTCTCATTGACTTGCCTTGTGAAGGGCTTCTACCCATCGGATATCGCC GTGGAATGGGAGTCCAACGGCCAGCCGGAAAACAACTACAAGACCACCCCTCCG GTGCTGGACTCAGACGGATCCTTCTTCCTCTACTCGCGGCTGACCGTGGATAAG AGCAGATGGCAGGAGGGAAATGTGTTCAGCTGTTCTGTGATGCATGAAGCCCTG CACAACCACTACACTCAGAAGTCCCTGTCCCTCTCCCTGGGA |
| | BAP058-Clone N LC | |
| SEQ ID NO: 295 (Kabat) | LCDR1 | KASQDVGTAVA |
| SEQ ID NO: 296 (Kabat) | LCDR2 | WASTRHT |
| SEQ ID NO: 297 (Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 352 | VL | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIK |
| SEQ ID NO: 384 | DNA VL | GACGTCGTGATGACTCAGTCACCCCTGAGCCTGCCCGTGACCCTGGGGCAGCCC GCCTCTATTAGCTGTAAAGCCTCTCAGGACGTGGGCACCGCCGTGGCCTGGTAT CAGCAGAAGCCAGGGCAAGCCCCTAGACTGCTGATCTACTGGGCCTCTACTAGA CACACCGGCGTGCCCTCTAGGTTTAGCGGTAGCGGTAGTGGCACCGAGTTCACC CTGACTATCTCTTCACTGCAGCCCGACGACTTCGCTACCTACTACTGTCAGCAG TATAATAGCTACCCCCTGACCTTCGGTCAAGGCACTAAGGTCGAGATTAAG |
| SEQ ID NO: 354 | Light Chain | DVVMTQSPLSLPVTLGQPASISCKASQDVGTAVAWYQQKPGQAPRLLIYWASTR HTGVPSRFSGSGSGTEFTLTISSLQPDDFATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 385 | DNA Light Chain | GACGTCGTGATGACTCAGTCACCCCTGAGCCTGCCCGTGACCCTGGGGCAGCCC GCCTCTATTAGCTGTAAAGCCTCTCAGGACGTGGGCACCGCCGTGGCCTGGTAT CAGCAGAAGCCAGGGCAAGCCCCTAGACTGCTGATCTACTGGGCCTCTACTAGA CACACCGGCGTGCCCTCTAGGTTTAGCGGTAGCGGTAGTGGCACCGAGTTCACC CTGACTATCTCTTCACTGCAGCCCGACGACTTCGCTACCTACTACTGTCAGCAG TATAATAGCTACCCCCTGACCTTCGGTCAAGGCACTAAGGTCGAGATTAAGCGT ACGGTGGCCGCTCCCAGCGTGTTCATCTTCCCCCCCAGCGACGAGCAGCTGAAG AGCGGCACCGCCAGCGTGGTGTGCCTGCTGAACAACTTCTACCCCCGGGAGGCC AAGGTGCAGTGGAAGGTGGACAACGCCCTGCAGAGCGGCAACAGCCAGGAGAGC GTCACCGAGCAGGACAGCAAGGACTCCACCTACAGCCTGAGCAGCACCCTGACC CTGAGCAAGGCCGACTACGAGAAGCATAAGGTGTACGCCTGCGAGGTGACCCAC CAGGGCCTGTCCAGCCCCGTGACCAAGAGCTTCAACAGGGGCGAGTGC |
| | BAP058-Clone O HC | |
| SEQ ID NO: 287 (Kabat) | HCDR1 | SYWMY |
| SEQ ID NO: 288 (Kabat) | HCDR2 | RIDPNSGSTKYNEKFKN |
| SEQ ID NO: 289 (Kabat) | HCDR3 | DYRKGLYAMDY |
| SEQ ID NO: 290 (Chothia) | HCDR1 | GYTFTSY |
| SEQ ID NO: 291 (Chothia) | HCDR2 | DPNSGS |
| SEQ ID NO: 289 (Chothia) | HCDR3 | DYRKGLYAMDY |
| SEQ ID NO: 364 | VH | EVQLVQSGAEVKKPGATVKISCKVSGYTFTSYWMYWVRQARGQRLEWIGRIDPN SGSTKYNEKFKNRFTISRDNSKNTLYLQMNSLRAEDTAVYYCARDYRKGLYAMD YWGQGTTVTVSS |
| SEQ ID NO: 386 | DNA VH | GAAGTGCAGCTGGTGCAGTCAGGCGCCGAAGTGAAGAAACCCGGCGCTACCGTG AAGATTAGCTGTAAAGTCTCAGGCTACACCTTCACTAGCTACTGGATGTACTGG GTCCGACAGGCTAGAGGGCAAAGACTGGAGTGGATCGGTAGAATCGACCCTAAT AGCGGCTCTACTAAGTATAACGAGAAGTTTAAGAATAGGTTCACTATTAGTAGG GATAACTCTAAGAACACCCTGTACCTGCAGATGAATAGCCTGAGAGCCGAGGAC ACCGCCGTCTACTACTGCGCTAGAGACTATAGAAAGGGCCTGTACGCTATGGAC TACTGGGGTCAAGGCACTACCGTGACCGTGTCTTCA |

TABLE 6-continued

Amino acid and nucleotide sequences for murine, chimeric and humanized antibody molecules. The antibody molecules include murine mAb BAP058, chimeric mAb BAP058-chi, and humanized mAbs BAP058-hum01 to BAP058-hum17 and BAP058-Clone-K to BAP058-Clone-O. The amino acid and nucleotide sequences of the heavy and light chain CDRs, the heavy and light chain variable regions, and the heavy and light chains are shown.

| | | |
|---|---|---|
| SEQ ID NO: 366 | Heavy Chain | EVQLVQSGAEVKKPGATVKISCKVSGYTFTSYWMYWVRQARGQRLEWIGRIDPN SGSTKYNEKFKNRFTISRDNSKNTLYLQMNSLRAEDTAVYYCARDYRKGLYAMD YWGQGTTVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVVDVSQED PEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVMHEAL HNHYTQKSLSLSLG |
| SEQ ID NO: 387 | DNA Heavy Chain | GAAGTGCAGCTGGTGCAGTCAGGCGCCGAAGTGAAGAAACCCGGCGCTACCGTG AAGATTAGCTGTAAAGTCTCAGGCTACACCTTCACTAGCTACTGGATGTACTGG GTCCGACAGGCTAGAGGGCAAAGACTGGAGTGGATCGGTAGAATCGACCCTAAT AGCGGCTCTACTAAGTATAACGAGAAGTTTAAGAATAGGTTCACTATTAGTAGG GATAACTCTAAGAACACCCTGTACCTGCAGATGAATAGCCTGAGAGCCGAGGAC ACCGCCGTCTACTACTGCGCTAGAGACTATAGAAAGGGCCTGTACGCTATGGAC TACTGGGGTCAAGGCACTACCGTGACCGTGTCTTCAGCTAGCACTAAGGGCCCG TCCGTGTTCCCCCTGGCACCTTGTAGCCGGAGCACTAGCGAATCCACCGCTGCC CTCGGCTGCCTGGTCAAGGATTACTTCCCGGAGCCCGTGACCGTGTCCTGGAAC AGCGGAGCCCTGACCTCCGGAGTGCACACCTTCCCCGCTGTGCTGCAGAGCTCC GGGCTGTACTCGCTGTCGTCGGTGGTCACGGTGCCTTCATCTAGCCTGGGTACC AAGACCTACACTTGCAACGTGGACCACAAGCCTTCCAACACTAAGGTGGACAAG CGCGTCGAATCGAAGTACGGCCCACCGTGCCCGCCTTGTCCCGCGCCGGAGTTC CTCGGCGGTCCCTCGGTCTTTCTGTTCCCACCGAAGCCCAAGGACACTTTGATG ATTTCCCGCACCCCTGAAGTGACATGCGTGGTCGTGGACGTGTCACAGGAAGAT CCGGAGGTGCAGTTCAATTGGTACGTGGATGGCGTCGAGGTGCACAACGCCAAA ACCAAGCCGAGGGAGGAGCAGTTCAACTCCACTTACCGCGTCGTGTCCGTGCTG ACGGTGCTGCATCAGGACTGGCTGAACGGGAAGGAGTACAAGTGCAAAGTGTCC AACAAGGGACTTCCTAGCTCAATCGAAAAGACCATCTCGAAAGCCAAGGGACAG CCCCGGGAACCCCAAGTGTATACCCTGCCACCGAGCCAGGAAGAAATGACTAAG AACCAAGTCTCATTGACTTGCCTTGTGAAGGGCTTCTACCCATCGGATATCGCC GTGGAATGGGAGTCCAACGGCCAGCCGGAAAACAACTACAAGACCACCCCTCCG GTGCTGGACTCAGACGGATCCTTCTTCCTCTACTCGCGGCTGACCGTGGATAAG AGCAGATGGCAGGAGGGAAATGTGTTCAGCTGTTCTGTGATGCATGAAGCCCTG CACAACCACTACACTCAGAAGTCCCTGTCCCTCTCCCTGGGA |

BAP058-Clone O LC

| | | |
|---|---|---|
| SEQ ID NO: 295 (Kabat) | LCDR1 | KASQDVGTAVA |
| SEQ ID NO: 296 (Kabat) | LCDR2 | WASTRHT |
| SEQ ID NO: 297(Kabat) | LCDR3 | QQYNSYPLT |
| SEQ ID NO: 298 (Chothia) | LCDR1 | SQDVGTA |
| SEQ ID NO: 299 (Chothia) | LCDR2 | WAS |
| SEQ ID NO: 300 (Chothia) | LCDR3 | YNSYPL |
| SEQ ID NO: 368 | VL | AIQLTQSPSSLSASVGDRVTITCKASQDVGTAVAWYLQKPGQSPQLLIYWASTR HTGVPSRFSGSGSGTDFTFTISSLEAEDAATYYCQQYNSYPLTFGQGTKVEIK |
| SEQ ID NO: 388 | DNA VL | GCTATTCAGCTGACTCAGTCACCTAGTAGCCTGAGCGCTAGTGTGGGCGATAGA GTGACTATCACCTGTAAAGCCTCTCAGGACGTGGGCACCGCCGTGGCCTGGTAT CTGCAGAAGCCTGGTCAATCACCTCAGCTGCTGATCTACTGGGCCTCTACTAGA CACACCGGCGTGCCCTCTAGGTTTAGCGGTAGCGGTAGTGGCACCGACTTCACC TTCACTATCTCTTCACTGGAAGCCGAGGACGCCGCTACCTACTACTGTCAGCAG TATAATAGCTACCCCCTGACCTTCGGTCAAGGCACTAAGGTCGAGATTAAG |
| SEQ ID NO: 370 | Light Chain | AIQLTQSPSSLSASVGDRVTITCKASQDVGTAVAWYLQKPGQSPQLLIYWASTR HTGVPSRFSGSGSGTDFTFTISSLEAEDAATYYCQQYNSYPLTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| SEQ ID NO: 389 | DNA Light Chain | GCTATTCAGCTGACTCAGTCACCTAGTAGCCTGAGCGCTAGTGTGGGCGATAGA GTGACTATCACCTGTAAAGCCTCTCAGGACGTGGGCACCGCCGTGGCCTGGTAT CTGCAGAAGCCTGGTCAATCACCTCAGCTGCTGATCTACTGGGCCTCTACTAGA CACACCGGCGTGCCCTCTAGGTTTAGCGGTAGCGGTAGTGGCACCGACTTCACC TTCACTATCTCTTCACTGGAAGCCGAGGACGCCGCTACCTACTACTGTCAGCAG TATAATAGCTACCCCCTGACCTTCGGTCAAGGCACTAAGGTCGAGATTAAGCGT ACGGTGGCCGCTCCCAGCGTGTTCATCTTCCCCCCCAGCGACGAGCAGCTGAAG AGCGGCACCGCCAGCGTGGTGTGCCTGCTGAACAACTTCTACCCCCGGGAGGCC AAGGTGCAGTGGAAGGTGGACAACGCCCTGCAGAGCGGCAACAGCCAGGAGAGC GTCACCGAGCAGGACAGCAAGGACTCCACCTACAGCCTGAGCAGCACCCTGACC CTGAGCAAGGCCGACTACGAGAAGCATAAGGTGTACGCCTGCGAGGTGACCCAC CAGGGCCTGTCCAGCCCCGTGACCAAGAGCTTCAACAGGGGCGAGTGC |

Therapeutic Application for Mesothelin Expressing Diseases and Disorders

The present invention provides compositions and methods for treating diseases and disorders associated with the expression of mesothelin. An example of a disease or disorder associated with mesothelin is mesothelioma.

Malignant mesothelioma is a type of cancer that occurs in the thin layer of cells lining the body's internal organs, known as the mesothelium. There are three recognized types of mesothelioma. Pleural mesothelioma (e.g., malignant pleural mesothelioma, or MPM) is the most common form of the disease, accounting for roughly 70% of cases, and occurs in the lining of the lung known as the pleura. Peritoneal mesothelioma occurs in the lining of the abdominal cavity, known as the peritoneum. Pericardial mesothelioma originates in the pericardium, which lines the heart.

A subject may be at risk to develop mesothelioma if the subject was exposed to asbestos. Exposure to asbestos and the inhalation of asbestos particles can cause mesothelioma. In most cases, mesothelioma symptoms will not appear in a subject exposed to asbestos until many years after the exposure has occurred.

Symptoms of pleural mesothelioma include, e.g., lower back pain or side chest pain, and shortness of breath. Other symptoms include difficulty swallowing, persistent cough, fever, weight loss or fatigue. Additional symptoms that some patients experience are muscle weakness, loss of sensory capability, coughing up blood, facial and arm swelling, and hoarseness. In the early stages of the disease, such as stage 1 mesothelioma, symptoms may be mild. Patients usually report pain in one area of the chest that never seems to go away, weight loss and fever.

Peritoneal mesothelioma originates in the abdomen and as a result, symptoms often include abdominal pain, weight loss, nausea, and vomiting. Fluid buildup may occur in the abdomen as well as a result of the cancer. Peritoneal mesothelioma originates in the abdomen and will frequently spread to other organs in area including the liver, spleen or bowel. Severe abdominal pain is the most common complaint that patients first experience. There may also be a discomfort level with fluid buildup in the abdomen as well. Other symptoms of peritoneal mesothelioma may include difficult bowel movements, nausea and vomiting, fever and swollen feet.

Pericardial mesothelioma is the least common form of mesothelioma. Pericardial mesothelioma, as the name suggests, involves the heart. This rare type of mesothelioma cancer invades the pericardium, the sac that surrounds the heart. As the cancer progresses, the heart is not able to deliver oxygen as efficiently to the body causing further decline in health at an increasingly rapid rate. The symptoms most commonly associated with pericardial mesothelioma mimic those of a heart attack: nausea, pain in the chest and shortness of breath.

Subjects benefiting from treatment according to the invention include subjects with a mesothelioma, or subjects suspected of having mesothelioma, e.g., as evidenced by the presence of one or more of the symptoms described herein and/or exposure to asbestos. In particular embodiments, the mesothelioma is pleural mesothelioma (e.g., malignant pleural mesothelioma). In other aspects, the subject may be treated that has a precancerous condition such as, e.g., pleural plaques, benign mesothelioma or mesothelial hyperplasia.

Another example of a disease or disorder associated with mesothelin is pancreatic cancer. Pancreatic cancers that can be treated with methods described herein include, but are not limited to, exocrine pancreatic cancers and endocrine pancreatic cancers. Exocrine pancreatic cancers include, but are not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma. Endocrine pancreatic cancers include, but are not limited to, insulinomas and glucagonomas.

In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting. In some embodiments, the pancreatic cancer is locally advanced pancreatic cancer, unresectable pancreatic cancer, or metastatic pancreatic ductal carcinoma. In some embodiments, the pancreatic cancer is resistant to the gemcitabine-based therapy. In some embodiments, the pancreatic cancer is refractory to the gemcitabine-based therapy.

In other aspects, the disorder associated with mesothelin expression is ovarian cancer. Ovarian cancer is classified according to the histology of the tumor. Surface epithelial-stromal tumor, also known as ovarian epithelial carcinoma, is the most common type of ovarian cancer. It includes serous tumor (including serous papillary cystadenocarcinoma), endometrioid tumor and mucinous cystadenocarcinoma.

The methods described herein can be used to treat various stages of ovarian cancer, e.g., stage I, stage II, stage III or stage IV. Staging can be performed, e.g., when the ovarian cancer is removed. Ovarian cancer is staged as follows:

Stage I cancer is confined to one or both ovaries. The cancer is stage II if either one or both of the ovaries is involved and has spread to the uterus and/or the fallopian tubes or other sites in the pelvis. The cancer is stage III cancer if one or both of the ovaries is involved and has spread to lymph nodes or other sites outside of the pelvis but is still within the abdominal cavity, such as the surface of the intestine or liver. The cancer is stage IV cancer if one or both ovaries are involved and the cancer has spread outside the abdomen or to the inside of the liver.

In some embodiments, the ovarian cancer is resistant to one or more chemotherapeutic agent. In some embodiments, the ovarian cancer is refractory to the one or more chemotherapeutic agent.

Other cancers that can be treated with the combination therapy described herein include, e.g., brain cancer, bladder cancer, breast cancer, cervical cancer, colorectal cancer, liver cancer, kidney cancer, lymphoma, leukemia, lung cancer (e.g., lung adenocarcinoma), melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In one aspect, the disclosure features a method of treating cancer in a subject. The method comprises administering to the subject a combination therapy that includes administering a mesothelin CAR-expressing cell and a PD-L1 inhibitor such that the cancer is treated in the subject. An example of a cancer that is treatable by the combination therapy described herein is a cancer associated with expression of mesothelin. In one aspect, the cancer associated with expression of mesothelin is selected from mesothelioma, pancreatic cancer, ovarian cancer and lung cancer, or a metastasis resulting from any of the aforesaid cancers.

In one embodiment, the combination therapy of a mesothelin CAR-expressing cell and a PD-L1 inhibitor described herein results in one or more of: improved or increased anti-tumor activity of the mesothelin CAR-epxressing cell; increased proliferation or persistence of the mesothelin CAR-expressing cell; improved or increased infiltration of the mesothelin CAR-expressing cell; improved inhibition of tumor progression; delay of tumor progression; inhibition or reduction in cancer cell proliferation; and/or reduction in tumor burden, e.g., tumor volume, or size, e.g., as compared to a monotherapy of mesothelin CAR-expressing cell or PD-L1 inhibitor alone.

The present invention provides methods for inhibiting the proliferation of or reducing a mesothelin-expressing cell population. In one embodiment, the methods comprise administering a combination therapy, e.g., a combination comprising a mesothelin CAR-expressing cell, or a population of mesothelin-CAR expressing cells, and a PD-L1 inhibitor. In certain embodiments, the combination therapy described herein reduces the quantity, number, amount or percentage of cells and/or cancer cells by at least at least 5%, 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% in a subject with or animal model of mesothelioma or another cancer associated with mesothelin-expressing cells relative to the quantity, number, amount, or percentage of cells and/or cancer cells in a subject treated with a mesothelin CAR-expressing cell or a PD-L1 inhibitor alone. In one aspect, the subject is a human.

The invention also provides methods for preventing, treating and/or managing a disorder associated with mesothelin-expressing cells (e.g., mesothelioma), the methods comprising administering to a subject in need a mesothelin CAR-expressing cell, or a population of mesothelin CAR-expressing cells, and a PD-L1 inhibitor. In one aspect, the subject is a human.

Combination Therapies

Any of the methods described herein may be used in combination with other known agents and therapies.

The combination described herein, e.g., a mesothelin CAR-expressing cell and a PD-L1 inhibitor, and the at least one additional therapeutic agent can be administered simultaneously, in the same or in separate compositions, or sequentially. For sequential administration, the CAR-expressing cell and/or the PD-L1 inhibitor described herein can be administered after the additional therapeutic agent, or the order of administration can be reversed where the additional therapeutic agent can be administered after the CAR-expressing cell and/or the PD-L1 inhibitor described herein. Alternatively, the additional therapeutic agent can be administered between administration of the CAR-expressing cell and the PD-L1 inhibitor.

In further aspects, the combination described herein, e.g., a mesothelin CAR-expressing cell and a PD-L1 inhibitor, may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, the combination described herein, e.g., a mesothelin CAR-expressing cell and a PD-L1 inhibitor, can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.$0^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 613), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, the combination described herein, e.g., a mesothelin CAR-expressing cell and a PD-L1 inhibitor, is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, the combination described herein, e.g., a mesothelin CAR-expressing cell and a PD-L1 inhibitor, is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 $mg/m^2$ (e.g., about 300-325, 325-350, 350-375, 375-400, 400-425, or 425-450 $mg/m^2$), e.g., intravenously. In embodiments, bendamustine is administered at a dosage of about 75-125 mg/m2 (e.g., 75-100 or 100-125 $mg/m^2$, e.g., about 90 $mg/m^2$), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1(2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s5311lbl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 $mg/m^2$ to 750 $mg/m^2$, e.g., about 150-175 $mg/m^2$, 175-200 $mg/m^2$, 200-225 $mg/m^2$, 225-250 $mg/m^2$, 250-300 $mg/m^2$, 300-325 $mg/m^2$, 325-350 $mg/m^2$, 350-375 $mg/m^2$, 375-400 $mg/m^2$, 400-425 $mg/m^2$, 425-450 $mg/m^2$, 450-475 $mg/m^2$, 475-500 $mg/m^2$, 500-525 $mg/m^2$, 525-550 $mg/m^2$, 550-575 $mg/m^2$, 575-600 $mg/m^2$, 600-625 $mg/m^2$, 625-650 $mg/m^2$, 650-675 $mg/m^2$, or 675-700 $mg/m^2$, where $m^2$ indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1κ human monoclonal antibody with a molecular weight of approximately 149 kDa. For example, ofatumumab is generated using transgenic mouse and hybridoma technology and is expressed and purified from a recombinant murine cell line (NS0). See, e.g., www.accessdata.fda.gov/drugsatfda_docs/label/2009/1253261bl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378(2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or R05072759) is a humanized and glyco-engineered anti-CD20 monoclonal antibody. See, e.g., Robak. Curr. Opin. Investig. Drugs. 10.6(2009):588-96; Clinical Trial Identifier Numbers: NCT01995669, NCT01889797, NCT02229422, and NCT01414205; and www.accessdata.fda.gov/drugsatfda_docs/label/2013/125486s0001bl.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1(2011):13-25; and Forero-Torres et al. Clin Cancer Res. 18.5(2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1(2011):13-25; and Casulo et al. Clin Immunol. 154.1(2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1(2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

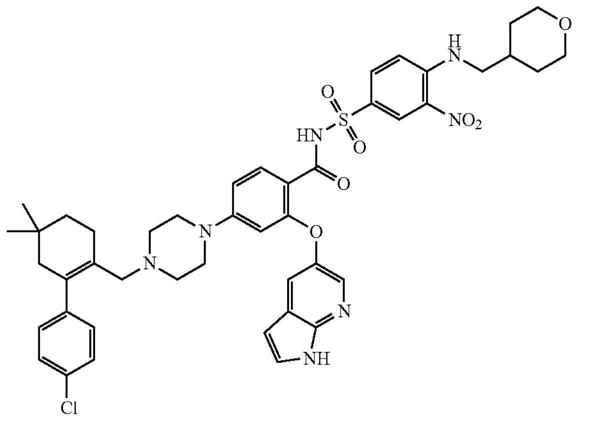 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously, e.g., monthly.

In some embodiments, the combination described herein, e.g., a mesothelin CAR-expressing cell and a PD-L1 inhibitor, is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following: Group B Oncolytic Adenovirus (ColoAd1) (PsiOxus Therapeutics Ltd.) (see, e.g., Clinical Trial Identifier: NCT02053220); ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129); VCN-01, which is a genetically modified oncolytic human adenovirus encoding human PH20 hyaluronidase (VCN Biosciences, S.L.) (see, e.g., Clinical Trial Identifiers: NCT02045602 and NCT02045589); Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759); Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661); CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); orDNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intraarterial, intravenous, intramuscular, intrathecal, or intraperitoneal injection. In embodiments, an oncolytic virus described herein is administered intratumorally, transdermally, transmucosally, orally, intranasally, or via pulmonary administration. In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse.

In one embodiment, the combination described herein, e.g., a mesothelin CAR-expressing cell and a PD-L1 inhibitor, is administered to a subject in combination with a molecule targeting GITR and/or modulating GITR functions, such as a GITR agonist and/or a GITR antibody that depletes regulatory T cells (Tregs). In one embodiment, the GITR binding molecules and/or molecules modulating GITR functions (e.g., GITR agonist and/or Treg depleting GITR antibodies) are administered prior to the CAR-expressing cell. For example, in one embodiment, the GITR agonist can be administered prior to apheresis of the cells. In one embodiment, the subject has CLL. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the combination described herein, e.g., a mesothelin CAR-expressing cell and a PD-L1 inhibitor, is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells. In one embodiment, the subject has CLL.

In one embodiment, the combination described herein, e.g., a mesothelin CAR-expressing cell and a PD-L1 inhibitor, is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells. In one embodiment, the subject has CLL.

In one embodiment, the combination described herein, e.g., a mesothelin CAR-expressing cell and a PD-L1 inhibitor, is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d]pyrimidine. The MNK inhibitor can be, e.g., a MNKla, MNK1b, MNK2a and/or MNK2b inhibitor. In one embodiment, the kinase inhibitor is a dual PI3K/mTOR inhibitor described herein, such as, e.g., PF-04695102.

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In embodiments, the combination described herein, e.g., a mesothelin CAR-expressing cell and a PD-L1 inhibitor, is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

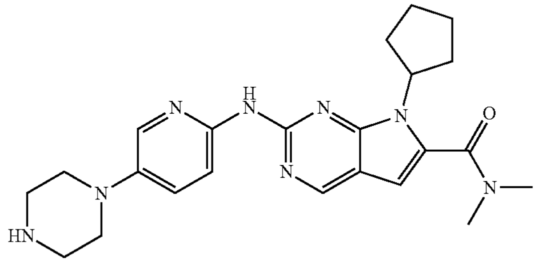 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

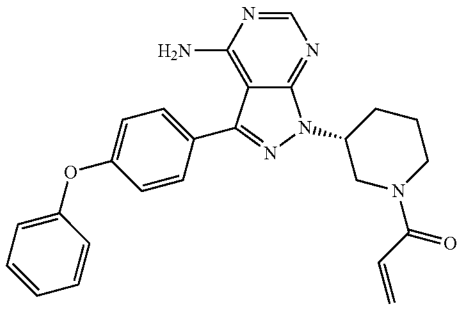 [SMILES: C=CC(=O)N1CCC[C@@H](n2nc(-c3ccc(Oc4ccccc4)cc3)c3c(N)ncnc32)C1]

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

(I)

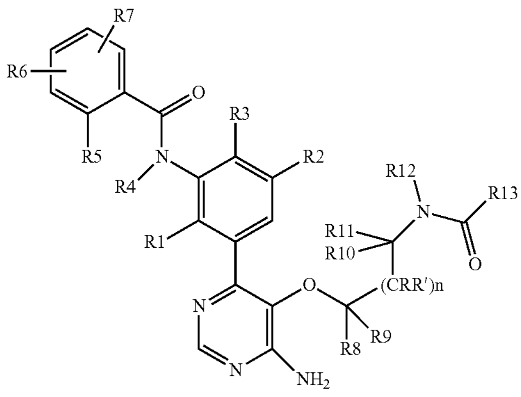

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2-, —CH2-CH2-, —CH═CH—, —CH═CH—CH2-; —CH2-CH═CH—; or —CH2-CH2-CH2-;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)

methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylacrylamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.$0^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 613), inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In embodiments, the combination described herein, e.g., a mesothelin CAR-expressing cell and a PD-L1 inhibitor, is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

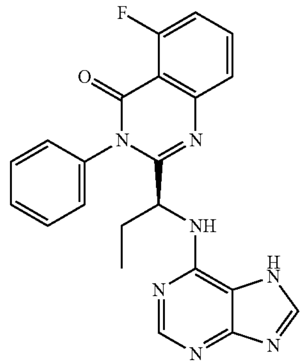 [SMILES: CC[C@H](Nc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

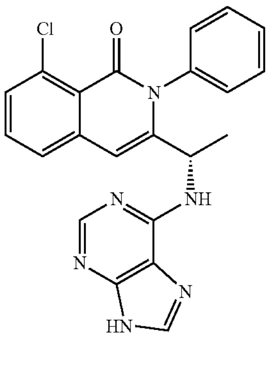 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 $mg/m^2$ (e.g., 350-375, 375-400, 400-425, 425-450, 450-475, or 475-500 $mg/m^2$), e.g., intravenously.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-$N^2$-[2-isopropoxy-5-methyl-4-(4-piperidinyl)phenyl]-$N^4$-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-$N^2$-{4-[4-(dimethylamino)-1-piperidinyl]-2-methoxyphenyl}-$N^4$-[2-(dimethylphosphoryl)phenyl]-2,4-pyrimidinediamine. The chemical name of entrectinib is N-(5-(3,5-difluorobenzyl)-1H-indazol-3-yl)-4-

(4-methylpiperazin-1-yl)-2-((tetrahydro-2H-pyran-4-yl) amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present disclosure may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

In embodiments, the combination described herein, e.g., a mesothelin CAR-expressing cell and a PD-L1 inhibitor, is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255)

In embodiments, the combination described herein, e.g., a mesothelin CAR-expressing cell and a PD-L1 inhibitor, is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19(2013): 1264-72. The structure of BLZ945 is shown below.

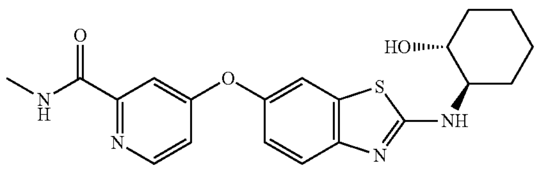 [SMILES: CNC(=O)c1cc(Oc2ccc3nc(N[C@@H]4CCCC[C@H]4O)sc3c2)ccn1]

In embodiments, the combination described herein, e.g., a mesothelin CAR-expressing cell and a PD-L1 inhibitor, herein is administered to a subject in combination with an agent that inhibits or reduces the activity of immunosuppressive plasma cells. Immunosuppressive plasma cells have been shown to impede T cell-dependent immunogenic chemotherapy, such as oxaliplatin (Shalapour et al., *Nature* 2015, 521:94-101). In an embodiment, immunosuppressive plasma cells can express one or more of IgA, interleukin (IL)-10, and PD-L1. In an embodiment, the agent is a CD19 CAR-expressing cell or a BCMA CAR-expressing cell.

In some embodiments, the combination described herein, e.g., a mesothelin CAR-expressing cell and a PD-L1 inhibitor, is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In embodiments, a subject having a disease described herein is administered a combination described herein, e.g., a mesothelin CAR-expressing cell and a PD-L1 inhibitor, in combination with an agent, e.g., cytotoxic or chemotherapy agent, a biologic therapy (e.g., antibody, e.g., monoclonal antibody, or cellular therapy), or an inhibitor (e.g., kinase inhibitor). In embodiments, the subject is administered a CAR-expressing cell described herein in combination with a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. CPX-351 is a liposomal formulation comprising cytarabine and daunorubicin at a 5:1 molar ratio. In embodiments, the subject is administered a CAR-expressing cell described herein in combination with a hypomethylating agent, e.g., a DNA methyltransferase inhibitor, e.g., azacitidine or decitabine. In embodiments, the subject is administered a CAR-expressing cell described herein in combination with a biologic therapy, e.g., an antibody or cellular therapy, e.g., 225Ac-lintuzumab (Actimab-A; Actinium Pharmaceuticals), IPH2102 (Innate Pharma/Bristol Myers Squibb), SGN-CD33A (Seattle Genetics), or gemtuzumab ozogamicin (Mylotarg; Pfizer). SGN-CD33A is an antibody-drug conjugate (ADC) comprising a pyrrolobenzodiazepine dimer that is attached to an anti-CD33 antibody. Actimab-A is an anti-CD33 antibody (lintuzumab) labeled with actinium. IPH2102 is a monoclonal antibody that targets killer immunoglobulin-like receptors (KIRs). In embodiments, the subject is administered a CAR-expressing cell described herein in combination a FLT3 inhibitor, e.g., sorafenib (Bayer), midostaurin (Novartis), quizartinib (Daiichi Sankyo), crenolanib (Arog Pharmaceuticals), PLX3397 (Daiichi Sankyo), AKN-028 (Akinion Pharmaceuticals), or ASP2215 (Astellas). In embodiments, the subject is administered a CAR-expressing cell described herein in combination with an isocitrate dehydrogenase (IDH) inhibitor, e.g., AG-221 (Celgene/Agios) or AG-120 (Agios/Celgene). In embodiments, the subject is administered a CAR-expressing cell described herein in combination with a cell cycle regulator, e.g., inhibitor of polo-like kinase 1 (Plk1), e.g., volasertib (Boehringer Ingelheim); or an inhibitor of cyclin-dependent kinase 9 (Cdk9), e.g., alvocidib (Tolero Pharmaceuticals/Sanofi Aventis). In embodiments, the subject is administered a CAR-expressing cell described herein in combination with a B cell receptor signaling network inhibitor, e.g., an inihibitor of B-cell lymphoma 2 (Bcl-2), e.g., venetoclax (Abbvie/Roche); or an inhibitor of Bruton's tyrosine kinase (Btk), e.g., ibrutinib (Pharmacyclics/Johnson & Johnson Janssen Pharmaceutical). In embodiments, the subject is administered a CAR-expressing cell described herein in combination with an inhibitor of M1 aminopeptidase, e.g., tosedostat (CTI BioPharma/Vernalis); an inhibitor of histone deacetylase (HDAC), e.g., pracinostat (MEI Pharma); a multi-kinase inhibitor, e.g., rigosertib (Onconova Therapeutics/Baxter/SymBio); or a peptidic CXCR4 inverse agonist, e.g., BL-8040 (BioLineRx).

Some patients may experience allergic reactions to the compounds of the present disclosure and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present disclosure and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid). The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present disclosure, can be prepared and administered as described in the art, such as in the documents cited above.

In one embodiment, the present disclosure provides pharmaceutical compositions comprising at least one compound of the present disclosure (e.g., a compound of the present disclosure) or a pharmaceutically acceptable salt thereof together with a pharmaceutically acceptable carrier suitable for administration to a human or animal subject, either alone or together with other anti-cancer agents.

In one embodiment, the present disclosure provides methods of treating human or animal subjects suffering from a cellular proliferative disease, such as cancer. The present disclosure provides methods of treating a human or animal subject in need of such treatment, comprising administering to the subject a therapeutically effective amount of a compound of the present disclosure (e.g., a compound of the present disclosure) or a pharmaceutically acceptable salt thereof, either alone or in combination with other anti-cancer agents.

In particular, compositions will either be formulated together as a combination therapeutic or administered separately.

In combination therapy, the compound of the present disclosure and other anti-cancer agent(s) may be administered either simultaneously, concurrently or sequentially with no specific time limits, wherein such administration provides therapeutically effective levels of the two compounds in the body of the patient.

In a preferred embodiment, the compound of the present disclosure and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present disclosure and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present disclosure, kits that include one or more compound of the present disclosure and a combination partner as disclosed herein are provided. Representative kits include (a) a compound of the present disclosure or a pharmaceutically acceptable salt thereof, (b) at least one combination partner, e.g., as indicated above, whereby such kit may comprise a package insert or other labeling including directions for administration.

A compound of the present disclosure may also be used to advantage in combination with known therapeutic processes, for example, the administration of hormones or especially radiation. A compound of the present disclosure may in particular be used as a radiosensitizer, especially for the treatment of tumors which exhibit poor sensitivity to radiotherapy. In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symsptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others.

In some embodiments, the subject is administered a vasopressor, such as, e.g., norepinephrine, dopamine, phenylephrine, epinephrine, vasopressin, or a combination thereof.

In an embodiment, the subject can be administered an antipyretic agent. In an embodiment, the subject can be administered an analgesic agent.

In one embodiment, the subject can be administered an agent which enhances the activity or fitness of a CAR-expressing cell. For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., Programmed Death 1 (PD-1), can, in some embodiments, decrease the ability of a CAR-expressing cell to mount an immune effector response. Examples of inhibitory molecules include PD-1, PD-L1, CTLA4, TIM3, CEACAM (e.g., CEACAM-1, CEACAM-3 and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta. Inhibition of a molecule that modulates or regulates, e.g., inhibits, T cell function, e.g., by inhibition at the DNA, RNA or protein level, can optimize a CAR-expressing cell performance. In embodiments, an agent, e.g., an inhibitory nucleic acid, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CAR-expressing cell. In an embodiment, the inhibitor is an shRNA.

In an embodiment, the agent that modulates or regulates, e.g., inhibits, T-cell function is inhibited within a CAR-expressing cell. In these embodiments, a dsRNA molecule that inhibits expression of a molecule that modulates or regulates, e.g., inhibits, T-cell function is linked to the nucleic acid that encodes a component, e.g., all of the components, of the CAR. In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. Configurations of exemplary vectors for expressing a component, e.g., all of the components, of the CAR with a dsRNA molecule that inhibits expression of the molecule that modulates or regulates, e.g., inhibits, T-cell function, is provided, e.g., in FIG. 47 of International Publication WO2015/090230, filed Dec. 19, 2014, which is herein incorporated by reference.

Examples of dsRNA molecules useful for inhibiting expression of a molecule that modulates or regulates, e.g., inhibits, T-cell function, wherein the molecule that modulates or regulates, e.g., inhibits, T-cell function is PD-1 include RNAi agents that target PD-1, as described, e.g., in paragraph [00489] and Tables 16 and 17 of International Publication WO2015/090230, filed Dec. 19, 2014, which is incorporated by reference in its entirety.

In one embodiment, the agent that modulates or regulates, e.g., inhibits, T-cell function can be, e.g., an antibody or antibody fragment that binds to an inhibitory molecule. For example, the agent can be an antibody or antibody fragment that binds to PD-1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present disclosure described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

In one embodiment, the anti-PD-1 antibody or fragment thereof is an anti-PD-1 antibody molecule as described in US 2015/0210769, entitled "Antibody Molecules to PD-1 and Uses Thereof," incorporated by reference in its entirety. In one embodiment, the anti-PD-1 antibody molecule includes at least one, two, three, four, five or six CDRs (or collectively all of the CDRs) from a heavy and light chain variable region from an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1, or a sequence substantially identical (e.g., at least 80%, 85%, 90%, 92%, 95%, 97%, 98%, 99% or higher identical) to any of the aforesaid sequences; or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1; or a sequence substantially identical (e.g., at least 80%, 85%, 90%, 92%, 95%, 97%, 98%, 99% or higher identical) to any of the aforesaid sequences.

TIM3 (T cell immunoglobulin-3) also negatively regulates T cell function, particularly in IFN-g-secreting CD4+T helper 1 and CD8+T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In one embodiment, the anti-TIM3 antibody or fragment thereof is an anti-TIM3 antibody molecule as described in US 2015/0218274, entitled "Antibody Molecules to TIM3 and Uses Thereof," incorporated by reference in its entirety. In one embodiment, the anti-TIM3 antibody molecule includes at least one, two, three, four, five or six CDRs (or collectively all of the CDRs) from a heavy and light chain variable region from an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-TIM3 antibody molecule comprises at least one, two, three or four variable regions from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. Cancer *Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BMS-986016 (Bristol-Myers Squib) is a monoclonal antibody that targets LAG3. IMP701 (Immutep) is an antagonist LAG3 antibody and IMP731 (Immutep and GlaxoSmithKlne) is a depleting LAW antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In one embodiment, the anti-LAG3 antibody or fragment thereof is an anti-LAG3 antibody molecule as described in US 2015/0259420, entitled "Antibody Molecules to LAG3 and Uses Thereof," incorporated by reference in its entirety. In one embodiment, the anti-LAG3 antibody molecule includes at least one, two, three, four, five or six CDRs (or collectively all of the CDRs) from a heavy and light chain variable region from an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420; or encoded by the nucleotide sequence in Table 1; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-LAG3 antibody molecule comprises at least one, two, three or four variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420; or encoded by the nucleotide sequence in Tables 1; or a sequence substantially identical (e.g., at least 80%, 85%, 90%, 92%, 95%, 97%, 98%, 99% or higher identical) to any of the aforesaid sequences. In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express a CAR of the present disclosure.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with the combination described herein, e.g., a mesothelin CAR-expressing cell and a PD-L1 inhibitor. The cytokine can be administered simultaneously or concurrently with the CAR-expressing cells, e.g., administered on the same day. The cytokine may be prepared in the same pharmaceutical composition as the CAR-expressing cells, or may be prepared in a separate pharmaceutical composition. Alternatively, the cytokine can be administered shortly after administration of the CAR-expressing cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing cells, or the first day of the cytokine dosing regimen can be 1 day, 2 days, 3 days, 4 days, 5 days, 6 days, or 7 days after administration of the CAR-expressing cells. In one embodiment, on the first day, the CAR-expressing cells are administered to the subject, and on the second day, a cytokine is administered once a day for the next 7 days. In a preferred embodiment, the cytokine to be administered in combination with CAR-expressing cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CART therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CAR-expressing cell therapy can be administered a cytokine. Administration of the cytokine to the subject that has sub-optimal response to the CAR-expressing cell therapy improves CAR-expressing cell efficacy or anti-tumor activity. In a preferred embodiment, the cytokine administered after administration of CAR-expressing cells is IL-7.

Combination with a Low Dose of an mTOR Inhibitor

In one embodiment, the combination described herein, e.g., a mesothelin CAR-expressing cell and a PD-L1 inhibitor, is administered in combination with a low, immune enhancing dose of an mTOR inhibitor.

In another embodiment, administration of a low, immune enhancing, dose of an mTOR inhibitor results in increased or prolonged proliferation of CAR-expressing cells, e.g., in culture or in a subject, e.g., as compared to non-treated CAR-expressing cells or a non-treated subject. In embodiments, increased proliferation is associated with in an increase in the number of CAR-expressing cells. Methods for measuring increased or prolonged proliferation are described in the Examples herein. In another embodiment, administration of a low, immune enhancing, dose of an mTOR inhibitor results in increased killing of cancer cells by CAR-expressing cells, e.g., in culture or in a subject, e.g., as compared to non-treated CAR-expressing cells or a non-treated subject. In embodiments, increased killing of cancer cells is associated with in a decrease in tumor volume.

In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

(A)

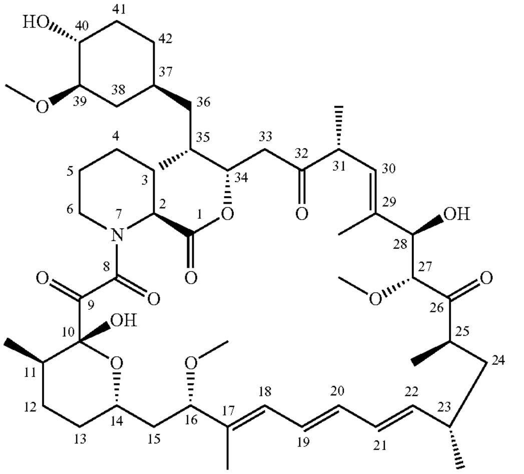

Other suitable rapamycin analogs include, but are not limited to, RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone,sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669).b Other examples of allosteric mTor inhibitors include zotarolimus (ABT578) and umirolimus as described in US2005/0101624 the contents of which are incorporated by reference. Other suitable mTOR inhibitors are described in paragraphs 946 to 964 of International Publication WO2015/142675, filed Mar. 13, 2015, which is incorporated by reference in its entirety. Low, immune enhancing doses of an mTOR inhibitor, suitable levels of mTOR inhibition associated with low doses of an mTOR inhibitor, methods for detecting the level of mTOR inhibition, and suitable pharmaceutical compositions thereof are further described in paragraphs 936 to 945 and 965 to 1003 of International Publication WO2015/142675, filed Mar. 13, 2015, which is incorporated by reference in its entirety.

Pharmaceutical Compositions

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

Methods of Treating

When "an immunologically effective amount," "an effective dose", "an anti-cancer effective amount," "a cancer-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject).

The dosage of the above treatments to be administered to a subject will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

The administration of the compositions described herein may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the compositions described herein, e.g., comprising a CAR-expressing cell and/or PD-L1 inhibitor, are administered to a patient by intradermal or subcutaneous injection. In one embodiment, the the compositions described herein, e.g., comprising a CAR-expressing cell and/or PD-L1 inhibitor, are administered by i.v. injection. The the compositions described herein, e.g., comprising a CAR-expressing cell and/or PD-L1 inhibitor, may be injected directly into a tumor, lymph node, or site of infection.

It can generally be stated that a pharmaceutical composition comprising the immune effector cells described herein may be administered at a dosage of $10^4$ to $10^9$ cells/kg body weight, in some instances $10^5$ to $10^6$ cells/kg body weight, including all integer values within those ranges. The immune effector cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells to a subject and then subsequently redraw blood (or have an apheresis performed), activate the cells therefrom according to the present invention, and reinfuse the patient with these activated and expanded cells. This process can be carried out multiple times every few weeks. In certain aspects, the cells can be activated from blood draws of from 10 cc to 400 cc. In certain aspects, the cells are activated from blood draws of 20 cc, 30 cc, 40 cc, 50 cc, 60 cc, 70 cc, 80 cc, 90 cc, or 100 cc.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR expressing cells of the present invention. In an additional aspect, expanded cells are administered before or following surgery.

In one embodiment, the CAR is introduced into immune effector cells, e.g., using in vitro transcription, and the subject (e.g., human) receives an initial administration of CAR-expressing cells of the invention, and one or more subsequent administrations of the CAR-expressing cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-expressing cells of the invention are administered to the subject (e.g., human) per week, e.g., 2, 3, or 4 administrations of the CAR-expressing cells of the invention are administered per week. In one embodiment, the subject (e.g., human subject) receives more than one administration of the CAR-expressing cells per week (e.g., 2, 3 or 4 administrations per week) (also referred to herein as a cycle), followed by a week of no CAR-expressing cells administration, and then one or more additional administration of the CAR-expressing cells (e.g., more than one administration of the CAR-expressing cells per week) is administered to the subject. In another embodiment, the subject (e.g., human subject) receives more than one cycle of CAR-expressing cells, and the time between each cycle is less than 10, 9, 8, 7, 6, 5, 4, or 3 days. In one embodiment, the CAR-expressing cells are administered every other day for 3 administrations per week. In one embodiment, the CAR-expressing cells of the invention are administered for at least two, three, four, five, six, seven, eight or more weeks.

In some embodiments, a dose of CAR-expressing cells described herein (e.g., mesothelin CAR-expressing cell) comprises about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, $3\times10^8$, or $5\times10^8$ cells/kg. In some embodiments, a dose of CAR cells (e.g., mesothelin CAR-expressing cell) comprises at least about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, $3\times10^8$, or $5\times10^8$ cells/kg. In some embodiments, a dose of CAR cells (e.g., mesothelin CAR-expressing cell) comprises up to about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, $3\times10^8$, or $5\times10^8$ cells/kg. In some embodiments, a dose of CAR cells (e.g., mesothelin CAR-expressing cell) comprises about $1.1\times10^6$-$1.8\times10^7$ cells/kg. In some embodiments, a dose of CAR cells (e.g., mesothelin CAR-expressing cell) comprises about $1\times10^7$, $2\times10^7$, $5\times10^7$, $1\times10^8$, $2\times10^8$, $3\times10^8$, $5\times10^8$, $1\times10^9$, $2\times10^9$, or $5\times10^9$ cells.

In some embodiments, a dose of CAR cells (e.g., e.g., mesothelin CAR-expressing cell) comprises at least about $1\times10^7$, $2\times10^7$, $5\times10^7$, $1\times10^8$, $2\times10^8$, $3\times10^8$, $5\times10^8$, $1\times10^9$, $2\times10^9$, or $5\times10^9$ cells. In some embodiments, a dose of CAR cells (e.g., e.g., mesothelin CAR-expressing cell) comprises up to about $1\times10^7$, $2\times10^7$, $5\times10^7$, $1\times10^8$, $2\times10^8$, $3\times10^8$, $5\times10^8$, $1\times10^9$, $2\times10^9$, or $5\times10^9$ cells.

In some embodiments, a dose of CAR cells (e.g., mesothelin CAR-expressing cell) comprises up to about $1\times10^7$, $1.5\times10^7$, $2\times10^7$, $2.5\times10^7$, $3\times10^7$, $3.5\times10^7$, $4\times10^7$, $5\times10^7$, $1\times10^8$, $1.5\times10^8$, $2\times10^8$, $2.5\times10^8$, $3\times10^8$, $3.5\times10^8$, $4\times10^8$, $5\times10^8$, $1\times10^9$, $2\times10^9$, or $5\times10^9$ cells. In some embodiments, a dose of CAR cells (e.g., mesothelin CAR-expressing cell) comprises up to about $1\text{-}3\times10^7$ to $1\text{-}3\times10^8$. In some embodiments, the subject is administered about $1\text{-}3\times10^7$ of mesothelin CAR-expressing cells. In other embodiments, the subject is administered about $1\text{-}3\times10^8$ of mesothelin-CAR-expressing cells.

In one aspect, mesothelin CAR-expressing cells are generated using lentiviral viral vectors, such as lentivirus. CAR-expressing cells generated that way will have stable CAR expression.

In one aspect, the CAR-expressing cells transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR-expressing cells (particularly with murine scFv bearing CAR-expressing cells) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CAR-expressing cell infusion breaks should not last more than ten to fourteen days.

Using CARs with human (instead of murine) scFvs can reduce the likelihood and intensity of a patient having an anti-CAR response.

Dosages and therapeutic regimens of the PD-L1 inhibitor, e.g., anti-PD-L1 antibody molecule, can be determined by a skilled artisan.

In certain embodiments where the PD-L1 inhibitor is an anti-PD-L1 antibody molecule, the anti-PD-L1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-L1 antibody molecule is administered at a dose from about 10 to 20 mg/kg every other week. In one embodiment, the anti-PD-L1 antibody molecule is administered, alone or in combination (e.g., in combination with an anti-LAG-3 antibody molecule), at a dose of less than, or about, 5 mg/kg; less than, or about, 4 mg/kg; less than, or about, 3 mg/kg; less than, or about, 2 mg/kg; less than, or about, 1 mg/kg, every other week. In one embodiment, the anti-PD-L1 antibody molecule is administered at a dose of 1 to 5 mg/kg every other week; 1 to 4 mg/kg every other week, 1 to 3 mg/kg every other week, or 1 to 2 mg/kg every other week. In one embodiment, the anti-PD-L1 antibody molecule is administered, alone or in combination (e.g., in combination with an anti-PD-L1 antibody molecule) at a dose of 1 to 5 mg/kg every other week; 1 to 4 mg/kg every other week, 1 to 3 mg/kg every other week, or 1 to 2 mg/kg every other week.

The antibody molecules can be administered by a variety of methods known in the art, although for many therapeutic applications, the preferred route/mode of administration is intravenous injection or infusion. For example, the antibody molecule can be administered by intravenous infusion at a rate of more than 20 mg/min, e.g., 20-40 mg/min, and typically greater than or equal to 40 mg/min to reach a dose of about 35 to 440 $mg/m^2$, typically about 70 to 310 $mg/m^2$, and more typically, about 110 to 130 $mg/m^2$. In embodiments, the infusion rate of about 110 to 130 $mg/m^2$ achieves a level of about 3 mg/kg. In other embodiments, the antibody molecule can be administered by intravenous infusion at a rate of less than 10 mg/min, e.g., less than or equal to 5 mg/min to reach a dose of about 1 to 100 $mg/m^2$, e.g., about 5 to 50 $mg/m^2$, about 7 to 25 $mg/m^2$, or, about 10 $mg/m^2$. In some embodiments, the antibody is infused over a period of about 30 min. The antibody molecule can be administered by intravenous infusion at a rate of less than 10 mg/min, preferably less than or equal to 5 mg/min to reach a dose of about 1 to 100 $mg/m^2$, preferably about 5 to 50 $mg/m^2$, about 7 to 25 $mg/m^2$, and more preferably, about 10 $mg/m^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Figure 1B:
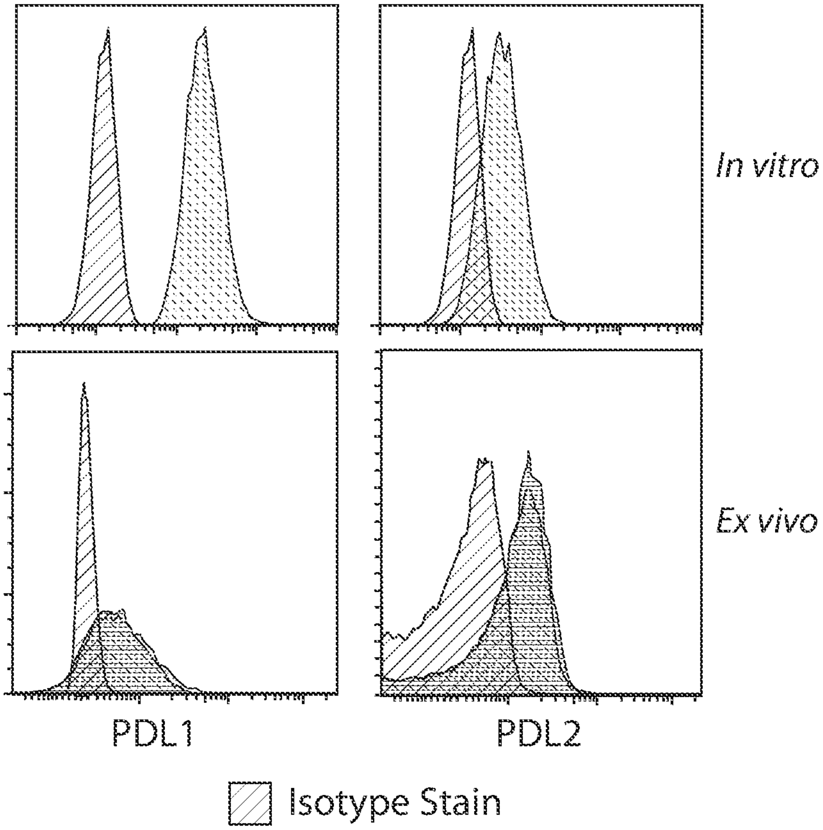
FIG. 1B shows flow cytometric analysis of the expression of PDL1 and PDL2 on Panc02.03 cancer cells. Shown is the expression of both PDL1 and PDL2 by Panc02.03 cancer cells when analyzed both in vitro and ex vivo, from the same tumors analyzed in FIG. 1A. Cancer cells were stained with anti-PDL1 (Biolegend, 29E.2A3) and anti-PDL2 (Biolegend, 24F.10C12).

Example 1: Efficacy of MSLN CART and PD-L1 Inhibitor Combination Therapy in Pancreatic Cancer The anti-tumor activity of mesothelin CART therapy in combination with PD-L1 antibodies was assessed in a mouse model of pancreatic cancer, PANC02.03. Previous studies with mesothelin CAR therapy in the PANC02.03 mouse model showed that mesothelin CAR T cells expanded and infiltrated the tumors. Analysis of these tumor-infiltrating CAR T cells by flow cytometry revealed expression of PD-1 (see FIG. 1A) and PD-L1. Additionally, the PAN02.03 cancer cells expressed express PD-L1 and PD-L2 when tested both in vitro and in vivo (see FIG. 1B).

In a subsequent experiment to test the synergy between mesothelin CAR T cells and PDL1 inhibition, $5\times10^6$ PANC02.03 pancreatic tumor cells were implanted subcutaneously into the flank of immunocompromised NSG mice. PANC02.03 mice were treated with CART therapy alone, PD-L1 therapy alone, or the combination of CART and PD-L1 inhibitor therapy. The effect of the order of administering PD-L1 inhibitor therapy with respect to the CART therapy on anti-tumor activity was assessed with the experiments described below.

Antibody Treatment Prior to CART Therapy

T cells were engineered to express the M5 mesothelin CAR construct (e.g., SEQ ID NO: 67 in Table 2) by lentiviral transduction. Control CAR T cells were engineered to express a CD19 CAR. Mice were divided into 9 groups and treated according to the dosage and treatment schedule below. Two doses of $4\times10^6$ CART cells were injected intravenously on day 23 and 28 after tumor implantation. PD-L1 antibody was injected intraperitoneally at day 21 after tumor implantation, e.g., 48 hours prior to CART therapy.

TABLE 7

| Group | Name | N | CAR T cells per dose | Schedule CAR T cells | Antibody Dose | Antibody Schedule | Route |
|---|---|---|---|---|---|---|---|
| 1 | PBS | 8 | N/A | N/A | N/A | N/A | IV |
| 2 | CAR19 | 8 | $4\times10^6$ | Matched to antibody groups | N/A | N/A | IV |
| 3 | M5 | 8 | $4\times10^6$ | Matched to antibody groups | N/A | N/A | IV |
| 4 | CAR19 + PD-L1 | 8 | $4\times10^6$ | 2 days post antibody dose; $2^{nd}$ dose 4 days after $1^{st}$ dose | 10 mg/kg PD-L1 | Tumor at 175-200 $mm^3$; q5d | IV |
| 5 | M5 + PD-L1 | 8 | $4\times10^6$ | 2 days post antibody dose; $2^{nd}$ dose 4 days after $1^{st}$ dose | 10 mg/kg PD-L1 | Tumor at 175-200 $mm^3$; q5d | IV |

Mice were weighed and calipered twice weekly prior to dosing with treatment to monitor tumor growth. After dosing, the mice were calipered twice weekly. At the end of the study, bone marrow (BM), tumor, and spleen will be collected for FACs analysis.

Figure 2:
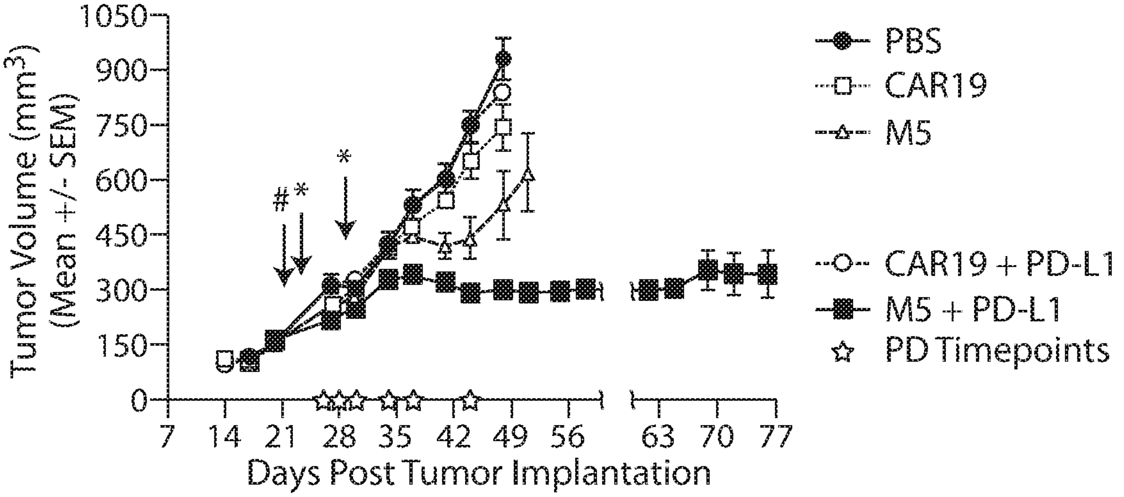
FIG. 2 is a graph showing the tumor progression after various combination treatments with mesothelin CART and a PD-L1 inhibitor, where the PD-L1 inhibitor was administered prior to CAR administration. PD-L1 antibody was administered at the timepoint designated by #. The indicated CAR-expressing cells were administered at the timepoints designated by *. The timepoints where tissues were harvested are designated by the stars on the X-axis.

The results shown in FIG. 2 show that the combination therapy of mesoCART and PD-L1 inhibitor showed transient tumor regression followed by tumor stasis. The combination treatment was shown to be more effective at inhibiting tumor progression than treatment with mesoCART alone. Treatment with CD19 CART alone, or in combination and PD-L1 inhibitor had no effect on tumor progression.

Antibody Treatment after CART Therapy

In the next experiment, PD-L1 inhibitor therapy was administered after mesothelin CART therapy. $4\times10^6$ M5 CART cells were administered 21 days after tumor implantation. PD-1 or PD-L1 antibodies were administered i.v. at 10 mg/kg weekly, with the first dose administered 24 hours after CART administration.

Figure 3:
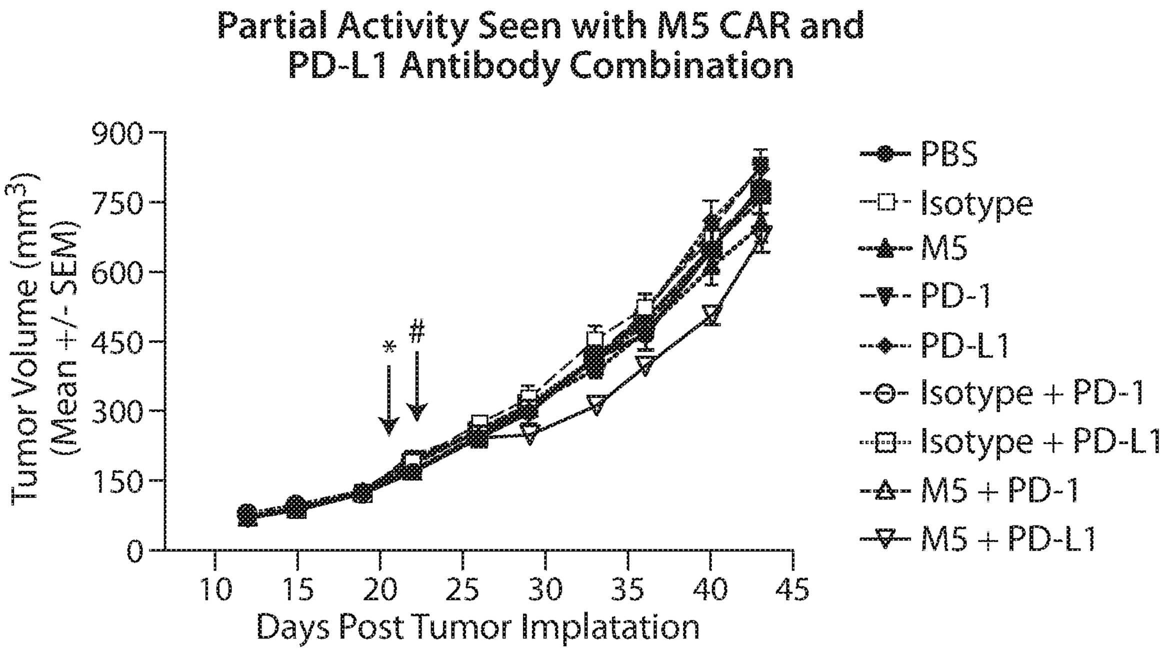
FIG. 3 is a graph the tumor progression after various combination treatments with mesothelin CART and PD-L1 inhibitors, where the PD-L1 inhibitor was administered after CAR administration. PD-L1 antibody was administered at the timepoint designated by #. The indicated CAR-expressing cells were administered at the timepoints designated by *.

The results of treatment on tumor progression are shown in FIG. 3. The combination of M5 CART therapy with PD-L1 antibody treatment only showed minimal and transient anti-tumor activity.

Taking together the data from the two experiments show that administering PD-L1 inhibitor prior to administering the CART therapy has a more robust anti-tumor effect.

Example 2: PD-L1 Expression in Cancer Patients

Further analysis was performed to better characterize the PANC02.03 tumors from NSG mice that were treated with $4\times10^6$ M5 mesothelin CAR positive T cells. PANC02.03 tumor samples were obtained at 35 days from mice that were treated with M5 mesothelin CART. The tumor samples were prepared and serial sections stained to analyze expression of mesothelin and PD-L1 in the tumors, as well as CART infiltration and apoptosis. A mesothelin antibody, anti-PD-L1 antibody (#SP263, Ventana Medical Systems, Tucson, Ariz.), anti-human CD3 antibody (#2GV6, Vetana Medical Systems), and anti-CC3 antibody (apoptosis marker) (#9661, Cell Signaling Technology, Danvers, Mass.) were used for immunohistochemical staining, e.g., using immunohistochemical techniques known in the art. In situ hybridization for mesothelin mRNA (#413101, ACDBio, Hayward, Calif.) was also performed.

Figure 4:
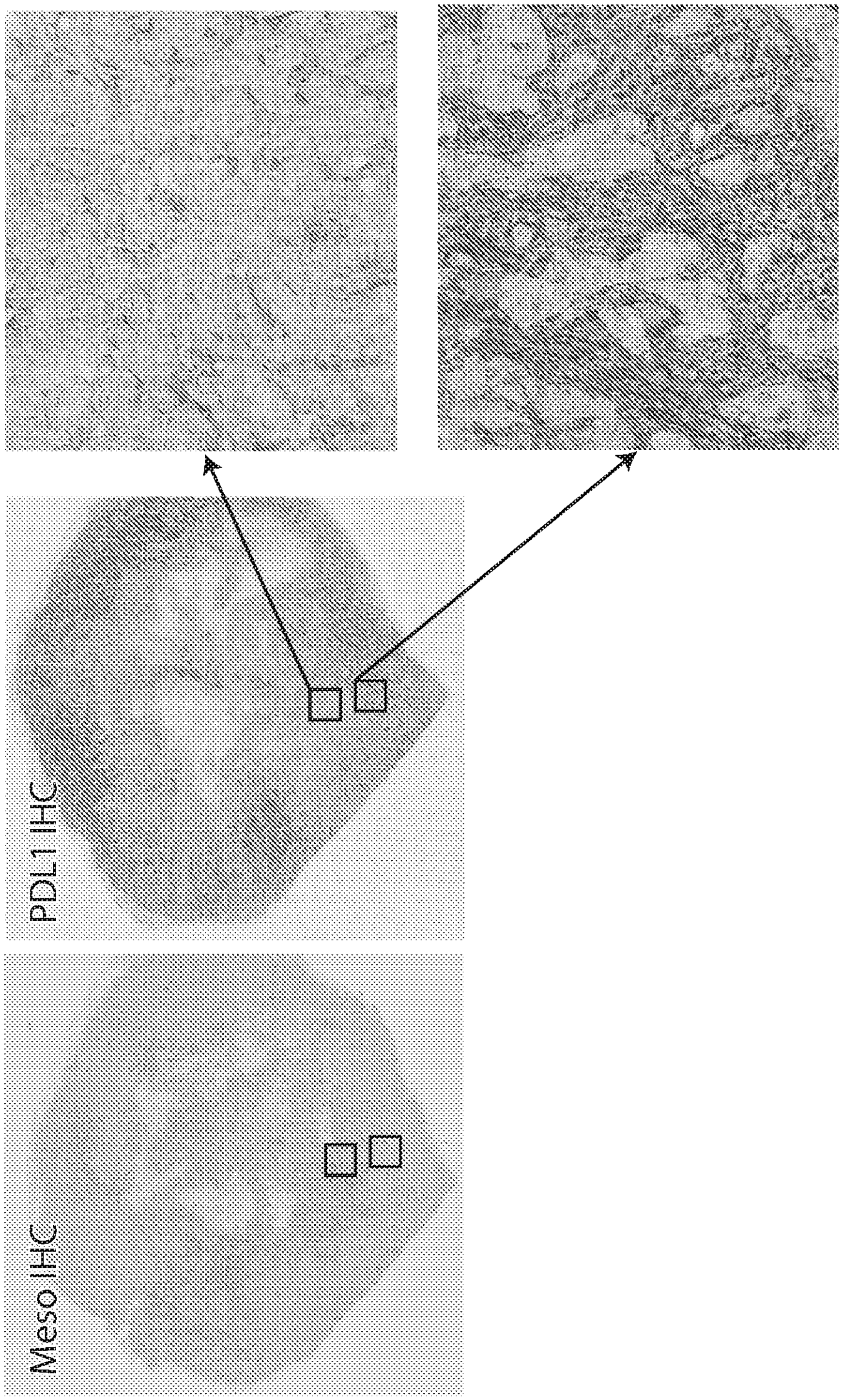
FIG. 4 is a series of images from immunohistochemical analysis of Panc xenograft tissue after treatment with M5 mesothelin CART.
Figure 5:
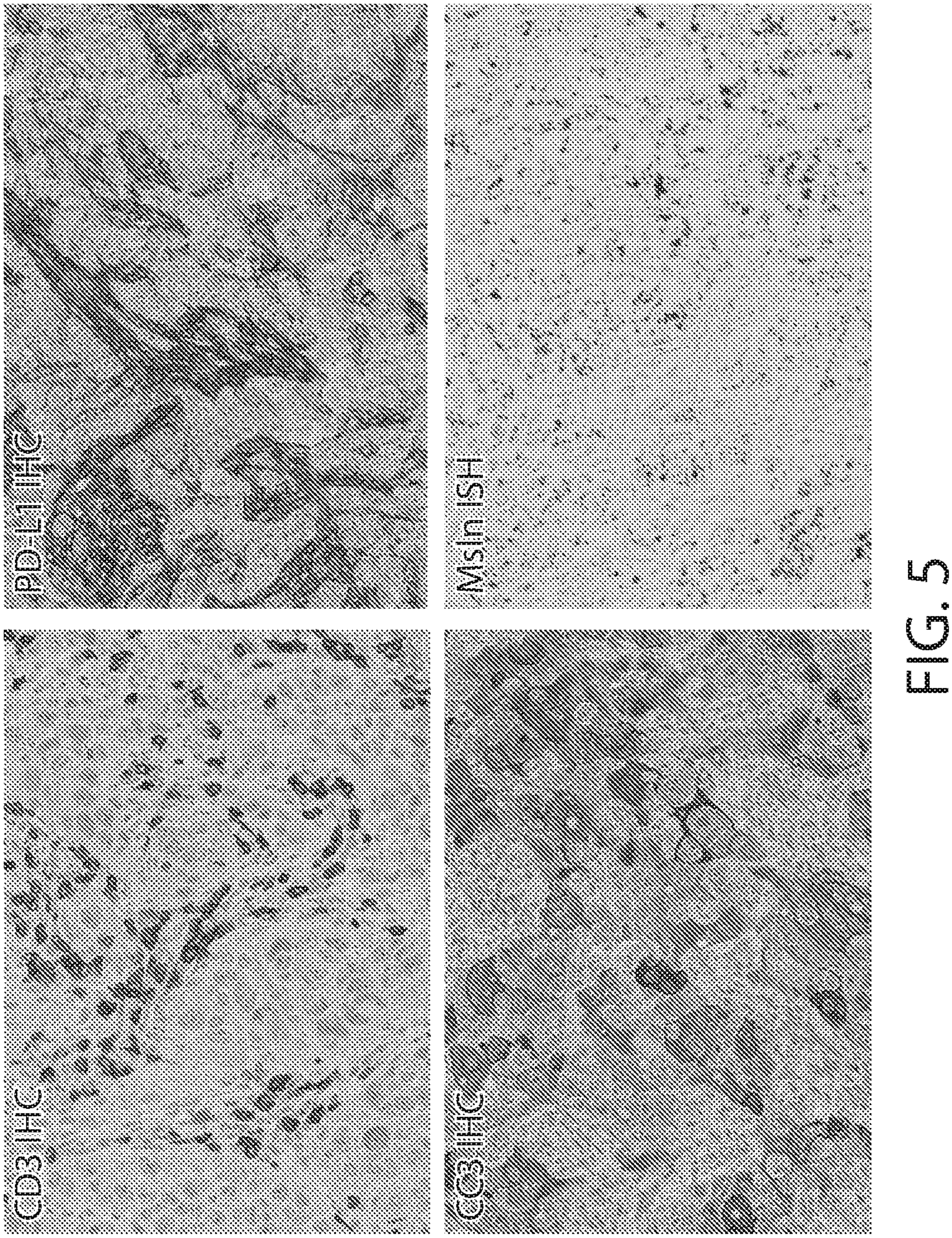
FIG. 5 is a series of images from immunohistochemical analysis of Panc xenograft tissue after treatment with M5 mesothelin CART.

FIG. 4 shows mesothelin expression and PD-L1 expression in the tumor. The tumor has regions of high PD-L1 staining which appear to be inversely correlated with levels of mesothelin protein expression. FIG. 5 shows CAR T cell infiltration (CD3 stained sample, top left panel), apoptosis (CC3 stained sample, bottom left panel), PD-L1 expression (top right panel), and mesothelin mRNA expression (bottom right panel). The results from this expression analysis show that PD-L1 expression is high in tumor regions with low mesothelin protein and mRNA expression (FIG. 4) and yet high CAR T cell infiltration (FIG. 5). These PD-L1-High mesothelin-Low cells are characterized by a spindleloid or mesenchymal morphology and have likely arisen through epithelial mesenchymal transformation. This process is well described in pancreatic tumors and likely contributes to the immunosuppressive tumor microenvironment and disease progression. Thus, these results suggest that a combination treatment using a mesothelin CART and a PD-L1 inhibitor could produce a synergistic effect enhancing efficacy in mesothelin-expressing tumors, where the mesothelin CART targets and kills the mesothelin-expressing tumor cells, while the PD-L1 inhibitor inhibits the immunosuppressive signals from, for example, cancer cells and tumor stromal cells.

Example 3: Low Dose RAD001 Stimulates CART Proliferation in a Cell Culture Model The effect of low doses of RAD001 on CAR T cell proliferation in vitro was evaluated by co-culturing CART-expressing cells with target cells in the presence of different concentrations of RAD001.

Materials and Methods

Generation of CAR-Transduced T Cells

A humanized, anti-human CD19 CAR (huCART19) lentiviral transfer vector was used to produce the genomic material packaged into VSVg pseudotyped lentiviral particles. The amino acid and nucleotide sequence of the humanized anti-human CD19 CAR (huCART19) is CAR 1, ID 104875 described in PCT publication, WO2014/153270, filed Mar. 15, 2014, and is designated SEQ ID NOs. 85 and 31 therein.

Lentiviral transfer vector DNA is mixed with the three packaging components VSVg env, gag/pol and rev in combination with lipofectamine reagent to transfect Lenti-X 293T cells. Medium is changed after 24 h and 30 h thereafter, the virus-containing media is collected, filtered and stored at −80° C. CARTs are generated by transduction of fresh or frozen naïve T cells obtained by negative magnetic selection of healthy donor blood or leukopak. T cells are activated by incubation with anti-CD3/anti-CD28 beads for 24 h, after which viral supernatant or concentrated virus (MOI=2 or 10, respectively) is added to the cultures. The modified T cells are allowed to expand for about 10 days. The percentage of cells transduced (expressing the CARs on the cell surface) and the level of CAR expression (relative fluorescence intensity, Geo Mean) are determined by flow cytometric analysis between days 7 and 9. The combination of slowing growth rate and T cell size approaching ~350 fL determines the state for T cells to be cryopreserved for later analysis.

Evaluating Proliferation of CARTs

To evaluate the functionality of CARTs, the T cells are thawed and counted, and viability is assessed by Cellometer. The number of CAR-positive cells in each culture is normalized using non-transduced T cells (UTD). The impact of RAD001 on CARTs was tested in titrations with RAD001, starting at 50 nM. The target cell line used in all co-culture experiments is Nalm-6, a human pre-B cell acute lymphoblastic leukemia (ALL) cell line expressing CD19 and transduced to express luciferase.

For measuring the proliferation of CARTs, T cells are cultured with target cells at a ratio of 1:1. The assay is run for 4 days, when cells are stained for CD3, CD4, CD8 and CAR expression. The number of T cells is assessed by flow cytometry using counting beads as reference.

Results

Figure 6:
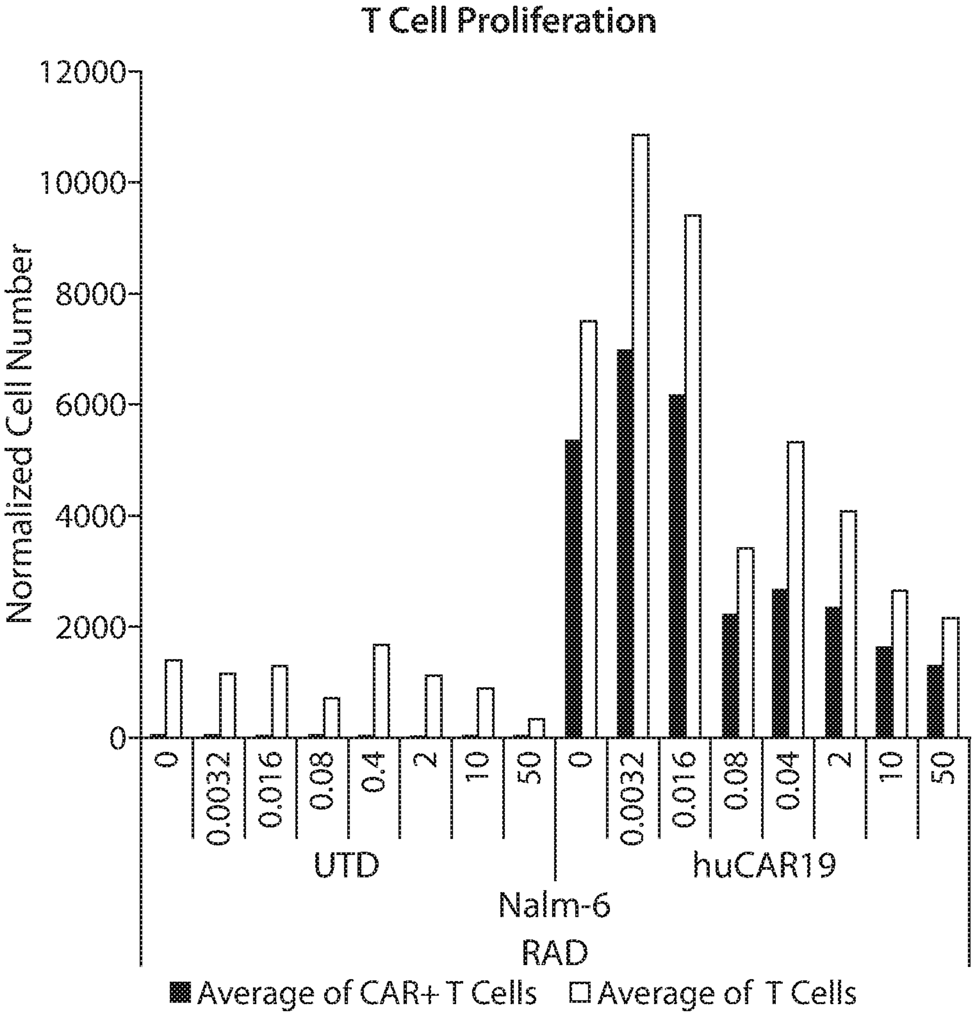
FIG. 6 shows that the proliferation of CAR-expressing, transduced T cells is enhanced by low doses of RAD001 in a cell culture system. CARTs were co-cultured with Nalm-6 cells in the presence of different concentrations of RAD001. The number of CAR-positive CD3-positive T cells (black) and total T cells (gray) was assessed after 4 days of co-culture.

The proliferative capacity of CART cells was tested in a 4 day co-culture assay. The number of CAR-positive CD3-positive T cells (dark bars) and total CD3-positive T cells (light bars) was assessed after culturing the CAR-transduced and non-transduced T cells with Nalm-6 (FIG. 6). huCART19 cells expanded when cultured in the presence of less than 0.016 nM of RAD001, and to a lesser extent at higher concentrations of the compound. Importantly, both at 0.0032 and 0.016 nM RAD001 the proliferation was higher than observed without the addition of RAD001. The non-transduced T cells (UTD) did not show detectable expansion.

Example 4: Low Dose RAD001 Stimulates CART Expansion In Vivo

This example evaluates the ability of huCAR19 cells to proliferate in vivo with different concentrations of RAD001.

Materials and Methods:

NALM6-Luc Cells:

The NALM6 human acute lymphoblastic leukemia (ALL) cell line was developed from the peripheral blood of a patient with relapsed ALL. The cells were then tagged with firefly luciferase. These suspension cells grow in RPMI supplemented with 10% heat inactivated fetal bovine serum.

Mice:

6 week old NSG (NOD.Cg-Prkdc$^{scid}$Il2rg$^{tm1\ Wjl}$/SzJ) mice were received from the Jackson Laboratory (stock number 005557).

Tumor Implantation:

NALM6-luc cells were grown and expanded in vitro in RPMI supplemented with 10% heat inactivated fetal bovine serum. The cells were then transferred to a 15 ml conical tube and washed twice with cold sterile PBS. NALM6-luc cells were then counted and resuspended at a concentration of 10×10$^6$ cells per milliliter of PBS. The cells were placed on ice and immediately (within one hour) implanted in the mice. NALM6-luc cells were injected intravenously via the tail vein in a 100 μl volume, for a total of 1×10$^6$ cells per mouse.

CAR T Cell Dosing:

Mice were administered 5×10$^6$ CAR T cells 7 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of 50×10$^6$ CAR T cells per ml of cold PBS and kept on ice until the mice were dosed. The mice were injected intravenously via the tail vein with 100 μl of the CAR T cells for a dose of 5×10$^6$ CAR T cells per mouse. Eight mice per group were treated either with 100 μl of PBS alone (PBS), or humanized CD19 CAR T cells.

Rad001 Dosing:

A concentrated micro-emulsion of 50 mg equal to 1 mg RAD001 was formulated and then resuspended in D5W (dextrose 5% in water) at the time of dosing. Mice were orally dosed daily (via oral gavage) with 200 μl of the desired doses of RAD001.

Pk Analysis:

Mice were dosed daily with RAD001 starting 7 days post tumor implantation. Dosing groups were as follows: 0.3 mg/kg, 1 mg/kg, 3 mg/kg, and 10 mg/kg. Mice were bled on days 0 and 14 following the first and last dose of RAD001, at the following time points for PK analysis: 15 minutes, 30 minutes, 1 hour, 2 hours, 4 hours, 8 hours, 12 hours, and 24 hours.

Figure 7:
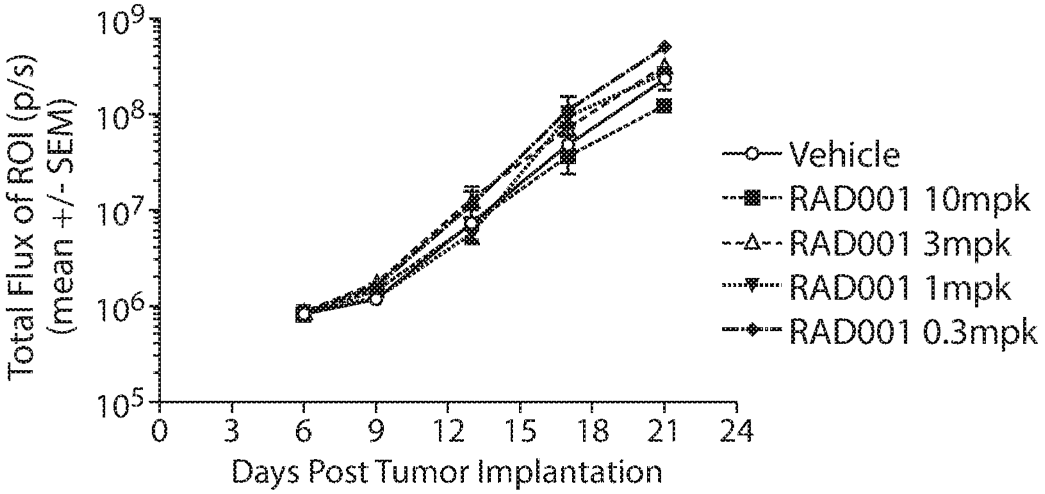
FIG. 7 depicts tumor growth measurements of NALM6-luc cells with daily RAD001 dosing at 0.3, 1, 3, and 10 mg/kg (mpk) or vehicle dosing. Circles denote the vehicle; squares denote the 10 mg/kg dose of RAD001; triangles denote the 3 mg/kg dose of RAD001, inverted triangles denote the 1 mg/kg dose of RAD001; and diamonds denote the 0.3 mg/kg dose of RAD001.
Figure 8A:
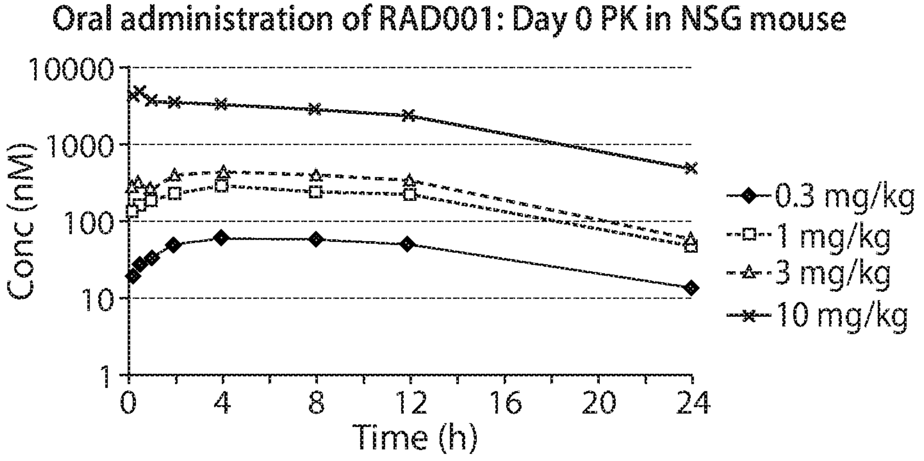
FIGS. 8A and 8B, shows pharmacokinetic curves showing the amount of RAD001 in the blood of NSG mice with NALM6 tumors.
Figure 8B:
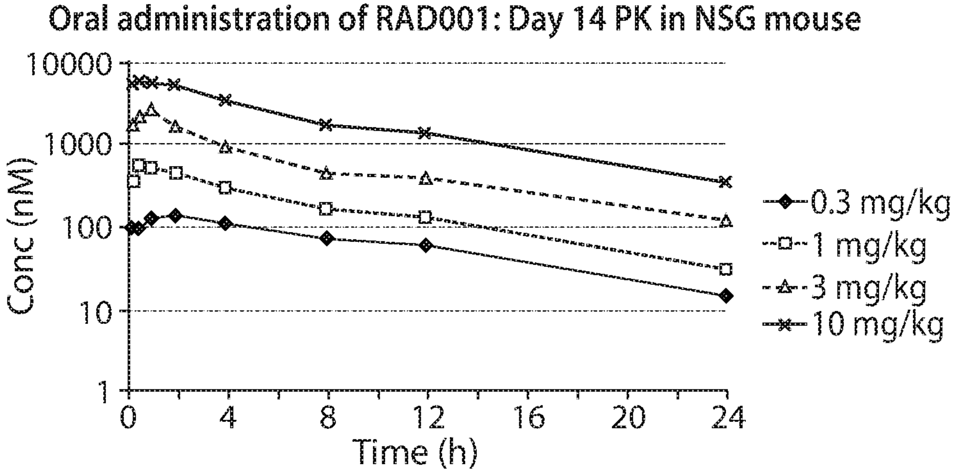

Results:

The expansion and pharmacokinetics of RAD001 was tested in NSG mice with NALM6-luc tumors. Daily oral dosing of RAD001 alone did not have an impact on the growth of NALM6-luc tumors (FIG. 7). The pharmacokinetic analysis of RAD001 shows that it is fairly stable in the blood of tumor bearing mice (FIGS. 8A and 8B). Both the day 0 and day 14 PK analyses show that the RAD001 concentrations in the blood is above 10 nm even 24 hours after dosing at the lowest dose tested (0.3 mg/kg).

Based on these doses, huCAR19 CAR T cells were dosed with and without RAD001 to determine the proliferative ability of these cells. The highest dose used was 3 mg/kg based on the levels of RAD001 in the blood 24 hours after dosing. As the concentration of RAD001 was above 10 nM 24 hours after the final dose of RAD001, several lower doses of RAD001 were used in the in vivo study with CAR T cells. The CAR T cells were dosed IV one day prior to the start of the daily oral RAD001 dosing. Mice were monitored via FACS for T cell expansion.

Figure 9A:
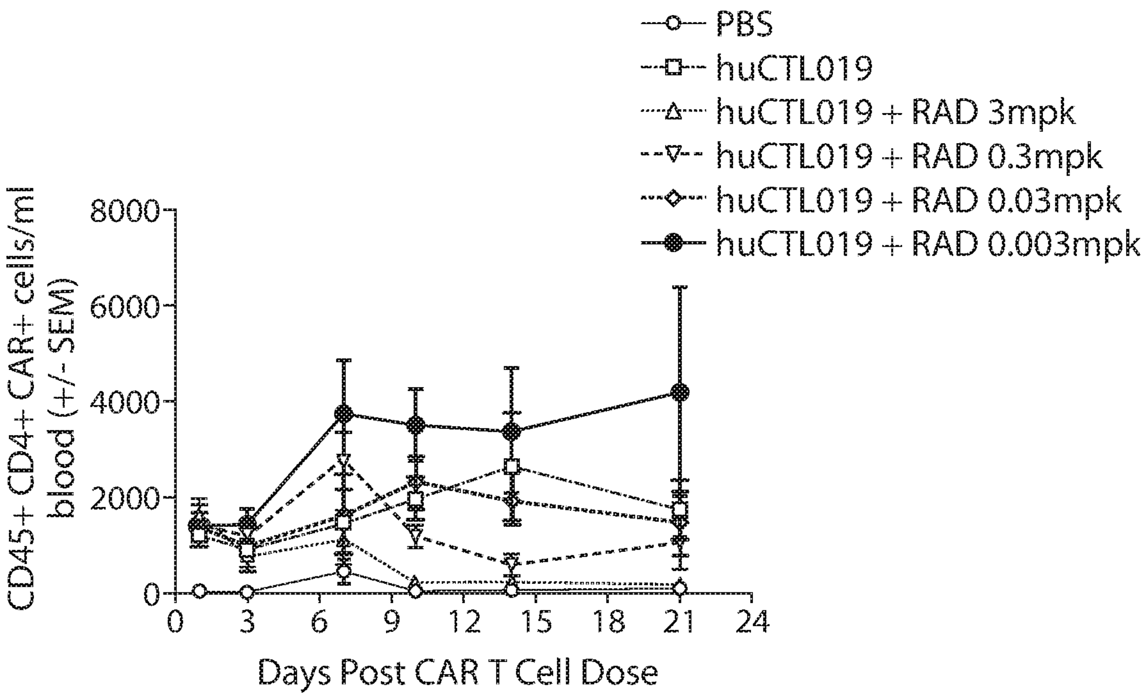
FIGS. 9A and 9B, shows in vivo proliferation of humanized CD19 CART cells with and without RAD001 dosing. Low doses of RAD001 (0.003 mg/kg) daily lead to an enhancement in CAR T cell proliferation, above the normal level of huCAR19 proliferation.
Figure 9B:
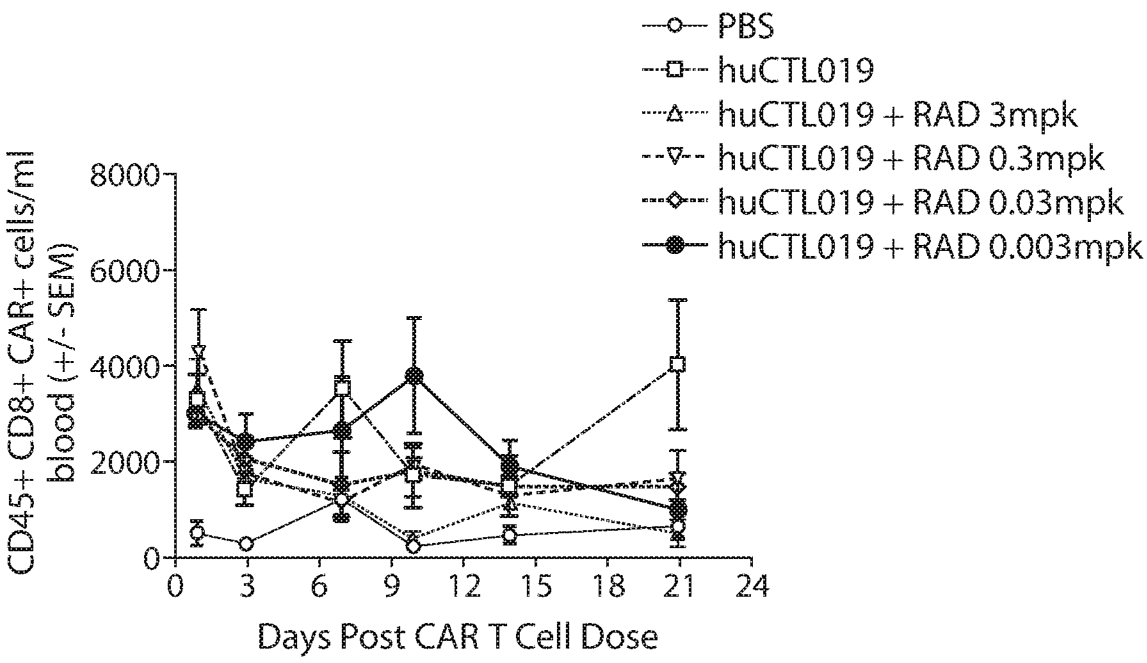

The lowest doses of RAD001 show an enhanced proliferation of the CAR T cells (FIGS. 9A and 9B). This enhanced proliferation is more evident and prolonged with the CD4$^+$ CAR T cells than the CD8$^+$ CAR T cells. However, with the CD8$^+$ CAR T cells, enhanced proliferation can be seen at early time points following the CAR T cell dose. In embodiments, a RNA CART cell can also be used in combination with checkpoint inhibitors.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A method of treating a subject having a disease associated with mesothelin expression, comprising administering to the subject:

i) a cell, or a population of immune effector cells expressing, a chimeric antigen receptor (CAR), wherein the CAR comprises a mesothelin binding domain, a transmembrane domain, and an intracellular signaling domain; wherein the mesothelin binding domain comprises:

(a) a heavy chain complementarity determining region 1 (HC CDR1), a heavy chain complementarity determining region 2 (HC CDR2), and a heavy chain complementarity determining region 3 (HC CDR3) of an anti-mesothelin antibody selected from the group consisting of M1, M2, M3, M4, M5, M6, M7, M8, M9, M10, M11, M12, M13, M14, M15, M16, M17, M18, M19, M20, M21, M22, M23, and M24; and (b) a light chain complementarity determining region 1 (LC CDR1), a light chain complementarity determining region 2 (LC CDR2), and a light chain complementarity determining region 3 (LC CDR3) of an anti-mesothelin antibody selected from the group consisting of M1, M2, M3, M4, M5, M6, M7, M8, M9, M10, M11, M12, M13, M14, M15, M16, M17, M18, M19, M20, M21, M22, M23, and M24; and ii) a PD-L1 inhibitor, wherein the PD-L1 inhibitor is administered prior to administration of the cell comprising a CAR; and wherein the PD-L1 inhibitor is an anti-PD-L1 antibody molecule selected from the group consisting of YW243.55.S70, MPDL3280A (atezolizumab), MEDI-4736, MSB-0010718C (avelumab), MDX-1105, and an anti-PD-L1 antibody molecule comprising:

(a) a heavy chain complementarity determining region 1 (HC CDR1) amino acid sequence selected from the group consisting of SEQ ID NO: 287, 290, or 195, a HC CDR2 amino acid sequence of SEQ ID NO: 288, and a HC CDR3 amino acid sequence of SEQ ID NO: 289; and a light chain complementarity determining region 1 (LC CDR1) amino acid sequence of SEQ ID NO: 295, a LC CDR2 amino acid sequence of SEQ ID NO: 296, and a LC CDR3 amino acid sequence of SEQ ID NO: 297; or (b) a HC CDR1 amino acid sequence selected from the group consisting of SEQ ID NOs: 287, 290, or 195, a HC CDR2 amino acid sequence of SEQ ID NO: 291, and a HC CDR3 amino acid sequence of SEQ ID NO: 292; and a LC CDR1 amino acid sequence of SEQ ID NO: 298, a LC CDR2 amino acid sequence of SEQ ID NO: 299, and a LC CDR3 amino acid sequence of SEQ ID NO: 300.

2. The method of claim 1, wherein the treatment comprises:

(i) administration of the CAR-expressing cell and the PD-L1 inhibitor for a treatment interval, and wherein the treatment interval comprises a single dose of the PD-L1 inhibitor and a single dose of the CAR-expressing cell; or (ii) a single dose of the CAR-expressing cell and a single dose of the PD-L1 inhibitor.

3. The method of claim 2, wherein the treatment or treatment interval:

(i) is initiated upon administration of the dose of the PD-L1 inhibitor and completed upon administration of the dose of the CAR-expressing cell;

(ii) further comprises one or more subsequent doses of the PD-L1 inhibitor.

4. The method of claim 2, wherein the dose of the CAR-expressing cell is administered:

(i) at least 2 days, 3 days, 4 days, 5 days, 6 days, 7 days, or 2 weeks after the dose of PDL1 inhibitor is administered; or (ii) 2 days after the dose of the PD-L1 inhibitor is administered.

5. The method of claim 1, wherein the CAR-expressing cell and the PD-L1 inhibitor is administered for a treatment interval, wherein the treatment interval comprises a first and second dose of the PD-L1 inhibitor and a dose of the CAR-expressing cell, and wherein the dose of the CAR-expressing cell is administered after administration of the first dose of the PD-L1 inhibitor but before the administration of the second dose of the PD-L1 inhibitor.

6. The method of claim 5, wherein:

(i) the treatment interval is initiated upon administration of the first dose of the PD-L1 inhibitor and completed upon administration of the second dose of the PD-L1 inhibitor;

(ii) the second dose of the PD-L1 inhibitor is administered at least 5 days, 7 days, 1 week, 2 weeks, or 3 weeks after administration of the first dose of the PD-L1 inhibitor;

(iii) the dose of the CAR-expressing cell is administered at least 2 days, 3 days, 4 days, 5 days, 6 days, 7 days, or 2 weeks after administration of the first dose of the PD-L1 inhibitor; or (iv) the second dose of the PD-L1 inhibitor is administered at least 2 days, 3 days, 4 days, 5 days, 6 days, 7 days, or 2 weeks after administration of the dose of the CAR-expressing cell.

7. The method of claim 2, wherein the treatment or treatment interval:

(i) is repeated one or more times; or (ii) is followed by one or more subsequent treatment intervals wherein the one or more subsequent treatment intervals is administered at least 1 day, 2 days, 3 days, 4 days, 5 days, 6 days, 7 days, or 2 weeks, after the completion of the first or previous treatment interval.

8. The method of claim 3, wherein one or more subsequent doses of the PD-L1 inhibitor is administered:

(i) after the completion of one or more treatment intervals;

(ii) after the administration of the single dose of the PD-L1 inhibitor;

(iii) at least 5 days, 7 days, 2 weeks, 3 weeks or 4 weeks, after the previous dose of PD-L1 inhibitor;

(iv) at least 1, 2, 3, 4, 5, 6, or 7 days, after the initial dose of the CAR-expressing cell; or (v) prior to the first dose of the CAR-expressing cell.

9. The method of claim 8, wherein a dose of the PD-L1 inhibitor is administered every 5 days, 7 days, 2 weeks, 3 weeks, or 4 days after the previous dose of PD-L1 inhibitor or after the completion of one or more treatment intervals.

10. The method of claim 2, wherein the treatment interval comprises a dose of CAR-expressing cells administered 2 days after the dose of the PD-L1 inhibitor is administered, and wherein the treatment interval is repeated twice, and wherein the treatment intervals are initiated 3 days after the completion of the previous treatment interval.

11. The method of claim 10, wherein one or more subsequent doses of the PDL1 inhibitor is administered every 5 days, 7 days, 2 weeks, 3 weeks, or 4 weeks, after the second treatment interval.

12. The method of claim 2, wherein one or more subsequent doses of a CAR-expressing cell is administered to the subject after the initial dose of the CAR-expressing cell.

13. The method of claim 12, wherein the one or more subsequent doses of the CAR-expressing cell are administered:

(i) at least 2 days, 3 days, 4 days, 5 days, 6 days, 7 days or 2 weeks, after the previous dose of the CAR-expressing cell;

(ii) at least 5 days after the previous dose of the CAR-expressing cell.

14. The method of claim 2, wherein the dose of CAR-expressing cells:

(i) comprises at least about $1\text{-}3\times10^7$ to $1\text{-}3\times10^8$ cells;

(ii) is about $1\text{-}3\times10^7$ cells; or (iii) is about $1\text{-}3\times10^8$ cells.

15. The method of claim 2, wherein the dose of the PD-L1 inhibitor is about 1 to 30 mg/kg, about 5 to 25 mg/kg, about 10 to 20 mg/kg, or about 1 to 5 mg/kg.

16. The method of claim 1, wherein the PD-L1 inhibitor comprises an antibody molecule, a small molecule, a polypeptide, a fusion protein, or an inhibitory nucleic acid.

17. The method of claim 1, wherein the anti PD-L1 antibody molecule is selected from the group consisting of BAP058-hum01, BAP058-hum02, BAP058-hum03, BAP058-hum04, BAP058-hum05, BAP058-hum06, BAP058-hum07, BAP058-hum08, BAP058-hum09, BAP058-hum010, BAP058-hum011, BAP058-hum012, BAP058-hum013, BAP058-hum014, BAP058-hum015, BAP058-hum016, BAP058-hum017, BAP058-Clone K, BAP058-Clone L, BAP058-Clone M, BAP058-Clone N, and BAP058-Clone O.

18. The method of claim 1, wherein the anti-PD-L1 antibody molecule comprises:

(a) a heavy chain variable region comprising:

(i) an amino acid sequence of a heavy chain variable region selected from the group consisting of SEQ ID NOs: 304, 306, 316, 318, 324, 326, 332, 334, 336, 338, 340, 342, 348, 350, 356, 358, 364, 366, 377, 382, 391, 393, and 398;

(ii) an amino acid sequence having at least one, two or three modifications but not more than 30, 20 or 10 modifications to the amino acid sequence of a heavy chain variable region selected from the group consisting of SEQ ID NOs: 304, 306, 316, 318, 324, 326, 332, 334, 336, 338, 340, 342, 348, 350, 356, 358, 364, 366, 377, 382, 391, 393, and 398; or (iii) an amino acid sequence with 95-99% identity to the amino acid sequence of a heavy chain variable region selected from the group consisting of SEQ ID NOs: 304, 306, 316, 318, 324, 326, 332, 334, 336, 338, 340, 342, 348, 350, 356, 358, 364, 366, 377, 382, 391, 393, and 398; and (b) a light chain variable region comprising:

(i) an amino acid sequence of a light chain variable region selected from the group consisting of SEQ ID NOs: 308, 310, 312, 314, 320, 322, 330, 328, 344, 346, 352, 354, 360, 362, 368, 370, 372 and 374;

(ii) an amino acid sequence having at least one, two or three modifications but not more than 30, 20 or 10 modifications to the amino acid sequence of a light chain variable region selected from the group consisting of SEQ ID NOs: 308, 310, 312, 314, 320, 322, 330, 328, 344, 346, 352, 354, 360, 362, 368, 370, 372 and 374; or (iii) an amino acid sequence with 95-99% identity to the amino acid sequence of a light chain variable region selected from the group consisting of SEQ ID NOs: 308, 310, 312, 314, 320, 322, 330, 328, 344, 346, 352, 354, 360, 362, 368, 370, 372 and 374.

19. The method of claim 1, wherein the anti-PD-L1 antibody molecule comprises:

i) a heavy chain variable domain comprising the amino acid sequence of SEQ ID NO: 304 and a light chain variable domain comprising the amino acid sequence of SEQ ID NO: 308;

ii) a heavy chain variable domain comprising the amino acid sequence of SEQ ID NO: 304 and a light chain variable domain comprising the amino acid sequence of SEQ ID NO: 312;

iii) a heavy chain variable domain comprising the amino acid sequence of SEQ ID NO: 304 and a light chain variable domain comprising the amino acid sequence of SEQ ID NO: 372;

iv) a heavy chain variable domain comprising the amino acid sequence of SEQ ID NO: 316 and a light chain variable domain comprising the amino acid sequence of SEQ ID NO: 320;

v) a heavy chain variable domain comprising the amino acid sequence of SEQ ID NO: 316 and a light chain variable domain comprising the amino acid sequence of SEQ ID NO: 352;
vi) a heavy chain variable domain comprising the amino acid sequence of SEQ ID NO: 324 and a light chain variable domain comprising the amino acid sequence of SEQ ID NO: 328;
vii) a heavy chain variable domain comprising the amino acid sequence of SEQ ID NO: 324 and a light chain variable domain comprising the amino acid sequence of SEQ ID NO: 360;
viii) a heavy chain variable domain comprising the amino acid sequence of SEQ ID NO: 332 and a light chain variable domain comprising the amino acid sequence of SEQ ID NO: 328;
ix) a heavy chain variable domain comprising the amino acid sequence of SEQ ID NO: 336 and a light chain variable domain comprising the amino acid sequence of SEQ ID NO: 328;
x) a heavy chain variable domain comprising the amino acid sequence of SEQ ID NO: 336 and a light chain variable domain comprising the amino acid sequence of SEQ ID NO: 308;
xi) a heavy chain variable domain comprising the amino acid sequence of SEQ ID NO: 336 and a light chain variable domain comprising the amino acid sequence of SEQ ID NO: 372;
xii) a heavy chain variable domain comprising the amino acid sequence of SEQ ID NO: 340 and a light chain variable domain comprising the amino acid sequence of SEQ ID NO: 344;
xiii) a heavy chain variable domain comprising the amino acid sequence of SEQ ID NO: 340 and a light chain variable domain comprising the amino acid sequence of SEQ ID NO: 372;
xiv) a heavy chain variable domain comprising the amino acid sequence of SEQ ID NO: 348 and a light chain variable domain comprising the amino acid sequence of SEQ ID NO: 352;
xv) a heavy chain variable domain comprising the amino acid sequence of SEQ ID NO: 348 and a light chain variable domain comprising the amino acid sequence of SEQ ID NO: 386;
xvi) a heavy chain variable domain comprising the amino acid sequence of SEQ ID NO: 356 and a light chain variable domain comprising the amino acid sequence of SEQ ID NO: 352; or
xvii) a heavy chain variable domain comprising the amino acid sequence of SEQ ID NO: 364 and a light chain variable domain comprising the amino acid sequence of SEQ ID NO: 368.

20. The method of claim 1, wherein the anti-PD-L1 antibody molecule comprises:
i) a heavy chain comprising the amino acid sequence of SEQ ID NO: 306 and a light chain comprising the amino acid sequence of SEQ ID NO: 310;
ii) a heavy chain comprising the amino acid sequence of SEQ ID NO: 306 and a light chain comprising the amino acid sequence of SEQ ID NO: 314;
iii) a heavy chain comprising the amino acid sequence of SEQ ID NO: 306 and a light chain comprising the amino acid sequence of SEQ ID NO: 374;
iv) a heavy chain comprising the amino acid sequence of SEQ ID NO: 318 and a light chain comprising the amino acid sequence of SEQ ID NO: 322;
v) a heavy chain comprising the amino acid sequence of SEQ ID NO: 318 and a light chain comprising the amino acid sequence of SEQ ID NO: 354;
vi) a heavy chain comprising the amino acid sequence of SEQ ID NO: 326 and a light chain comprising the amino acid sequence of SEQ ID NO: 330;
vii) a heavy chain comprising the amino acid sequence of SEQ ID NO: 326 and a light chain comprising the amino acid sequence of SEQ ID NO: 362;
viii) a heavy chain comprising the amino acid sequence of SEQ ID NO: 334 and a light chain comprising the amino acid sequence of SEQ ID NO: 330;
ix) a heavy chain comprising the amino acid sequence of SEQ ID NO: 338 and a light chain comprising the amino acid sequence of SEQ ID NO: 330;
x) a heavy chain comprising the amino acid sequence of SEQ ID NO: 338 and a light chain comprising the amino acid sequence of SEQ ID NO: 310;
xi) a heavy chain comprising the amino acid sequence of SEQ ID NO: 338 and a light chain comprising the amino acid sequence of SEQ ID NO: 374;
xii) a heavy chain comprising the amino acid sequence of SEQ ID NO: 342 and a light chain comprising the amino acid sequence of SEQ ID NO: 346;
xiii) a heavy chain comprising the amino acid sequence of SEQ ID NO: 342 and a light chain comprising the amino acid sequence of SEQ ID NO: 374;
xiv) a heavy chain comprising the amino acid sequence of SEQ ID NO: 350 and a light chain comprising the amino acid sequence of SEQ ID NO: 354;
xv) a heavy chain comprising the amino acid sequence of SEQ ID NO: 350 and a light chain comprising the amino acid sequence of SEQ ID NO: 374;
xvi) a heavy chain comprising the amino acid sequence of SEQ ID NO: 358 and a light chain comprising the amino acid sequence of SEQ ID NO: 354;
xvii) a heavy chain comprising the amino acid sequence of SEQ ID NO: 366 and a light chain comprising the amino acid sequence of SEQ ID NO:370;
xviii) a heavy chain comprising the amino acid sequence of SEQ ID NO: 393 and a light chain comprising the amino acid sequence of SEQ ID NO: 322;
xix) a heavy chain comprising the amino acid sequence of SEQ ID NO: 377 and a light chain comprising the amino acid sequence of SEQ ID NO: 330; or
xx) a heavy chain comprising the amino acid sequence of SEQ ID NO: 382 and a light chain comprising the amino acid sequence of SEQ ID NO: 354.

21. The method of claim 1, wherein the mesothelin binding domain comprises:
(a) a heavy chain variable region comprising:
i) an amino acid sequence of a heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62;
ii) an amino acid sequence having at least one, two or three modifications but not more than 30, 20 or 10 modifications to the amino acid sequence of a heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62; or iii) an amino acid sequence with 95-99% identity to the amino acid sequence of a heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62; and (b) a light chain variable region comprising:

i) the amino acid sequence of a light chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62;

ii) an amino acid sequence having at least one, two or three modifications but not more than 30, 20 or 10 modifications to the amino acid sequence of a light chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62; or iii) an amino acid sequence with 95-99% identity to the amino acid sequence of a heavy chain variable region of a mesothelin binding domain of an scFv selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62.

22. The method of claim 1, wherein the mesothelin binding domain comprises:

i) the amino acid sequence selected from the group consisting of SEQ ID NO: 43, SEQ ID NO: 49, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62;

ii) an amino acid sequence having at least one, two or three modifications but not more than 30, 20 or 10 modifications to any of SEQ ID NO: 43, SEQ ID NO: 49, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62; or iii) an amino acid sequence with 95-99% identity to the amino acid sequence to any of SEQ ID NO: 43, SEQ ID NO: 49, SEQ ID NO: 39, SEQ ID NO: 40, SEQ ID NO: 41, SEQ ID NO: 42, SEQ ID NO: 44, SEQ ID NO: 45, SEQ ID NO: 46, SEQ ID NO: 47, SEQ ID NO: 48, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, or SEQ ID NO: 62.

23. The method of claim 1, wherein the transmembrane domain comprises a transmembrane domain from a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

24. The method of claim 1, wherein the transmembrane domain comprises (i) the amino acid sequence of SEQ ID NO: 6, (ii) an amino acid sequence comprises at least one, two or three modifications but not more than 20, 10 or 5 modifications of the amino acid sequence of SEQ ID NO:6, or (iii) a sequence with 95-99% identity to the amino acid sequence of SEQ ID NO:6.

25. The method of claim 1, wherein the intracellular signaling domain comprises a costimulatory signaling domain comprising a functional signaling domain obtained from a protein selected from the group consisting of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, ICAM-1, LFA-1 (CD11a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

26. The method of claim 25, wherein the costimulatory domain comprises:
(i) the amino acid sequence of SEQ ID NO:7,
(ii) an amino acid sequence having at least one, two or three modifications but not more than 20, 10 or 5 modifications of the amino acid sequence of SEQ ID NO:7, or
(iii) an amino acid sequence with 95-99% identity to the amino acid sequence of SEQ ID NO:7.

27. The method of claim 1, wherein the intracellular signaling domain comprises a functional signaling domain of 4-1BB and/or a functional signaling domain of CD3 zeta.

28. The method of claim 27, wherein the intracellular signaling domain comprises:
(i) the amino acid sequence of SEQ ID NO: 7 and/or the amino acid sequence of SEQ ID NO:9 or SEQ ID NO:10;
(ii) an amino acid sequence having at least one, two or three modifications but not more than 20, 10 or 5 modifications of the amino acid sequence of SEQ ID NO:7 and/or the amino acid sequence of SEQ ID NO:9 or SEQ ID NO:10; or
(iii) an amino acid sequence with 95-99% identity to the amino acid sequence of SEQ ID NO:7 and/or the amino acid sequence of SEQ ID NO:9 or SEQ ID NO:10.

29. The method of claim 1, wherein the intracellular signaling domain comprises the amino acid sequence of SEQ ID NO:7 and the amino acid sequence of SEQ ID NO:9 or SEQ ID NO:10, wherein the amino acid sequences comprising the intracellular signaling domain are expressed in the same frame and as a single polypeptide chain.

30. The method of claim 1, wherein the CAR comprises:
(i) the amino acid sequence of any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86;
(ii) an amino acid sequence having at least one, two or three modifications but not more than 30, 20 or 10 modifications to any of SEQ ID NO: 67, SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86; or
(iii) an amino acid sequence with 95-99% identity to any of SEQ ID NO: 67; SEQ ID NO: 73, SEQ ID NO: 278, SEQ ID NO: 63, SEQ ID NO: 64, SEQ ID NO: 65, SEQ ID NO: 66, SEQ ID NO: 68, SEQ ID NO: 69, SEQ ID NO: 70, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86.

31. The method of claim 1, wherein the cell is a T cell, an autologous T cell, an allogeneic T cell, or an NK cell.

32. The method of claim 1, wherein the disease associated with mesothelin expression is a cancer chosen from one or more of mesothelioma, malignant pleural mesothelioma, non-small cell lung cancer, small cell lung cancer, squamous cell lung cancer, or large cell lung cancer, pancreatic cancer, pancreatic ductal adenocarcinoma, pancreatic metastatic, ovarian cancer, or colorectal cancer and bladder cancer, or a metastasis thereof.

* * * * *